(12) United States Patent
Wang et al.

(10) Patent No.: US 11,919,969 B2
(45) Date of Patent: Mar. 5, 2024

(54) BISPECIFIC ANTIBODIES FOR FACTOR IX AND FACTOR X

(71) Applicant: KYMAB LIMITED, Cambridge (GB)

(72) Inventors: Wei Wang, Cambridge (GB); E-Chiang Lee, Cambridge (GB); John Kenneth Blackwood, Cambridge (GB); Roberto Magliozzi, Cambridge (GB)

(73) Assignee: KYMAB LIMITED, Cambridge (GB)

( * ) Notice: Subject to any disclaimer, the term of this patent is extended or adjusted under 35 U.S.C. 154(b) by 362 days.

(21) Appl. No.: 16/625,109

(22) PCT Filed: Jun. 22, 2018

(86) PCT No.: PCT/EP2018/066836
§ 371 (c)(1),
(2) Date: Dec. 20, 2019

(87) PCT Pub. No.: WO2018/234575
PCT Pub. Date: Dec. 27, 2018

(65) Prior Publication Data
US 2020/0148787 A1    May 14, 2020

(30) Foreign Application Priority Data

Jun. 22, 2017 (GB) .................................. 1709970.6

(51) Int. Cl.
*C07K 16/36* (2006.01)
*A61P 7/04* (2006.01)
*C07K 16/40* (2006.01)

(52) U.S. Cl.
CPC ............. *C07K 16/36* (2013.01); *A61P 7/04* (2018.01); *C07K 16/40* (2013.01); *C07K 2317/21* (2013.01); *C07K 2317/31* (2013.01); *C07K 2317/55* (2013.01); *C07K 2317/56* (2013.01); *C07K 2317/64* (2013.01); *C07K 2317/75* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,731,168 A | 3/1998 | Carter et al. | |
| 8,062,635 B2 * | 11/2011 | Hattori | A61P 7/04 514/14.1 |
| 9,334,331 B2 * | 5/2016 | Igawa | C07K 16/40 |
| 10,815,308 B2 * | 10/2020 | Wang | A61P 7/02 |
| 2002/0146411 A1 * | 10/2002 | Blackburn | C07K 16/36 536/23.53 |
| 2003/0219441 A1 | 11/2003 | Thorpe | |
| 2005/0058640 A1 | 3/2005 | Kerschbaumer et al. | |
| 2010/0003254 A1 | 1/2010 | Hattori et al. | |
| 2014/0356377 A1 | 12/2014 | Hack et al. | |
| 2016/0222129 A1 | 8/2016 | Igawa | |
| 2016/0289299 A1 | 10/2016 | Griffin et al. | |
| 2020/0199250 A1 | 6/2020 | Wang et al. | |
| 2021/0101997 A1 | 4/2021 | Wang et al. | |
| 2022/0064327 A1 | 3/2022 | Wang et al. | |

FOREIGN PATENT DOCUMENTS

| | | |
|---|---|---|
| CA | 3027018 A1 | 2/2018 |
| CN | 1390258 A | 1/2003 |
| CN | 103930129 A | 7/2014 |
| WO | WO 1998/050431 A2 | 11/1998 |
| WO | 0119992 | 3/2001 |
| WO | WO 2002/060919 A2 | 8/2002 |
| WO | 2005025615 | 3/2005 |
| WO | 2005035753 | 4/2005 |
| WO | 2005035754 | 4/2005 |
| WO | 2005035756 | 4/2005 |
| WO | 2006109592 | 10/2006 |
| WO | WO 2006/106905 A1 | 10/2006 |
| WO | WO 2007/003421 A2 | 1/2007 |
| WO | WO 2007/110205 A2 | 10/2007 |
| WO | WO 2010/151792 A1 | 12/2010 |
| WO | WO 2011/143545 A1 | 11/2011 |
| WO | 2012067176 | 5/2012 |
| WO | WO 2013/157954 A1 | 10/2013 |
| WO | WO 2014/058389 A1 | 4/2014 |
| WO | WO 2015/103072 A1 | 7/2015 |
| WO | 2015194233 | 12/2015 |
| WO | 2016047656 | 3/2016 |
| WO | 2016166014 | 10/2016 |
| WO | 2016171202 | 10/2016 |
| WO | WO 2017/072310 A1 | 2/2017 |
| WO | 2017110980 | 6/2017 |
| WO | 2017136820 | 8/2017 |

(Continued)

OTHER PUBLICATIONS

Church et al., Blood. Dec. 1988;72(6):1911-21.*
Hsia et al., Am. J. Hematol. 1008, 83:318-320.*
Janeway et al., Immunobiology, 3rd edition, Garland Publishing Inc., 1997, pp. 3:1-3:21.*
Rudikoff et al., Proc Natl Acad Sci USA. Mar. 1982;79(6):1979-83.*
Edwards et al.,J Mol Biol. Nov. 14, 2003;334(1): 103-18.*
Llyod et al., Protein Eng Des Sel. Mar. 2009;22(3):159-68. doi: 10.1093/protein/gzn058. Epub Oct. 29, 2008.*

(Continued)

*Primary Examiner* — Michael Szperka
(74) *Attorney, Agent, or Firm* — LATHROP GPM LLP; James H. Velema, Esq.

(57) ABSTRACT

Bispecific antigen binding molecules (e.g., antibodies) that bind blood clotting factors, factor IXa (FIXa) and factor X (FX), and enhance the FIXa-catalysed activation of FX to FXa. Use of the bispecific antigen binding molecules to control bleeding, by replacing natural cofactor FVIIIa which is deficient in patients with haemophilia A.

9 Claims, 14 Drawing Sheets
Specification includes a Sequence Listing.

(56) References Cited

FOREIGN PATENT DOCUMENTS

| WO | 2017200981 | 11/2017 |
| WO | 2018021450 | 2/2018 |
| WO | 2018047813 | 3/2018 |
| WO | 2018098363 | 5/2018 |
| WO | 2018141863 | 8/2018 |
| WO | 2018145125 | 8/2018 |
| WO | WO 2018/209265 A1 | 11/2018 |
| WO | WO 2018/234575 A1 | 12/2018 |
| WO | 2019065795 | 4/2019 |
| WO | 2019096874 | 5/2019 |
| WO | WO 2020/128049 A1 | 6/2020 |

OTHER PUBLICATIONS

Goel et al., J Immunol. Dec. 15, 2004; 173(12):7358-67.*
Kanyavuz et al., Nat Rev Immunol. Jun. 2019;19(6):355-368. doi: 10.1038/S41577-019-0126-7.*
Aleman, Maria M., et al. "Phospholipid-Independent Activity of Fviiia Mimetic Bispecific Antibodies in Plasma." Blood 132. Supplement 1 (2018): 2461-2461.
Haemophilia (2014), 20(suppl. 3), 1-186.
Knappe, Sabrine et al. "Biospecific antibodies with light chain specificity for factor IXa and X improve thrombingeneration in hemophilia A plasma." 27th congress of the international society of thrombosis and homeostasis, Jul. 6-10, 2019, Melbourne, Australia, 1 pg.
Knobe, Karin, and Erik Berntorp. "New treatments in hemophilia: insights for the clinician." Therapeutic advances in hematology 3.3 (2012): 165-175.
Leksa, Nina C., et al. "Intrinsic differences between FVIII a mimetic bispecific antibodies and FVIII prevent assignment of FVIII equivalence." Journal of Thrombosis and Haemostasis 17.7 (2019): 1044-1052 Supplementary Material.
Leksa, Nina C., et al. "Intrinsic differences between FVIII a mimetic bispecific antibodies and FVIII prevent assignment of FVIII equivalence." Journal of Thrombosis and Haemostasis 17.7 (2019): 1044-1052.
Muto, Atsushi, et al. "Anti-factor IXa/X bispecific antibody ACE910 prevents joint bleeds in a long-term primate model of acquired hemophilia A." Blood, The Journal of the American Society of Hematology 124.20 (2014): 3165-3171.
Oldenburg J, Mahlangu JN, Kim B, et al. Emicizumab prophylaxis in hemophilia A with inhibitors. N Engl J Med. DOI: 10.1056/NEJMoa1703068, 29 pages.
Oldenburg, Johannes, et al. "Emicizumab prophylaxis in hemophilia A with inhibitors." New England Journal of Medicine 377.9 (2017): 809-818.
Sampei, Zenjiro, et al. "Identification and multidimensional optimization of an asymmetric bispecific IgG antibody mimicking the function of factor VIII cofactor activity." PloS one 8.2 (2013), 13 pages.
Shima, Midori, et al. "Factor VIII-mimetic function of humanized bispecific antibody in hemophilia A." New England Journal of Medicine 374.21 (2016): 2044-2053.
Tripodi, Armando. "Thrombin generation assay and its application in the clinical laboratory." Clinical chemistry 62.5 (2016): 699-707.
Uchida, Naoki, et al. "A first-in-human phase 1 study of ACE910, a novel factor VIII-mimetic bispecific antibody, in healthy subjects." Blood, The Journal of the American Society of Hematology 127.13 (2016): 1633-1641.
International Search Report and Written Opinion for PCT International Patent Application No. PCT/EP2018/066836, dated Nov. 27, 2018.
International Preliminary Report on Patentability for PCT International Patent Application No. PCT/EP2018/066836, dated Dec. 24, 2019.
Kitazawa et al., "A bispecific antibody to factors IXa and X restores factor VIII hemostatic activity in a hemophilia A model", Nature Medicine, Sep. 30, 2012, 18(10): 1570-1574.
Roche, "Information on neutralising anti-drug antibody to Hemlibra", Apr. 23, 2018, Retrieved from url: <https://aiceonline.org/wp-content/uploads/2019/03/2018-04-20-ADA-Case-Roche-Statement.pdf>.
"Abstracts of the WFH 2014 World Congress, May 11-15, Melbourne, Australia", Haemophilia, The Official Journal of the World Federation of Hemophilia, 2014, 20(Supplement 3): 1-186.
Aleman et al., "Phospholipid-Independent Activity of Fviiia Mimetic Bispecific Antibodies in Plasma", Program: Oral and Poster Abstracts, Session: 321, Blood Coagulation and Fibrinolytic Factors: Poster II, Hematology Disease Topics & Pathways: Biological, antibodies, Therapies, Dec. 2, 2018.
Hoad et al., "Characterisation of monoclonal antibodies to human factor X/Xa initial observations with a quantitative ELISA procedure", Journal of Immunological Methods, Feb. 15, 1991, 136(2): 269-278.
International Search Report and Written Opinion for PCT International Patent Application No. PCT/EP2019/086808, dated Apr. 17, 2020.
Kymab, "Kymab Announces Presentation on KY1049 at the European Congress on Thrombosis and Haemostasis", News Release, Cambridge, U.K., Oct. 3, 2019.
Lloyd et al., "Modelling the human immune response: performance of a 10" human antibody repertoire against a broad panel of therapeutically relevant antigens", Protein Eng Des Sel., Mar. 2009, 22(3): 159-168, Epublished Oct. 29, 2008.
Oldenburg et al., "Emicizumab prophylaxis in Hemophilia A with inhibitors", New England Journal of Medicine, 2017, 377(9): 809-818.
Oldenburg et al., "HAVEN 1 Supplementary Appendix for Emicizumab prophylaxis in Hemophilia A with inhibitors", New England Journal of Medicine, 2017, pp. 1-29.
Paz-Priel et al., "Immunogenicity of Emicizumab in People with Hemophilia A (PwHA): Results from the HAVEN 1-4 Studies", Blood, Nov. 29, 2018, 132: 633.
Powell et al., "Compendium of excipients for parenteral formulations", PDA Journal of Pharmaceutical Science and Technology, Sept. 1, 1998, 52(5): 238-311.
Roche, "Roche's emicizumab continued to show promising safety and efficacy profile in long-term study in people with severe haemophilia A", Jul. 28, 2016, Retrieved from url: < https://www.roche.com/investors/updates/inv-update-2016-07-28.htm>.
Sampei et al., "Identification and Multidimensional Optimization of an Asymmetric Bispecific IgG Antibody Mimicking the Function of Factor VIII Cofactor Activity", PLOS One, Feb. 28, 2013, 8(2): 1-13.
Uchida et al., "A first-in-human phase 1 study of ACE910, a novel factor VIII-mimetic bispecific antibody, in healthy subjects", Blood, Mar. 31, 2016, 127: 1633-1641.
Gibson et al., "N-terminal or signal peptide sequence engineering prevents truncation of human monoclonal antibody light chains," Biotechnology and Bioengineering, Sep. 2017, 114(9): 1970-1977.
Kotia et al., "Analysis of monoclonal antibody product heterogeneity resulting from alternate cleavage sites of signal peptide," Analytical Biochemistry, Apr. 15, 2010, 399(2): 190-195.
Ponraj et al., "Expressed antibody repertoires in human cord blood cells: 454 sequencing and IMGT/HighV-QUEST analysis of germline gene usage, junctional diversity, and somatic mutations," Immunogenics, May 2012, 64: 337-350.
Song et al., "Alteration of amino acid residues at the L-chain N-terminus and in complementarity-determining region 3 increases affinity of a recombinant F(ab) for the human N blood group antigen," The Journal of AABB, Transfusion, Feb. 2004, 44(2): 173-186.
Spidel et al., "Rapid high-throughput cloning and stable expression of antibodies in HEK293 cells," Journal of Immunological Methods, Dec. 2016, 439: 50-58.

* cited by examiner a
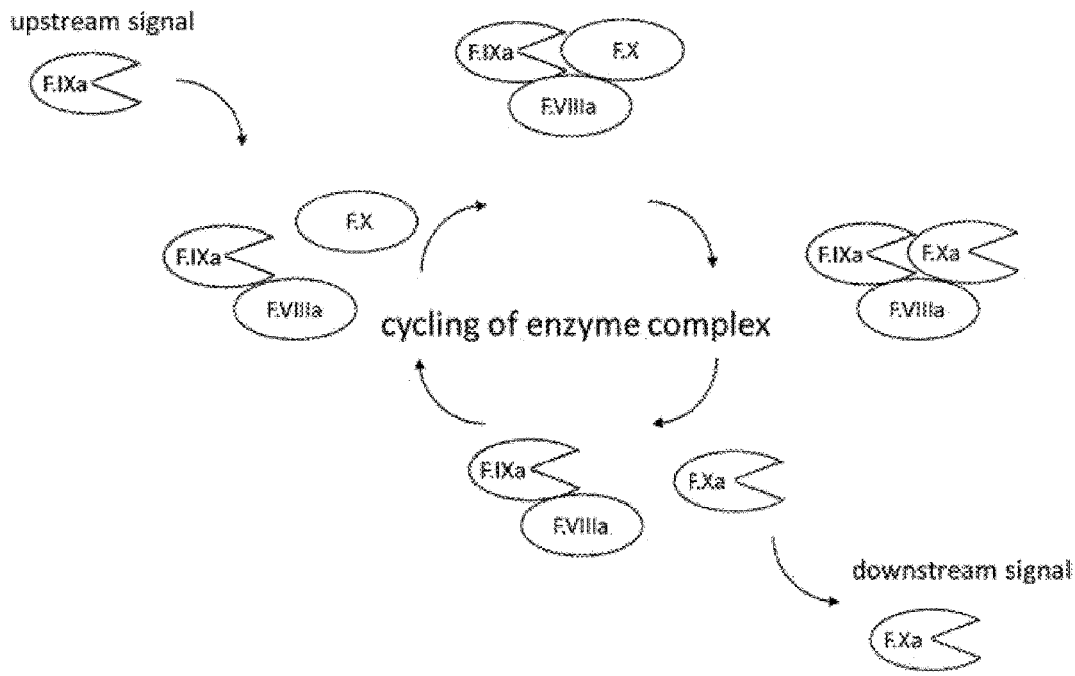
b
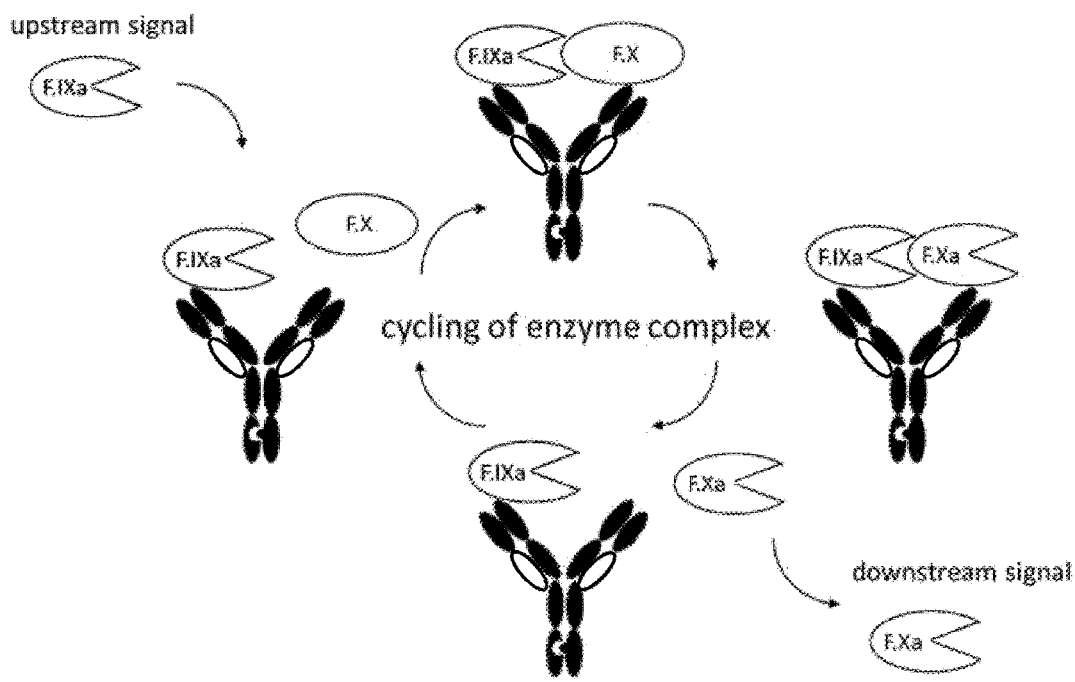
Figure 2

MQRVNMIMAESPGLITICLLGYLLSAECTVFLDHENANKILNRPKR

| | | | | |
|---|---|---|---|---|
| YNSGKLEEFV | QGNLERECME | EKCSFEEARE | VFENTERTTE | 40 |
| FWKQYVDGDQ | CESNPCLNGG | SCKDDINSYE | CWCPFGFEGK | 80 |
| NCELDVTCNI | KNGRCEQFCK | NSADNKVVCS | CTEGYRLAEN | 120 |
| QKSCEPAVPF | PCGRVSVSQT | SKLTR AETVF | PDVDYVNSTE | 160 |
| AETILDNITQ STQSFNDFTR | VVGGEDAKPG | QFPWQVVLNG | | 200 |
| KVDAFCGGSI | VNEKWIVTAA | HCVETGVKIT | VVAGEHNIEE | 240 |
| TEHTEQKRNV | IRIIPHHNYN | AAINKYNHDI | ALLELDEPLV | 280 |
| LNSYVTPICI | ADKEYTNIFL | KFGSGYVSGW | GRVFHKGRSA | 320 |
| LVLQYLRVPL | VDRATCLRST | KFTIYNNMFC | AGFHEGGRDS | 360 |
| CQGDSGGPHV | TEVEGTSFLT | GIISWGEECA | MKGKYGIYTK | 400 |
| VSRYVNWIKE | KTKLT | | | 415 |

Figure 3

```
          10         20         30         40         50
MGRPLHLVLL SASLAGLLLL GESLFIRREQ ANNILARVTR ANSFLEEMKK
          60         70         80         90        100
GHLERECMEE TCSYEEAREV FEDSDKTNEF WNKYKDGDQC ETSPCQNQGK
         110        120        130        140        150
CKDGLGEYTC TCLEGFEGKN CELFTRKLCS LDNGDCDQFC HEEQNSVVCS
         160        170        180        190        200
CARGYTLADN GKACIPTGPY PCGKQTLERR KRSVAQATSS SGEAPDSITW
         210        220        230        240        250
KPYDAADLDP TENPFDLLDF NQTQPERGDN NLTRIVGGQE CKDGECPWQA
         260        270        280        290        300
LLINEENEGF CGGTILSEFY ILTAAHCLYQ AKRFKVRVGD RNTEQEEGGE
         310        320        330        340        350
AVHEVEVVIK HNRFTKETYD FDIAVLRLKT PITFRMNVAP ACLPERDWAE
         360        370        380        390        400
STLMTQKTGI VSGFGRTHEK GRQSTRLKML EVPYVDRNSC KLSSSFIITQ
         410        420        430        440        450
NMFCAGYDTK QEDACQGDSG GPHVTRFKDT YFVTGIVSWG EGCARKGKYG
         460        470        480
IYTKVTAFLK WIDRSMKTRG LPKAKSHAPE VITSSPLK
```

Figure 4

A) With common light chain
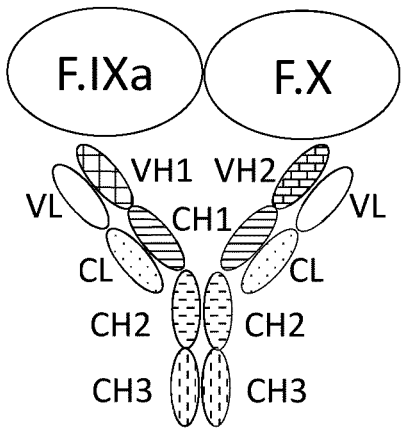
B) Without common light chain
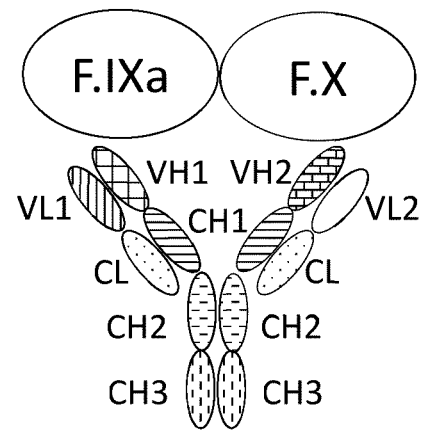
Figure 5 A and B C)
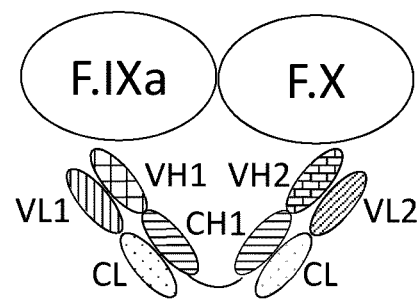
D)
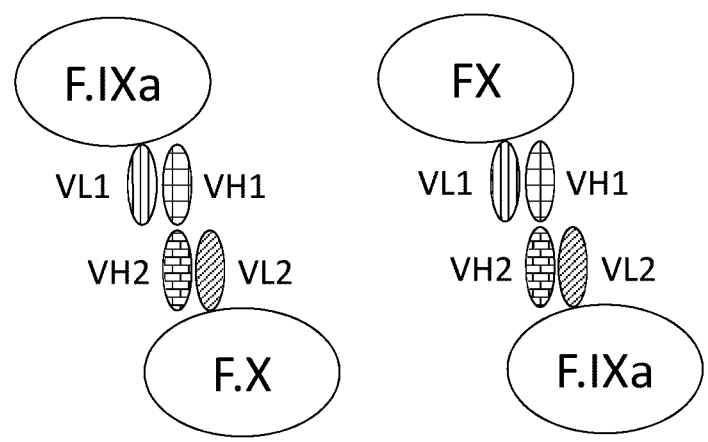
Figure 5 C and D i)
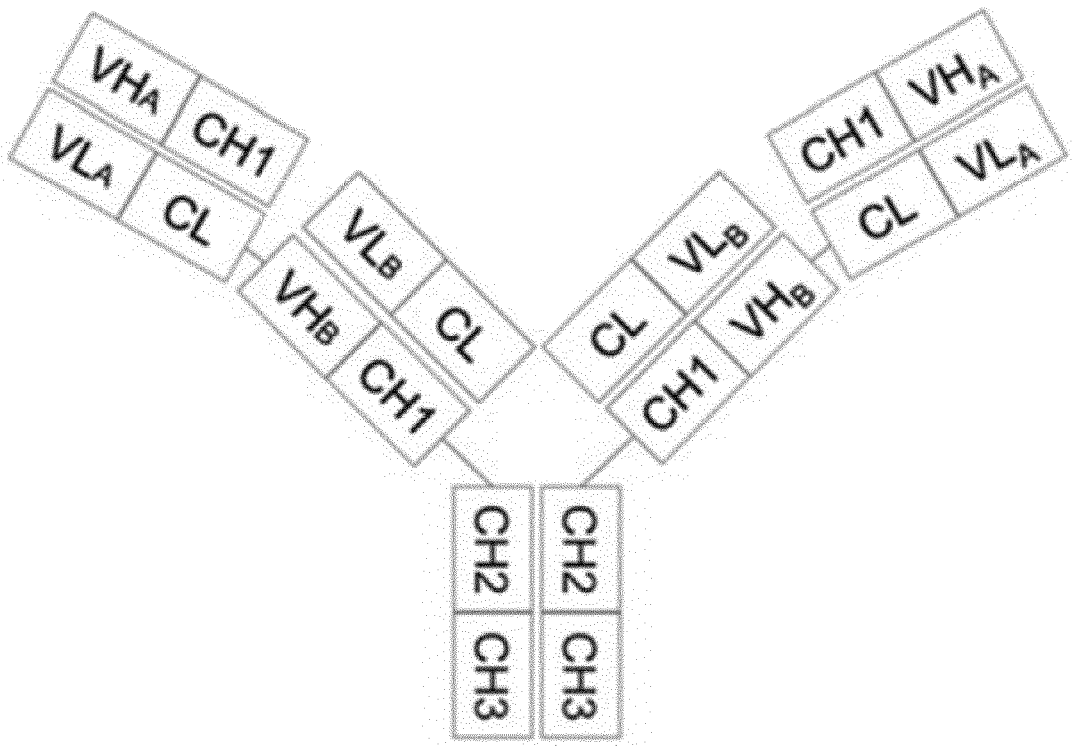
ii)
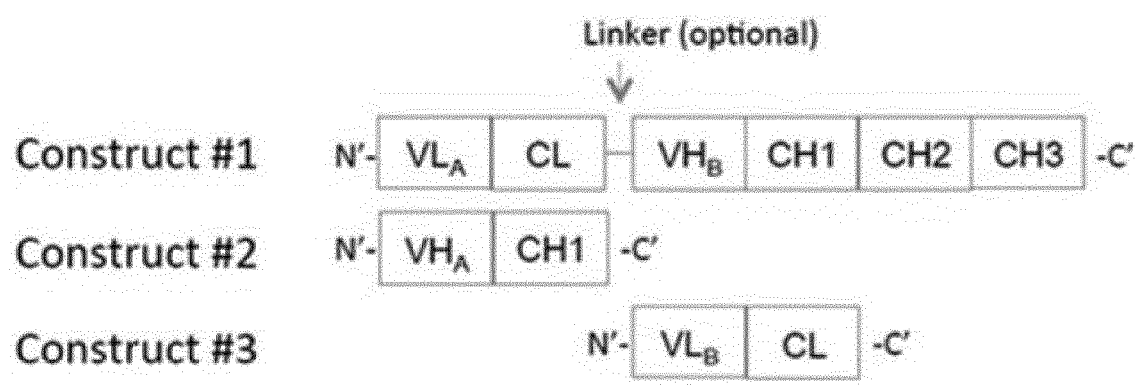
Figure 6

A
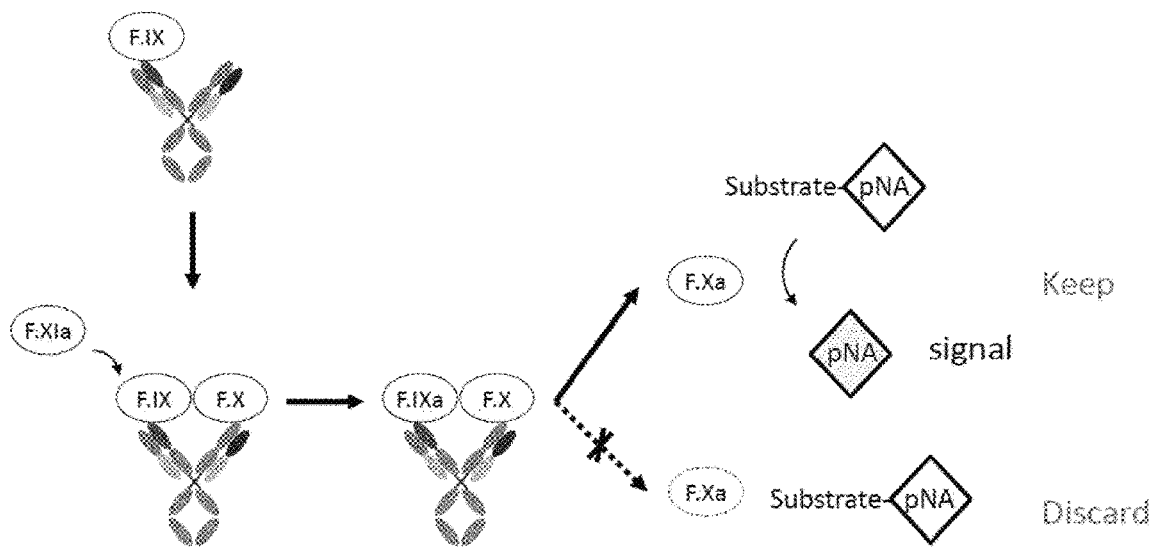
B
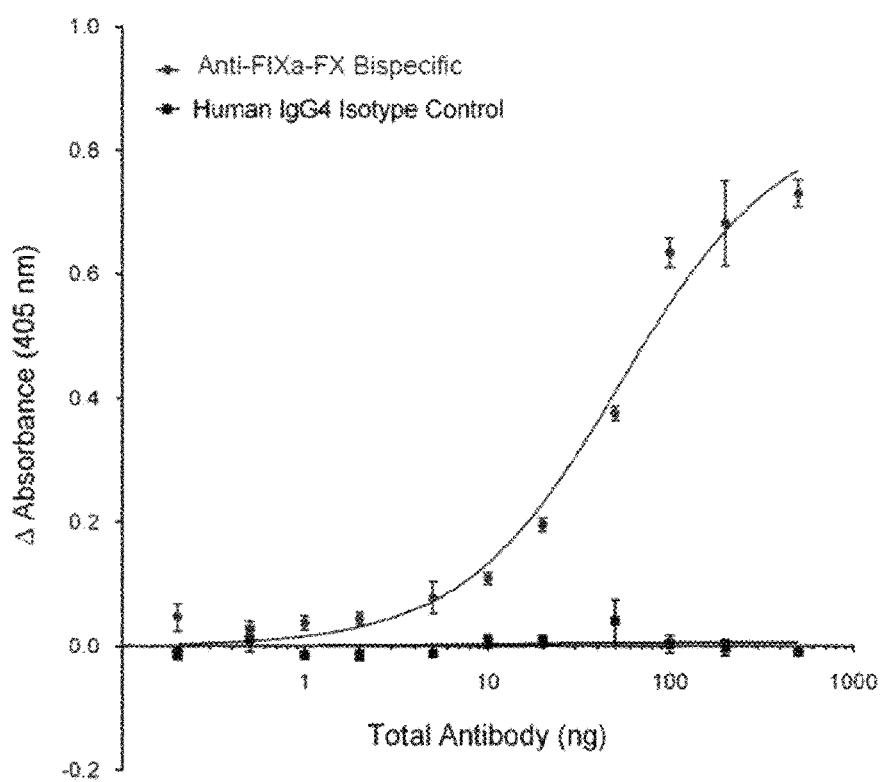
Figure 7

| | A | C | D | E | F | G | H | I | K | L |
|---|---|---|---|---|---|---|---|---|---|---|
| AREGYSSSSYYGMDV | N420H | N467H | N468H | N469H | N470H | N471H | N472H | N473H | N474H | N475H |
| AREGYSSSSYYGMDV | N421H | N485H | N486H | N487H | N488H | N489H | N490H | N491H | N492H | N493H |
| AREGYSSSSYYGMDV | N422H | N430H | N431H | N432H | N433H | N434H | N435H | N436H | N437H | N438H |
| AREGYSSSSYYGMDV | N423H | N448H | N449H | N450H | N451H | N452H | N453H | N454H | N455H | N456H |

| | M | N | P | Q | R | S | T | V | W | Y |
|---|---|---|---|---|---|---|---|---|---|---|
| AREGYSSSSYYGMDV | N476H | N477H | N478H | N479H | N480H | *N128H* | N481H | N482H | N483H | N484H |
| AREGYSSSSYYGMDV | N494H | N495H | N496H | N497H | N498H | *N128H* | N499H | N500H | N501H | N502H |
| AREGYSSSSYYGMDV | N439H | N440H | N441H | N442H | N443H | *N128H* | N444H | N445H | N446H | N447H |
| AREGYSSSSYYGMDV | N457H | N458H | N459H | N460H | N461H | N462H | N463H | N464H | N465H |

Figure 9

BISPECIFIC ANTIBODIES FOR FACTOR IX AND FACTOR X

CROSS-REFERENCE TO RELATED APPLICATIONS

This application is the U.S. national phase application filed under 35 U.S.C. § 371 claiming benefit to International Patent Application No. PCT/EP2018/066836, filed on Jun. 22, 2018, which is entitled to priority under to Great Britain Patent Application No. 1709970.6, filed Jun. 22, 2017, the disclosure of which is incorporated herein by reference in their entireties.

FIELD OF THE INVENTION

This invention relates to bispecific antigen-binding molecules (e.g., antibodies) that bind factor IXa and factor X clotting factors in the blood coagulation cascade. Such bispecifics functionally substitute for factor VIII by activating factor X, restoring blood clotting ability to patients who are deficient in FVIII, i.e., patients who have type A haemophilia.

BACKGROUND

Haemophilia is an inherited condition in which the blood has a reduced ability to clot, owing to loss of function (partial or total) of one of the many clotting factors. Haemophilia A is a deficiency in blood clotting factor VIII (FVIII). The disease has mild, moderate and severe forms, depending on the degree to which the patient retains any residual FVIII function and on the balance of other components in the blood coagulation cascade. If untreated, haemophilia A leads to uncontrolled bleeding, which can result in severe disability, especially through damage to joints from haemarthrosis events. The disease is often life-limiting and can be life-threatening. The global incidence of haemophilia A is believed to be around 1:10,000. Haemophilia B (deficiency of a different blood clotting factor, factor IX) is less common, with an incidence of around 1:50,000. Both diseases are X-linked so are usually found in males, the incidence of haemophilia A in male births thus being around 1 in 5,000.

Preventing bleeding episodes is essential to improving patients' quality of life and reducing the risk of fatal blood loss. For haemophilia A, the missing co-factor can be replaced by administration of FVIII. FVIII for administration to a patient may be recombinantly expressed or it may be purified from blood plasma. Typically, patients on this treatment self-inject with FVIII every 48 hours or 3× per week.

Treatment with FVIII is not a perfect solution. A serious drawback is that it can trigger production of alloantibodies in the body. This renders treatment with FVIII ineffective, as the alloantibodies bind the FVIII and prevent its activity, putting the patient in a dangerous situation if a bleed occurs. Such inhibitory antibodies develop in about 30% of patients treated with FVIII for severe haemophilia.

Treatment with plasma-derived FVIII, rather than the recombinant form, has been reported to have a lower risk of triggering inhibitory antibodies in patients. This may be due to the plasma-derived form retaining Von Willebrand factor (VWF), which is found naturally in association with FVIII and may mask immunogenic epitopes. However, no form of FVIII has yet been produced that completely avoids the risk of inhibitory antibodies.

Despite being possibly more immunogenic, recombinant FVIII offers some advantages over the plasma-derived form, since being more stable it is easier and cheaper to store and transport. The risk of transmitting infections via products from donated blood plasma is now much reduced compared with the 1980s when viruses such as hepatitis C and HIV were inadvertently spread to recipients of infected blood products, but of course the need for strict safety controls remains.

New recombinant forms of FVIII have been developed, such as the B-domain truncated polypeptide turoctocog alfa (NovoEight®). However, such products are ineffective for patients that develop neutralising antibodies against FVIII. Some patients successfully undergo immune tolerance induction to prevent anti-FVIII antibodies from developing. However, there remains a substantial demand for alternatives to FVIII for use in patients who have, or are at risk of developing, inhibitory antibodies.

One such alternative is recombinant factor VIIa, known as activated eptacog alfa (NovoSeven®). However, it has a short half-life and must be injected every few hours. Its use is largely restricted to rescue therapy or providing haemostatic cover during surgery in haemophiliacs who have inhibitory antibodies, rather than being a viable option for long term protective treatment.

Another available product is FEIBA (Factor Eight Inhibitor Bypassing Activity), an activated prothrombin complex concentrate (aPCC), which similarly can be used to control bleeding episodes and to prevent bleeding during surgical interventions in haemophiliac patients who have inhibitors to factor VIII.

A variety of other alternative therapies are currently being pursued, such as gene therapy, suppression of anti-thrombin using siRNA, and an antibody to TFPI (Tissue factor Pathway Inhibitor), concizumab.

One new approach is a humanised bispecific IgG antibody targeting both factor IXa (FIXa) and factor X (FX). The bispecific antibody binds FIXa with one arm and FX with the other arm, bringing these two co-factors together and thereby promoting FIXa-catalysed activation of FX in the same way that FVIII does. Thus, the antibody functionally replaces FVIII in the blood coagulation cascade (FIG. 1). As its structure is completely different from FVIII, the antibody cannot be neutralised by anti-FVIII antibodies and so is suitable for patients who have developed, or are at risk of developing, alloantibodies to administered FVIII.

In 2012, Kitazawa et al reported isolation of a FIXa/X bispecific antibody which was able to activate FX, from a screen of approximately 40,000 anti-FIXa/X bispecific antibodies that had been produced by immunising 92 laboratory animals with human FIXa or FX and co-transfecting the anti-FIXa and anti-FX antibody genes into host cells for expression [1]. The selected antibody was refined to generate a humanised antibody designated hBS23, which showed coagulation activity in FVIII-deficient plasma and in vivo haemostatic activity in primates [1]. A more potent version of this antibody, designated hBS910 [2], entered clinical trials under the investigational drug name ACE910, INN emicizumab. The development of ACE910 took place in one of the leading antibody groups globally. Nevertheless, it took more than 7 years to engineer a molecule with the appropriate in vivo efficacy and with biochemical and biophysical properties suitable for clinical scale manufacturing.

In a phase I study of 48 healthy male subjects receiving ACE910 subcutaneously at doses up to 1 mg/kg, 2 subjects tested positive for anti-ACE910 antibodies [3]. The antibody was reported to have a linear pharmacokinetic profile and a half-life of about 4-5 weeks [3]. Emicizumab was subsequently administered to 18 Japanese patients with severe haemophilia A, at weekly subcutaneous doses of up to 3 mg/kg, and was reported to reduce the episodic use of clotting factors to control bleeding in these patients [4]. In December 2016, emicizumab was reported to have met its primary endpoint in a phase III clinical trial for reducing bleeding in patients with haemophilia A (the "HAVEN 1" study). A statistically significant reduction in the number of bleeds was reported for patients treated with emicizumab prophylaxis compared with those receiving no prophylactic treatment. The study was also reported to have met all secondary endpoints, including a statistically significant reduction in the number of bleeds over time with emicizumab prophylaxis treatment in an intra-patient comparison in people who had received prior bypassing agent prophylaxis treatment. The efficacy data on emicizumab are therefore encouraging, although safety concerns were heightened by the death of a patient on the HAVEN 1 study. The approved drug carries a boxed warning regarding the risk of thrombotic microangiopathy and thromboembolism in patients receiving aPCC in combination with emicizumab. As noted above, aPCC is used to control bleeding in patients who have inhibitory antibodies to FVIII, a key patient group for treatment with the bispecific antibody.

It is important to note that management of haemophilia requires continuous treatment for a patient's lifetime, beginning at the point of diagnosis—which is usually in infancy—and calls for a therapy that will be tolerated without adverse effects and that will remain effective over several decades or even a century. Long term safety, including low immunogenicity, is therefore of greater significance for an anti-haemophilia antibody compared with antibodies that are intended to be administered over a shorter duration such as a period of weeks, months or even a few years.

Recently, WO2018/098363 described bispecific antibodies binding to FIX and FX, isolated from a human antibody yeast library (Adimab). WO2018/098363 disclosed that increasing the affinity of the anti-FIXa arm of a bispecific antibody results in an increase in FVIIIa activity (represented by decreased blood clotting time in an assay). A bispecific antibody "BS-027125" was generated by affinity maturation of an initially selected "parent" antibody, which increased the affinity of its FIXa-binding arm. BS-027125 was reported to achieve approximately 90% FVIIIa-like activity in a one-stage clotting assay. When compared with emicizumab, BS-027125 was reported to exhibit much higher affinity binding to factor FIX zymogen, FIXa and FX zymogen, and much lower binding (no detected binding) to FXa. The FIX-binding arm, "BIIB-9-1336" reportedly showed selective binding for FIXa (activated FIX) in preference to FIX zymogen (mature FIX prior to proteolytic activation), and was found to bind an epitope overlapping with the FIXa epitope bound by FVIIIa. The FX-binding arm, "BIIB-12-917", reportedly showed selective binding to FX zymogen, lacked detectable binding to (activated) FXa, and bound an epitope of FX that lies within the activation peptide (which is present in FX zymogen but not FXa). Further mutations were then introduced into selected FIX-binding antibodies, including BIIB-9-1336, to generate libraries from which to select for antibodies with even further increased specificity and/or affinity for FIXa.

SUMMARY OF THE INVENTION

The present invention relates to improved bispecific antigen-binding molecules that bind blood clotting factors FIXa and FX. The bispecific antigen-binding molecules of the present invention enhance the FIXa-catalysed activation of FX to FXa, and can effectively replace the natural cofactor FVIIIa which is missing in patients with haemophilia A, to restore the ability of the patients' blood to clot. See FIG. 2b.

As reported here, the inventors succeeded in generating a number of bispecific antigen-binding molecules having suitable qualities for development as therapeutic products, including very high potency in enhancing FX activation. Described are bispecific antigen-binding molecules having novel binding sites for anti-FIXa and anti-FX, which can be used to effectively substitute for FVIIIa in the blood clotting cascade. In particular, an anti-FIXa binding site is described which is highly active in combination with an array of different anti-FX binding sites and can thus be incorporated into a variety of different FIXa-FX bispecifics, providing flexibility for selection of bispecific antibodies with further desired characteristics such as ease of manufacture.

In a first aspect, the present invention relates to bispecific antigen-binding molecules comprising (i) a FIXa binding polypeptide arm comprising a FIXa binding site, and (ii) a FX binding polypeptide arm comprising a FX binding site. The FIXa and/or the FX binding polypeptide arm may comprise an antibody Fv region comprising the FIXa or FX binding site respectively. An antibody Fv region is an antibody VH-VL domain pair. The VH domain comprises HCDR1, HCDR2 and HCDR3 in a VH domain framework, and the VL domain comprises LCDR1, LCDR2 and LCDR3 in a VL domain framework. The polypeptide arm may comprise an antibody heavy chain (optionally one comprising an IgG constant region) and/or an antibody light chain.

Antigen-binding molecules of the present invention may thus comprise
  first and second antibody Fv regions, the first and second
    antibody Fv regions comprising binding sites for FIXa
    and for FX respectively, and
  a half-life extending region for prolonging the half-life of
    the molecule in vivo.

The half-life extending region may be a heterodimerisation region, comprising a first polypeptide covalently linked (e.g., as a fusion protein) to the first antibody Fv region and a second polypeptide covalently linked (e.g., as a fusion protein) to the second antibody Fv region, wherein the two polypeptides pair covalently and/or non-covalently with one another. The first and second polypeptides of the heterodimerisation region may have identical or different amino acid sequences. The heterodimerisation region may comprise one or more antibody constant domains, e.g., it may be an antibody Fc region.

Bispecific antigen-binding molecules of the present invention are able to bind FIXa through the FIXa binding site of the FIXa binding polypeptide arm and to bind FX through the FX binding site of the FX binding polypeptide arm, and thereby enhance the FIXa-catalysed activation of FX to FXa. This may be determined in an in vitro FX activation assay as described herein.

The FIXa binding site may be provided by a set of complementarity determining regions (CDRs) in the FIXa binding polypeptide arm, the set of CDRs comprising HCDR1, HCDR2, HCDR3 and/or LCDR1, LCDR2 and LCDR3, wherein
  HCDR1 is SEQ ID NO: 1
  HCDR2 is SEQ ID NO: 2
  HCDR3 is SEQ ID NO: 400
  LCDR1 is SEQ ID NO: 6
  LCDR2 is SEQ ID NO: 7 and
  LCDR3 is SEQ ID NO: 8.

The set of CDRs in the FIXa binding polypeptide arm may be a set of CDRs wherein
   HCDR1 is SEQ ID NO: 1
   HCDR2 is SEQ ID NO: 2
   HCDR3 is SEQ ID NO: 401, SEQ ID NO: 402, or SEQ ID NO: 403.
   LCDR1 is SEQ ID NO: 6
   LCDR2 is SEQ ID NO: 7 and
   LCDR3 is SEQ ID NO: 8.

The set of CDRs in the FIXa binding polypeptide arm may be a set of CDRs wherein
   HCDR1 is SEQ ID NO: 1
   HCDR2 is SEQ ID NO: 2
   HCDR3 is SEQ ID NO: 171
   LCDR1 is SEQ ID NO: 6
   LCDR2 is SEQ ID NO: 7 and
   LCDR3 is SEQ ID NO: 8.

The FIXa binding site may be provided by a set of complementarity determining regions (CDRs) in the FIXa binding polypeptide arm, the set of CDRs comprising HCDR1, HCDR2, HCDR3 and/or LCDR1, LCDR2 and LCDR3, wherein
   HCDR1 is SEQ ID NO: 140
   HCDR2 is SEQ ID NO: 141
   HCDR3 is SEQ ID NO: 142
   LCDR1 is SEQ ID NO: 6
   LCDR2 is SEQ ID NO: 7 and
   LCDR3 is SEQ ID NO: 8.

Optionally, one or more amino acids in the set of CDRs may be mutated to differ from these sequences. For example, the set of CDRs may comprise 1, 2, 3, 4 or 5 amino acid alterations, the altered residue or residues being in any one or more of the heavy or light chain CDRs. For example the set of CDRs may comprise one or two conservative substitutions. The choice of mutations, e.g., substitutions, can be informed by the analysis in Example 14 herein (e.g., for HCDR3) and/or by experimental testing to confirm biological properties of the resulting variants. Mutation in a VH domain, in a set of HCDRs, or in HCDR3, may comprise or consist of substitution of a hydrophobic or positively charged residue for the Ile at IMGT position 111.1 in HCDR3 SEQ ID NO: 171 or the Ser in IMGT position 111.1 of HCDR3 SEQ ID NO: 171. Preferably, the HCDR3 comprises a hydrophobic residue at this position, for example Ile, Leu, Val or Trp. Ile is especially preferred.

The FIXa binding polypeptide arm may comprise an antibody VH domain comprising a set of HCDRs HCDR1, HCDR2 and HCDR3. The sequence of HCDR1 may be SEQ ID NO: 140, optionally with one or two amino acid alterations (e.g., substitutions). The sequence of HCDR2 may be SEQ ID NO: 141, optionally with one or two amino acid alterations (e.g., substitutions). The sequence of HCDR3 may be SEQ ID NO: 142, optionally with one or two amino acid alterations (e.g., substitutions). The sequence of HCDR1 may be SEQ ID NO: 1, optionally with one or two amino acid alterations (e.g., substitutions). The sequence of HCDR2 may be SEQ ID NO: 2, optionally with one or two amino acid alterations (e.g., substitutions). The sequence of HCDR3 may be SEQ ID NO: 3, optionally with one or two amino acid alterations (e.g., substitutions). Optionally, the HCDR1 sequence is SEQ ID NO: 140 or SEQ ID NO: 1. Optionally, the HCDR2 sequence is SEQ ID NO: 141 or SEQ ID NO: 2. Optionally, the HCDR3 sequence is SEQ ID NO: 400, SEQ ID NO: 401, SEQ ID NO: 402, SEQ ID NO: 403 or SEQ ID NO: 171. The sequence of HCDR1 may be SEQ ID NO: 1. The sequence of HCDR2 may be SEQ ID NO: 2. The sequence of HCDR3 may be SEQ ID NO: 171.

In a preferred embodiment, the VH domain comprises HCDR1 SEQ ID NO: 1, HCDR2 SEQ ID NO: 2 and HCDR3 SEQ ID NO: 171.

The FIXa binding polypeptide arm may comprise an antibody VL domain comprising a set of LCDRs LCDR1, LCDR2 and LCDR3. The sequence of LCDR1 may be SEQ ID NO: 6, optionally with one or two amino acid alterations (e.g., substitutions). The sequence of LCDR2 may be SEQ ID NO: 7, optionally with one or two amino acid alterations (e.g., substitutions). The sequence of LCDR3 may be SEQ ID NO: 8, optionally with one or two amino acid alterations (e.g., substitutions).

The antibody Fv region of the FIXa binding polypeptide arm may comprise a VH domain generated through recombination of immunoglobulin heavy chain v, d and j gene segments, wherein the v gene segment is VH3-7 (e.g., VH3-7*01), the d gene segment is DH1-26 (e.g., DH1-26*01) and/or wherein the j gene segment is JH6 (e.g. JH6*02), and/or it may comprise a VL domain generated through recombination of immunoglobulin light chain v and j gene segments, wherein the v gene segment is VL3-21 (e.g., VL3-21*d01) and the j gene segment is JL3 (e.g., JL3*02). The antibody Fv region of the FIXa binding polypeptide arm may comprise a VL domain generated through recombination of immunoglobulin light chain v and j gene segments, wherein the v gene segment is VL3-21 (e.g., VL3-21d*01) and the j gene segment is JL2 (e.g., JL2*01).

A VH domain of the FIXa binding polypeptide arm in the present invention may comprise HCDR1, HCDR2 and HCDR3 in a framework, the framework comprising a set of framework regions FR1, FR2, FR3 and FR4, wherein:
   FR1 is SEQ ID NO: 132
   FR2 is SEQ ID NO: 133
   FR3 is SEQ ID NO: 134 and
   FR4 is SEQ ID NO: 135,
   or comprising that set of framework regions with up to 10 amino acid alterations, e.g., there may be one or two conservative substitutions in any one or more framework region.

FR1 may have amino acid sequence SEQ ID NO: 132, optionally with a substitution of L for F, a substitution of V for A and/or a substitution of A for V in the AVS motif.

FR2 may have amino acid sequence SEQ ID NO: 133.

FR3 may have amino acid sequence SEQ ID NO: 134, optionally with a substitution of Y for F at the first residue position of that sequence, a substitution of D for A at the fourth residue position, a substitution of I for M at the twelfth residue position, a substitution of N for K at the nineteenth residue position, a substitution of L for V at the twenty first residue position and/or a substitution of L for V at the twenty third residue position of that sequence.

FR4 may have amino acid sequence SEQ ID NO: 135, optionally with a substitution of S for T at the eighth residue position.

The amino acid sequence of the VH domain of a FIXa polypeptide binding arm may share at least 90% sequence identity with SEQ ID NO: 324. Sequence identity may be at least 95%, at least 97%, at least 98% or at least 99%. It is preferred that the VH domain has a hydrophobic or positively charged residue at IMGT position 111.1 in HCDR3. The HCDR3 may be 15 amino acids in length. Preferably, the HCDR3 comprises a hydrophobic residue at this position, for example Ile, Leu, Val or Trp. Ile is especially preferred. The HCDR3 may comprise Ser at IMGT position 110, position 111 and/or position 112.1, for example it may comprise Ser two or three of positions 110, 111 and 112.1.

The amino acid sequence of an HCDR3 of a VH domain in the present invention is optionally SEQ ID NO: 400, SEQ ID NO: 401, SEQ ID NO: 402, SEQ ID NO: 403 or SEQ ID NO: 171.

The amino acid sequence of the VH domain may share at least 90% sequence identity with SEQ ID NO: 5. Sequence identity may be at least 95%, at least 97%, at least 98% or at least 99%.

Optionally the VH domain amino acid sequence is SEQ ID NO: 324. Optionally the VH domain amino acid sequence is SEQ ID NO: 5.

A VL domain of the FIXa binding polypeptide arm in the present invention may comprise LCDR1, LCDR2 and LCDR3 in a framework, the framework comprising a set of framework regions FR1, FR2, FR3 and FR4, wherein:
FR1 is SEQ ID NO: 136
FR2 is SEQ ID NO: 137
FR3 is SEQ ID NO: 138 and
FR4 is SEQ ID NO: 139,
or comprising that set of framework regions with up to 10 amino acid alterations, e.g., there may be one or two conservative substitutions in any one or more framework region.

The amino acid sequence of the VL domain may share at least 90% sequence identity with SEQ ID NO: 10. Sequence identity may be at least 95%, at least 97%, at least 98% or at least 99%. Optionally the VL domain amino acid sequence is SEQ ID NO: 10.

The FIXa binding polypeptide arm of bispecific antigen-binding molecules of the present invention may, even when provided in monospecific form outside the context of the bispecific molecule, be capable of enhancing the FIXa-catalysed activation of FX to FXa. This may be determined in an in vitro FX activation assay as described herein.

Surface plasmon resonance may be used to determine binding to FIXa and FX, and to quantify the affinity of a polypeptide arm for antigen binding.

The FX binding site may be provided by a set of CDRs in the FX binding polypeptide arm. The FX binding polypeptide arm may comprise an antibody VH-VL domain pair (i.e., an antibody Fv region), the VH domain comprising HCDR1, HCDR2 and HCDR3 in a framework, and the VL domain comprising LCDR1, LCDR2 and LCDR3 in a framework.

The FX binding site may be provided by the CDRs of antibody T02, i.e., a set of CDRs comprising HCDR1, HCDR2, HCDR3 and/or LCDR1, LCDR2 and LCDR3, wherein
HCDR1 is SEQ ID NO: 57
HCDR2 is SEQ ID NO: 58
HCDR3 is SEQ ID NO: 59
LCDR1 is SEQ ID NO: 62
LCDR2 is SEQ ID NO: 63 and
LCDR3 is SEQ ID NO: 64.

The FX binding polypeptide arm may comprise a VH domain having at least 90% amino acid sequence identity with the T02 VH domain SEQ ID NO: 61 and/or may comprise a VL domain having at least 90% amino acid sequence identity with the T02 VL domain SEQ ID NO: 66. Sequence identity may be at least 95%, at least 97%, at least 98% or at least 99%. Optionally the VH domain amino acid sequence is SEQ ID NO: 61. Optionally the VL domain amino acid sequence is SEQ ID NO: 66.

The FX binding site may be provided by the CDRs of antibody T05, i.e., a set of CDRs comprising HCDR1, HCDR2, HCDR3 and/or LCDR1, LCDR2 and LCDR3, wherein
HCDR1 is SEQ ID NO: 67
HCDR2 is SEQ ID NO: 68
HCDR3 is SEQ ID NO: 69
LCDR1 is SEQ ID NO: 72
LCDR2 is SEQ ID NO: 73 and
LCDR3 is SEQ ID NO: 74.

The FX binding polypeptide arm may comprise a VH domain having at least 90% amino acid sequence identity with the T05 VH domain SEQ ID NO: 71 and/or may comprise a VL domain having at least 90% amino acid sequence identity with the T05 VL domain SEQ ID NO: 76. Sequence identity may be at least 95%, at least 97%, at least 98% or at least 99%. Optionally the VH domain amino acid sequence is SEQ ID NO: 61. Optionally the VL domain amino acid sequence is SEQ ID NO: 76.

The FX binding site may be provided by the CDRs of antibody T14, i.e., a set of CDRs comprising HCDR1, HCDR2, HCDR3 and/or LCDR1, LCDR2 and LCDR3, wherein
HCDR1 is SEQ ID NO: 96
HCDR2 is SEQ ID NO: 97
HCDR3 is SEQ ID NO: 98
LCDR1 is SEQ ID NO: 101
LCDR2 is SEQ ID NO: 92 and
LCDR3 is SEQ ID NO: 102.

The FX binding polypeptide arm may comprise a VH domain having at least 90% amino acid sequence identity with the T14 VH domain SEQ ID NO: 100 and/or may comprise a VL domain having at least 90% amino acid sequence identity with the T14 VL domain SEQ ID NO: 104. Sequence identity may be at least 95%, at least 97%, at least 98% or at least 99%. Optionally the VH domain amino acid sequence is SEQ ID NO: 100. Optionally the VL domain amino acid sequence is SEQ ID NO: 104.

The FX binding polypeptide arm may comprise an antibody Fv region comprising:
(a) a VH domain generated through recombination of immunoglobulin heavy chain v, d and j gene segments, wherein the v and j gene segments are VH1-3 (e.g., VH1-3*01) and JH6 (e.g., JH6*02), and
a VL domain generated through recombination of immunoglobulin light chain v and j gene segments, wherein the v and j gene segments are VL1-47, (e.g., VL1-47*01) and JL1 (e.g., JL1*01); or
(b) a VH domain generated through recombination of immunoglobulin heavy chain v, d and j gene segments, wherein the v and j gene segments are VH3-30 (e.g., VH3-30*18) and JH6 (e.g., JH6*02), and
a VL domain generated through recombination of immunoglobulin light chain v and j gene segments, wherein the v and j gene segments are VL2-8, (e.g., VL2-8*01) and JL2 (e.g., JL2*01); or
(c) a VH domain generated through recombination of immunoglobulin heavy chain v, d and j gene segments, wherein the v and j gene segments are VH4-61 (e.g., VH4-61*01) and JH1 (e.g., JH1*01), and
a VL domain generated through recombination of immunoglobulin light chain v and j gene segments, wherein the v and j gene segments are VK3-11, (e.g., VK3-11*01) and JK5 (e.g., JK5*01).

The FX binding polypeptide arm may comprise an antibody Fv region comprising a VH domain generated through recombination of immunoglobulin heavy chain v, d and j gene segments, wherein the v and j gene segments are:
VH1-3 (e.g., VH1-3*01) and JH6 (e.g., JH6*02),
VH3-30 (e.g., VH3-30*18) and JH6 (e.g., JH6*02),
VH3-33 (e.g., VH3-33*01) and JH6 (e.g., JH6*02), VH4-31 (e.g., VH4-31*03) and JH4 (e.g., JH4*02), or VH4-59 (e.g., VH4-59*01) and JH4 (e.g., JH4*02), and a VL domain.

The FX binding polypeptide arm may comprise an antibody Fv region comprising a VL domain generated through recombination of immunoglobulin light chain v and j gene segments, wherein the v gene segment is VL3-21 (e.g., VL3-21*d01) and the j gene segment is JL3 (e.g., JL3*02).

The FIXa binding polypeptide arm and the FX binding polypeptide arm may each comprise an antibody Fv, wherein the VL domain of each Fv has an identical amino acid sequence, i.e. the bispecific antigen-binding molecule has a common VL domain. The molecule may have a common light chain comprising a variable region and a constant region, optionally a human lambda constant region.

The bispecific antigen-binding molecule may be a tetrameric immunoglobulin comprising
a first pair of antibody heavy and light chains (heavy-light chain pair) comprising a FIXa binding Fv region,
a second heavy-light chain pair comprising a FX binding Fv region,
wherein each heavy chain comprises a VH domain and a constant region, and each light chain comprises a VL domain and a constant region, and wherein the first and second heavy-light chain pairs associate through heterodimerisation of their heavy chain constant regions to form the immunoglobulin tetramer. As noted, the light chain may be a common light chain, i.e., the light chain of the first and second heavy-light chain pairs has an identical amino acid sequence. Exemplary immunoglobulin isotypes include human IgG, e.g., IgG4, optionally with engineered constant domains such as IgG4 PE.

An advantageous feature of bispecific antibodies exemplified here is that they have been generated from human immunoglobulin gene segments, using the Kymouse platform. Unlike antibodies generated from immunisation of normal laboratory animals, which may require "humanisation" steps such as grafting of mouse CDRs into human antibody variable domains and iterative refinement of the engineered variable domains to mitigate a loss of function resulting from these changes, the antibodies of the present invention were generated and selected from the outset with fully human antibody variable domains. The use of a fully human antibody is of special relevance in the context of haemophilia treatment, where low immunogenicity is paramount, as noted above. The low immunogenicity of the bispecific antibodies of the present invention renders them suitable for treatment of haemophilia A patients, including those with or without inhibitory antibodies to other treatments such as FVIII. Patients receiving antigen-binding molecules of the present invention should be at minimal risk of developing an immunogenic response to the therapy.

The mode of action of the bispecific molecules is also associated with a good safety profile, with low risk of complications such as deep vein thrombosis and pulmonary embolism. Activity of the bispecific molecules is comparable with that of natural FVIII and a mechanism of action that is integrated within the existing blood coagulation pathway, being activated only in the context of upstream triggering of the natural clotting cascade.

Other desirable features include long-half life (reducing the required frequency of administration) and amenability of the molecules to formulation at high concentration (facilitating subcutaneous injection in the home setting).

Further aspects of the invention relate to pharmaceutical compositions comprising the bispecific antigen-binding molecules, their encoding nucleic acids, the individual polypeptide binding arms, systems and methods for production of the molecules, and their use in medicine including for the treatment of haemophilia A, as set out in the appended claims and described in the present disclosure.

BRIEF DESCRIPTION OF THE DRAWINGS

FIG. 2 A. Co-factor action of FVIIIa interacting with FIXa and FX.
B. Co-factor action of bispecific antibody interacting with FIXa and FX.

FIG. 3 Amino acid sequence of factor IX, with residue numbering for the mature protein. The signal peptide (straight underlined) is cleaved after secretion. The propeptide (wave underlined) is cleaved on maturation. Mature factor IX contains a light chain (residues 1-145) and a heavy chain (residues 146-415). The activation peptide (boxed) is cleaved on activation, generating activated factor IXa which contains a light chain (residues 1-145) and a heavy chain (residues 181-415, bold) joined by a disulphide bridge between Cys132 and Cys289.

FIG. 4 Amino acid sequence of factor X, with residue numbering. Residues 1-31 are a signal peptide (straight underlined). Residues 32-40 are a propeptide (wave underlined). The FX light chain is residues 41-179. The FX heavy chain is residues 183-488. The FXa heavy chain is residues 235-488 (bold).

FIG. 5 A, B Bispecific IgGs. (A) Bispecific IgG with common light chain. (B) Bispecific IgG with different light chains.

FIG. 5 C, D Bispecific IgG fragments. (C) F(ab')2. (D) Tandem-linked scFv.

FIG. 6 FIT-Ig format of bispecific antibodies. (i) Assembled FIT-Ig antibody (ii) Polypeptide chains included in FIT-Ig antibody. Construct #1 is a polypeptide containing, in the N to C direction, the light variable (VL) and light constant (CL) regions of antibody "A", fused to the heavy variable (VH) and heavy constant regions (CH1, CH2, CH3) of antibody "B". Preferably, no linker is included between the CL and VHB domain. Construct #2 is a polypeptide fusion of the heavy variable (VH) region and CH1 of antibody "A". Construct #3 is a polypeptide fusion of the light variable (VL) and light constant (CL) regions of antibody "B". The FIT-Ig may be constructed with antibody "A" being anti-FIXa and antibody "B" being anti-FX, or with antibody "A" being FX and antibody "B" being anti-FIXa.

FIG. 7 A. Principles of in vitro assay for FVIII mimetic activity of a bispecific molecule as described in Example 9.
B. Example data from the assay as described in Example 9 showing positive result for FIXa-FX bispecific molecule compared with negative control.

FIG. 9 Table of N128H mutants.

DETAILED DESCRIPTION

Blood Coagulation

Figure 1:
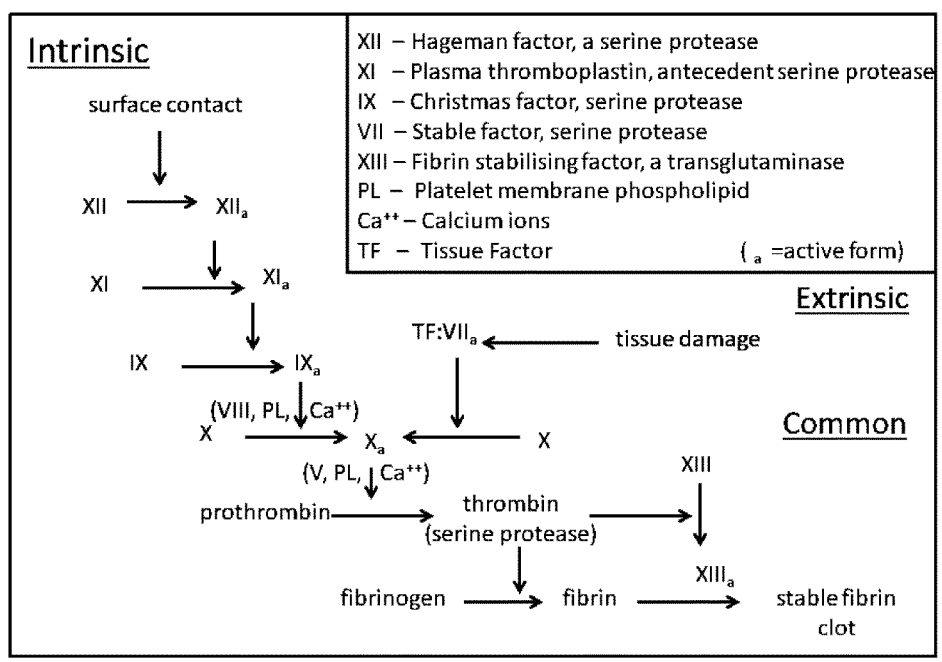
FIG. 1 Blood coagulation cascade [5].

The blood coagulation cascade is diagrammed in FIG. 1. Coagulation or clotting is one of the most important biological processes which stops blood loss from a damaged vessel to allow the vessel to be repaired. The mechanism of coagulation involves activation, adhesion, and aggregation of platelets along with deposition and maturation of fibrin. Misregulation of coagulation can result in excessive bleeding (haemophilia) or obstructive clotting (thrombosis). Coagulation is highly conserved in all mammals. It is controlled by a complex network of coagulation factors. Coagulation is initiated when the endothelium lining the blood vessel is damaged. The exposure of subendothelial tissue factor (TF) to plasma factor VII (FVII) leads to primary haemostasis (extrinsic pathway): a loose plug is formed at the site of injury. Activation of additional coagulation factors, especially factor IX (FIX) and factor VIII (FVIII), leads to secondary haemostasis (intrinsic pathway): fibrin strands are formed to strengthen the plug. Extrinsic and intrinsic pathways ultimately converge to a common point: the formation of the factor Xa/Va complex which together with calcium and bound on a phospholipid surface generate thrombin (factor IIa) from prothrombin (factor II).

FVIII is cleaved by thrombin or factor Xa (FXa), and the resultant factor VIIIa (FVIIIa) presents a heterotrimeric structure consisting of the A1 subunit, the A2 subunit, and the light chain. Upon activation and in the presence of calcium ions and a phospholipid surface (on platelets), FVIIIa binds via its light chain and A2 subunit to FIXa and simultaneously binds via its A1 subunit to FX, forming an active intrinsic "tenase" or "Xase" complex in which the FVIIIa cofactor brings FIXa and FX into proximity and also allosterically enhances the catalytic rate constant of FIXa. See FIG. 2a. Factor X is activated by the serine protease activity of FIXa, and the clotting cascade continues, culminating in the deposition of fibrin, the structural polymer of the blood clot.

Haemophilia arise through a deficiency in the Xase complex, due either to a lack of FVIII cofactor activity (haemophilia A) or a lack of FIX enzyme activity (haemophilia B).

Factor IX (FIX)

Factor IX is a serine protease which requires factor VIII as a cofactor. It circulates in blood as an inactive precursor, which is activated through intrinsic or extrinsic pathway at the time of haemostatic challenge, as discussed above.

Unless the context requires otherwise, factor IX referred to herein is human factor IX, and factor IXa is human factor IXa.

The amino acid sequence of human factor IX are shown in FIG. 3. The factor IX gene is approximately 34 kb in length and contains 8 exons. The transcript comprises a short 5' untranslated region, an open reading frame plus stop codon and a 3' untranslated region. The ORF encodes a 461 amino acid pre-pro-protein in which the pre-sequence (signal peptide) directs factor IX for secretion, the propeptide sequence provides a binding domain for a vitamin K dependent carboxylase, which carboxylates certain glutamic acid residues in the adjacent GLA domain, and the remainder represents the factor IX zymogen, which enters into circulation after removal of the pre- and pro-sequences. The mature 415 residue FIX protein contains, from N to C terminus: a GLA domain in which 12 glutamic acid residues are post-translationally γ-carboxylated, two epidermal growth factor (EGF)-like domains, an activation peptide sequence and a catalytic serine protease domain. FIX is activated by either activated factor XI generated through the intrinsic pathway, or by the TF/FVIIa complex of the extrinsic pathway. Either way, activation involves cleavage of the peptide bond following R145 (α-cleavage) and of the peptide bond following R180 (β-cleavage), releasing an activation peptide corresponding to the intervening sequence, and thereby generating the activated FIXa molecule, which has an N terminal light chain (GLA-EGF-EGF) and a C terminal heavy chain (catalytic domain) joined by a disulphide bridge between C132 of the light chain and C289 of the heavy chain. Residue numbering refers to amino acids in the mature FIX polypeptide sequence. On the phospholipid surface where the Xase complex forms, it is the GLA domain of FIXa which associates with the phospholipid, while the catalytic domain stands high (>70 Å) above the phospholipid surface and is modulated by the A2 domain of FVIIIa [6, 7].

The molecular basis of haemophilia B—deficiency in FIXa activity—is diverse, including a variety of point mutations, nonsense mutations, mRNA splice site mutations, deletions, insertions, or mis-sense mutations at activation cleavage sites [8].

The catalytic (protease) domain of activated FIX (FIXa) is involved in binding to FVIIIa. Residue E245 in this domain binds calcium ions, and mutations at this position may reduce binding to FVIII and lead to haemophilia B, for example the substitution E245V. Mutations within the FIX helix formed by residues 330-338 are also linked with reduced binding to FVIII and consequently to haemophilia B.

Non-pathogenic mutations in factor IX have also been reported, including single nucleotide polymorphisms (SNPs) and length polymorphisms—reviewed in [8]. These include the MnII SNP in exon 6, resulting in T/A substitution at residue 148 (Malmö polymorphism), which is relatively common among white and black American populations [8].

Factor X (FX)

Unless the context requires otherwise, factor X referred to herein is human factor X, and factor Xa is human factor Xa. The amino acid sequence of human FX is shown in FIG. 4.

FX is also known as Stuart-Prower factor. It is a serine endopeptidase. FX can be activated, by hydrolysis, into factor Xa by either factor IX (together with its cofactor, factor FVIII, as described above) or factor VII (with its cofactor, tissue factor). FX acts by cleaving prothrombin in two places—at an Arg-Thr bond and then at an Arg-Ile bond, to yield the active thrombin.

Antigen-Binding

A desirable feature of the bispecific antigen-binding molecule is that it binds FIXa and FX in a manner that allows the bound FIXa to activate the bound FX.

To bring FIXa and FX together and thereby promote the activation of FX by FIXa, the bispecific antigen-binding molecule may bind these two cofactors simultaneously. Binding may occur sequentially, e.g., an initial binary complex may form between a first binding arm and its cognate antigen, followed by binding of the second binding arm to its cognate antigen. In principle these two binding events may occur in either sequence, i.e., FIXa followed by FX, or FX followed by FIXa. The molecular choreography is influenced by the relative affinities of the two binding sites for their respective antigens. In a population of bispecific antigen-binding molecules, FIXa and FX, a number of different complexes are expected to exist in parallel. Thus the pool will comprise free antigen-binding molecule, free FIXa, free FX, FIXa complexed with antigen-binding molecule, FX complexed with antigen-binding molecule, and a tertiary complex of FIX, FX and antigen-binding molecule, with each of these species being present in different proportions according to the relative on-rates and off-rates of the individual interactions.

It may be preferable for a bispecific antigen-binding molecule to have a higher affinity for FIXa than for FX. Such a bispecific molecule would be envisaged to form an initial complex with FIXa, which in turn would bind and activate FX. The relatively low affinity for FX reduces the proportion of FX that is bound in incomplete antibody-antigen complexes (i.e., without FIXa). A potential advantage of this is that it allows a greater proportion of FX to remain free to engage with any FVIII that may be present in a patient's blood. Haemophilia A encompasses a range of deficiencies in FVIII, ranging from mild deficiency to total absence of functional FVIII. For those patients who retain some functional FVIII, it may be desirable to retain this natural activity as far as possible. Thus, it may be desirable to provide a bispecific antigen-binding molecule in which the FX binding arm does not compete with FVIII for binding to FX.

Preferably the FX binding arm has a higher affinity for FX than for FXa. A low affinity for FXa promotes release of the activated product, completing the role of the FVIII-mimetic molecule in the coagulation cascade and freeing the FX binding site for re-use.

FIXa Binding

The FIXa binding arm of a bispecific antigen-binding molecule may bind the light chain and/or the heavy chain of FIXa. Initial studies indicated that FIXa binding arms of the N128 lineage described in the Examples do not bind the FIXa light chain in isolation (in the absence of the heavy chain).

A bispecific antigen-binding molecule of the present invention (or FIXa binding polypeptide arm thereof) may thus be one which binds a FIXa molecule comprising a heavy chain and a light chain, and which does not bind the FIX light chain in the absence of the heavy chain. Optionally, the FIXa binding arm recognises an epitope formed by, or stabilised by, the combination of the FIXa heavy and light chains. It may for example make contact only with the light chain in the FIXa molecule, binding an epitope that is exposed or stabilised only when the light chain is present in combination with the heavy chain in the FIXa molecule. Alternatively, it may contact an epitope comprising one or more residues from both the light chain and the heavy chain, or comprising residues of the heavy chain alone.

An antigen-binding molecule according to the present invention, or a FIXa-binding polypeptide arm thereof, may bind the EC domain of human FIXa with an affinity (measured as $K_D$) of 10 mM or less, preferably 5 mM or less, more preferably 1 mM or less. For example, $K_D$ may be between 1 nM and 3 µM.

The $K_D$ for binding human FIXa may be between 0.1 µM and 1 µM, e.g., between 0.15 and 0.3 µM. The $K_D$ may be 0.6 µM or less, 0.5 µM or less, 0.4 µM or less, 0.3 µM or less, 0.25 µM or less, or 2 µM or less. The $K_D$ may be at least 0.1 µM, for example at least 0.2 µM.

The $K_D$ may be 50 nM or less, 10 nM or less, 5 nM or less, 2 nM or less, or 1 nM or less. The $K_D$ may be 0.9 nM or less, 0.8 nM or less, 0.7 nM or less, 0.6 nM or less, 0.5 nM or less, 0.4 nM or less, 0.3 nM or less, 0.2 nM or less, or 0.1 nM or less. The $K_D$ may be at least 0.001 nM, for example at least 0.01 nM or at least 0.1 nM. The $K_D$ may be between 0.1-10 nM.

An antigen-binding molecule according to the present invention, or a FIXa-binding polypeptide arm thereof, may bind human FIX with an affinity (measured as $K_D$) between 0.1 µM and 1 µM, e.g., between 0.15 and 0.3 µM. The $K_D$ may be 0.6 µM or less, 0.5 µM or less, 0.4 µM or less, 0.3 µM or less, 0.25 µM or less, or 2 µM or less. The $K_D$ may be at least 0.1 µM, for example at least 0.2 µM.

The $K_D$ of interaction with FIX may be comparable to the $K_D$ of interaction with FIXa, e.g., there may be difference of less than 25%, optionally less than 10%, in the FIXa-binding arm's affinity for FIX compared with the affinity for FIXa. There may be no statistically significant difference in $K_D$ of interaction with FIX compared with FIXa.

As described elsewhere herein, affinity may be determined using surface plasmon resonance (SPR), e.g., with the binding arm coupled to a solid surface, optionally as a dimer (e.g., as monospecific IgG), with the antigen in solution as analyte, at 25° C.

FX Binding

An antigen-binding molecule according to the present invention, or a FX-binding polypeptide arm thereof, may bind the EC domain of human FX with a $K_D$ of 10 mM or less, preferably 5 mM or less, more preferably 1 mM or less. For example, $K_D$ may be between 5 µM and 1 nM, e.g., between 5 µM and 10 nM.

The $K_D$ may be between 0.1 µM and 1 µM, e.g., between 0.15 and 0.3 µM. The $K_D$ may be 0.6 µM or less, 0.5 µM or less, 0.4 µM or less, 0.3 µM or less, or 0.25 µM or less. The $K_D$ may be at least 0.1 µM.

The $K_D$ may be 50 nM or less, 10 nM or less, 5 nM or less, 2 nM or less, or 1 nM or less. The $K_D$ may be 0.9 nM or less, 0.8 nM or less, 0.7 nM or less, 0.6 nM or less, 0.5 nM or less, 0.4 nM or less, 0.3 nM or less, 0.2 nM or less, or 0.1 nM or less. The $K_D$ may be at least 0.001 nM, for example at least 0.01 nM or at least 0.1 nM. For example, the $K_D$ may be between 1-100 nM. $K_D$ may be between 1-10 nM.

As described elsewhere herein, affinity may be determined using surface plasmon resonance (SPR), e.g., with the binding arm coupled to a solid surface, optionally as a dimer (e.g., as monospecific IgG), with the antigen in solution as analyte, at 25° C.

Measurement of Antigen-Binding Affinity

The affinity of an antigen-binding molecule for binding FIX, FIXa, FX and FXa may be quantified in terms of the equilibrium dissociation constant $K_D$, the ratio Ka/Kd of the association or on-rate (Ka) and the dissociation or off-rate (kd) of the binding interaction. $K_D$, Ka and Kd for antigen binding can be measured using surface plasmon resonance (SPR).

Quantification of affinity may be performed using SPR with the antigen-binding polypeptide arm in monovalent form, e.g., antibody Fab or Fv comprising the antigen binding site, or heterodimeric immunoglobulin (e.g., IgG) having a single antigen-binding arm for the antigen in question. Alternatively, as shown in Example 3 and Example 6, or in Examples 15-16, it may be convenient to determine affinity for the antigen-binding polypeptide arm in bivalent form, for example IgG comprising homodimeric antigen-binding arms. SPR may comprise coating dimers of the antigen-binding polypeptide arm on to a biosensor chip (directly or indirectly), exposing the antigen-binding polypeptide arms to antigen in buffered solution at a range of concentrations, detecting binding, and calculating the equilibrium dissociation constant $K_D$ for the binding interaction. SPR may be performed at 25° C. A suitable buffered solution is 150 mM NaCl, 0.05% detergent (e.g., P20) and 3 mM EDTA, pH 7.6. HBS-P 1× (10 mM HEPES pH 7.4, 150 mM NaCl, 3 mM EDTA, 0.05% polysorbate 20 pH 7.6) with 2.5 mM CaCl$_2$). is an example buffer. The binding data can be fitted to a 1:1 model using standard algorithms, which may be inherent to the instrument used. A variety of SPR instruments are known, such as Biacore™, ProteOn XPR36™ (Bio-Rad®), and KinExA® (Sapidyne Instruments, Inc).

Cross-Reactivity

Regulatory bodies may require candidate therapeutic molecules to have demonstrated therapeutic efficacy in laboratory animals before they advance to human clinical trials. An example of an acquired haemophilia A animal model is a cynomolgus monkey that is rendered deficient in blood clotting through administration of a FVIII-neutralising antibody or a small molecule inhibitor against FVIII, thereby replicating the phenotype of a human haemophilia A patient. To enable testing of bispecific antigen-binding molecules in animal models, it is desirable for the binding site of each arm to be cross-reactive with the corresponding antigen from one or more non-human mammals. Thus, the FIXa binding site of the antigen-binding molecule may bind murine (e.g., mouse or rat), rabbit or non-human primate (e.g., cynomolgus monkey) FIXa as well as human FIXa, and the FX binding site may bind murine (e.g., mouse or rat), rabbit or non-human primate (e.g., cynomolgus monkey) FXa as well as human FXa.

One way to quantify the extent of species cross-reactivity of an antigen-binding molecule (or, more precisely, of its antigen binding site) is as the fold-difference in its affinity for antigen or one species compared with antigen of another species, e.g., fold difference in affinity for human antigen vs cynomolgus antigen. Affinity may be quantified as K$_D$, referring to the equilibrium dissociation constant of the binding of the antigen to the antigen-binding molecule. K$_D$ may be determined by SPR as described elsewhere herein.

A species cross-reactive binding molecule may have a fold-difference in affinity for binding human and non-human antigen that is 30-fold or less, 25-fold or less, 20-fold or less, 15-fold or less, 10-fold or less or 5-fold or less. To put it another way, the K$_D$ of binding the extracellular domain of the human antigen may be within 30-fold, 25-fold, 20-fold, 15-fold, 10-fold or 5-fold of the K$_D$ of binding the extracellular domain of the non-human antigen.

Preferably, the binding affinities of human and non-human antigen are within a range of 10-fold or less, more preferably within 5-fold or within 2-fold. K$_D$ for binding non-human FIXa, e.g., as determined by surface plasmon resonance, may be up to 10-fold (preferably up to 5-fold or up to 2-fold) greater or up to 10-fold lower (preferably up to 5-fold or up to 2-fold lower) than the Kd for binding human FIXa. Similarly, K$_D$ for binding non-human FX, e.g., as determined by SPR, may be up to 10-fold (preferably up to 5-fold or up to 2-fold) greater or up to 10-fold (preferably up to 5-fold or up to 2-fold) lower than the Kd for binding human FX. Methods of determining affinity are described elsewhere herein.

Binding molecules can also be considered species cross-reactive if the K$_D$ for binding antigen of both species meets a threshold value, e.g., if the K$_D$ of binding human antigen and the K$_D$ of binding non-human antigen are both 10 mM or less, preferably 5 mM or less, more preferably 1 mM or less. The K$_D$ may be 10 nM or less, 5 nM or less, 2 nM or less, or 1 nM or less. The K$_D$ may be 0.9 nM or less, 0.8 nM or less, 0.7 nM or less, 0.6 nM or less, 0.5 nM or less, 0.4 nM or less, 0.3 nM or less, 0.2 nM or less, or 0.1 nM or less.

While species cross-reactivity for binding antigen of different species may be advantageous, selectivity of the FIXa binding arm and the FX binding arm for their respective antigens is nevertheless desirable to avoid unwanted side effects. Thus, within the body, FIX/FIXa and FX/FXa are preferably the only antigens bound by the antigen-binding molecule.

Enhancement of FIXa-Mediated Activation of FX

The ability of a bispecific antigen-binding molecule to enhance the FIXa-mediated activation of FX to FXa may be determined in assays in vitro or in vivo.

A suitable in vitro assay is the FX activation assay exemplified in Example 9 and illustrated in FIG. 7. The assay comprises
(i) contacting the bispecific antigen-binding molecule with FIXa and FX under conditions suitable for formation of FXa (e.g., in the presence of phospholipid, in buffered solution at 37° C.)
(ii) adding substrate that is cleavable by FXa to generate a detectable product, and
(iii) detecting, and optionally quantifying, the presence of the detectable product.

The level of product may be compared with a control assay in which FIXa-FX bispecific antigen-binding molecule is absent from the reaction mixture. Significant difference in product level in the assay with the bispecific compared with control indicates that the bispecific is able to enhance FIXa-mediated activation of FX. FVIII may be included as a positive control.

The level of product may be compared with an assay in which the FIXa-FX bispecific antigen-binding molecule is emicizumab. A bispecific according to the present invention may enhance the FIXa-mediated activation of FX to FXa to the same or similar extent (e.g., within 10% difference or within 5% difference) as emicizumab, or to a greater extent (e.g., more than 10% more activation of FX to FXa than is achieved with emicizumab as measured by the level of detectable product).

Another suitable assay is to measure the activated partial thromboplastin time (aPTT) in FVIII-deficient plasma, which may be performed in the presence or the absence of inhibitors and can be used to compare the activity of bispecific molecules with recombinant human FVIII. This assay is exemplified in Example 10 and Example 18. aPTT is an end point assay which provides a global overview of blood clot formation and provides coagulation time as the assay read-out. FVIII-deficient plasma would typically have a coagulation time of around 80-90 seconds in the aPTT assay. Bispecific antigen binding molecules of the present invention are effective to reduce the coagulation time in an aPTT assay (compared with a negative control). The coagulation time of human FVIII-deficient in an aPTT assay with a bispecific antigen binding molecule according to the present invention may for example be the same as or less than that of the coagulation time with recombinant human FVIIIa. Physiological clotting time for normal (FVIII+) human plasma is typically <40 seconds, e.g., in the range of 37-34 s. Similar values are achievable with FVIII-deficient plasma upon provision of activated FVIIIa, which provides a convenient way of standardising the assay through calibration of the apparatus/measurement against reference values. Alternatively, coagulation time of normal (FVIII+) human plasma may be used for reference, the aPTT assay being begun by induction of coagulation through the addition of calcium.

A bispecific antigen-binding molecule of the present invention may give a coagulation time in the aPTT assay of within 10 seconds of that of FVIIIa (i.e., up to 10 seconds more than or up to 10 seconds less than the coagulation time of the aPTT assay with FVIIIa). Preferably, the coagulation time in the aPTT assay with a bispecific antigen binding molecule of the invention is less than that with FVIIIa. The bispecific antigen-binding molecule may reduce the coagulation time to less than 40 seconds, less than 35 seconds, or less than 30 seconds. The coagulation time may be between 20 and 40 seconds, e.g., between 20 and 30 seconds.

Bispecific Antigen-Binding Molecules

The bispecific antigen-binding molecule comprises a FIXa binding polypeptide arm and a FX binding polypeptide arm. It may be a multi-chain or single-chain polypeptide molecule. While the FIXa binding polypeptide arm and the FX binding polypeptide arm represent different moieties of the bispecific molecule, one polypeptide can optionally form all or part of both the FIXa binding arm and the FX binding arm.

A polypeptide binding arm is the region of the bispecific molecule that comprises the binding site for one of the antigens (FIXa or FX). One or both antigen-binding sites of a bispecific molecule can be provided by a set of complementarity determining regions (or peptide loops) in a polypeptide arm, wherein the polypeptide arm is any suitable scaffold polypeptide whether that of an antibody (e.g., an antibody Fv region) or a non-antibody molecule. A binding arm may comprise one or more than one (e.g., two) polypeptides or parts (e.g., domains) thereof.

The invention is described in detail herein with reference to bispecific antibodies, wherein at least one of the antigen binding polypeptide arms is provided by a set of CDRs in an antibody VH and/or VL domain, optionally an Fv region.

Antibodies are immunoglobulins or molecules comprising immunoglobulin domains. Antibodies may be IgG, IgM, IgA, IgD or IgE molecules or molecules including antigen-specific antibody fragments thereof. The term "antibody" covers any polypeptide or protein comprising an antibody antigen-binding site. An antibody antigen-binding site (paratope) is the part of an antibody that binds to and is complementary to the epitope of its target antigen. The term "epitope" refers to a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

An antibody antigen-binding site is provided by a set of complementarity determining regions (CDRs) in an antibody VH and/or VL domain, and is capable of binding the antigen. In an example, the antibody binding site is provided by a single variable domain, e.g., a heavy chain variable domain (VH domain) or a light chain variable domain (VL domain). In another example, the binding site is provided by a VH/VL pair (an Fv) or two or more such pairs.

The antibody variable domains are the portions of the light and heavy chains of antibodies that include amino acid sequences of complementarity determining regions (CDRs; ie., CDR1, CDR2, and CDR3), and framework regions (FRs). Thus, within each of the VH and VL domains are CDRs and FRs. A VH domain comprises a set of HCDRs, and a VL domain comprises a set of LCDRs. VH refers to the variable domain of the heavy chain. VL refers to the variable domain of the light chain. Each VH and VL is typically composed of three CDRs and four FRs, arranged from amino-terminus to carboxy-terminus in the following order: FR1, CDR1, FR2, CDR2, FR3, CDR3, FR4. Amino acid positions assigned to CDRs and FRs may be defined according to IMGT nomenclature. An antibody may comprise an antibody VH domain comprising a VH CDR1, CDR2 and CDR3 and a framework. It may alternatively or also comprise an antibody VL domain comprising a VL CDR1, CDR2 and CDR3 and a framework. Example sequences of antibody VH and VL domains and CDRs form part of the present disclosure. The CDRs are defined according to the IMGT system [9]. All VH and VL sequences, CDR sequences, sets of CDRs and sets of HCDRs and sets of LCDRs disclosed herein represent aspects and embodiments of the invention. As described herein, a "set of CDRs" comprises CDR1, CDR2 and CDR3. Thus, a set of HCDRs refers to HCDR1, HCDR2 and HCDR3, and a set of LCDRs refers to LCDR1, LCDR2 and LCDR3. Unless otherwise stated, a "set of CDRs" includes HCDRs and LCDRs.

An antibody may comprise one or more CDRs, e.g. a set of CDRs, within an antibody framework. The framework regions may be of human germline gene segment sequences. Thus, the antibody may be a human antibody having a VH domain comprising a set of HCDRs in a human germline framework. Normally the antibody also has a VL domain comprising a set of LCDRs, e.g. in a human germline framework. An antibody "gene segment", e.g., a VH gene segment, D gene segment, or JH gene segment refers to oligonucleotide having a nucleic acid sequence from which that portion of an antibody is derived, e.g., a VH gene segment is an oligonucleotide comprising a nucleic acid sequence that corresponds to a polypeptide VH domain from FR1 to part of CDR3. Human v, d and j gene segments recombine to generate the VH domain, and human v and j segments recombine to generate the VL domain. The D domain or region refers to the diversity domain or region of an antibody chain. J domain or region refers to the joining domain or region of an antibody chain. Somatic hypermutation may result in an antibody VH or VL domain having framework regions that do not exactly match or align with the corresponding gene segments, but sequence alignment can be used to identify the closest gene segments and thus identify from which particular combination of gene segments a particular VH or VL domain is derived. When aligning antibody sequences with gene segments, the antibody amino acid sequence may be aligned with the amino acid sequence encoded by the gene segment, or the antibody nucleotide sequence may be aligned directly with the nucleotide sequence of the gene segment. Germline gene segments corresponding to framework regions of example antibodies described herein are indicated in Table 12.

An antibody may be a whole immunoglobulin, including constant regions, or may be an antibody fragment. An antibody fragment is a portion of an intact antibody, for example comprising the antigen binding and/or variable region of the intact antibody. The antibody fragment may include one or more constant region domains.

An antibody of the invention may be a human antibody or a chimaeric antibody comprising human variable regions and non-human (e.g., mouse) constant regions. The antibody of the invention for example has human variable regions, and optionally also has human constant regions.

Thus, antibodies optionally include constant regions or parts thereof, e.g., human antibody constant regions or parts thereof, such as a human IgG4 constant region. For example, a VL domain may be attached at its C-terminal end to antibody light chain kappa or lambda constant domains. Similarly, an antibody VH domain may be attached at its C-terminal end to all or part (e.g. a CH1 domain or Fc region) of an immunoglobulin heavy chain constant region derived from any antibody isotype, e.g. IgG, IgA, IgE and IgM and any of the isotype sub-classes, such as IgG1 or IgG4.

Antibodies may be generated with non-human constant regions. For example, when antibodies are produced in transgenic animals (examples of which are described elsewhere herein), chimaeric antibodies may be produced comprising human variable regions and non-human constant regions. The constant regions may be those endogenous to the host animal, e.g., mouse. Some transgenic animals generate fully human antibodies. Others have been engineered to generate antibodies comprising chimaeric heavy chains and fully human light chains. Where antibodies comprise one or more non-human constant regions, these may be replaced with human constant regions to provide antibodies more suitable for administration to humans as therapeutic compositions, as their immunogenicity is thereby reduced.

Digestion of whole (bivalent) immunoglobulins with the enzyme papain results in two identical (monovalent) antigen-binding fragments known as "Fab" fragments, and an "Fc" fragment. The Fc has no antigen-binding activity but has the ability to crystallize. "Fab" when used herein refers to a fragment of an antibody that includes one constant and one variable domain of each of the heavy and light chains. The term "Fc region" herein is used to define a C-terminal region of an immunoglobulin heavy chain, including native-sequence Fc regions and variant Fc regions. The "Fc fragment" refers to the carboxy-terminal portions of both H chains held together by disulfides.

Digestion of antibodies with the enzyme pepsin results in a bivalent F(ab')2 fragment in which the two arms of the antibody molecule remain linked. The F(ab')2 fragment is a bivalent fragment including two Fab fragments linked by a disulfide bridge at the hinge region. Single-chain antibodies (e.g., scFv) are another fragment. Two different monovalent monospecific antibody fragments such as scFv may be linked together to form a bivalent bispecific antibody.

"Fv" when used herein refers to the minimum fragment of an antibody that retains both antigen-recognition and antigen-binding sites. This region consists of a dimer of one heavy and one light chain variable domain in tight, non-covalent or covalent association. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognise and bind antigen, although usually at a lower affinity than the entire binding site.

Bispecific antibodies can have many possible formats. For a review, see Spiess, Zhai & Carter, Mol. Immunol. 67:95-106 2015, which illustrates 5 categories of bispecific antibodies:

Bispecific IgG (approx 150 kDa), exemplified by CrossMab, DAF (2-in-1), DAF (4-in-1), DutaMab, DT-IgG, Knobs in holes (KIH) with common light chain, KIH assembly, charge pair, Fab-arm exchange, SEEDbody, Triomab, LUZ-Y, mAb$^2$ (referred to as "Fcab" in this review), κλ-body, orthogonal Fab;

Appended IgG (>150 kDa), exemplified by DVD-IgG, IgG(H)-scFv, scFv-(H)IgG, IgG(L)-scFv, scFv-(L)IgG, IgG(L,H)-Fv, IgG(H)-V, V(H)—IgG, IgG(L)-V, V(L)-IgG, KIH IgG-scFab, 2scFv-IgG, IgG-2scFv, scFv4-Ig, zybody, DVI-IgG (4-in-1);

Bispecific antibody fragments, exemplified by nanobody, nanobody-HSA, tandem-linked scFv (exemplified as "BiTE" in this review), Diabody, DART, TandAb, scDiabody, scDiabody-CH3, Diabody-CH3, Triple Body, Miniantibody, Minibody, TriBi minibody, scFv-CH3 KIH, Fab-scFv, scFv-CH-CL-scFv, F(ab')2, F(ab')2-scFv2, scFv-KIH, Fab-scFv-Fc, Tetravalent HCAb, scDiabody-Fc, Diabody-Fc, tandem scFv-Fc; intrabody;

Bispecific fusion proteins, exemplied by Dock and Lock, ImmTAC, HSAbody, scDiabody-HSA, Tandem scFv-toxin;

Bispecific antibody conjugates, exemplified by IgG-IgG, Cov-X-Body, scFv1-PEG-scFv2.

While the bispecific antigen binding molecules of the present invention are not restricted to any particular format or formats, some bispecific antibody formats are described here in more detail as examples of especially suitable molecules.

Preferably, the bispecific antibody is a dual binding antibody, i.e., a bispecific antibody in which both antigen binding domains are formed by a VH/VL pair. Dual binding antibodies include FIT-Ig (see WO2015/103072, incorporated herein by reference), mAb-dAb, dock and lock, Fab-arm exchange, SEEDbody, Triomab, LUZ-Y, Fcab, κλ-body, orthogonal Fab, scDiabody-Fc, diabody-Fc, tandem scFv-Fc, Fab-scFv-Fc, Fab-scFv, intrabody, BiTE, diabody, DART, TandAb, scDiabody, scDiabody-CH3, Diabody-CH3, Triple body, Miniantibody, minibody, scFv-CH3 KIH, scFv-CH-CL-scFv, F(ab')2-scFv, scFv-KIH, Fab-scFv-Fc, tetravalent HCab, ImmTAC, knobs-in-holes, knobs-in-holes with common light chain, knobs-in-holes with common light chain and charge pairs, charge pairs, charge pairs with common light chain, DT-IgG, DutaMab, IgG(H)-scFv, scFv-(H)IgG, IgG(L)-scFv, scFv-(L)IgG, IgG (L,H)-Fv, IgG(H)-V, V(H)-IgG, IgG(L)-V, V(L)-IgG, KIH IgG-scFab, 2scFv-IgG, IgG-2scFv and scFv4-Ig.

In one embodiment, the bispecific antibody is a bispecific IgG comprising a FIXa-binding polypeptide arm and a FX-binding polypeptide arm, each polypeptide arm comprising a heavy chain and a light chain. The IgG is a tetrameric immunoglobulin comprising
- a first pair of antibody heavy and light chains (heavy-light chain pair) comprising a FIXa binding Fv region,
- a second heavy-light chain pair comprising a FX binding Fv region,
- wherein each heavy chain comprises a VH domain and a constant region, and each light chain comprises a VL domain and a constant region, and wherein the first and second heavy-light chain pairs associate through heterodimerisation of their heavy chain constant regions to form the immunoglobulin tetramer.

Optionally, the two polypeptide arms comprise a common light chain, so the light chain of the first and second heavy-light chain pairs has an identical amino acid sequence (FIG. 5(A)). Alternatively the two polypeptide arms may comprise different light chains (FIG. 5(B)).

In another embodiment, the bispecific antibody is a linked pair of Fabs (bispecific F(ab')2), comprising a FIXa-binding Fab and a FX-binding Fab, in which the Fab heavy chains are covalently coupled (FIG. 5(C)). Fab can be connected at their CH1 domains via disulphide bonding. One polypeptide binding arm (e.g., FIXa-binding arm) comprises a heavy-light chain pair VH1-CH1 and VL1-CL, and the other polypeptide binding arm (e.g., FX-binding arm) comprises a heavy-light chain pair VH2-CH1 and VL2-CL. Optionally, the two light chains (VL-CL) are identical in sequence, i.e., a common light chain is present.

In another embodiment, the bispecific antibody is a tandem-linked scFv pair, comprising a first scFv connected to a second scFv, optionally via a linker. The molecule can be produced with the antigen-binding arms in either orientation, i.e., the first scFv VL1-VH1 binding FIXa and the second scFv VL2-VH2 binding FX, or the first scFv VL1-VH1 binding FX and the second scFv VL2-VH2 binding FIXa. See FIG. 5(D).

As illustrated in the above embodiments, bispecific antibody may be monovalent for binding FIXa and for binding FX. In alternative embodiments, the bispecific antibody may be bivalent for one or both target antigens. For example, the antibody may be a FIT-Ig comprising two FIXa-binding Fab domains and two FX-binding Fab domains (FIG. 6). This format thus comprises two FIXa binding polypeptide arms and two FX binding polypeptide arms. The FIXa binding Fabs may be the "inner" Fab pair and the FX binding Fabs the "outer" Fab pair, or vice versa. FIT-Ig format was described in WO2015/103072—the description of the FIT-Ig scaffold is incorporated herein by reference.

Alternatively, bispecific antibody may be presented in DVD-Ig format. DVD-Ig was described by DiGiammarino et al., "Design and generation of DVD-Ig™ molecules for dual-specific targeting", Meth. Mo. Biol., 889:145-156 2012.

Another doubly bivalent format for a bispecific antibody is mAb$^2$, comprising two Fab domains and an Fc region in which the two CH3 domains each have three binding loops forming an antigen binding site, the engineered CH3 domains being referred to as the Fcab region. The technology behind the Fcab/mAb$^2$ format is described in more detail in WO2008/003103, and the description of the mAb2 format is incorporated herein by reference.

Antibody Constant Regions

As discussed above, antibodies can be provided in various isotypes and with different constant regions. The Fc region of antibodies is recognised by Fc receptors and determines the ability of the antibody to mediate cellular effector functions, including antibody-dependent cell-mediated cytotoxicity (ADCC) activity, complement dependent cytotoxicity (CDC) activity and antibody-dependent cell phagocytosis (ADCP) activity. These cellular effector functions involve recruitment of cells bearing Fc receptors to the site of the target cells, resulting in killing of the antibody-bound cell.

In the context of the present invention it is desirable to avoid cellular effector functions such as ADCC, ADCP and/or CDC. Therefore, bispecific antigen-binding molecules according to the present invention may lack Fc effector function, for example they may contain Fc regions that do not mediate ADCC, ADCP and/or CDC, or they may lack Fc regions or lack antibody constant regions entirely. An antibody may have a constant region which is effector null.

An antibody may have a heavy chain constant region that binds one or more types of Fc receptor but does not induce cellular effector functions, i.e., does not mediate ADCC, CDC or ADCP activity. Such a constant region may be unable to bind the particular Fc receptor(s) responsible for triggering ADCC, CDC or ADCP activity.

An antibody may have a heavy chain constant region that does not bind Fcγ receptors, for example the constant region may comprise a Leu235Glu mutation (i.e., where the wild type leucine residue is mutated to a glutamic acid residue), which may be referred to as an "E" mutation, e.g., IgG4-E. Another optional mutation for a heavy chain constant region is Ser228Pro ("P" mutation), which increases stability by reducing Fab arm exchange. A heavy chain constant region may be an IgG4 comprising both the Leu235Glu mutation and the Ser228Pro mutation. This "IgG4-PE" heavy chain constant region is effector null. An alternative effector null human constant region is a disabled IgG1.

As discussed below, in bispecific IgG formats or other antibody formats where the different antigen binding arms are heterodimerised via constant regions, the constant regions may be engineered to promote heterodimer formation over homodimer formation and/or to facilitate purification of heterodimers from a mixture of different species.

Engineering of Bispecific Antibodies to Facilitate Heterodimer Formation and/or Purification One of the difficulties with using bispecific antibodies in the clinic has historically been the difficulty of producing them in large quantities and at pharmaceutical grade purity. The "traditional" bispecific IgG format comprises two different pairs of heavy and light chains, thus 4 different polypeptide chains, which if expressed together could assemble into 10 different potential antibody molecules. The mixture of species will include homodimers (homodimeric anti-FIXa binding arms and homodimeric anti-FX binding arms), molecules in which one or both light chains are swapped between the H-L pairs, as well as the "correct" bispecific heterodimeric structure.

Alternative molecular formats have been developed which avoid this potential mis-pairing, and several examples are provided herein. These include F(ab')2, e.g., prepared by chemical coupling or leucine zipper (fos:jun) assembly, diabodies, and scFv heterodimers. Nevertheless, it remains desirable to be able to use bispecific IgG, to reflect the native structure of antibodies in the bloodstream and to minimise immunogenicity of the administered therapeutic molecule. Additionally, a full length bispecific antibody may have a longer serum half-life.

"Knobs into holes" technology for making bispecific antibodies was described in [12] and in U.S. Pat. No. 5,731,168, both incorporated herein by reference. The principle is to engineer paired CH3 domains of heterodimeric heavy chains so that one CH3 domain contains a "knob" and the other CH3 domains contains a "hole" at a sterically opposite position. Knobs are created by replacing small amino acid side chain at the interface between the CH3 domains, while holes are created by replacing large side chains with smaller ones. The knob is designed to insert into the hole, to favour heterodimerisation of the different CH3 domains while destabilising homodimer formation. In in a mixture of antibody heavy and light chains that assemble to form a bispecific antibody, the proportion of IgG molecules having paired heterodimeric heavy chains is thus increased, raising yield and recovery of the active molecule Mutations Y349C and/or T366W may be included to form "knobs" in an IgG CH3 domain. Mutations E356C, T366S, L368A and/or Y407V may be included to form "holes" in an IgG CH3 domain. Knobs and holes may be introduced into any human IgG CH3 domain, e.g., an IgG1, IgG2, IgG3 or IgG4 CH3 domain. A preferred example is IgG4. As noted, the IgG4 may include further modifications such as the "P" and/or "E" mutations. An example IgG4-PE sequence and other example constant regions including knobs-into-holes mutations are shown in Table 11. The IgG4 type a ("ra") sequence contains substitutions Y349C and T366W ("knobs"), and the IgG4 type b ("γb") sequence contains substitutions E356C, T366S, L368A, and Y407V ("holes"). Both ra and γb also contain the "P" substitution at position 228 in the hinge (S228P), to stabilise the hinge region of the heavy chain. Both ra and γb also contain the "E" substitution in the CH2 region at position 235 (L235S), to abolish binding to FcγR. Thus the relevant sequence of the IgG4-PE heavy chain is ppcpPcpapefEggps (SEQ ID NO: 401). A bispecific antigen binding molecule of the present invention may contain an IgG4 PE human heavy chain constant region (e.g., SEQ ID NO: 143), optionally two such paired constant regions, optionally wherein one has "knobs" mutations and one has "holes" mutations, e.g., wherein one heavy chain constant region has a sequence SEQ ID NO: 144 (knobs) and one heavy chain constant region has a sequence SEQ ID NO: 145 (holes).

A further advance in bispecific IgG engineering was the idea of using a common light chain, as described in WO98/50431. Bispecific antibodies comprising two heavy-light chain pairs were described, in which the variable light chains of both heavy-light chain pairs had a common sequence. WO98/50431 described combining the common light chain approach with specific complementary interactions in the heavy chain heterodimerisation interface (such as knobs-into-holes) to promote heterodimer formation and hinder homodimer formation. In combination, these approaches enhance formation of the desired heterodimer relative to undesired heterodimers and homodimers.

While knobs-into-holes technology involves engineering amino acid side chains to create complementary molecular shapes at the interface of the paired CH3 domains in the bispecific heterodimer, another way to promote heterodimer formation and hinder homodimer formation is to engineer the amino acid side chains to have opposite charges. Association of CH3 domains in the heavy chain heterodimers is favoured by the pairing of oppositely charged residues, while paired positive charges or paired negative charges would make homodimer formation less energetically favourable. WO2006/106905 described a method for producing a heteromultimer composed of more than one type of polypeptide (such a heterodimer of two different antibody heavy chains) comprising a substitution in an amino acid residue forming an interface between said polypeptides such that heteromultimer association will be regulated, the method comprising:
  (a) modifying a nucleic acid encoding an amino acid residue forming the interface between polypeptides from the original nucleic acid, such that the association between polypeptides forming one or more multimers will be inhibited in a heteromultimer that may form two or more types of multimers;
  (b) culturing host cells such that a nucleic acid sequence modified by step (a) is expressed; and
  (c) recovering said heteromultimer from the host cell culture,
  wherein the modification of step (a) is modifying the original nucleic acid so that one or more amino acid residues are substituted at the interface such that two or more amino acid residues, including the mutated residue(s), forming the interface will carry the same type of positive or negative charge.

An example of this is to suppress association between heavy chains by introducing electrostatic repulsion at the interface of the heavy chain homodimers, for example by modifying amino acid residues that contact each other at the interface of the CH3 domains, including:
  positions 356 and 439
  positions 357 and 370
  positions 399 and 409,
the residue numbering being according to the EU numbering system.

By modifying one or more of these pairs of residues to have like charges (both positive or both negative) in the CH3 domain of a first heavy chain, the pairing of heavy chain homodimers is inhibited by electrostatic repulsion. By engineering the same pairs or pairs of residues in the CH3 domain of a second (different) heavy chain to have an opposite charge compared with the corresponding residues in the first heavy chain, the heterodimeric pairing of the first and second heavy chains is promoted by electrostatic attraction.

In one example, introduction of charge pairs in the antibody VH and VL domains was used to inhibit the formation of "incorrect" VH-VL pairs (pairing of VH from one antibody with VL of the other antibody). In one example, Q residues in the VH and VL were changed to K or R (positive), or to E or D (negative), to inhibit hydrogen bonding between the Q side chains and to introduce electrostatic repulsion. In another example, amino acids at the heavy chain constant region CH3 interface were modified to introduce charge pairs, the mutations being listed in Table 1 of WO2006/106905. It was reported that modifying the amino acids at heavy chain positions 356, 357, 370, 399, 409 and 439 to introduce charge-induced molecular repulsion at the CH3 interface had the effect of increasing efficiency of formation of the intended bispecific antibody. WO2006/106905 also exemplified bispecific IgG antibodies binding FX and FIXa in which the CH3 domains of IgG4 were engineered with knobs-into-holes mutations. Type a Type a (IgG4γa) was an IgG4 substituted at Y349C and T366W, and type b (IgG4γb) was an IgG4 substituted at E356C, T366S, L368A, and Y407V.

Further examples of charge pairs were disclosed in WO2013/157954, which described a method for producing a heterodimeric CH3 domain-comprising molecule from a single cell, the molecule comprising two CH3 domains capable of forming an interface. The method comprised providing in the cell
  (a) a first nucleic acid molecule encoding a first CH3 domain-comprising polypeptide chain, this chain comprising a K residue at position 366 according to the EU numbering system and
  (b) a second nucleic acid molecule encoding a second CH3 domain-comprising polypeptide chain, this chain comprising a D residue at position 351 according to the EU numbering system,
  the method further comprising the step of culturing the host cell, allowing expression of the two nucleic acid molecules and harvesting the heterodimeric CH3 domain-comprising molecule from the culture.

Further methods of engineering electrostatic interactions in polypeptide chains to promote heterodimer formation over homodimer formation were described in WO2011/143545.

Another example of engineering at the CH3-CH3 interface is strand-exchange engineered domain (SEED) CH3 heterodimers. The CH3 domains are composed of alternating segments of human IgA and IgG CH3 sequences, which form pairs of complementary SEED heterodimers referred to as "SEED-bodies" [10; WO2007/110205].

Bispecifics have also been produced with heterodimerised heavy chains that are differentially modified in the CH3 domain to alter their affinity for binding to a purification reagent such as Protein A. WO2010/151792 described a heterodimeric bispecific antigen-binding protein comprising a first polypeptide comprising, from N-terminal to C-terminal, a first epitope-binding region that selectively binds a first epitope, an immunoglobulin constant region that comprises a first CH3 region of a human IgG selected from IgG1, IgG2, and IgG4; and a second polypeptide comprising, from N-terminal to C-terminal, a second epitope-binding region that selectively binds a second epitope, an immunoglobulin constant region that comprises a second CH3 region of a human IgG selected from IgG1, IgG2, and IgG4, wherein the second CH3 region comprises a modification that reduces or eliminates binding of the second CH3 domain to Protein A.

The bispecifics of the present invention may employ any of these techniques and molecular formats as desired.

Generating and Modifying Antibodies

Methods for identifying and preparing antibodies are well known. Antibodies that bind an antigen of interest may be generated using transgenic mice (eg, the Kymouse™, Velocimouse®, Omnimouse®, Xenomouse®, HuMab Mouse® or MeMo Mouse®), rats (e.g., the Omnirat®), camelids, sharks, rabbits, chickens or other non-human animals immunised with the antigen, followed optionally by humanisation of the constant regions and/or variable regions to produce human or humanised antibodies. In an example, display technologies can be used, such as yeast, phage or ribosome display, as will be apparent to the skilled person. Standard affinity maturation, e.g., using a display technology, can be performed in a further step after isolation of an antibody lead from a transgenic animal, phage display library or other library. Representative examples of suitable technologies are described in US20120093818 (Amgen, Inc), which is incorporated by reference herein in its entirety, eg, the methods set out in paragraphs [0309] to [0346].

Following generation of antibodies, whether by immunisation or screening of in vitro libraries, nucleic acid encoding an antibody heavy chain variable domain and/or an antibody light chain variable domain of a selected antibody may be isolated. Such nucleic acid may encode the full antibody heavy chain and/or light chain, or the variable domain(s) without associated constant region(s). Encoding nucleotide sequences may be obtained directly from antibody-producing cells of a mouse, or B cells may be immortalised or fused to generate hybridomas expressing the antibody, and encoding nucleic acid obtained from such cells. Optionally, nucleic acid encoding the variable domain(s) is then conjugated to a nucleotide sequence encoding a human heavy chain constant region and/or human light chain constant region, to provide nucleic acid encoding a human antibody heavy chain and/or human antibody light chain, e.g., encoding an antibody comprising both the heavy and light chain. This step is particularly useful where the immunised mammal produces chimaeric antibodies with non-human constant regions, which are preferably replaced with human constant regions to generate an antibody that will be less immunogenic when administered to humans as a medicament. Provision of particular human isotype constant regions is also significant for determining the effector function of the antibody, and a number of suitable heavy chain constant regions are discussed herein.

Other alterations to nucleic acid encoding the antibody heavy and/or light chain variable domain may be performed, such as mutation of residues and generation of variants, as described herein.

The isolated (optionally mutated) nucleic acid may be introduced into host cells, e.g., CHO cells as discussed. Host cells are then cultured under conditions for expression of the antibody, or of the antibody heavy and/or light chain variable domain, in any desired antibody format. Some possible antibody formats are described herein, e.g., whole immunoglobulins, antigen-binding fragments, and other designs.

Variable domain amino acid sequence variants of any of the VH and VL domains or CDRs whose sequences are specifically disclosed herein may be employed in accordance with the present invention, as discussed.

There are many reasons why it may be desirable to create variants, which include optimising the antibody sequence for large-scale manufacturing, facilitating purification, enhancing stability or improving suitability for inclusion in a desired pharmaceutical formulation. Protein engineering work can be performed at one or more target residues in the antibody sequence, e.g., to substituting one amino acid with an alternative amino acid (optionally, generating variants containing all naturally occurring amino acids at this position, with the possible exception of Cys and Met), and monitoring the impact on function and expression to determine the best substitution. It is in some instances undesirable to substitute a residue with Cys or Met, or to introduce these residues into a sequence, as to do so may generate difficulties in manufacturing—for instance through the formation of new intramolecular or intermolecular cysteine-cysteine bonds. Where a lead candidate has been selected and is being optimised for manufacturing and clinical development, it will generally be desirable to change its antigen-binding properties as little as possible, or at least to retain the affinity and potency of the parent molecule. However, variants may also be generated in order to modulate key antibody characteristics such as affinity, cross-reactivity or neutralising potency.

One or more amino acid mutations may optionally be made in framework regions of an antibody VH or VL domain disclosed herein. For example, one or more residues that differ from the corresponding human germline segment sequence may be reverted to germline. Human germline gene segment sequences corresponding to VH and VL domains of example antibodies herein are indicated in Table 12.

In a bispecific antigen binding molecule, an antigen-binding site may comprise a set of H and/or L CDRs of any of the disclosed anti-FIX or anti-FX antibodies with one or more amino acid mutations within the disclosed set of H and/or L CDRs. The mutation may be an amino acid substitution, deletion or insertion. Thus for example there may be one or more amino acid substitutions within the disclosed set of H and/or L CDRs. For example, there may be up to 12, 11, 10, 9, 8, 7, 6, 5, 4, 3 or 2 mutations e.g. substitutions, within the set of H and/or L CDRs. For example, there may be up to 6, 5, 4, 3 or 2 mutations, e.g. substitutions, in HCDR3 and/or there may be up to 6, 5, 4, 3, or 2 mutations, e.g. substitutions, in LCDR3.

An antibody may comprise a VH domain that has at least 60, 70, 80, 85, 90, 95, 98 or 99% amino acid sequence identity with a VH domain as shown in the Tables, and/or comprising a VL domain that has at least 60, 70, 80, 85, 90, 95, 98 or 99% amino acid sequence identity with a VL domain of any of those antibodies. Algorithms that can be used to calculate % identity of two amino acid sequences include e.g. BLAST, FASTA, or the Smith-Waterman algorithm, e.g. employing default parameters. Particular variants may include one or more amino acid sequence alterations (addition, deletion, substitution and/or insertion of an amino acid residue).

Alterations may be made in one or more framework regions and/or one or more CDRs. Variants are optionally provided by CDR mutagenesis. The alterations normally do not result in loss of function, so an antibody comprising a thus-altered amino acid sequence may retain an ability to bind its antigen. It may retain the same quantitative binding ability as an antibody in which the alteration is not made, e.g. as measured in an assay described herein. The antibody comprising a thus-altered amino acid sequence may have an improved ability to bind its antigen.

Alteration may comprise replacing one or more amino acid residue with a non-naturally occurring or non-standard amino acid, modifying one or more amino acid residue into a non-naturally occurring or non-standard form, or inserting one or more non-naturally occurring or non-standard amino acid into the sequence. Examples of numbers and locations of alterations in sequences of the invention are described elsewhere herein. Naturally occurring amino acids include the 20 "standard" L-amino acids identified as G, A, V, L, I, M, P, F, W, S, T, N, Q, Y, C, K, R, H, D, E by their standard single-letter codes. Non-standard amino acids include any other residue that may be incorporated into a polypeptide backbone or result from modification of an existing amino acid residue. Non-standard amino acids may be naturally occurring or non-naturally occurring.

The term "variant" as used herein refers to a peptide or nucleic acid that differs from a parent polypeptide or nucleic acid by one or more amino acid or nucleic acid deletions, substitutions or additions, yet retains one or more specific functions or biological activities of the parent molecule. Amino acid substitutions include alterations in which an amino acid is replaced with a different naturally-occurring amino acid residue. Such substitutions may be classified as "conservative", in which case an amino acid residue contained in a polypeptide is replaced with another naturally occurring amino acid of similar character either in relation to polarity, side chain functionality or size. Such conservative substitutions are well known in the art. Substitutions encompassed by the present invention may also be "non-conservative", in which an amino acid residue which is present in a peptide is substituted with an amino acid having different properties, such as naturally-occurring amino acid from a different group (e.g., substituting a charged or hydrophobic amino; acid with alanine), or alternatively, in which a naturally-occurring amino acid is substituted with a non-conventional amino acid. In some embodiments amino acid substitutions are conservative. Also encompassed within the term variant when used with reference to a polynucleotide or polypeptide, refers to a polynucleotide or polypeptide that can vary in primary, secondary, or tertiary structure, as compared to a reference polynucleotide or polypeptide, respectively (e.g., as compared to a wild-type polynucleotide or polypeptide).

In some aspects, one can use "synthetic variants", "recombinant variants", or "chemically modified" polynucleotide variants or polypeptide variants isolated or generated using methods well known in the art. "Modified variants" can include conservative or non-conservative amino acid changes, as described below. Polynucleotide changes can result in amino acid substitutions, additions, deletions, fusions and truncations in the polypeptide encoded by the reference sequence. Some aspects use include insertion variants, deletion variants or substituted variants with substitutions of amino acids, including insertions and substitutions of amino acids and other molecules) that do not normally occur in the peptide sequence that is the basis of the variant, for example but not limited to insertion of ornithine which do not normally occur in human proteins. The term "conservative substitution," when describing a polypeptide, refers to a change in the amino acid composition of the polypeptide that does not substantially alter the polypeptide's activity. For example, a conservative substitution refers to substituting an amino acid residue for a different amino acid residue that has similar chemical properties (e.g., acidic, basic, positively or negatively charged, polar or nonpolar, etc.). Conservative amino acid substitutions include replacement of a leucine with an isoleucine or valine, an aspartate with a glutamate, or a threonine with a serine. Conservative substitution tables providing functionally similar amino acids are well known in the art. For example, the following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). (See also Creighton, Proteins, W. H. Freeman and Company (1984), incorporated by reference in its entirety.) In some embodiments, individual substitutions, deletions or additions that alter, add or delete a single amino acid or a small percentage of amino acids can also be considered "conservative substitutions" if the change does not reduce the activity of the peptide. Insertions or deletions are typically in the range of about 1 to 5 amino acids. The choice of conservative amino acids may be selected based on the location of the amino acid to be substituted in the peptide, for example if the amino acid is on the exterior of the peptide and expose to solvents, or on the interior and not exposed to solvents.

One can select the amino acid that will substitute an existing amino acid based on the location of the existing amino acid, including its exposure to solvents (i.e., if the amino acid is exposed to solvents or is present on the outer surface of the peptide or polypeptide as compared to internally localized amino acids not exposed to solvents). Selection of such conservative amino acid substitutions are well known in the art, for example as disclosed in Dordo et al, J. Mol Biol, 1999, 217, 721-739 and Taylor et al, J. Theor. Biol. 119(1986); 205-218 and S. French and B. Robson, J. Mol. Evol. 19(1983) 171. Accordingly, one can select conservative amino acid substitutions suitable for amino acids on the exterior of a protein or peptide (i.e. amino acids exposed to a solvent), for example, but not limited to, the following substitutions can be used: substitution of Y with F, T with S or K, P with A, E with D or Q, N with D or G, R with K, G with N or A, T with S or K, D with N or E, I with L or V, F with Y, S with T or A, R with K, G with N or A, K with R, A with S, K or P.

In alternative embodiments, one can also select conservative amino acid substitutions encompassed suitable for amino acids on the interior of a protein or peptide, for example one can use suitable conservative substitutions for amino acids is on the interior of a protein or peptide (i.e. the amino acids are not exposed to a solvent), for example but not limited to, one can use the following conservative substitutions: where Y is substituted with F, T with A or S, I with L or V, W with Y, M with L, N with D, G with A, T with A or S, D with N, I with L or V, F with Y or L, S with A or T and A with S, G, T or V. In some embodiments, non-conservative amino acid substitutions are also encompassed within the term of variants.

The invention includes methods of producing polypeptide binding arms containing VH and/or VL domain variants of the antibody VH and/or VL domains shown in the Tables herein. FIXa binding polypeptide arms comprising variant VH domains may be produced by a method comprising
  (i) providing, by way of addition, deletion, substitution or insertion of one or more amino acids in the amino acid sequence of a parent antibody VH domain, an antibody VH domain that is an amino acid sequence variant of the parent antibody VH domain,
    wherein the parent antibody VH domain is the VH domain N192H, N212H, N205H, N211H, N203H, N128H, N215H, N216H, N217H, N218H, N219H, N220H, N221H, N222H, N223H, N224H, N225H, N226H, N227H, N228H or N229H or is a VH domain comprising the heavy chain complementarity determining regions of any of those VH domains,
  (ii) optionally combining the VH domain thus provided with a VL domain, to provide a VH/VL combination, and
  (iii) testing the VH domain or VH/VL domain combination thus provided to identify an antibody with one or more desired characteristics.

The VH domain may be any VH domain whose sequence is shown in Table 9A, or any VH domain comprising a set of HCDRs (HCDR1, HCDR2 and HCDR3) of a VH domain shown in Table 9A. The VH domain may be the N436 VH domain (SEQ ID NO: 324). The VH domain may be the N128 VH domain (SEQ ID NO: 5).

Desired characteristics of FIXa-binding polypeptide arms, and of bispecific anti-FIXa/FX binding molecules comprising them, are detailed elsewhere herein. For example, the method may comprise confirming that the VH domain or VH/VL domain combination binds FIXa as described herein.

When VL domains are included in the method, the VL domain may be the N128L VL domain or may be a variant provided by way of addition, deletion, substitution or insertion of one or more amino acids in the amino acid sequence of the N128L VL domain, or may be a VL domain comprising the light chain complementarity determining regions of the N128L VL domain.

Methods of generating variant antibodies may optionally comprise producing copies of the antibody or VH/VL domain combination. Methods may further comprise producing a bispecific antibody comprising the FIXa binding polypeptide arm, for example by expression of encoding nucleic acid. Suitable methods of expression, including recombinant expression in host cells, are set out in detail herein.

Encoding Nucleic Acids and Methods of Expression

Isolated nucleic acid may be provided, encoding bispecific antigen binding molecules, e.g., bispecific antibodies, according to the present invention. Nucleic acid may be DNA and/or RNA. Genomic DNA, cDNA, mRNA or other RNA, of synthetic origin, or any combination thereof can encode an antibody.

The present invention provides constructs in the form of plasmids, vectors, transcription or expression cassettes which comprise at least one polynucleotide as above. Exemplary nucleotide sequences are included in the Tables. Reference to a nucleotide sequence as set out herein encompasses a DNA molecule with the specified sequence, and encompasses a RNA molecule with the specified sequence in which U is substituted for T, unless context requires otherwise.

The present invention also provides a recombinant host cell that comprises one or more nucleic acids encoding the antigen binding molecule. Methods of producing the encoded molecule may comprise expression from the nucleic acid, e.g., by culturing recombinant host cells containing the nucleic acid. The bispecific molecule may thus be obtained, and may be isolated and/or purified using any suitable technique, then used as appropriate. A method of production may comprise formulating the product into a composition including at least one additional component, such as a pharmaceutically acceptable excipient.

Systems for cloning and expression of a polypeptide in a variety of different host cells are well known. Suitable host cells include bacteria, mammalian cells, plant cells, filamentous fungi, yeast and baculovirus systems and transgenic plants and animals.

The expression of antibodies and antibody fragments in prokaryotic cells is well established in the art. A common bacterial host is *E. coli*. Expression in eukaryotic cells in culture is also available to those skilled in the art as an option for production. Mammalian cell lines available in the art for expression of a heterologous polypeptide include Chinese hamster ovary (CHO) cells, HeLa cells, baby hamster kidney cells, NS0 mouse melanoma cells, YB2/0 rat myeloma cells, human embryonic kidney cells, human embryonic retina cells and many others.

Vectors may contain appropriate regulatory sequences, including promoter sequences, terminator sequences, polyadenylation sequences, enhancer sequences, marker genes and other sequences as appropriate. Nucleic acid encoding an antibody can be introduced into a host cell. Nucleic acid can be introduced to eukaryotic cells by various methods, including calcium phosphate transfection, DEAE-Dextran, electroporation, liposome-mediated transfection and transduction using retrovirus or other virus, e.g. vaccinia or, for insect cells, baculovirus. Introducing nucleic acid in the host cell, in particular a eukaryotic cell may use a viral or a plasmid based system. The plasmid system may be maintained episomally or may be incorporated into the host cell or into an artificial chromosome. Incorporation may be either by random or targeted integration of one or more copies at single or multiple loci. For bacterial cells, suitable techniques include calcium chloride transformation, electroporation and transfection using bacteriophage. The introduction may be followed by expressing the nucleic acid, e.g., by culturing host cells under conditions for expression of the gene, then optionally isolating or purifying the antibody.

Nucleic acid of the invention may be integrated into the genome (e.g. chromosome) of the host cell. Integration may be promoted by inclusion of sequences that promote recombination with the genome, in accordance with standard techniques.

The present invention also provides a method that comprises using nucleic acid described herein in an expression system in order to express the bispecific antigen binding molecule. Desirably, the antigen-binding molecules are expressed at a yield of at least 0.5 g/L in the cell supernatant after initial fermentation, preferably at a yield of >2 g/L. Solubility should be >10 mg/ml, preferably >50 mg/ml, without significant aggregation or degradation of the molecules.

Formulation and Administration

The bispecific antigen-binding molecules ("bispecifics") according to the present invention, and their encoding nucleic acid molecules, will usually be provided in isolated form. The bispecifics VH and/or VL domains, and nucleic acids may be provided purified from their natural environment or their production environment. Isolated antigen-binding molecules and isolated nucleic acid will be free or substantially free of material with which they are naturally associated, such as other polypeptides or nucleic acids with which they are found in vivo, or the environment in which they are prepared (e.g., cell culture) when such preparation is by recombinant DNA technology in vitro. Optionally an isolated antigen-binding molecule or nucleic acid (1) is free of at least some other proteins with which it would normally be found, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is operably associated (by covalent or noncovalent interaction) with a polypeptide with which it is not associated in nature, or (6) does not occur in nature.

Bispecifics or their encoding nucleic acids may be formulated with diluents or adjuvants and still for practical purposes be isolated—for example they may be mixed with carriers if used to coat microtitre plates for use in immunoassays, and may be mixed with pharmaceutically acceptable carriers or diluents when used in therapy. As described elsewhere herein, other active ingredients may also be included in therapeutic preparations. The antigen binding molecules may be glycosylated, either naturally in vivo or by systems of heterologous eukaryotic cells such as CHO cells, or they may be (for example if produced by expression in a prokaryotic cell) unglycosylated. The invention encompasses antibodies having a modified glycosylation pattern.

Typically, an isolated product constitutes at least about 5%, at least about 10%, at least about 25%, or at least about 50% of a given sample. A bispecific may be substantially free from proteins or polypeptides or other contaminants that are found in its natural or production environment that would interfere with its therapeutic, diagnostic, prophylactic, research or other use.

The invention provides therapeutic compositions comprising the bispecifics described herein. Therapeutic compositions comprising nucleic acid encoding such bispecifics are also provided. Encoding nucleic acids are described in more detail elsewhere herein and include DNA and RNA, e.g., mRNA. In therapeutic methods described herein, use of nucleic acid encoding the bispecific, and/or of cells containing such nucleic acid, may be used as alternatives (or in addition) to compositions comprising the bispecific molecule itself. Cells containing nucleic acid encoding the bispecific, optionally wherein the nucleic acid is stably integrated into the genome, thus represent medicaments for therapeutic use in a patient. Nucleic acid encoding the bispecific may be introduced into human cells derived from the intended patient and modified ex vivo. Administration of cells containing the encoding nucleic acid to the patient provides a reservoir of cells capable of expressing the bispecific, which may provide therapeutic benefit over a longer term compared with administration of isolated nucleic acid or the isolated bispecific molecule. Nucleic acid encoding the bispecific may be provided for use in gene therapy, comprising introducing the encoding nucleic acid into cells of the patient in vivo, so that the nucleic acid is expressed in the patient's cells and provides a therapeutic effect such as compensating for hereditary factor VIII deficiency.

Compositions may contain suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311. Compositions may comprise the antibody or nucleic acid in combination with medical injection buffer and/or with adjuvant.

Bispecifics, or their encoding nucleic acids, may be formulated for the desired route of administration to a patient, e.g., in liquid (optionally aqueous solution) for injection.

Various delivery systems are known and can be used to administer the pharmaceutical composition of the invention. Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. The antigen-binding molecules are preferably administered by subcutaneous injection.

The pharmaceutical composition can be also delivered in a vesicle, in particular a liposome (see Langer (1990) Science 249:1527-1533; Treat et al. (1989) in Liposomes in the Therapy of Infectious Disease and Cancer, Lopez Berestein and Fidler (eds.), Liss, New York, pp. 353-365; Lopez-Berestein, ibid., pp. 317-327; see generally ibid.).

In certain situations, the pharmaceutical composition can be delivered in a controlled release system. In one embodiment, a pump may be used (see Langer, supra; Sefton (1987) CRC Crit. Ref. Biomed. Eng. 14:201). In another embodiment, polymeric materials can be used; see, Medical Applications of Controlled Release, Langer and Wise (eds.), CRC Pres., Boca Raton, Fla. (1974). In yet another embodiment, a controlled release system can be placed in proximity of the composition's target, thus requiring only a fraction of the systemic dose (see, e.g., Goodson, in Medical Applications of Controlled Release, supra, vol. 2, pp. 115-138, 1984).

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared can be filled in an appropriate ampoule. A pharmaceutical composition of the present invention can be delivered subcutaneously or intravenously with a standard needle and syringe. It is envisaged that treatment will not be restricted to use in the clinic. Therefore, subcutaneous injection using a needle-free device is also advantageous. With respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded. Numerous reusable pen and autoinjector delivery devices have applications in the subcutaneous delivery of a pharmaceutical composition of the present invention. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPENT™, OPTIPEN PRO™, OPTIPEN STARLET™, and OPTICLIKT™ (Sanofi-Aventis, Frankfurt, Germany), to name only a few. Examples of disposable pen delivery devices having applications in subcutaneous delivery of a pharmaceutical composition of the present invention include, but certainly are not limited to the SOLOSTAR™ pen (Sanofi-Aventis), the FLEXPEN™ (Novo Nordisk), and the KWIKPEN™ (Eli Lilly).

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, the aforesaid antibody may be contained in about 5 to about 100 mg and in about 10 to about 250 mg for the other dosage forms.

The bispecific, nucleic acid, or composition comprising it, may be contained in a medical container such as a phial, syringe, IV container or an injection device. In an example, the bispecific, nucleic acid or composition is in vitro, and may be in a sterile container. In an example, a kit is provided comprising the bispecific, packaging and instructions for use in a therapeutic method as described herein.

One aspect of the invention is a composition comprising a bispecific or nucleic acid of the invention and one or more pharmaceutically acceptable excipients, examples of which are listed above. "Pharmaceutically acceptable" refers to approved or approvable by a regulatory agency of the USA Federal or a state government or listed in the U.S. Pharmacopeia or other generally recognized pharmacopeia for use in animals, including humans. A pharmaceutically acceptable carrier, excipient, or adjuvant can be administered to a patient, together with a bispecific agent, e.g., any antibody or polypeptide molecule described herein, and does not destroy the pharmacological activity thereof and is nontoxic when administered in doses sufficient to deliver a therapeutic amount of the agent.

In some embodiments, the bispecific will be the sole active ingredient in a composition according to the present invention. Thus, a composition may consist of the antibody or it may consist of the bispecific with one or more pharmaceutically acceptable excipients. However, compositions according to the present invention optionally include one or more additional active ingredients. Other therapeutic agents that it may be desirable to administer with bispecific or nucleic acids according to the present invention include analgesic agents. Any such agent or combination of agents may be administered in combination with, or provided in compositions with antibodies or nucleic acids according to the present invention, whether as a combined or separate preparation. The bispecific or nucleic acid according to the present invention may be administered separately and sequentially, or concurrently and optionally as a combined preparation, with another therapeutic agent or agents such as those mentioned.

Multiple compositions can be administered separately or simultaneously. Separate administration refers to the two compositions being administered at different times, e.g. at least 10, 20, 30, or 10-60 minutes apart, or 1, 2, 3, 4, 5, 6, 7, 8, 9, 10, 12 hours apart. One can also administer compositions at 24 hours apart, or even longer apart. Alternatively, two or more compositions can be administered simultaneously, e.g. less than 10 or less than 5 minutes apart. Compositions administered simultaneously can, in some aspects, be administered as a mixture, with or without similar or different time release mechanism for each of the components.

Bispecifics, and their encoding nucleic acids, can be used as therapeutic agents. Patients herein are generally mammals, typically humans. A bispecific or nucleic acid may be administered to a mammal, e.g., by any route of administration mentioned herein.

Administration is normally in a "therapeutically effective amount", this being an amount that produces the desired effect for which it is administered, sufficient to show benefit to a patient. The exact amount will depend on the purpose of the treatment, and will be ascertainable by one skilled in the art using known techniques (see, for example, Lloyd (1999) The Art, Science and Technology of Pharmaceutical Compounding). Prescription of treatment, e.g. decisions on dosage etc, is within the responsibility of general practitioners and other medical doctors and may depend on the severity of the symptoms and/or progression of a disease being treated. A therapeutically effective amount or suitable dose of bispecific or nucleic acid can be determined by comparing its in vitro activity and in vivo activity in an animal model. Methods for extrapolation of effective dosages in mice and other test animals to humans are known.

Bispecifics may be administered in an amount in one of the following ranges per dose:
about 10 µg/kg body weight to about 100 mg/kg body weight,
about 50 µg/kg body weight to about 5 mg/kg body weight,
about 100 µg/kg body weight to about 10 mg/kg body weight,
about 100 µg/kg body weight to about 20 mg/kg body weight,
about 0.5 mg/kg body weight to about 20 mg/kg body weight, or about 5 mg/kg body weight or lower, for example less than 4, less than 3, less than 2, or less than 1 mg/kg of the antibody.

The dose of antigen-binding molecule administered may be up to 1 mg/kg. It may be formulated at lower strength for paediatric populations, for example 30-150 mg/mL. The bispecific molecule may be packaged in smaller quantities for a paediatric population, e.g., it may be provided in phials of 25-75 mg, e.g., 30 or 60 mg.

In methods of treatment described herein, one or more doses may be administered. In some cases, a single dose may be effective to achieve a long-term benefit. Thus, the method may comprise administering a single dose of the bispecific, its encoding nucleic acid, or the composition. Alternatively, multiple doses may be administered, usually sequentially and separated by a period of days, weeks or months. Optionally, the bispecific may be administered to a patient once a month, or less frequently, e.g., every two months or every three months.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder. The term "treating" includes reducing or alleviating at least one adverse effect or symptom of a condition, disease or disorder. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilised (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment). For treatment to be effective a complete cure is not contemplated. The method can in certain aspects include cure as well. In the context of the invention, treatment may be preventative treatment.

Long half-life is a desirable feature in the bispecifics of the present invention. Extended half-life translates to less frequent administration, with fewer injections being required to maintain a therapeutically effective concentration of the molecule in the bloodstream. The in vivo half life of antigen-binding molecules of the present invention in humans may be 7, 8, 9, 10, 11, 12, 13, 14, 15, 16, 17, 18, 19, 20 or 21 days, or longer. The in vivo half life of antigen-binding molecules in non-human primates such as cynomolgus monkeys may be 7, 8, 9, 10, 11, 12, 13, 14, 15, 16, 17, 18, 19, 20 or 21 days, or longer.

Antigen-binding molecules may be provided for administration at regular intervals of one week, two weeks, three weeks, four weeks, or one month.

Therapeutic Use

The bispecific antigen-binding molecules of the present invention may be used in a method of treatment of the human or animal body by therapy. Therapeutic indications for the molecules include:
  use to treat haemophilia A,
  use to treat hereditary factor VIII deficiency,
  use to significantly decrease the number of bleeding incidents in haemophilia A patients,
  use to substitute for factor VIII function,
  and/or
  use to promote blood coagulation.

Patients are typically human patients. The patient may be a human diagnosed with haemophilia A or hereditary factor VIII deficiency, or a human who has lower (or absent) factor VIII expression or activity compared with wild type. The patient may be a paediatric patient (e.g., from 2 to less than 18 years of age) or may be an adult. The patient may or may not have inhibitors to factor VIII.

A bispecific molecule of the present invention, or a composition comprising such an bispecific molecule or its encoding nucleic acid, may be used or provided for use in any such method. Use of the bispecific molecule, or of a composition comprising it or its encoding nucleic acid, for the manufacture of a medicament for use in any such method is also envisaged. The method typically comprises administering the antibody or composition to a mammal, e.g., a human patient. Suitable formulations and methods of administration are described elsewhere herein.

There is a presently unmet need for treatment of haemophilia A patients who develop inhibitory alloantibodies to FVIII. Antigen-binding molecules of the present invention are suitable for use in such patients. Accordingly, in some aspects, a patient treated with a bispecific antigen binding molecule according to the present invention may be resistant to treatment with FVIII owing to the presence of inhibitory antibodies in the bloodstream. Resistance to treatment can be manifested in a reduction of efficacy of the therapy. Such resistance may be detected in in vitro assays (e.g. aPTT assay) with a blood plasma sample from the patient, wherein the therapeutic molecule does not reduce coagulation time to the same level as in an assay with control FVIII-deficient plasma (the latter lacking inhibitory antibodies to the therapeutic molecule).

Patients receiving other treatments for haemophilia, such as bispecific antibodies to FIXa and FX, may also develop inhibitory antibodies to those therapeutic antibodies. As noted, use of human antibodies such as those of the present invention should minimise the risk of this, but inhibitory antibodies may nevertheless be generated in some patients who receive antigen binding molecules of the present invention or other bispecific antigen binding molecules to FIXa and FX. A patient treated with a bispecific antigen binding molecule according to the present invention may be resistant to treatment to a different bispecific antigen binding molecule for FIXa and FX owing to the presence of inhibitory antibodies in the bloodstream. The patient may be resistant to treatment with emicizumab.

Since inhibitory antibodies may be generated through long term therapeutic administration of a drug product, it may be beneficial for patients to alternate or cycle between multiple different treatments, to reduce the risk of their developing inhibitory antibodies. Thus, a bispecific antigen binding molecule of the present invention may be administered to a patient who has previously received treatment with a different FVIIIa-activity replacing polypeptide drug, e.g., a bispecific antigen binding molecule for FIXa and FX, optionally emicizumab, even where the patient has not (yet) developed inhibitory antibodies. Similarly, emicizumab or other bispecific antigen binding molecules for FIXa and FX, and other FVIIIa-activity replacing polypeptide drugs generally, may be administered to patients who were previously treated with a bispecific antigen binding molecule of the present invention. Regiments of treatment may comprise administration of a first FVIII-activity replacing polypeptide drug for a first period (e.g., between one and six months, or between six months and one year), followed by switching to a different FVIII-activity replacing polypeptide drug for a second period (e.g. between one and six months, or between six months and one year), followed by switching back to the first drug or switching to yet another FVIII-activity replacing polypeptide drug. The different amino acid sequences of the different drug treatments should ensure that a patient at risk of developing inhibitory antibodies to one drug is no longer at risk of developing inhibitory antibodies to the first drug (e.g., emicizumab) following switching to a different drug (e.g., a molecule of the present invention). The cycling period may be varied or shortened, according to convenience and the preferences of the patient and doctor.

It will be recognised that administration of the encoding nucleic acid represents an alternative therapy, and may be performed in place of administering the polypeptide drug directly.

As noted, the bispecific antigen-binding molecules of the present invention are believed to have a strong safety profile, associated with no (or minimal) incidents of hypersensitivity reactions, development of alloantibodies, organ toxicity or other adverse events leading to discontinuation of the therapy.

The following numbered clauses and statements represent embodiments of the invention and are part of the description.

CLAUSES

Clause 1. A bispecific antigen-binding molecule comprising
  a FIXa binding polypeptide arm comprising a FIXa binding site, and
  a FX binding polypeptide arm comprising a FX binding site, characterised in that
  (i) the FIXa binding site is provided by a set of complementarity determining regions (CDRs) in the FIXa binding polypeptide arm, the set of CDRs comprising HCDR1, HCDR2, HCDR3 and/or LCDR1, LCDR2 and LCDR3, wherein
  HCDR1 is SEQ ID NO: 140
  HCDR2 is SEQ ID NO: 141
  HCDR3 is SEQ ID NO: 142
  LCDR1 is SEQ ID NO: 6
  LCDR2 is SEQ ID NO: 7 and
  LCDR3 is SEQ ID NO: 8,
  or comprising that set of CDRs with 1, 2, 3, 4 or 5 amino acid alterations;
  (ii) the FIXa binding polypeptide arm comprises an antibody Fv region comprising
    a VH domain generated through recombination of immunoglobulin heavy chain v, d and j gene segments, wherein the v gene segment is VH3-7 and/or wherein the j gene segment is JH6, and/or
    a VL domain generated through recombination of immunoglobulin light chain v and j gene segments, wherein the v gene segment is VL3-21 and the j gene segment is JL3; and/or
  (iii) the FIXa binding polypeptide arm is capable, when provided in monospecific form, of enhancing FIXa-catalysed activation of FX to FXa.

Clause 2. A bispecific antigen-binding molecule according to clause 1, wherein the FIXa binding polypeptide arm comprises a VH domain generated through recombination of immunoglobulin heavy chain v, d and j gene segments, wherein the v gene segment is VH3-7, the d gene segment DH1-26 and the j gene segment is JH6.

Clause 3. A bispecific antigen-binding molecule according to clause 1 or clause 2, wherein the FIXa binding polypeptide arm comprises a VH domain generated through recombination of immunoglobulin heavy chain v, d and j gene segments, wherein the v gene segment is VH3-7*01 and the j gene segment is JH6*02.

Clause 4. A bispecific antigen-binding molecule according to any preceding clause, wherein the FIXa binding polypeptide arm comprises an antibody Fv region comprising a FIXa binding site provided by a set of CDRs, the set of CDRs comprising HCDR1, HCDR2, HCDR3 and/or LCDR1, LCDR2 and LCDR3, wherein
  HCDR1 is SEQ ID NO: 140
  HCDR2 is SEQ ID NO: 141
  HCDR3 is SEQ ID NO: 142
  LCDR1 is SEQ ID NO: 6
  LCDR2 is SEQ ID NO: 7 and
  LCDR3 is SEQ ID NO: 8,
  or comprising that set of CDRs with 1, 2, 3, 4 or 5 amino acid alterations.

Clause 5. A bispecific antigen-binding molecule according to any preceding clause, wherein the FIXa binding polypeptide arm comprises an antibody VH domain comprising HCDR1, HCDR2 and HCDR3, wherein
  HCDR1 is SEQ ID NO: 140
  HCDR2 is SEQ ID NO: 141 and
  HCDR3 is SEQ ID NO: 142.

Clause 6. A bispecific antigen-binding molecule according to any preceding clause, wherein HCDR1 is SEQ ID NO: 1, HCDR2 is SEQ ID NO: 2 and HCDR3 is SEQ ID NO: 3.

Clause 7. A bispecific antigen-binding molecule according to any preceding clause, wherein the FIXa binding polypeptide arm comprises a VL domain generated through recombination of VL3-21*d01 gene segment and a JL3*02 gene segment.

Clause 8. A bispecific antigen-binding molecule according to any preceding clause, wherein the FIXa binding polypeptide arm comprises an antibody VL domain comprising LCDR1, LCDR2 and LCDR3, wherein
  LCDR1 is SEQ ID NO: 6
  LCDR2 is SEQ ID NO: 7 and
  LCDR3 is SEQ ID NO: 8.

Clause 9. A bispecific antigen-binding molecule according to any preceding clause, wherein the FIXa binding polypeptide arm comprises a VH domain comprising HCDR1, HCDR2 and HCDR3 in a framework, the framework comprising a set of framework regions FR1, FR2, FR3 and FR4, wherein:
  FR1 is SEQ ID NO: 132
  FR2 is SEQ ID NO: 133
  FR3 is SEQ ID NO: 134 and
  FR4 is SEQ ID NO: 135,
  or wherein the framework comprises that set of framework regions with up to 10 amino acid alterations.

Clause 10. A bispecific antigen-binding molecule according to clause 9, wherein
  FR1 is SEQ ID NO: 132, optionally with a substitution of L for F at residue 11, a substitution of V for A at residue 24 and/or a substitution of A for V at residue 24
  FR2 is SEQ ID NO: 133
  FR3 is SEQ ID NO: 134, optionally with a substitution of Y for F at residue 59, a substitution of D for A at residue 62, a substitution of I for M at residue 70, a substitution of N for K at residue 77, a substitution of L for V at residue 79 and/or a substitution of L for V at residue 81, and FR4 is SEQ ID NO: 135, optionally with a substitution of S for Tat residue 119,
wherein residue numbering is according to the IMGT system.

Clause 11. A bispecific antigen-binding molecule according to clause 10, wherein:
FR1 is SEQ ID NO: 132
FR2 is SEQ ID NO: 133
FR3 is SEQ ID NO: 134 and
FR4 is SEQ ID NO: 135.

Clause 12. A bispecific antigen-binding molecule according to any preceding clause, wherein the FIXa binding polypeptide arm comprises a VL domain comprising LCDR1, LCDR2 and LCDR3 in a framework, the framework comprising a set of framework regions FR1, FR2, FR3 and FR4, wherein:
FR1 is SEQ ID NO: 136
FR2 is SEQ ID NO: 137
FR3 is SEQ ID NO: 138 and
FR4 is SEQ ID NO: 139,
or wherein the framework comprises that set of framework regions with up to 10 amino acid alterations.

Clause 13. A bispecific antigen-binding molecule according to clause 12, wherein:
FR1 is SEQ ID NO: 136
FR2 is SEQ ID NO: 137
FR3 is SEQ ID NO: 138 and
FR4 is SEQ ID NO: 139.

Clause 14. A bispecific antigen-binding molecule according to any preceding clause, wherein the FIXa binding polypeptide arm comprises a VH domain having amino acid sequence SEQ ID NO: 5.

Clause 15. A bispecific antigen-binding molecule according to any preceding clause, wherein the FIXa binding polypeptide arm VL domain comprises amino acid sequence SEQ ID NO: 10.

Clause 16. A bispecific antigen-binding molecule according to any preceding clause, wherein the FIXa binding polypeptide arm comprises an antibody heavy chain comprising, from N to C terminus, a VH domain, a CH1 domain, a CH2 domain and a CH3 domain.

Clause 17. A bispecific antigen-binding molecule according to clause 16, wherein the antibody heavy chain comprises an IgG constant region.

Clause 18. A bispecific antigen-binding molecule according to any preceding clause, wherein the FIXa binding polypeptide arm comprises an antibody light chain comprising, from N to C terminus, a VL domain and a CL domain.

Clause 19. A bispecific antigen-binding molecule according to any preceding clause, wherein the FX binding polypeptide arm comprises an antibody Fv region comprising a FIXa binding site provided by a set of CDRs.

Clause 20. A bispecific antigen-binding molecule according to clause 19, wherein the antibody Fv region comprises a VH domain generated through recombination of immunoglobulin heavy chain v, d and j gene segments, wherein the v and j gene segments are:
VH1-3 (e.g., VH1-3*01) and JH6 (e.g., JH6*02),
VH3-30 (e.g., VH3-30*18) and JH6 (e.g., JH6*02),
VH3-33 (e.g., VH3-33*01) and JH6 (e.g., JH6*02),
VH4-31 (e.g., VH4-31*03) and JH4 (e.g., JH4*02), or
VH4-59 (e.g., VH4-59*01) and JH4 (e.g., JH4*02).

Clause 21. A bispecific antigen-binding molecule according to clause 19 or clause 20, wherein the antibody Fv region comprises a VL domain generated through recombination of immunoglobulin light chain v and j gene segments, wherein the v gene segment is VL3-21 (e.g., VL3-21*d01) and the j gene segment is JL3 (e.g., JL3*02).

Clause 22. A bispecific antigen-binding molecule according to any preceding clause, wherein the FIXa binding polypeptide arm and the FX binding polypeptide arm comprise a common antibody light chain.

Clause 23. A bispecific antigen-binding molecule according to clause 22, wherein the light chain comprises a lambda constant region.

Clause 24. A bispecific antigen-binding molecule according to any preceding clause, wherein the antigen-binding molecule is a tetrameric immunoglobulin comprising
a first heavy-light chain pair comprising a FIXa binding Fv region,
a second heavy-light chain pair comprising a FX binding Fv region,
wherein each heavy chain comprises a VH domain and a constant region, and each light chain comprises a VL domain and a constant region, and wherein the first and second heavy-light chain pairs associate to form the tetrameric immunoglobulin through heterodimerisation of their heavy chain constant regions.

Clause 25. A bispecific antigen-binding molecule according to clause 24, wherein the immunoglobulin is an IgG, e.g., IgG4.

Clause 26. An isolated FIXa binding polypeptide comprising a FIXa binding site, wherein the FIXa binding polypeptide is as defined in any of the preceding clauses.

Clause 27. A kit for production of the bispecific antigen-binding molecule of any of clauses 1 to 25, comprising
a FIXa binding polypeptide comprising a FIXa binding site, or nucleic acid encoding said polypeptide, wherein the FIXa binding polypeptide is a FIXa binding polypeptide arm as defined in any of clauses 1 to 25, and
a FX binding polypeptide comprising a FX binding site, or nucleic acid encoding said polypeptide, wherein the FX binding polypeptide is a FX binding polypeptide arm as defined defined in any of clauses 1 to 25.

Clause 28. A composition comprising an antigen-binding molecule according to any of clauses 1 to 25 in combination with a pharmaceutically acceptable excipient.

Clause 29. A composition according to clause 28, wherein the antigen-binding molecule is in sterile aqueous solution.

Clause 30. Isolated nucleic acid encoding a bispecific antigen-binding molecule according to any of clauses 1 to 25.

Clause 31. Isolated nucleic acid encoding the FIXa binding polypeptide arm of a bispecific antigen-binding molecule according to any of clauses 1 to 25.

Clause 32. A host cell comprising recombinant nucleic acid encoding a bispecific antigen-binding molecule according to any of clauses 1 to 25, or encoding the FIXa binding polypeptide arm or the FX binding polypeptide arm of said bispecific antigen-binding molecule, wherein the encoding nucleic acid is operably linked to a promoter for expression.

Clause 33. A method of producing an antigen-binding molecule according to any of clauses 1 to 25, or producing the FIXa binding polypeptide arm or the FX binding polypeptide arm of said bispecific antigen-binding molecule, comprising culturing host cells according to clause 32 under conditions for expression of the antigen-binding molecule, and recovering the antigen-binding molecule or binding arm from the host cell culture.

Clause 34. A method of controlling bleeding in a patient, comprising administering a composition according to clause 29 or clause 30 to the patient.

Clause 35. A bispecific antigen-binding molecule according to any of clauses 1 to 25 for use in a method of treatment of the human or animal body by therapy.

Clause 36. A bispecific antigen-binding molecule according to any of clauses 1 to 25 for use in controlling bleeding in a patient.

Clause 37. A method according to clause 34, or a bispecific antigen-binding molecule for use according to clause 35 or clause 36, wherein the patient is a haemophilia A patient.

Clause 38. A method or a bispecific antigen-binding molecule for use according to clause 37, wherein the patient is resistant to treatment with FVIII owing to the presence of inhibitory antibodies in the bloodstream.

Clause 39. Use of a bispecific antigen-binding molecule according to any of clauses 1 to 25 for binding FIXa and FX in vitro.

Clause 40. Use of a bispecific antigen-binding molecule according to any of clauses 1 to 25 to substitute for FVIII function in a patient with haemophilia A.

STATEMENTS

1. A bispecific antigen-binding molecule comprising
    a FIXa binding polypeptide arm comprising a FIXa binding site, and
    a FX binding polypeptide arm comprising a FX binding site,
    characterised in that the FIXa binding polypeptide arm comprises a VH domain having at least 90% amino acid sequence identity with SEQ ID NO: 324 and a VL domain having at least 90% amino acid sequence identity with SEQ ID NO: 10, optionally wherein the VH domain comprises an HCDR3 having a hydrophobic or positively charged residue at IMGT position 111.1, optionally wherein the HCDR3 amino acid sequence is SEQ ID NO: 400, SEQ ID NO: 401, SEQ ID NO: 402, SEQ ID NO: 403 or SEQ ID NO: 171; and/or
    characterised in that the FIXa binding site is provided by a set of complementarity determining regions (CDRs) in the FIXa binding polypeptide arm, the set of CDRs comprising HCDR1, HCDR2, HCDR3 and/or LCDR1, LCDR2 and LCDR3, wherein
    HCDR1 is SEQ ID NO: 1
    HCDR2 is SEQ ID NO: 2
    HCDR3 is SEQ ID NO: 400
    LCDR1 is SEQ ID NO: 6
    LCDR2 is SEQ ID NO: 7 and
    LCDR3 is SEQ ID NO: 8.

2. A bispecific antigen-binding molecule according to statement 1, wherein the FIXa binding site is provided by a set of complementarity determining regions (CDRs) in the FIXa binding polypeptide arm, the set of CDRs comprising HCDR1, HCDR2, HCDR3 and/or LCDR1, LCDR2 and LCDR3, wherein
    HCDR1 is SEQ ID NO: 1
    HCDR2 is SEQ ID NO: 2
    HCDR3 is SEQ ID NO: 401, SEQ ID NO: 402, SEQ ID NO: 403 or SEQ ID NO: 171
    LCDR1 is SEQ ID NO: 6
    LCDR2 is SEQ ID NO: 7 and
    LCDR3 is SEQ ID NO: 8.

3. A bispecific antigen-binding molecule comprising
    (i) a FIXa binding polypeptide arm comprising a FIXa binding site, wherein the FIXa binding polypeptide arm comprises an antibody Fv region comprising
        a VH domain generated through recombination of immunoglobulin heavy chain v, d and j gene segments, wherein the v gene segment is VH3-7 (e.g., VH3-7*01) and/or wherein the j gene segment is JH6 (e.g., JH6*02), and
        a VL domain generated through recombination of immunoglobulin light chain v and j gene segments, wherein the v gene segment is VL3-21 (e.g., VL3-21*d01) and the j gene segment is JL2 (e.g., JL2*01) or JL3, and
    (ii) a FX binding polypeptide arm comprising a FX binding site, wherein the FX binding polypeptide arm comprises an antibody Fv region comprising
        (a) a VH domain generated through recombination of immunoglobulin heavy chain v, d and j gene segments, wherein the v and j gene segments are VH1-3 (e.g., VH1-3*01) and JH6 (e.g., JH6*02), and
            a VL domain generated through recombination of immunoglobulin light chain v and j gene segments, wherein the v and j gene segments are VL1-47, (e.g., VL1-47*01) and JL1 (e.g., JL1*01); or
        (b) a VH domain generated through recombination of immunoglobulin heavy chain v, d and j gene segments, wherein the v and j gene segments are VH3-30 (e.g., VH3-30*18) and JH6 (e.g., JH6*02), and
            a VL domain generated through recombination of immunoglobulin light chain v and j gene segments, wherein the v and j gene segments are VL2-8, (e.g., VL2-8*01) and JL2 (e.g., JL2*01); or
        (c) a VH domain generated through recombination of immunoglobulin heavy chain v, d and j gene segments, wherein the v and j gene segments are VH4-61 (e.g., VH4-61*01) and JH1 (e.g., JH1*01), and
            a VL domain generated through recombination of immunoglobulin light chain v and j gene segments, wherein the v and j gene segments are VK3-11, (e.g., VK3-11*01) and JK5 (e.g., JK5*01).

4. A bispecific antigen-binding molecule according to any preceding statement, wherein the FIXa binding polypeptide arm comprises a VH domain having at least 95% amino acid sequence identity with SEQ ID NO: 324.

5. A bispecific antigen-binding molecule according to any preceding statement, wherein the FIXa binding polypeptide arm comprises a VL domain having at least 95% amino acid sequence identity with SEQ ID NO: 10.

6. A bispecific antigen-binding molecule according to any preceding statement, wherein the
    FIXa binding site is provided by a set of complementarity determining regions (CDRs) in the FIXa binding polypeptide arm, the set of CDRs comprising HCDR1, HCDR2, HCDR3 and/or LCDR1, LCDR2 and LCDR3, wherein
    HCDR1 is SEQ ID NO: 1
    HCDR2 is SEQ ID NO: 2
    HCDR3 is SEQ ID NO: 171
    LCDR1 is SEQ ID NO: 6
    LCDR2 is SEQ ID NO: 7 and
    LCDR3 is SEQ ID NO: 8.

7. A bispecific antigen-binding molecule according any preceding statement, wherein the FIXa binding polypeptide arm comprises a VH domain amino acid sequence SEQ ID NO: 324 and a VL domain amino acid sequence SEQ ID NO: 10.

8. A bispecific antigen-binding molecule according to any preceding statement, which reduces the coagulation time of FVIII-deficient human blood plasma to less than 40 seconds in an aPTT assay.

9. A bispecific antigen-binding molecule according to any preceding statement, wherein the FIXa binding polypeptide arm is capable, when provided in monospecific form, of enhancing FIXa-catalysed activation of FX to FXa.

10. A bispecific antigen-binding molecule according to any preceding statement, wherein
the FX binding polypeptide arm comprises a VH domain having at least 90% amino acid sequence identity with SEQ ID NO: 61 and a VL domain having at least 90% amino acid sequence identity with SEQ ID NO: 66; and/or wherein the FX binding site is provided by a set of complementarity determining regions (CDRs) in the FX binding polypeptide arm, the set of CDRs comprising HCDR1, HCDR2, HCDR3 and/or LCDR1, LCDR2 and LCDR3, wherein HCDR1 is SEQ ID NO: 57
HCDR2 is SEQ ID NO: 58
HCDR3 is SEQ ID NO: 59
LCDR1 is SEQ ID NO: 62
LCDR2 is SEQ ID NO: 63 and
LCDR3 is SEQ ID NO: 64.

11. A bispecific antigen-binding molecule according to statement 10, wherein the FX binding polypeptide arm comprises a VH domain amino acid sequence SEQ ID NO: 61 and a VL domain amino acid sequence SEQ ID NO: 66.

12. A bispecific antigen-binding molecule according to any of statements 1 to 9, wherein the FX binding polypeptide arm comprises a VH domain having at least 90% amino acid sequence identity with SEQ ID NO: 71 and a VL domain having at least 90% amino acid sequence identity with SEQ ID NO: 76; and/or wherein the FX binding site is provided by a set of complementarity determining regions (CDRs) in the FX binding polypeptide arm, the set of CDRs comprising HCDR1, HCDR2, HCDR3 and/or LCDR1, LCDR2 and LCDR3, wherein HCDR1 is SEQ ID NO: 67
HCDR2 is SEQ ID NO: 68
HCDR3 is SEQ ID NO: 69
LCDR1 is SEQ ID NO: 72
LCDR2 is SEQ ID NO: 73 and
LCDR3 is SEQ ID NO: 74.

13. A bispecific antigen-binding molecule according to statement 12, wherein the FX binding polypeptide arm comprises a VH domain amino acid sequence SEQ ID NO: 71 and a VL domain amino acid sequence SEQ ID NO: 76.

14. A bispecific antigen-binding molecule according to any of statements 1 to 9, wherein the FX binding polypeptide arm comprises a VH domain having at least 90% amino acid sequence identity with SEQ ID NO: 100 and a VL domain having at least 90% amino acid sequence identity with SEQ ID NO: 104; and/or wherein the FX binding site is provided by a set of complementarity determining regions (CDRs) in the FX binding polypeptide arm, the set of CDRs comprising HCDR1, HCDR2, HCDR3 and/or LCDR1, LCDR2 and LCDR3, wherein HCDR1 is SEQ ID NO: 96
HCDR2 is SEQ ID NO: 97
HCDR3 is SEQ ID NO: 98
LCDR1 is SEQ ID NO: 101
LCDR2 is SEQ ID NO: 92 and
LCDR3 is SEQ ID NO: 102.

15. A bispecific antigen-binding molecule according to statement 14, wherein the FX binding polypeptide arm comprises a VH domain amino acid sequence SEQ ID NO: 100 and a VL domain amino acid sequence SEQ ID NO: 104.

16. A bispecific antigen-binding molecule according to any preceding statement, wherein the FIXa binding polypeptide arm and/or the FX binding polypeptide arm comprises an antibody heavy chain comprising, from N to C terminus, a VH domain, a CH1 domain, a CH2 domain and a CH3 domain, and an antibody light chain comprising, from N to C terminus, a VL domain and a CL domain.

17. A bispecific antigen-binding molecule according to statement 16, wherein the antibody heavy chain comprises an IgG constant region.

18. A bispecific antigen-binding molecule according to any preceding statement, wherein the antigen-binding molecule is a tetrameric immunoglobulin comprising a first heavy-light chain pair comprising a FIXa binding Fv region, a second heavy-light chain pair comprising a FX binding Fv region, wherein each heavy chain comprises a VH domain and a constant region, and each light chain comprises a VL domain and a constant region, and wherein the first and second heavy-light chain pairs associate to form the tetrameric immunoglobulin through heterodimerisation of their heavy chain constant regions.

19. A bispecific antigen-binding molecule according to statement 18, wherein the immunoglobulin is an IgG, e.g., IgG4.

20. A bispecific antigen-binding molecule according to statement 19, wherein the IgG comprises the IgG4-PE human heavy chain constant region SEQ ID NO: 143, optionally engineered with one or more amino acid substitutions to promote heterodimerisation.

21. An isolated FIXa binding polypeptide comprising a FIXa binding site, wherein the FIXa binding polypeptide is as defined in any of the preceding statements.

22. Isolated nucleic acid encoding the FIXa binding polypeptide arm or the FX binding polypeptide arm of a bispecific antigen-binding molecule according to any of statements 1 to 20.

23. Isolated nucleic acid encoding a bispecific antigen-binding molecule according to any of statements 1 to 20.

24. A kit for production of the bispecific antigen-binding molecule of any of statements 1 to 20, comprising a FIXa binding polypeptide comprising a FIXa binding site, or nucleic acid encoding said polypeptide, wherein the FIXa binding polypeptide is a FIXa binding polypeptide arm as defined in any of statements 1 to 20, and a FX binding polypeptide comprising a FX binding site, or nucleic acid encoding said polypeptide, wherein the FX binding polypeptide is a FX binding polypeptide arm as defined defined in any of statements 1 to 20.

25. A composition comprising an antigen-binding molecule according to any of statements 1 to 20, or isolated nucleic acid according to statement 23, in combination with a pharmaceutically acceptable excipient.

26. A composition according to statement 25, wherein the antigen-binding molecule or nucleic acid is in sterile aqueous solution.

27. A host cell comprising recombinant nucleic acid encoding a bispecific antigen-binding molecule according to any of statements 1 to 20, or encoding the FIXa binding polypeptide arm and/or the FX binding polypeptide arm of said bispecific antigen-binding molecule, wherein the encoding nucleic acid is operably linked to a promoter for expression.

28. A method of producing an antigen-binding molecule according to any of statements 1 to 20, or producing the FIXa binding polypeptide arm or the FX binding polypeptide arm of said bispecific antigen-binding molecule, comprising culturing host cells according to statement 27 under conditions for expression of the antigen-binding molecule, and recovering the antigen-binding molecule or binding arm from the host cell culture.

29. A method of controlling bleeding in a patient, comprising administering a composition according to statement 25 or statement 26 to the patient.

30. A bispecific antigen-binding molecule according to any of statements 1 to 20 or a composition according to statement 25 or statement 26, for use in a method of treatment of the human or animal body by therapy.

31. A bispecific antigen-binding molecule according to any of statements 1 to 20 of a composition according to statement 25 or statement 26, for use in controlling bleeding in a patient.

33. A method according to statement 29, or a bispecific antigen-binding molecule for use according to statement 30 or statement 31, wherein the patient is a haemophilia A patient.

34. A method or a bispecific antigen-binding molecule for use according to statement 33, wherein the patient is resistant to treatment with FVIII owing to the presence of inhibitory antibodies in the bloodstream.

35. A method or a bispecific antigen-binding molecule for use according to statement 33 or statement 34, wherein the patient is resistant to treatment with another bispecific antigen-binding molecule for FIXa and FX owing to the presence of inhibitory antibodies in the bloodstream.

36. A method or a bispecific antigen-binding molecule for use according to statement 35, wherein the patient is resistant to treatment with emicizumab.

37. A method of reducing development of inhibitory anti-drug antibodies in a haemophilia A patient undergoing treatment with a polypeptide that replaces FVIIIa activity, comprising
    administering a first FVIIIa-activity replacing polypeptide drug to the patient for a period of 1-12 months,
    switching the patient to a second, different FVIIIa-activity replacing polypeptide drug for a period of 1-12 months, and
    switching the patient to either the first antigen-binding molecule or to a third, different FVIIIa-activity replacing polypeptide drug for a period of 1-12 months,
    wherein in each case the FVIIIa-activity replacing polypeptide drug or its encoding nucleic acid is administered in a therapeutically effective amount to functionally replace FVIIIa in the patient, and wherein the risk of the patient developing inhibitory anti-drug antibodies to any of the FVIIIa-activity replacing polypeptide drug is reduced compared with a patient continuing to receive treatment with that FVIIIa-activity replacing polypeptide drug.

38. A composition comprising a FVIIIa-activity replacing polypeptide drug or its encoding nucleic acid, for use in a method of treating a haemophilia A patient while reducing development of inhibitory anti-drug antibodies, the method comprising
    administering a first FVIIIa-activity replacing polypeptide drug to the patient for a period of 1-12 months,
    switching the patient to a second, different FVIIIa-activity replacing polypeptide drug for a period of 1-12 months, and
    switching the patient to either the first antigen-binding molecule or to a third, different FVIIIa-activity replacing polypeptide drug for a period of 1-12 months,
    wherein in each case the FVIIIa-activity replacing polypeptide drug or its encoding nucleic acid is administered in a therapeutically effective amount to functionally replace FVIIIa in the patient, and wherein the risk of the patient developing inhibitory anti-drug antibodies to any of the FVIIIa-activity replacing polypeptide drug is reduced compared with a patient continuing to receive treatment with that FVIIIa-activity replacing polypeptide drug.

39. A method according to statement 37 or a composition for use according to statement 38, wherein the first, second and/or third FVIIIa-activity replacing polypeptide drug is a bispecific antigen-binding molecule for FIXa and FX.

40. A method or a composition for use according to any of statements 37 to 39, wherein the first, second and/or third FVIIIa-activity replacing polypeptide drug is emicizumab.

41. A method or a composition for use according to any of statements 37 to 40, wherein the first, second and/or third FVIIIa-activity replacing polypeptide drug is a bispecific antigen-binding molecule according to any of statements 1 to 20.

42. A method or a composition for use according to any of statements 37 to 41, wherein the first, second or third FVIIIa-activity replacing polypeptide drug is recombinant FVIII or plasma-derived FVIII.

43. Use of a bispecific antigen-binding molecule according to any of statements 1 to 20 for binding FIXa and FX in vitro.

44. Use of a bispecific antigen-binding molecule according to any of statements 1 to 20 to substitute for FVIII function in a patient with haemophilia A.

Various further aspects and embodiments of the present invention will be apparent to those skilled in the art in view of the present disclosure. All documents mentioned in this specification, including published US counterparts of any patents or patent applications referred to, are incorporated herein by reference in their entirety.

EXAMPLES

The following Examples describe the generation, characterisation and performance of anti-FIXa antibodies, anti-FX antibodies, and bispecific antibodies generated from combination of FIXa binding polypeptide arms and FX binding polypeptide arms of the anti-FIXa and anti-FX antibodies respectively. Antibodies were generated using the Kymouse™, a transgenic mouse platform capable of generating antibodies with human variable domains. Antibodies from the Kymouse have human variable domains, generated from human v (d) and j segments, and mouse constant domains. The endogenous mouse variable genes have been silenced and make up a very small portion of the repertoire (less than 0.5% of all heavy chain variable regions are of mouse origin). The Kymouse system is described in Lee et al 2014 [11], WO2011/004192, WO2011/158009 and WO2013/061098. This project employed the Kymouse HK strain in which the heavy chain locus and light chain kappa locus are humanised, and the Kymouse HL strain in which the heavy chain locus and the light chain lambda locus are humanised. The mice have a full repertoire of human v, d and j heavy chain gene segments and a full repertoire of human v and j kappa or lambda light chain gene segments.

Example 1. Production of Antibodies to Factor IXa (FIXa)

Four Kymouse HK mice (male, aged 4 months at the initiation of immunisation) and four Kymouse HL mice (male, aged 3 months at the initiation of immunisation) were immunised against human Factor IXa (Enzyme Research Laboratories, Inc.).

Spleen tissues were harvested from the immunised mice, and spleen cells were suspended and sorted by FACS to isolate antigen-specific B cells. A total of 2,460 factor IXa specific B cells were sorted from the 8 immunised animals. Coupled antibody heavy and light chain variable domain sequences were recovered from the B cells by reverse transcription of RNA and PCR amplification of the variable regions.

Antibody-encoding nucleic acid was transfected into the human cell line Expi293F for expression and supernatants were harvested.

Example 2. HTRF® (Homogeneous Time-Resolved Fluorescence) Screen of Factor IXa Antibodies An HTRF assay was used to screen the anti-FIXa antibodies for binding to FIXa. FIXa and antibody were labelled with two different fluorophores, a donor and an acceptor. When two entities come close enough to each other, excitation of the donor by an energy source triggers an energy transfer towards the acceptor, which in turn emits specific fluorescence at a given wavelength. Therefore the binding of FIXa by its specific antibodies can be detected by detection at the emission wavelength of the acceptor.

Serial dilutions of an anti-human factor IX reference antibody AbN and CM7 isotype control antibody were prepared using Expi293 expression media (Invitrogen). 5 µL of supernatants from each of the 2,460 antibody-secreting human cells generated in Example 1 were transferred to assay plates. 5 µL of AbN and CM7 isotype control antibody were transferred to each assay plate as positive and negative controls respectively. 5 µL (80 nM) of Alexa 647-labelled human factor IX, factor IXa or factor IX light chain was added to each well of the assay plates and incubated at room temperature (RT) for 1 hour. 10 µL of 2×M24-K solution (1:2000 dilution from stock solution) was added to each well of assay plates, and incubated at RT in the dark for 2 hours. Assay plates were read using HTRF 100 flashes protocol of Envision (Excitation wavelength: 340 nm; Emission wavelength 1: 620 nm; Emission wavelength 2: 665 nm). Data were analysed and normalized to the AbN positive control.

Of the 2,460 antibodies originating from the anti-FIXa specific B cells, 732 were identified as binders to factor IX, factor IXa and/or the factor IX light chain in this assay.

Example 3. SPR Analysis of Factor IX Antibodies

Anti-mouse IgG chip was prepared according to manufacturer's instruction.

Supernatants from Example 1 were diluted 1:5 with HBS-EP running buffer (diluted from 20×HBS-EP+ Buffer, pH 7.6 (Bioquote)). Antibodies were captured on the anti-mouse IgG surface. Varying concentrations (256 nM and 1024 nM) of human factor IX, human factor IXa, or human factor IX light chain were used as analyte. The surface was regenerated with 10 mM glycine (pH 1.7). Binding sensorgrams were double referenced with a buffer injection (0 nM). Data was fitted to the 1:1 model inherent to the ProteOn analysis software. Assays were performed at 25° C. and HBS-EP buffer was used as running buffer.

Example 4. Production of Antibody to Factor X (FX)

Four Kymouse HK version 2 mice (male, aged 3 months at the initiation of immunisation) and four Kymouse HL version 2 mice (male, aged 3 months at the initiation of immunisation) were immunised against human Factor X (Enzyme Research Laboratories, Inc.). Spleen tissues were harvested from the immunised mice, and spleen cells were suspended and sorted by FACS to isolate antigen-specific B cells. A total of 1,722 factor X specific B cells were sorted from the 8 immunised animals. Coupled antibody heavy and light chain variable domain sequences were recovered from the B cells by reverse transcription of RNA and PCR amplification of the variable regions.

Antibody-encoding nucleic acid was transfected into the human cell line Expi293F for expression and supernatants were harvested.

Example 5. HTRF Screen of Factor X Antibodies

Serial dilutions of a reference anti-human Factor X antibody, AbT and CM7 isotype control antibody were prepared using Expi293 expression media (Invitrogen). 5 µL of supernatants from each of the 1,722 antibody-secreting human cells generated in Example 4 were transferred to assay plates. 5 µL of AbT and CM7 isotype control antibody were transferred to each assay plates as positive and negative controls respectively. 5 µL (80 nM) of Alexa 647-labelled human factor X, factor Xa or factor X light chain was added to each well of the assay plates, and incubated at RT for 1 hour. 10 µL of 2×M24-K solution (1:2000 dilution from stock solution) was added to each well and incubated at RT in the dark for 2 hours. Assay plates were read using HTRF 100 flashes protocol of Envision (Excitation wavelength: 340 nm; Emission wavelength 1: 620 nm; Emission wavelength 2: 665 nm). Data was analysed and normalized to the AbT positive control.

Of the 1,722 antibodies originating from the anti-FX specific B cells, 497 were identified as binders to factor X, factor Xa and/or the factor X light chain in this assay.

Example 6. SPR Analysis of Factor X Antibodies

Anti-mouse IgG chip was prepared according to manufacturer's instruction. Supernatants from Example 4 were diluted 1: 5 with HBS-EP running buffer (diluted from 20×HBS-EP+ Buffer, pH 7.6 (Bioquote)). Antibodies were captured on anti-mouse IgG surface. Varying concentrations (256 nM and 1024 nM) of human factor X, human factor Xa, or human Factor X light chain were used as analyte. The surface was regenerated with 10 mM Glycine (pH 1.7). Binding sensorgrams were double referenced with a buffer injection (0 nM). Data was fitted to the 1:1 model inherent to the ProteOn analysis software. Assays were performed at 25° C. and HBS-EP buffer was used as running buffer.

Example 7. Construction of Bispecific Antibody Expression Vectors

Plasmids for expression of bispecific human IgG antibodies were constructed as follows. DNA fragments encoding antibody variable regions were prepared from PCR products generated as described in Example 1 and Example 4. To prepare antibody variable region DNA fragments for cloning, after performing PCR, the reaction solution was subjected to 0.8% agarose gel electrophoresis. Amplified fragments of the desired size (about 400 bp) were purified using QIAquick Gel Extraction Kit (QIAGEN) by the method described in the attached instruction manual and eluted using 30 mL of elution buffer (EB).

Amino acid substitution products in the CH3 region of IgG4 were prepared with reference to the knobs-into-holes technique of IgG1 [12] to form heterogeneous molecules of each H chain. Type a (IgG4ra) is a substitution product of Y349C and T366W, and type b (IgG4yb) is a substitution product of E356C, T366S, L368A and Y407V. Furthermore, the substitutions (-ppcpScp- and -ppcpPcp-) were introduced in the hinge region of both types of substitution products. According to the present technique, almost all of the H chains may form heterodimers.

For expression of the FIXa arm of the bispecific antibody, VH domains were cloned into plasmid vector pTT5_Cam_ccdB_hIgG4ra to provide DNA encoding the VH domain in a full length human IgG4ra antibody heavy chain, VL kappa domains were cloned into pTT5_Cam_ccdB_hIgK to provide DNA encoding the VL domain in a full length human kappa antibody light chain, and VL lambda domains were cloned into pTT5_Cam_ccdB to provide DNA encoding the VL domain in a full length human lambda antibody light chain.

H and L chain variable region (VH and VL) DNA fragments were digested with AarI (Invitrogen), and purified using QIAquick PCR Purification Kit (QIAGEN) according to the manufacturer's instructions. pTT5_Cam_ccdB_hIgG4ra (for VH), pTT5_Cam_ccdB_hIgK (for VL from κ clones) or pTT5_Cam_ccdB (for VL from λ clones) was digested with restriction AarI whose cleavage site is in the multicloning site. After digestion, the vectors were purified using QIAquick PCR Purification Kit (QIAGEN) according to the manufacturer's instructions.

The AarI-digested VH or VL fragments and pTT5_Cam_ccdB_hIgG4ra (for VH), pTT5_Cam_ccdB_hIgK (for VL from κ clones) or pTT5_Cam_ccdB (for VL from λ clones) which had been digested with AarI were ligated using T4 ligase (New England Biolabs) according to the manufacturer's instructions. E. coli DH10B strain (ElectroMax DH10B (Invitrogen)) was transformed with the ligation solution. Respective plasmid DNAs were isolated from the obtained ampicillin resistant clones using QIAprep Spin Miniprep Kit (QIAGEN). The resulting respective ampicillin resistant transformants were confirmed to have the insertion of the desired VH and VL by Sanger sequencing.

Plasmid DNAs for anti-FIX binding arms and anti-FX binding arms were isolated from the desired clones using QIAprep Spin Miniprep Kit (QIAGEN) according to the manufacturer's instructions and dissolved in 100 mL of elution buffer (EB) initially. Plasmid DNA solutions were quantified by Nano-drop (Thermo Scientific) and normalized to 50 ng/mL. Anti-FIXa antibody H chain expression vector, anti-FIXa antibody L chain expression vector, anti-FX antibody H chain expression vector, and anti-FX antibody L chain expression vector were dubbed as Nn-IgG4ra, Nn-IgL (or IgK), Tn-IgG4rb, and Tn-IgL (or IgK). DNA minipreps were confirmed to have the insertion of the desired VH or VL by Sanger sequencing. The respective plasmid solutions were preserved at 4° C. until use.

Example 8. Expression of Bispecific Antibodies 8-1. Preparation of DNA Solutions Mixed solutions containing four kinds of plasmid DNA were prepared for transfection of HEK cells. For 1 mL of cell culture, 250 ng each of Nn-IgG4ra, Nn-IgL (or IgK), Tn-IgG4rb, and Tn-IgL (or IgK) were used.

8-2. Transfection of Host Cells

One day before transfection, cultured Expi293F cells (HEK cell line) were counted for cell seeding calculation. Expi293F cells were pelleted at 300 rpm for 10 minutes. Cells were resuspended in pre-warmed fresh Expi293 expression media to give a final dilution of $2.4 \times 10^6$ cells/ml. 200 ml of cell suspension was incubated overnight in a Kuhner Shaking Incubator (37° C., 140 rpm, 8% $CO_2$).

On the day of transfection, cultured Expi293F cells were counted and diluted to $4 \times 10^6$ cells/ml using fresh Expi293 expression media. 500 μl of cell suspension was aliquoted into each well of 96-well deep well plates using Multidrop Combi. After dispensing, the plates were covered with Duetz sandwich covers and incubated in a Kuhner Shaking Incubator (37° C., 300 rpm, 50 mm orbital throw, humidity 80%) for 2-2.5 hours.

For each transfection, two mixtures were prepared.

Mix 1: 25 μl B cell bridge product (the 4 plasmid mixture)+55 μl RSM+100 ng HyperPBase per well Mix 2: 1 μl ExpiFectamine™ 293+79 μl RSM Mix 2 was added to Mix 1 and incubated at room temperature for 15 minutes. The incubated mixture was then added to the 500 μl of cell culture solution and incubated in a Kuhner Shaking Incubator (37° C., 300 rpm, 50 mm orbital throw) for a week.

Example 9. Activation Coagulation Factor VIII (FVIIIa)-Like Activity Assay

The FVIIIa-mimetic activity of a bispecific antibody, i.e., its ability to enhance the FIXa-mediated activation of FX, was assessed in vitro by enzymatic assay. In this assay, the test bispecific molecule is contacted with FIXa and FX in the presence of phospholipid, under conditions suitable for formation of FXa. A substrate for FXa is added which, when cleaved by FXa, generates a detectable product. Detection of this product in the presence of test bispecific antibody is compared with a negative control in which no test antibody is present (a control antibody may be included). The detected signal is quantified by recording absorbance of the reaction solution at 405 nm. Absorbance is measured across a range of antibody concentrations in the assay and an EC50 value calculated as a measure of the bispecific antibody potency in this assay. Significant difference of EC50 between test antibody and control indicates that the test antibody is able to enhance FIXa-mediated activation of FX. See FIG. 7.

Materials & Methods

All reactions were performed at 37° C. unless otherwise stated.

7.5 μL FIX (3.75 μg/mL) and 5 μL supernatant from the Expi293 cells producing the recombinant antibodies (Example 8) were added to each well of an assay plate and incubated at room temperature for 1 hour. A mixture of 2.5 μL FXIa (10 ng/mL), 5 μL FX (50 ng/mL), 0.05 μL phospholipid (10 mg/mL) and 5 µL TBSB-S buffer was added to each well to initiate enzymatic reaction (FIXa cleavage of FX to generate FXa), and incubated at 37° C. for 1 hour. After 60 minutes, the reaction was terminated by adding 5 µL of 0.5 M EDTA. After adding 10 µL S2765 substrate solution to each well, absorbance at 405 nm (reference wavelength 655 nm) was measured for 30 minutes (one reading per 10 minutes).
TBSB:
Tris buffered saline containing 0.1% bovine serum albumin
To make 7.5 mL TBSB:
0.1 mL 7.5% BSA solution (Sigma)
7.4 mL 1×TBS solution (diluted from 20×TBS solution ThermoFisher)
TBSB-S:
TBSB containing 5 mM CaCl2) and 1 mM MgCl2
To make 100 mL TBSB-S:
99.4 mL TBSB
0.5 mL 1M CaCl2 (Sigma)
0.1 mL 1M MgCl2 (Sigma)
FXIa STOCK solution (10 µg/mL):
Add 10 mL TBSB-S to 0.1 mg FXIa (Enzyme Research Laboratories) to make 10 µg/mL stock solution.
Dilute to 10 ng/mL (1:1,000) working solution before use.
FIX Stock Solution (37.5 µg/mL):
Add 13.3 mL TBSB-S to 0.5 mg FIX (Enzyme Research Laboratories) to make 37.5 µg/mL stock solution.
Dilute to 3.75 µg/mL (1:10) working solution before use.
FX Working Solution (50 µg/mL):
Add 16 mL TBSB-S to 0.8 mg FX (Enzyme Research Laboratories) to make 50 µg/mL working solution.
No further dilution is needed before use.
S2765 Stock Solution:
25 mg S2765 (Chromogenix) chromogenic substrate (0.035 mmol)
To make 2 mM stock solution:
Add 17.493 mL water to the vial and dissolve with shaking.
Pefafluor FXa Stock Solution:
10 µmol Pefafluor FXa fluorogenic substrate (0.010 mmol)
To make 1.5 mM stock solution:
Add 6.667 mL water to the vial and dissolve by shaking.
Polybrene Solution:
To make 0.6 g/L hexadimethrine bromide stock solution:
Add 0.15 g hexadimethrine bromide (Sigma) to 250 mL water.
Dilute to 0.6 mg/L (1:1,000) working solution before use.
S2765 Substrate Working Solution
A 1:1 mixture of 2 mM S-2765 stock solution and 0.6 mg/L polybrene solution.

Example 10. Plasma Coagulation Assay

To determine the ability of the bispecific antibodies of the present invention to correct the coagulation ability of the blood of haemophilia A patients, the effect of these antibodies on the activated partial thromboplastin time (aPTT) using FVIII deficient plasma was examined.

A mixture of 50 mL of bispecific antibody solution having a variety of concentrations, 50 mL of FVIII deficient plasma (Biomerieux), and 50 mL of aPTT reagent (Dade Behring) was warmed at 37° C. for 3 minutes. The coagulation reaction was initiated by adding 50 mL of 20 mM CaCl$_2$) (Dade Behring) to the mixture. The time period until coagulation was measured. Apparatus used for this was KC10A (Amelung) connected to CR-A (Amelung).

Concentration dependency was subsequently determined for bispecific antibodies that exhibited the highest coagulation time-reducing effect.

Example 11: Summary of Initial Screening

Figure 8:
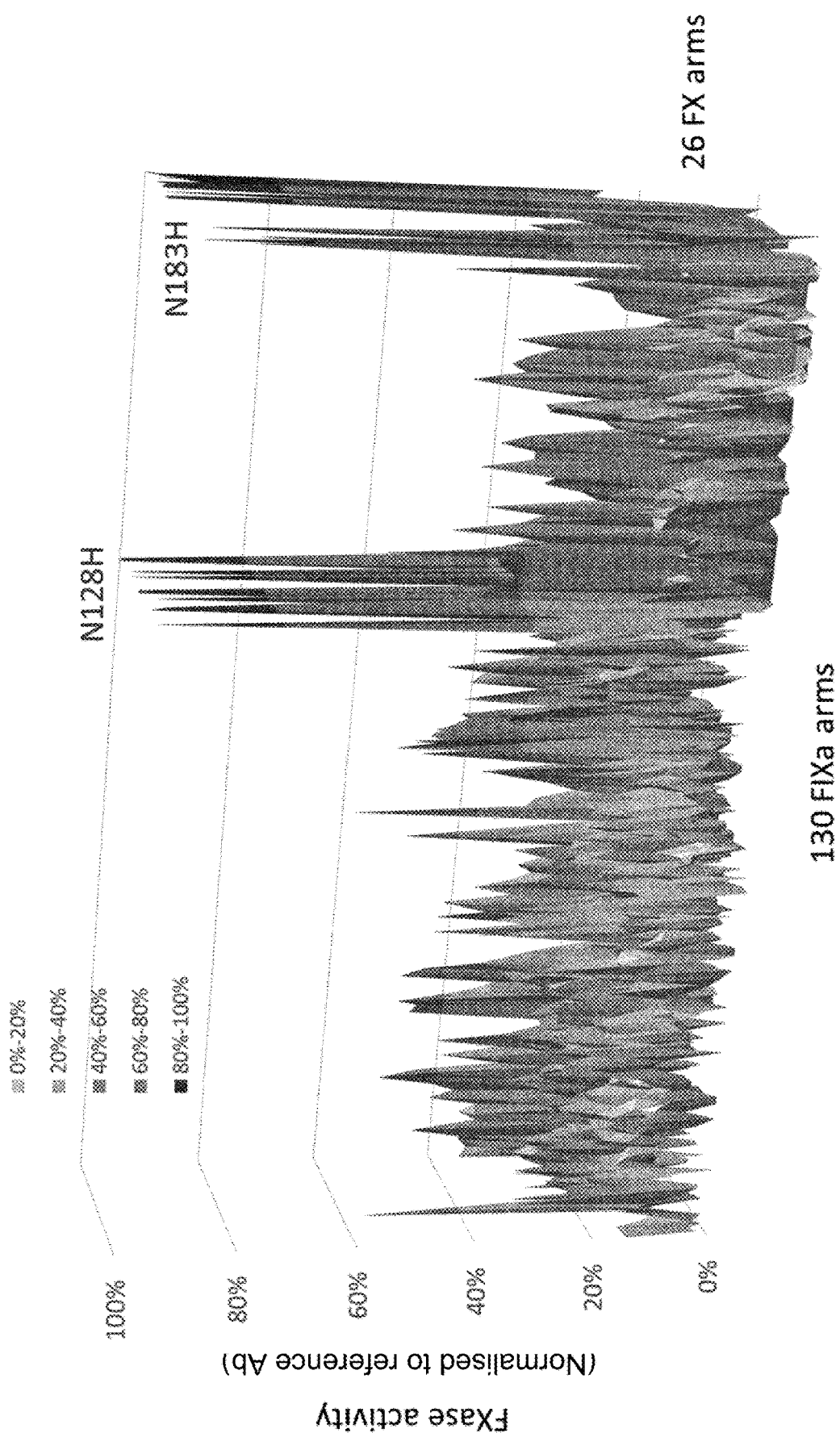
FIG. 8 Results of initial high-throughput functional screening of bispecific antibodies in tenase assay.

Bispecific antibodies containing the N128H FIX-binding arm were dramatically more active in the FXase assay than the majority of other bispecifics, and the N128H FIX-binding arm showed an ability to form active bispecifics with a range of FX-binding arms. FIG. 8.

Example 12: Generation of N128H Mutants

Anti-FIX antibody "N128", having heavy and light chain variable domains designated N128H and N128L respectively, was selected for further assessment and optimisation. The N128H CDR3 (SEQ ID NO: 3) contains a series of four serine residues, at IMGT residue positions 110, 111, 111.1 and 112.1 respectively. Each Ser was individually mutated to all other naturally occurring amino acids, generating mutations in the N128H HCDR3 as summarised in FIG. 9.

This work produced an array of bispecific antibodies containing variants of the N128 FIXa-binding arm, providing a basis to research the further potential of the FIXa-binding arm for:
1) bringing factor IXa to the ideal proximity of Factor X;
2) orientating factor IXa in a way to maximize the catalytical activity of Factor IXa.

As reported below, bispecific antibodies, each containing a FIXa binding arm having a single point mutation in the HCDR3 compared with N128, were expressed in mammalian cells, purified by Protein A (Example 13) and functionally characterised (Example 14). Selected bispecific antibodies exhibiting better activities than the bispecific antibody with N128H arm were then further analysed to confirm their binding properties and biological activity (Examples 15 to 18).

Example 13: Expression and Purification of Antibodies for Functional Assays

The following procedure was used for preparation of antibodies (monospecific and bispecific) for use in the experiments described in the subsequent Examples.
Expression:
Antibodies were transiently expressed in human (Expi293) cells, then purified from cell culture supernatants.
The day before transfection, Expi293 cells were counted by an automated cell counter (Eve cell counter) seeded in pre-warmed expression media at the density of ~1.7×10$^6$ cells/ml and incubated overnight in an orbital shaker incubator (37° C., 8% CO2, 140 rpm).
On the day of transfection, cells were counted and adjusted the cell number to 2.5×10$^6$ cells/ml. 2000 µl of cell suspension were dispensed into 24 Deep Well Plates and placed into Kuhner shaking incubator (37° C., 8% CO2, 225 rpm).
DNA solutions were prepared. 2 µg of DNA plasmid mixture diluted in ultrapure water was used for each transfection of Expi293 cells.
In the case of bispecific antibodies, mixed solutions containing four kinds of plasmid DNA were prepared. For 2 mL of cell culture, 500 ng each of Nn-IgG4ra, Nn-IgL (or IgK), Tn-IgG4γb, and Tn-IgL (or IgK) were used. In the case of monospecific antibodies, for 2 mL of cell culture, 1 µg each of Nn-IgG4PE and Nn-IgL (or IgK) or Tn-IgG4PE and Tn-IgL (or IgK) were used.

DNA encoding monospecific or bispecific antibodies was transfected by the same procedure. Two mixtures were prepared for transfection:
Mix 1: 2 µg of plasmid DNA diluted in 40 µl of Opti-MEM® I medium.
Mix 2: 80 µl of ExpiFectamine™ 293 transfection reagent+ 40 µl of OptiMEM I medium.
Mix 2 was combined with Mix 1 and incubated for 20-30 minutes at room temperature. After the incubation was complete 165 µl of DNA-ExpiFectamine™ 293 Reagent complex was dispensed to each well of the 24 deep well plate. Cells were incubated in the Kuhner shaking incubator (37° C., 8% CO2, 225 rpm) for 6 days. Cell culture supernatants were harvested 6 days after transfection.

Purification:

A 96-well plate purification was employed to purify antibodies (bispecific or monospecific) from Expi293F cell culture supernatants. This method allows rapid small-scale affinity antibody purification of multiple samples in antibody screening experiments. To achieve high % of recovery MabSelect Sure LX was used which is a protein A affinity with very dynamic binding activity (60 mg human IgG/ml medium), an extended residence time, alkali tolerant and low ligand leakage.

Procedure
1. MabSelect Sure LX resin (GE Healthcare) was equilibrated in 1×PBS (Gibco) to remove the storage buffer, to a final concentration of 10% slurry.
2. 600 µl of 10% slurry is added to each well of the 96 well plate AcroPrep™ Advance (Pall)
3. The resin was centrifuged 70×rcf for 1 min at 4 C.
4. The resin was washed with 300 µl 1×PBS, spin 70×rcf for 1 min. This step was repeated twice.
5. 2 ml of cell culture supernatants (pH 7-8) were loaded onto the MabSelect Sure LX resin into the 96 well purification plate and centrifuged at 70-100×rcf for 1 minute.
6. Plate was washed using 600 µl of 1×PBS and centrifuged at 70-100×rcf for 1 minute. This step is performed four times in total.
7. 70 µl of elution buffer (IgG Elute Pierce) was added to each well and incubated for 1 min.
8. The plate was centrifuged at 70-100×rcf for 1 minute to collect the eluate. This step is performed twice in total.

Example 14: Functional Analysis of N128H CDR3 Mutants

The functional activity the bispecific antibodies newly generated according to Example 12 was determined using the in vitro chromogenic factor X activation (FXase) assay and the plasma coagulation assay (as described previously). To standardise comparison of the variants, all FIXa-binding arms (variant VH paired with N128 VL) were heterodimerised with the same FX-binding arm.

Figure 10:
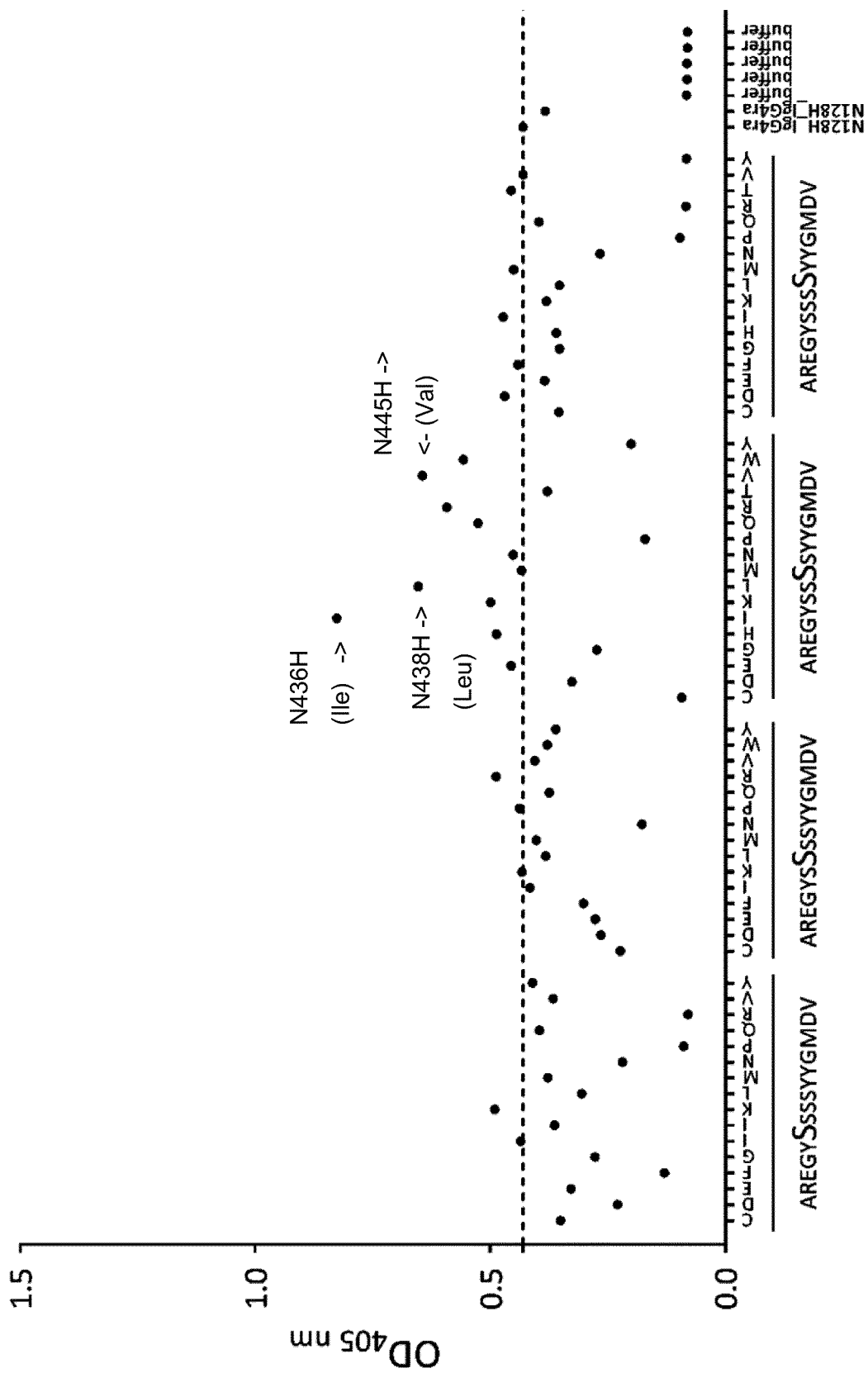
FIG. 10 FXase activity of N128H CDR3 mutants.

From the mutagenesis analysis of the CDRH3, it was noted that the 3rd serine residue in the series of 4 serines in the N128H CDR3 appears to substantially contribute to the FVIII-mimetic activity. Strikingly, several sequence variations at this position greatly improved the FVIII-mimetic activity of the bispecific antibody compared with the original N128 FIX binding arm (FIG. 10). In particular, variants N436H, N438H and N445H, in which the 3rd serine of the N128H CDR3 had been replaced by isoleucine, leucine and valine respectively (FIG. 9), showed a dramatic increase (approximately 2-3 fold) in FXase activity. Significant increase in FXase activity was also observed with N435H, N437H, N442H, N443H and N446H variants, in which the 3rd serine was mutated into histidine, lysine, glutamine, arginine and tryptophan respectively. Mutagenesis analysis also revealed that substitution of specific amino acids in the HCDR3 at this position decreased the FXase activity of the bispecific antibody compared with the original anti-FIX arm N128H. The tenase activity of variants N430H (Cys), N441H (Pro), N447H (Tyr), again indicating the significance of the residue at this position.

Substitution of certain other amino acids for the serine at other positions in the (Ser)4 motif also reduced activity compared with the original anti-FIX arm, most notably in variants N459H (4th Ser to Pro), N461H (4th Ser to Arg), N465H (4th Ser to Tyr), N470H (1st Ser to Phe), N478H (1st Ser to Pro), N480H (1st Ser to Arg), N495H (2nd Ser to Asn).

Figure 11:
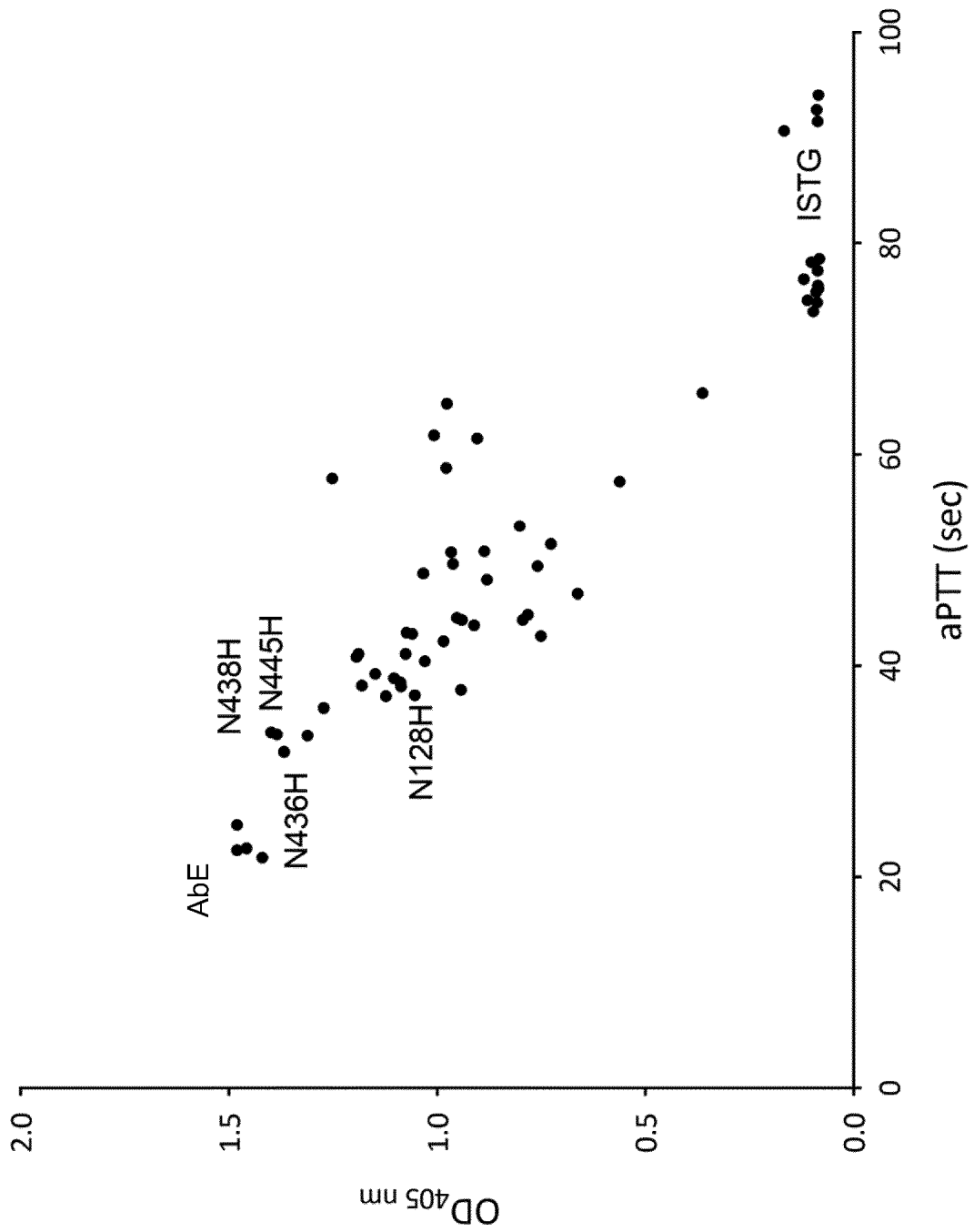
FIG. 11 FVIII mimetic activities of N128H CDR3 mutants in aPTT assay.

In FIG. 11 the tenase activities (as absorbance at 405 nm) of N128H variants is plotted against the clotting time (aPTT in seconds). The FVIII-mimetic activity of the N128H variants is compared against bispecific antibody AbE and an ISTC. The isotype control (negative control, ISTC) showed no tenase activity and poor ability to form the clot as indicated by high aPTT values. N436H, N438H and N445H variants exhibited strong ability to generate FXa (high OD405 values) and to quickly result in clotting in FVIII-immunodepleted plasma (low aPTT values—approximately 30 seconds).

Taking into account these functional data, consensus sequences can be generated for the residues at the sequential IMGT positions 110, 111, 111.1 and 112.1 in HCDR3 (see Table 9A). Considering IMGT position 111.1 (corresponding to the third Ser in N128H), a hydrophobic residue (e.g., Ile, Leu, Val, Trp) or positively charged residue (e.g., Arg, Gln, Lys) was associated with strong functional activity. Other residues which could be substituted at this position without loss of activity (and with potentially improved activity) included His, Glu, Asn and Met.

FIXa binding arms of bispecific antibodies showing the highest activity in the above screens were selected for further characterisation as reported in the following Examples.

Example 15. SPR Analysis of Purified Anti-FIX Antibodies

SPR was used to determine the binding affinity ($K_D$) of the FIXa binding arm to FIX, the kinetic constants on-rate ($k_{on}$) and off-rate ($k_{off}$). The analysis was performed using a Biacore 8K (GE Healthcare) system.

An anti-human IgG Fc antibody was immobilised on CM4 chip (GE Healthcare catalog number BR100534) according to manufacturer's instructions. Amine coupling kit (BioRad) was used to activate the surface of the chip. The surface was subsequently blocked with 1M ethanolamine. The immobilisation run was performed at 25° C. using HBS-EP (10 mM HEPES pH 7.4, 150 mM NaCl, 3 mM EDTA, 0.05% Polysorbate 20 pH 7.6) as immobilisation running buffer.

Purified monospecific antibodies (referred to as ligand) from Example 13 were captured on the anti-human IgG Fc CM4 surface at approximately 2 µg/ml. The ligands were injected for 60 sec at 10 µl/min in all the active channels of all 8 flow channels. The run was performed at 25° C. using neutral pH (pH 7.4) HBS-P 1× (0.01 M HEPES pH 7.4, 0.15

M NaCl, 0.05% Polysorbate 20 pH 7.6)+CaCl$_2$) 2.5 mM as running buffer. Human factor IX (FIX) (Enzyme Research Laboratories cat n. HFIX 47064) was reconstituted at 1 mg/ml (MW ~55 KDa) in the running buffer and used as analyte. Factor IX was injected in multiple cycle kinetics (MCK) mode at 3 concentrations (1.5 µM, 500 µM and 166.7 nM) with 120 seconds association phase and 200 seconds dissociation phase, at flow rate 30 µl/sec in both active and reference channels. Three injections of 10 mM glycine pH 1.5 for 60 sec at 10 µl/min were used for the regeneration phase.

An isotype control (ISTC) antibody hIgG4PE was captured at 1 µg/ml for 60 sec at 10 µl/min in the reference channel. hIgG4PE ISTC and hIgG1 ISTC were also captured in the active channel as a negative control. The anti-FIX monospecific antibody AbN was included for comparison.

The data were reference and buffer subtracted and fitted into Langmuir 1:1 model. The first 30 seconds of dissociation were evaluated in the model.

Results:

The anti-FIX antibodies analysed showed binding to FIX with the affinity shown in Table 1 and fast association ($k_{on}$) and dissociation ($k_{off}$) rate for FIX. No binding to FIX was observed with ISTC. The anti-FIX antibodies analysed showed approximately 10-fold higher affinity for FIX compared with AbN.

As this assay used FIX, not FIXa, the kinetic data here refer to the affinity of the binding arm's interaction with FIX. In view of the close structural similarity between FIX and FIXa, the affinity of the antibodies for binding FIXa may be similar to their affinity for binding FIX.

Example 16. SPR Analysis of Purified Anti-FX Antibodies

SPR was used to determine the binding affinity ($K_D$) of the FX binding arm to FX, the kinetic constants on-rate ($k_{on}$) and off-rate ($k_{off}$). The analysis was performed using a Biacore 8K (GE Healthcare) system.

An anti-human IgG Fc antibody was immobilised on CM5 chip (GE Healthcare catalog number 29104988) according to manufacturer's instructions. Amine coupling kit (BioRad) was used to activate the surface of the chip. The surface was subsequently blocked with 1M ethanolamine. The immobilisation run was performed at 25° C. using HBS-EP (10 mM HEPES pH 7.4, 150 mM NaCl, 3 mM EDTA, 0.05% Polysorbate 20 pH 7.6) as immobilisation running buffer.

Purified monospecific antibodies (referred to as ligand) from Example 13 were captured on the anti-human IgG Fc CM5 surface at approximately 1 µg/ml. The ligands were injected for 60 seconds at 10 µl/min in all the 8 active channels of all 8 flow cells. The run was performed at 25° C. using neutral pH (pH 7.4) HBS-P 1× (0.01 M HEPES pH 7.4, 0.15 M NaCl, 0.05% Polysorbate 20 pH 7.6)+CaCl$_2$) 2.5 mM as running buffer.

Human Factor X (FX) (Enzyme Research Laboratories cat n. HFX1010) was reconstituted at 1 mg/ml (MW ~58 KDa) and used as analyte. Factor X was injected in multiple

TABLE 1

Binding affinity and kinetic constants on-rate ($k_{on}$) and off-rate ($k_{off}$) of anti-FIX antibodies. The association and dissociation data of the interaction were fitted using biomolecular reaction model (1:1 Langmuir model). The values for association rate constant ($k_{on}$), dissociation rate constant ($k_{off}$) and dissociation constant ($K_D$) were calculated from the binding data by BIAevaluation software.

| Captured anti-FIX antibody | $k_{on}$ (1/Ms) | $k_{off}$ (1/s) | $K_D$ (M) |
|---|---|---|---|
| N128H_IgG4PE + N128L_IgL (n = 2) | 2.92 × 10$^5$ | 5.76 × 10$^{-2}$ | 1.98 × 10$^{-7}$ |
| N192H_IgG4PE + N128L_IgL | 5.46 × 10$^4$ | 4.70 × 10$^{-2}$ | 8.62 × 10$^{-7}$ |
| N203H_IgG4PE + N128L_IgL | 1.02 × 10$^5$ | 4.60 × 10$^{-2}$ | 4.52 × 10$^{-7}$ |
| N205H_IgG4PE + N128L_IgL | 9.50 × 10$^4$ | 3.97 × 10$^{-2}$ | 4.18 × 10$^{-7}$ |
| N211H_IgG4PE + N128L_IgL | 8.86 × 10$^4$ | 4.03 × 10$^{-2}$ | 4.54 × 10$^{-7}$ |
| N212H_IgG4PE + N128L_IgL | 9.89 × 10$^4$ | 4.02 × 10$^{-2}$ | 4.07 × 10$^{-7}$ |
| N215H_IgG4PE + N128L_IgL | 7.00 × 10$^4$ | 4.68 × 10$^{-2}$ | 6.68 × 10$^{-7}$ |
| N216H_IgG4PE + N128L_IgL | 9.09 × 10$^4$ | 4.28 × 10$^{-2}$ | 4.71 × 10$^{-7}$ |
| N217H_IgG4PE + N128L_IgL | 8.36 × 10$^4$ | 3.25 × 10$^{-2}$ | 3.89 × 10$^{-7}$ |
| N218H_IgG4PE + N128L_IgL | 8.02 × 10$^4$ | 3.24 × 10$^{-2}$ | 4.04 × 10$^{-7}$ |
| N219H_IgG4PE + N128L_IgL | 7.94 × 10$^4$ | 3.49 × 10$^{-2}$ | 4.40 × 10$^{-7}$ |
| N220H_IgG4PE + N128L_IgL | 7.89 × 10$^4$ | 3.36 × 10$^{-2}$ | 4.26 × 10$^{-7}$ |
| N221H_IgG4PE + N128L_IgL | 6.67 × 10$^4$ | 3.45 × 10$^{-2}$ | 5.17 × 10$^{-7}$ |
| N222H_IgG4PE + N128L_IgL | 8.54 × 10$^4$ | 3.14 × 10$^{-2}$ | 3.68 × 10$^{-7}$ |
| N223H_IgG4PE + N128L_IgL | 7.30 × 10$^4$ | 3.10 × 10$^{-2}$ | 4.25 × 10$^{-7}$ |
| N224H_IgG4PE + N128L_IgL | 7.80 × 10$^4$ | 3.36 × 10$^{-2}$ | 4.31 × 10$^{-7}$ |
| N225H_IgG4PE + N128L_IgL | 7.23 × 10$^4$ | 3.10 × 10$^{-2}$ | 4.28 × 10$^{-7}$ |
| N226H_IgG4PE + N128L_IgL | 5.90 × 10$^4$ | 2.94 × 10$^{-2}$ | 4.98 × 10$^{-7}$ |
| N227H_IgG4PE + N128L_IgL | 7.54 × 10$^4$ | 2.68 × 10$^{-2}$ | 3.56 × 10$^{-7}$ |
| N228H_IgG4PE + N128L_IgL | 6.05 × 10$^4$ | 2.94 × 10$^{-2}$ | 4.86 × 10$^{-7}$ |
| N229H_IgG4PE + N128L_IgL | 6.61 × 10$^4$ | 2.89 × 10$^{-2}$ | 4.37 × 10$^{-7}$ |
| N436H_IgG4PE + N128L_IgL | 2.46 × 10$^5$ | 4.53 × 10$^{-2}$ | 1.84 × 10$^{-7}$ |
| N438H_IgG4PE + N128L_IgL | 2.30 × 10$^5$ | 6.73 × 10$^{-2}$ | 2.93 × 10$^{-7}$ |
| N440H_IgG4PE + N128L_IgL | 1.85 × 10$^5$ | 5.35 × 10$^{-2}$ | 2.89 × 10$^{-7}$ |
| N442H_IgG4PE + N128L_IgL | 1.94 × 10$^5$ | 4.71 × 10$^{-2}$ | 2.42 × 10$^{-7}$ |
| N444H_IgG4PE + N128L_IgL | 2.16 × 10$^5$ | 4.45 × 10$^{-2}$ | 2.06 × 10$^{-7}$ |
| N445H_IgG4PE + N128L_IgL | 2.04 × 10$^5$ | 5.44 × 10$^{-2}$ | 2.67 × 10$^{-7}$ |
| N456H_IgG4PE + N128L_IgL | 1.51 × 10$^5$ | 3.96 × 10$^{-2}$ | 2.63 × 10$^{-7}$ |
| N460H_IgG4PE + N128L_IgL | 1.75 × 10$^5$ | 3.18 × 10$^{-2}$ | 1.81 × 10$^{-7}$ |
| AbN | 3.06 × 10$^4$ | 4.26 × 10$^{-2}$ | 1.39 × 10$^{-6}$ |
| ISTC | | | NB |

"NB" = no binding observed.

cycle kinetics (MCK) mode at 3 concentrations (1.5 μM, 375 nM, 93.75 nM) with 120 seconds association phase and 300 seconds dissociation phase at the flow rate 30 μl/sec in both active and reference channels. Three injections of 10 mM glycine pH 1.5 for 60 sec. at 10 ul/min were used for the regeneration phase.

hIgG4PE ISTC was captured in the active channel as a negative control. The anti-FX monospecific antibody AbT was included for comparison.

The data were reference and buffer subtracted and fitted into Langmuir 1:1 model. The first 30 seconds of dissociation were evaluated in the model.

Results:

The anti-FX antibodies analysed showed binding to FX with the affinity shown in Table 2 and fast association ($k_{on}$) and dissociation ($k_{off}$) rate for FX. No binding to FX was observed with ISTC.

The anti-FX antibodies analysed showed between approximately 10-fold to 1000-fold higher binding affinity to FX compared with AbT. Antibody T14 (VH domain T14H, VL domain T14L) had an affinity of approximately 0.18 μM for FX. Two other anti-FX antibody VH domains, T19H and T20H, which were identified from the immunised mice with sequences similar to T14, were paired with the T14 VL domain for comparison. These bound FX with a $K_D$ of approximately 0.2 and 0.05 μM respectively. The other tested anti-FX antibodies, T15, T23 and T25, had a $K_D$ in the nanomolar range.

TABLE 2

Binding affinity and kinetic constants on-rate ($k_{on}$) and off-rate ($k_{off}$) of anti-FX antibodies. The association and dissociation data of the interaction were fitted using biomolecular reaction model (1:1 Langmuir model). The values for association rate constant ($k_{on}$), dissociation rate constant ($k_{off}$) and dissociation constant ($K_D$) were calculated from the binding data by BIAevaluation software.

| Captured anti-FX antibody | $k_{on}$ (1/MS) | $k_{off}$ (1/S) | $K_D$ (M) |
|---|---|---|---|
| AbT | $1.40 \times 10^4$ | $3.26 \times 10^{-2}$ | $2.33 \times 10^{-6}$ |
| T14H_IgG4PE + T14_VL_IgK | $5.62 \times 10^4$ | $1.01 \times 10^{-2}$ | $1.79 \times 10^{-7}$ |
| T19H_IgG4PE + T14_VL_IgK | $6.29 \times 10^4$ | $1.21 \times 10^{-2}$ | $1.93 \times 10^{-7}$ |
| T20H_IgG4PE + T14_VL_IgK | $9.00 \times 10^4$ | $4.19 \times 10^{-3}$ | $4.66 \times 10^{-3}$ |
| T15H_IgG4PE + T15L_IgK | $9.94 \times 10^4$ | $2.94 \times 10^{-4}$ | $2.96 \times 10^{-9}$ |
| T23H_IgG4PE + T23L_IgK | $1.06 \times 10^4$ | $6.03 \times 10^{-4}$ | $5.70 \times 10^{-9}$ |
| T25H_IgG4PE + T25L_IgK | $7.03 \times 10^4$ | $2.51 \times 10^{-3}$ | $3.57 \times 10^{-9}$ |
| hIgG4PE ISTC | | | NB |

"NB" = no binding observed.

Example 17: Tenase (FXase) Assay with FIX Binding Arm N436 Paired with a Range of FX Binding Arms Ability of N436H_IgG4_ra Factor IX antibody arm heterodimerised with different Factor X arms to catalyse Factor IXa activation of Factor X was determined using in vitro tenase (FXase) assay using coagulation factors purified from human plasma.

The FXase assay protocol used for initial screening (see Example 9) was refined for the present experiments, which used bispecific antibody purified by Protein A (rather than cell supernatant). Pre-activated factor IXa was added in this updated assay protocol, rather than factor IX and factor XIa, and FIX was not pre-incubated with the antibody solution before adding the assay mixture. Incubation at 37 deg C. was reduced from 1 hour to 10 minutes.

In brief, the method was as follows, with all reactions being performed at 37° C. unless otherwise stated:

Recombinantly expressed antibodies were purified from supernatant from the recombinant Expi293 cells using Protein A as described in Example 13.

5 μL purified recombinant antibody was added to each well of an assay plate. A mixture of 1.5 μL FIXa (1 μg/ml), 5 μL FX (50 μg/mL), 0.05 μL phospholipid (10 mg/mL) and 13.45 μL TBSB-S buffer was added to each well to initiate enzymatic reaction (FIXa cleavage of FX to generate FXa), and incubated at 37° C. for 10 minutes. After 10 minutes, the reaction was terminated by adding 5 μL of 0.5 M EDTA. After adding 10 μL S2765 substrate solution to each well, absorbance at 405 nm (reference wavelength 655 nm) was measured for 25 minutes (one reading per 5 minutes).

Chromogenix S-2765 is a chromogenic substrate used to determine the generation of activated Factor X. Factor Xa cleaves S2765, releasing the chromophoric group p-nitroaniline (pNA), resulting in a colour change which can be monitored photometrically at 405 nm. The absorbance reading at 405 nm is proportional to the amount of Factor Xa generated. FIG. 7 illustrates the principles of the assay.

Bispecific antibodies tested in this assay had a FIX binding arm comprising the VH domain of N436H and the VL domain of N128L. These were expressed as the heavy and light chain constructs N436H_IgG4_ra and N128L_IgL respectively, and heterodimerised with the following heavy and light chain constructs providing the FX binding arm:

T02H_IgG4rb+T02L_IgL;
T05H_IgG4rb+T05L_IgL; or
T14H_IgG4rb+T14L_IgK.

Also included for reference were a positive control FIX-FX bispecific antibody (Ab_E) and an isotype control (ISTC).

Figure 12:
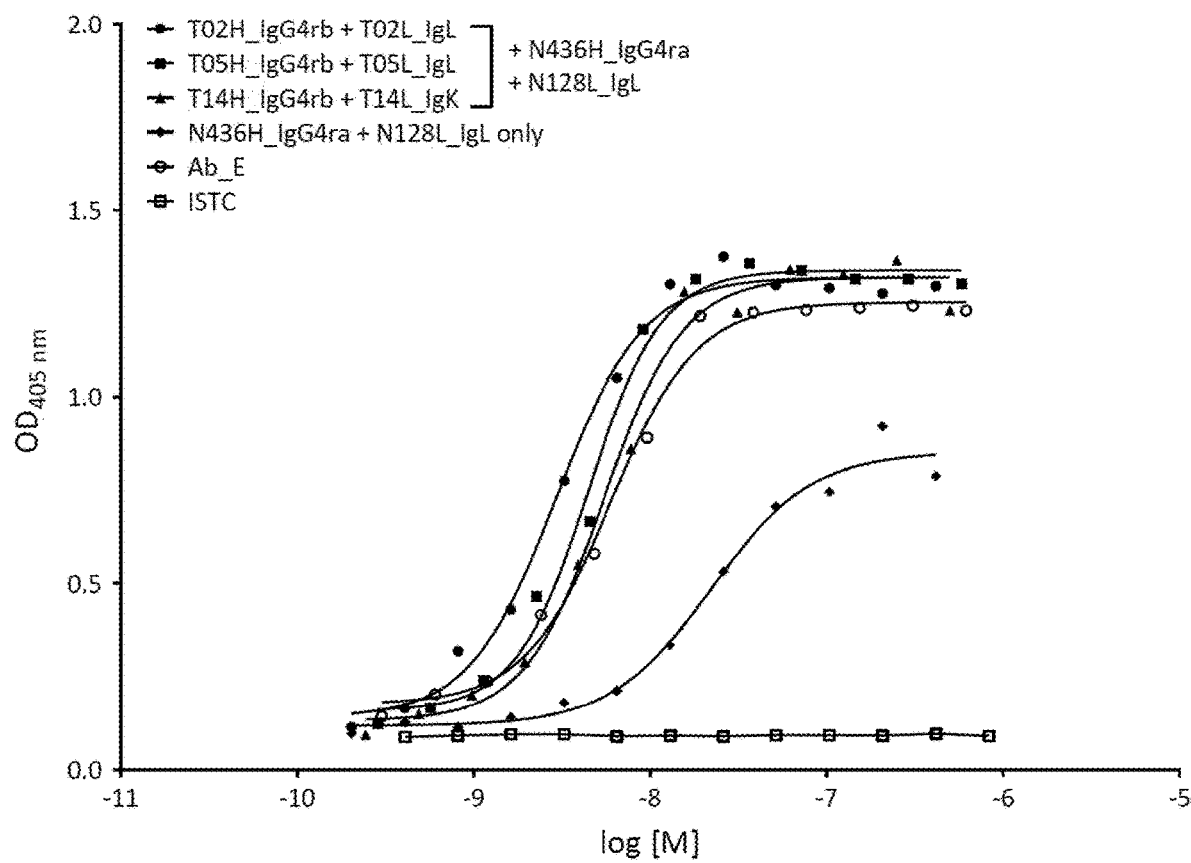
FIG. 12 In vitro tenase (FXase) assay activity of Factor IX specific arm N436.

Results are illustrated in FIG. 12.

N436H_IgG4ra, N128L_IgL demonstrated a dose dependent increase in FXase activity as a bispecific antibody heterodimerised with either T02H_IgG4rb+T02L_IgL, T05H_IgG4rb+T05L_IgL or T14H_IgG4rb+T14L_IgK. FX activation observed was comparable to the bispecific antibody Ab_E. N436H_IgG4ra, N128L_IgL expressed alone in the absence of an anti-Factor X arm was still capable of activating Factor X, albeit at a reduced level. The isotype control demonstrated no FXase activity.

Example 18: Plasma Coagulation (aPTT) Assay with FIX Binding Arm N436 Paired with a Range of FX Binding Arms In this plasma coagulation assay, aPTT measurements are derived using a photo-optical coagulation system. As a clot forms, the amount of light able to pass through the sample decreases. This decrease is plotted as a function of time, generating a waveform. Once a fibrin clot has been formed the end-point of the clotting reaction is complete and the clotting time is automatically calculated. Plasma used in the present aPTT assay is deficient in FVIII, so the effect of adding the FIX-FX bispecific antibody is measurable by its ability to substitute for FVIII in the clotting cascade. Clotting time in the presence of the bispecific antibody can be compared against a negative control and against clotting time in the presence of FVIII.

A mixture of 5 μL bispecific antibody solution having a variety of concentrations, 20 μL FVIII deficient human plasma (Helena Biosciences) and 25 μL Si L Minus aPTT reagent (Helena Biosciences) was warmed at 37° C. for 2 minutes. The coagulation reaction was initiated by adding 25

µL 20 mM CaCl$_2$) (Helena Biosciences) to the mixture. The time period until coagulation was measured. Apparatus used for this was a semi-automated coagulometer, specifically the C-series photo-optical coagulation system (Helena Biosciences). The aPTT reagent contains phospholipid and a contact activator (near-colloidal particle activator, namely magnesium-aluminium-silicate) which provides the "surface contact" activation of the intrinsic blood clotting cascade (see FIG. 1 for reference). Concentration dependency was subsequently determined for bispecific antibodies that exhibited the highest coagulation time-reducing effect.

Figure 13:
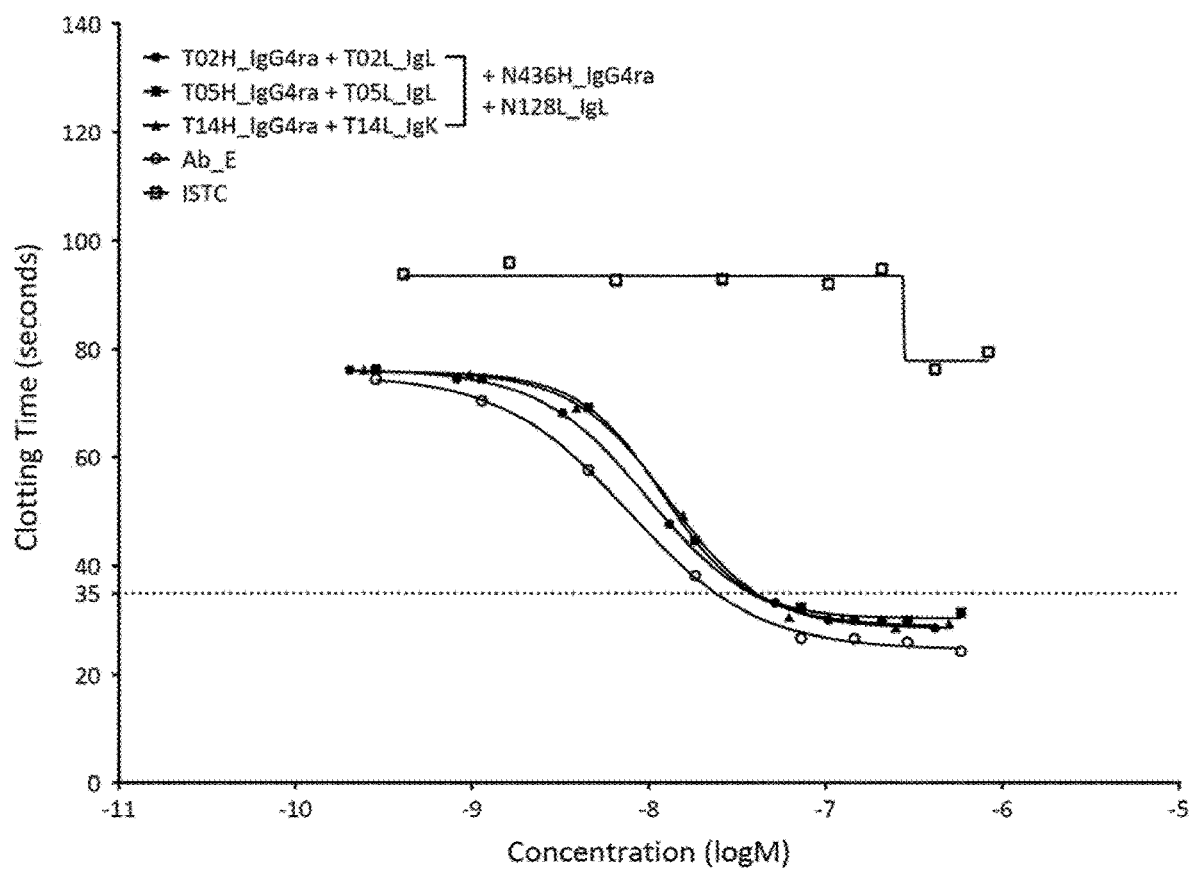
FIG. 13 aPTT assay activity of bispecific antibodies comprising N436H VH domain and N128L VL domain (providing FIX binding site) heterodimerised with FX binding site provided by (i) T02H VH domain and T02L VL domain, (ii) T05H VH domain and T05L VL domain or (iii) T14H VH domain and T14L VL domain.

Results are shown in FIG. 13. In this one-stage aPTT clotting assay using FVIII-depleted human plasma, N436H_IgG4ra, N128L_IgL demonstrated a dose dependent decrease in aPTT time as a bispecific antibody heterodimerised with either T02H_IgG4rb+T02L_IgL, T05H_IgG4rb+T05L_IgL or T14H_IgG4rb+T14L_IgK. The dose dependent decrease in aPTT time was comparable to Ab_E. No reduction in aPTT was observed for the isotype control.

REFERENCES

1 Kitazawa et al., A bispecific antibody to factors IXa and X restores factor VIII hemostatic activity in hemophilia A model, Nat. Med. 18(10):1570-1574 2012
2 Sampei et al., Identification and Multidimensional Optimization of an Asymmetric Bispecific IgG Antibody Mimicking the Function of Factor VIII Cofactor Activity, PLOS ONE 8(2) 2013
3 Uchida et al., A first-in-human phase 1 study of ACE910, a novel factor VIII-mimetic bispecific antibody, in healthy subjects, Blood 127(13):1633-1641 2015
4 Shima et al., Factor VIII-Mimetic Function of Humanized Bispecific Antibody in Hemophilia A, N Engl J Med 374:2044-2053 2016
5 Diagram by Dr Graham Beards, based on information in Pallister C J and Watson M S (2010) Haematology, UK: Scion Publishing, pp. 336-347 ISBN: 1-904842-39-9
6 Fay, Activation of factor VIII and mechanisms of cofactor action, Blood Reviews, 18:1-15 2004
7 Brandstetter et al., X-ray structure of clotting factor IXa: Active site and module structure related to Xase activity and hemophilia B, PNAS 92:9796-9800 1995
8 Bowen, Haemophilia A and haemophilia B: molecular insights, Mol. Pathol. 55:1-18 2002
9 Lefranc M P, IMGT unique numbering for immunoglobulin and T cell receptor variable domains and Ig superfamily V-like domains, Dev Comp Immunol. 27(1):55-77 2003
10 Davis J H et al., PEDS 23:195-202)
11 Lee et al, Nature Biotechnology, 32:6-363, 2014
12 Ridgway et al., Protein Eng. 9:617-621 1996

FIXa Binding Arm Polypeptide Sequences

TABLE 9A

| | | Anti-FIXa VH domain sequences and CDRs | | | |
|---|---|---|---|---|---|
| Ab VH | HCDR1 | HCDR2 | HCDR3 | VH nucleotide sequence | VH amino acid sequence |
| N192H | SEQ ID NO: 11 GFTFSSYW | SEQ ID NO: 12 IKQDGSEK | SEQ ID NO: 13 AREGYSSYYYYGMDV | SEQ ID NO: 14 GAGGTGCAGCTGGTGGAGTCTG GGGGAGGCTTGGTCCAGCCTGG GGGGTCCCTGAGACTCTCCTGT GCAGCCTCTGGATTCACCTTTA GTAGCTATTGGATGAGCTGGGT CCGCCAGGCTCCAGGGAAGGGG CTGGAGTGGGTGGCCAACATAA AGCAAGATGGAAGTGAGAAATA CTATGTGGACTCTGTGAAGGGC CGATTCACCATCTCCAGAGACA ACGCCAAGAACTCACTGTATCT GCAAATGAACAGCCTGAGAGCC GAGGACACGGCTGTGTATTACT GTGCGAGAGAGGGGTATAGCAG TTACTACTACTACGGTATGGAC GTCTGGGGCCAAGGGACCACG TCACCGTCTCCTCA | SEQ ID NO: 15 EVQLVESGGGLVQPGGSL RLSCAASGFTFSSYWMSW VRQAPGKGLEWVANIKQD GSEKYYVDSVKGRFTISR DNAKNSLYLQMNSLRAED TAVYYCAREGYSSYYYYG MDVWGQGTTVTVSS |
| N212H | SEQ ID NO: 11 GFTFSSYW | SEQ ID NO: 2 INQDGSEK | SEQ ID NO: 3 AREGYSSSSYYGMDV | SEQ ID NO: 16 GAGGTGCAGCTGGTGGAGTCTG GGGGAGGCTTGGTCCAGCCTGG GGGGTCCCTGAGACTCTCCTGT GCAGCCTCTGGATTCACCTTTA GTAGCTATTGGATGAGCTGGGT CCGCCAGGCTCCAGGGAAGGGG CTGGAGTGGGTGGCCAACATAA ACCAAGATGGAAGTGAGAAATA CTATGTGGACTCTGTGAAGGGC CGATTCACCATCTCCAGAGACA ACGCCAAGAACTCACTGTATCT ACAAATGAACAGCCTGAGAGCC GAGGACACGGCTGTGTATTACT GTGCGAGAGAGGGGTATAGTAG TTCGTCCTATTATGGTATGGAC GTCTGGGGCCAAGGGACCACG TCACCGTCTCCTCA | SEQ ID NO: 17 EVQLVESGGGLVQPGGSL RLSCAASGFTFSSYWMSW VRQAPGKGLEWVANINQD GSEKYYVDSVKGRFTISR DNAKNSLYLQMNSLRAED TAVYYCAREGYSSSSYYG MDVWGQGTTVTVSS |

TABLE 9A-continued

Anti-FIXa VH domain sequences and CDRs

| Ab VH | HCDR1 | HCDR2 | HCDR3 | VH nucleotide sequence | VH amino acid sequence |
|---|---|---|---|---|---|
| N205H | SEQ ID NO: 18 GFIFSSYW | SEQ ID NO: 2 INQDGSEK | SEQ ID NO: 3 AREGYSSSSYYGMDV | SEQ ID NO: 19 GAGGTGCAGCTGGTGGAGTCTG GGGGAGGCTTGGTCCAGCCTGG GGGGTCCCTGAGACTCTCCTGT GTAGCCTCTGGATTCATCTTTA GTAGCTATTGGATGAGCTGGGT CCGCCAGGCTCCAGGGAAGGGG CTGGAGTGGGTGGCCAATATAA ATCAAGATGGAAGTGAGAAATA CTATGTGGACTCTGTGAAGGGC CGATTCACCATCTCCAGAGACA ACGCCAAGAACTCACTGTATCT GCAAATGAACAGCCTGAGAGCC GAGGACACGGCTGTGTATTACT GTGCGAGAGAGGGGTATAGCAG TTCGTCCTATTATGGTATGGAC GTCTGGGGCCAAGGGACCACGG TCACCGTCTCCTCA | SEQ ID NO: 20 EVQLVESGGGLVQPGGSL RLSCVASGFIFSSYWMSW VRQAPGKGLEWVANINQD GSEKYYVDSVKGRFTISR DNAKNSLYLQMNSLRAED TAVYYCAREGYSSSSYYG MDVWGQGTTVTVSS |
| N211H | SEQ ID NO: 1 GFTFNSYW | SEQ ID NO: 2 INQDGSEK | SEQ ID NO: 3 AREGYSSSSYYGMDV | SEQ ID NO: 21 GAGGTGCAGCTGGTGGAGTCTG GGGGAGGCTTGGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATCTCCAGAGACA ACGCCAAGAACTCAGTGTATCT ACAAATGAACAGCCTGAGAGCC GAGGACACGGCTGTGTATTACT GTGCGAGAGAGGGGTATAGTAG TTCGTCCTATTATGGTATGGAC GTCTGGGGCCAAGGGACCACGG TCACCGTCTCCTCA | SEQ ID NO: 22 EVQLVESGGGLVQPGGSL RLSCVASGFTFNSYWMSW VRQAPGKGLEWVANINQD GSEKFYVASVKGRFTISR DNAKNSVYLQMNSLRAED TAVYYCAREGYSSSSYYG MDVWGQGTTVTVSS |
| N203H | SEQ ID NO: 23 GFTFNNYW | SEQ ID NO: 2 INQDGSEK | SEQ ID NO: 24 AREGYTDSSYYGMDV | SEQ ID NO: 25 GAGGTGCAGCTGGTGGAGTCTG GGGGAGGCGCTGGTCCAGCCTGG GGGGTCCCTGAGACTCTCCTGT GCAGTCTCTGGATTCACCTTTA ATAACTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCATCATCTCCAGAGACA ACGCCAAAAATTCAGTGTATCT ACAAATGAACAGCCTGAGAGCC GAGGACACGGCTGTGTATTACT GTGCGAGAGAGGGGTATACCGA TTCGTCCTATTATGGAATGGAC GTCTGGGGCCAAGGGACCACGG TCTCCGTCTCCTCA | SEQ ID NO: 26 EVQLVESGGGLVQPGGSL RLSCVASGFTFNNYWMSW VRQAPGKGLEWVANINQD GSEKFYVASVKGRFIISR DNAKNSVYLQMNSLRAED TAVYYCAREGYTDSSYYG MDVWGQGTTVSVSS |
| N128H | SEQ ID NO: 1 GFTFNSYW | SEQ ID NO: 2 INQDGSEK | SEQ ID NO: 3 AREGYSSSSYYGMDV | SEQ ID NO: 4 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATAGTAG | SEQ ID NO: 5 EVQLVESGGGFVQPGGSL RLSCVASGFTFNSYWMSW VRQAPGKGLEWVANINQD GSEKFYVASVKGRFTMSR DNAKKSVYVQMNSLRAED TAVYYCAREGYSSSSYYG MDVWGQGTTVTVSS |

TABLE 9A-continued

Anti-FIXa VH domain sequences and CDRs

| Ab VH | HCDR1 | HCDR2 | HCDR3 | VH nucleotide sequence | VH amino acid sequence |
|---|---|---|---|---|---|
| | | | | TTCGTCCTATTATGGTATGGAC GTCTGGGGCCAAGGGACCACGG TCACCGTCTCCTCAG | |
| N215H | SEQ ID NO: 11 GFTFSSYW | SEQ ID NO: 12 IKQDGSEK | SEQ ID NO: 3 AREGYSSSSYYGMDV | SEQ ID NO: 27 GAGGTGCAGCTGGTGGAGTCTG GGGGAGGCTTGGTCCAGCCTGG GGGGTCCCTGAGACTCTCCTGT GCAGCCTCTGGATTCACCTTTA GTAGCTATTGGATGAGCTGGGT CCGCCAGGCTCCAGGGAAGGGG CTGGAGTGGGTGGCCAACATAA AGCAAGATGGAAGTGAGAAATA CTATGTGGACTCTGTGAAGGGC CGATTCACCATCTCCAGAGACA ACGCCAAGAACTCACTGTATCT GCAAATGAACAGCCTGAGAGCC GAGGACACGGCTGTGTATTACT GTGCGAGAGAGGGGTATAGCAG TTCGTCCTACTACGGTATGGAC GTCTGGGGCCAAGGGACCACGG TCACCGTCTCCTCA | SEQ ID NO: 28 EVQLVESGGGLVQPGGSL RLSCAASGFTFSSYWMSW VRQAPGKGLEWVANIKQD GSEKYYVDSVKGRFTISR DNAKNSLYLQMNSLRAED TAVYYCAREGYSSSSYYG MDVWGQGTTVTVSS |
| N216H | SEQ ID NO: 1 GFTFNSYW | SEQ ID NO: 2 INQDGSEK | SEQ ID NO: 3 AREGYSSSSYYGMDV | SEQ ID NO: 29 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATCTCCAGAGACA ACGCCAAGAACTCAGTGTATCT ACAAATGAACAGCCTGAGAGCC GAGGACACGGCTGTGTATTACT GTGCGAGAGAGGGGTATAGTAG TTCGTCCTATTATGGTATGGAC GTCTGGGGCCAAGGGACCACGG TCACCGTCTCCTCA | SEQ ID NO: 30 EVQLVESGGGFVQPGGSL RLSCAVSGFTFNSYWMSW VRQAPGKGLEWVANINQD GSEKFYVASVKGRFTISR DNAKNSVYLQMNSLRAED TAVYYCAREGYSSSSYYG MDVWGQGTTVTVSS |
| N217H | SEQ ID NO: 1 GFTFNSYW | SEQ ID NO: 2 INQDGSEK | SEQ ID NO: 3 AREGYSSSSYYGMDV | SEQ ID NO: 31 GAGGTGCAGCTGGTGGAGTCTG GGGGAGGCTTGGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAACTCAGTGTATCT ACAAATGAACAGCCTGAGAGCC GAGGACACGGCTGTGTATTACT GTGCGAGAGAGGGGTATAGTAG TTCGTCCTATTATGGTATGGAC GTCTGGGGCCAAGGGACCACGG TCACCGTCTCCTCA | SEQ ID NO: 32 EVQLVESGGGLVQPGGSL RLSCAVSGFTFNSYWMSW VRQAPGKGLEWVANINQD GSEKFYVASVKGRFTMSR DNAKNSVYLQMNSLRAED TAVYYCAREGYSSSSYYG MDVWGQGTTVTVSS |
| N218H | SEQ ID NO: 1 GFTFNSYW | SEQ ID NO: 2 INQDGSEK | SEQ ID NO: 3 AREGYSSSSYYGMDV | SEQ ID NO: 33 GAGGTGCAGCTGGTGGAGTCTG GGGGAGGCTTGGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATCTCCAGAGACA ACGCCAAGAAATCAGTGTATCT ACAAATGAACAGCCTGAGAGCC GAGGACACGGCTGTGTATTACT | SEQ ID NO: 34 EVQLVESGGGLVQPGGSL RLSCAVSGFTFNSYWMSW VRQAPGKGLEWVANINQD GSEKFYVASVKGRFTISR DNAKKSVYLQMNSLRAED TAVYYCAREGYSSSSYYG MDVWGQGTTVTVSS |

TABLE 9A-continued

Anti-FIXa VH domain sequences and CDRs

| Ab VH | HCDR1 | HCDR2 | HCDR3 | VH nucleotide sequence | VH amino acid sequence |
|---|---|---|---|---|---|
| | | | | GTGCGAGAGAGGGGTATAGTAG TTCGTCCTATTATGGTATGGAC GTCTGGGGCCAAGGGACCACGG TCACCGTCTCCTCA | |
| N219H | SEQ ID NO: 1 GFTFNSYW | SEQ ID NO: 2 INQDGSEK | SEQ ID NO: 3 AREGYSSSSYYGMDV | SEQ ID NO: 35 GAGGTGCAGCTGGTGGAGTCTG GGGGAGGCTTGGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATCTCCAGAGACA ACGCCAAGAACTCAGTGTATGT ACAAATGAACAGCCTGAGAGCC GAGGACACGGCTGTGTATTACT GTGCGAGAGAGGGGTATAGTAG TTCGTCCTATTATGGTATGGAC GTCTGGGGCCAAGGGACCACGG TCACCGTCTCCTCA | SEQ ID NO: 36 EVQLVESGGGLVQPGGSL RLSCAVSGFTFNSYWMSW VRQAPGKGLEWVANINQD GSEKFYVASVKGRFTISR DNAKNSVYVQMNSLRAED TAVYYCAREGYSSSSYYG MDVWGQGTTVTVSS |
| N220H | SEQ ID NO: 1 GFTFNSYW | SEQ ID NO: 2 INQDGSEK | SEQ ID NO: 3 AREGYSSSSYYGMDV | SEQ ID NO: 37 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATCTCCAGAGACA ACGCCAAGAAATCAGTGTATGT ACAAATGAACAGCCTGAGAGCC GAGGACACGGCTGTGTATTACT GTGCGAGAGAGGGGTATAGTAG TTCGTCCTATTATGGTATGGAC GTCTGGGGCCAAGGGACCACGG TCACCGTCTCCTCA | SEQ ID NO: 38 EVQLVESGGGFVQPGGSL RLSCAVSGFTFNSYWMSW VRQAPGKGLEWVANINQD GSEKFYVASVKGRFTISR DNAKKSVYVQMNSLRAED TAVYYCAREGYSSSSYYG MDVWGQGTTVTVSS |
| N221H | SEQ ID NO: 1 GFTFNSYW | SEQ ID NO: 2 INQDGSEK | SEQ ID NO: 3 AREGYSSSSYYGMDV | SEQ ID NO: 39 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAACTCAGTGTATGT ACAAATGAACAGCCTGAGAGCC GAGGACACGGCTGTGTATTACT GTGCGAGAGAGGGGTATAGTAG TTCGTCCTATTATGGTATGGAC GTCTGGGGCCAAGGGACCACGG TCACCGTCTCCTCA | SEQ ID NO: 40 EVQLVESGGGFVQPGGSL RLSCAVSGFTFNSYWMSW VRQAPGKGLEWVANINQD GSEKFYVASVKGRFTMSR DNAKNSVYVQMNSLRAED TAVYYCAREGYSSSSYYG MDVWGQGTTVTVSS |
| N222H | SEQ ID NO: 1 GFTFNSYW | SEQ ID NO: 2 INQDGSEK | SEQ ID NO: 3 AREGYSSSSYYGMDV | SEQ ID NO: 41 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATCT ACAAATGAACAGCCTGAGAGCC | SEQ ID NO: 42 EVQLVESGGGFVQPGGSL RLSCAVSGFTFNSYWMSW VRQAPGKGLEWVANINQD GSEKFYVASVKGRFTMSR DNAKKSVYLQMNSLRAED TAVYYCAREGYSSSSYYG MDVWGQGTTVTVSS |

TABLE 9A-continued

Anti-FIXa VH domain sequences and CDRs

| Ab VH | HCDR1 | HCDR2 | HCDR3 | VH nucleotide sequence | VH amino acid sequence |
|---|---|---|---|---|---|
| | | | | GAGGACACGGCTGTGTATTACT GTGCGAGAGAGGGGTATAGTAG TTCGTCCTATTATGGTATGGAC GTCTGGGGCCAAGGGACCACGG TCACCGTCTCCTCA | |
| N223H | SEQ ID NO: 1 GFTFNSYW | SEQ ID NO: 2 INQDGSEK | SEQ ID NO: 3 AREGYSSSSYYGMDV | SEQ ID NO: 43 GAGGTGCAGCTGGTGGAGTCTG GGGGAGGCTTGGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATAGTAG TTCGTCCTATTATGGTATGGAC GTCTGGGGCCAAGGGACCACGG TCACCGTCTCCTCA | SEQ ID NO: 44 EVQLVESGGGLVQPGGSL RLSCAVSGFTFNSYWMSW VRQAPGKGLEWVANINQD GSEKFYVASVKGRFTMSR DNAKKSVYVQMNSLRAED TAVYYCAREGYSSSSYYG MDVWGQGTTVTVSS |
| N224H | SEQ ID NO: 1 GFTFNSYW | SEQ ID NO: 2 INQDGSEK | SEQ ID NO: 3 AREGYSSSSYYGMDV | SEQ ID NO: 45 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAACTCAGTGTATCT ACAAATGAACAGCCTGAGAGCC GAGGACACGGCTGTGTATTACT GTGCGAGAGAGGGGTATAGTAG TTCGTCCTATTATGGTATGGAC GTCTGGGGCCAAGGGACCACGG TCACCGTCTCCTCA | SEQ ID NO: 46 EVQLVESGGGFVQPGGSL RLSCAVSGFTFNSYWMSW VRQAPGKGLEWVANINQD GSEKFYVASVKGRFTMSR DNAKNSVYLQMNSLRAED TAVYYCAREGYSSSSYYG MDVWGQGTTVTVSS |
| N225H | SEQ ID NO: 1 GFTFNSYW | SEQ ID NO: 2 INQDGSEK | SEQ ID NO: 3 AREGYSSSSYYGMDV | SEQ ID NO: 47 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATCTCCAGAGACA ACGCCAAGAAATCAGTGTATCT ACAAATGAACAGCCTGAGAGCC GAGGACACGGCTGTGTATTACT GTGCGAGAGAGGGGTATAGTAG TTCGTCCTATTATGGTATGGAC GTCTGGGGCCAAGGGACCACGG TCACCGTCTCCTCA | SEQ ID NO: 48 EVQLVESGGGFVQPGGSL RLSCAVSGFTFNSYWMSW VRQAPGKGLEWVANINQD GSEKFYVASVKGRFTISR DNAKKSVYLQMNSLRAED TAVYYCAREGYSSSSYYG MDVWGQGTTVTVSS |
| N226H | SEQ ID NO: 1 GFTFNSYW | SEQ ID NO: 2 INQDGSEK | SEQ ID NO: 3 AREGYSSSSYYGMDV | SEQ ID NO: 49 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATCTCCAGAGACA ACGCCAAGAACTCAGTGTATGT | SEQ ID NO: 50 EVQLVESGGGFVQPGGSL RLSCAVSGFTFNSYWMSW VRQAPGKGLEWVANINQD GSEKFYVASVKGRFTISR DNAKNSVYVQMNSLRAED TAVYYCAREGYSSSSYYG MDVWGQGTTVTVSS |

TABLE 9A-continued

Anti-FIXa VH domain sequences and CDRs

| Ab VH | HCDR1 | HCDR2 | HCDR3 | VH nucleotide sequence | VH amino acid sequence |
|---|---|---|---|---|---|
| | | | | ACAAATGAACAGCCTGAGAGCC GAGGACACGGCTGTGTATTACT GTGCGAGAGAGGGGTATAGTAG TTCGTCCTATTATGGTATGGAC GTCTGGGGCCAAGGGACCACGG TCACCGTCTCCTCA | |
| N227H | SEQ ID NO: 1 GFTFNSYW | SEQ ID NO: 2 INQDGSEK | SEQ ID NO: 3 AREGYSSSSYYGMDV | SEQ ID NO: 51 GAGGTGCAGCTGGTGGAGTCTG GGGGAGGCTTGGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAAATCAGTGTATCT ACAAATGAACAGCCTGAGAGCC GAGGACACGGCTGTGTATTACT GTGCGAGAGAGGGGTATAGTAG TTCGTCCTATTATGGTATGGAC GTCTGGGGCCAAGGGACCACGG TCACCGTCTCCTCA | SEQ ID NO: 52 EVQLVESGGGLVQPGGSL RLSCAVSGFTFNSYWMSW VRQAPGKGLEWVANINQD GSEKFYVASVKGRFTMSR DNAKKSVYLQMNSLRAED TAVYYCAREGYSSSSYYG MDVWGQGTTVTVSS |
| N228H | SEQ ID NO: 1 GFTFNSYW | SEQ ID NO: 2 INQDGSEK | SEQ ID NO: 3 AREGYSSSSYYGMDV | SEQ ID NO: 53 GAGGTGCAGCTGGTGGAGTCTG GGGGAGGCTTGGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAACTCAGTGTATGT ACAAATGAACAGCCTGAGAGCC GAGGACACGGCTGTGTATTACT GTGCGAGAGAGGGGTATAGTAG TTCGTCCTATTATGGTATGGAC GTCTGGGGCCAAGGGACCACGG TCACCGTCTCCTCA | SEQ ID NO: 54 EVQLVESGGGLVQPGGSL RLSCAVSGFTFNSYWMSW VRQAPGKGLEWVANINQD GSEKFYVASVKGRFTMSR DNAKNSVYVQMNSLRAED TAVYYCAREGYSSSSYYG MDVWGQGTTVTVSS |
| N229H | SEQ ID NO: 1 GFTFNSYW | SEQ ID NO: 2 INQDGSEK | SEQ ID NO: 3 AREGYSSSSYYGMDV | SEQ ID NO: 55 GAGGTGCAGCTGGTGGAGTCTG GGGGAGGCTTGGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATCTCCAGAGACA ACGCCAAGAAAATCAGTGTATGT ACAAATGAACAGCCTGAGAGCC GAGGACACGGCTGTGTATTACT GTGCGAGAGAGGGGTATAGTAG TTCGTCCTATTATGGTATGGAC GTCTGGGGCCAAGGGACCACGG TCACCGTCTCCTCA | SEQ ID NO: 56 EVQLVESGGGLVQPGGSL RLSCAVSGFTFNSYWMSW VRQAPGKGLEWVANINQD GSEKFYVASVKGRFTISR DNAKKSVYVQMNSLRAED TAVYYCAREGYSSSSYYG MDVWGQGTTVTVSS |
| | SEQ ID NO: 140 HCCDR1 consensus GFTFSSYM I NN GF(T/I)F(S/N)(S/N)YM | SEQ ID NO: 141 HCDR2 consensus INQDGSEK K I(N/K)QDGSEK | SEQ ID NO: 142 HCDR3 consensus AREGYSSSSYYGMDV TDYY AREGY(S/T)(S/D)(S/Y)GMDV | | |

TABLE 9A-continued

Anti-FIXa VH domain sequences and CDRs

| Ab VH | HCDR1 | HCDR2 | HCDR3 | VH nucleotide sequence | VH amino acid sequence |
|---|---|---|---|---|---|
| N420H | SEQ ID NO: 1 | SEQ ID NO: 2 | SEQ ID NO: 161 AREGYASSSYYGMDV | SEQ ID NO: 238 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATGCCAG TTCGTCCTATTATGGTATGGAC GTCTGGGGCCAAGGGACCACGG TCACCGTCTCCTCAG | SEQ ID NO: 314 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYASSSYYG MDVWGQGTTVTVSS |
| N421H | SEQ ID NO: 1 | SEQ ID NO: 2 | SEQ ID NO: 162 AREGYSASSYYGMDV | SEQ ID NO: 239 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATAGTGC CTCGTCCTATTATGGTATGGAC GTCTGGGGCCAAGGGACCACGG TCACCGTCTCCTCAG | SEQ ID NO: 315 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSASSYYG MDVWGQGTTVTVSS |
| N422H | SEQ ID NO: 1 | SEQ ID NO: 2 | SEQ ID NO: 163 AREGYSSASYYGMDV | SEQ ID NO: 240 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATAGTAG TGCCTCCTATTATGGTATGGAC GTCTGGGGCCAAGGGACCACGG TCACCGTCTCCTCAG | SEQ ID NO: 316 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSSASYYG MDVWGQGTTVTVSS |
| N423H | SEQ ID NO: 1 | SEQ ID NO: 2 | SEQ ID NO: 164 AREGYSSSAYYGMDV | SEQ ID NO: 241 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATAGTAG | SEQ ID NO: 317 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSSSAYYG MDVWGQGTTVTVSS |

TABLE 9A-continued

Anti-FIXa VH domain sequences and CDRs

| Ab VH | HCDR1 | HCDR2 | HCDR3 | VH nucleotide sequence | VH amino acid sequence |
|---|---|---|---|---|---|
| | | | | TTCGGCCTATTATGGTATGGAC GTCTGGGGCCAAGGGACCACGG TCACCGTCTCCTCAG | |
| N430H | SEQ ID NO: 1 | SEQ ID NO: 2 | SEQ ID NO: 165 AREGYSSCSYYGMDV | SEQ ID NO: 242 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATAGTAG TTGCTCCTATTATGGTATGGAC GTCTGGGGCCAAGGGACCACGG TCACCGTCTCCTCAG | SEQ ID NO: 318 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSSCSYYG MDVWGQGTTVTVSS |
| N431H | SEQ ID NO: 1 | SEQ ID NO: 2 | SEQ ID NO: 166 AREGYSSDSYYGMDV | SEQ ID NO: 243 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATAGTAG TGACTCCTATTATGGTATGGAC GTCTGGGGCCAAGGGACCACGG TCACCGTCTCCTCAG | SEQ ID NO: 319 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSSDSYYG MDVWGQGTTVTVSS |
| N432H | SEQ ID NO: 1 | SEQ ID NO: 2 | SEQ ID NO: 167 AREGYSSESYYGMDV | SEQ ID NO: 244 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATAGTAG TGAGTCCTATTATGGTATGGAC GTCTGGGGCCAAGGGACCACGG TCACCGTCTCCTCAG | SEQ ID NO: 320 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSSESYYG MDVWGQGTTVTVSS |
| N433H | SEQ ID NO: 1 | SEQ ID NO: 2 | SEQ ID NO: 168 AREGYSSFSYYGMDV | SEQ ID NO: 245 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT | SEQ ID NO: 321 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSSFSYYG MDVWGQGTTVTVSS |

TABLE 9A-continued

Anti-FIXa VH domain sequences and CDRs

| Ab VH | HCDR1 | HCDR2 | HCDR3 | VH nucleotide sequence | VH amino acid sequence |
|---|---|---|---|---|---|
| | | | | GTGCGAGAGAGGGGTATAGTAG TTTCTCCTATTATGGTATGGAC GTCTGGGGCCAAGGGACCACGG TCACCGTCTCCTCAG | |
| N434H | SEQ ID NO: 1 | SEQ ID NO: 2 | SEQ ID NO: 169 AREGYSSGSYYGMDV | SEQ ID NO: 246 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATAGTAG TGGCTCCTATTATGGTATGGAC GTCTGGGGCCAAGGGACCACGG TCACCGTCTCCTCAG | SEQ ID NO: 322 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSSGSYYG MDVWGQGTTVTVSS |
| N435H | SEQ ID NO: 1 | SEQ ID NO: 2 | SEQ ID NO: 170 AREGYSSHSYYGMDV | SEQ ID NO: 247 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATAGTAG TCACTCCTATTATGGTATGGAC GTCTGGGGCCAAGGGACCACGG TCACCGTCTCCTCAG | SEQ ID NO: 323 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSSHSYYG MDVWGQGTTVTVSS |
| N436H | SEQ ID NO: 1 | SEQ ID NO: 2 | SEQ ID NO: 171 AREGYSSISYYGMDV | SEQ ID NO: 248 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATAGTAG TATCTCCTATTATGGTATGGAC GTCTGGGGCCAAGGGACCACGG TCACCGTCTCCTCAG | SEQ ID NO: 324 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSSISYYG MDVWGQGTTVTVSS |
| N437H | SEQ ID NO: 1 | SEQ ID NO: 2 | SEQ ID NO: 172 AREGYSSKSYYGMDV | SEQ ID NO: 249 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC | SEQ ID NO: 325 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSSKSYYG MDVWGQGTTVTVSS |

TABLE 9A-continued

Anti-FIXa VH domain sequences and CDRs

| Ab VH | HCDR1 | HCDR2 | HCDR3 | VH nucleotide sequence | VH amino acid sequence |
|---|---|---|---|---|---|
| | | | | GAGGACACGGCTGTGTATTACT GTGCGAGAGAGGGGTATAGTAG TAAGTCCTATTATGGTATGGAC GTCTGGGGCCAAGGGACCACGG TCACCGTCTCCTCAG | |
| N438H | SEQ ID NO: 1 | SEQ ID NO: 2 | SEQ ID NO: 173 AREGYSSLSYYGMDV | SEQ ID NO: 250 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATAGTAG TCTGTCCTATTATGGTATGGAC GTCTGGGGCCAAGGGACCACGG TCACCGTCTCCTCAG | SEQ ID NO: 326 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSSLSYYG MDVWGQGTTVTVSS |
| N439H | SEQ ID NO: 1 | SEQ ID NO: 2 | SEQ ID NO: 174 AREGYSSMSYYGMDV | SEQ ID NO: 251 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATAGTAG TATGTCCTATTATGGTATGGAC GTCTGGGGCCAAGGGACCACGG TCACCGTCTCCTCAG | SEQ ID NO: 327 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSSMSYYG MDVWGQGTTVTVSS |
| N440H | SEQ ID NO: 1 | SEQ ID NO: 2 | SEQ ID NO: 175 AREGYSSNSYYGMDV | SEQ ID NO: 252 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATAGTAG TAACTCCTATTATGGTATGGAC GTCTGGGGCCAAGGGACCACGG TCACCGTCTCCTCAG | SEQ ID NO: 328 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSSNSYYG MDVWGQGTTVTVSS |
| N441H | SEQ ID NO: 1 | SEQ ID NO: 2 | SEQ ID NO: 176 AREGYSSPSYYGMDV | SEQ ID NO: 253 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT | SEQ ID NO: 329 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSSPSYYG MDVWGQGTTVTVSS |

TABLE 9A-continued

Anti-FIXa VH domain sequences and CDRs

| Ab VH | HCDR1 | HCDR2 | HCDR3 | VH nucleotide sequence | VH amino acid sequence |
|---|---|---|---|---|---|
| | | | | ACAAATGAACAGCCTGAGAGCC GAGGACACGGCTGTGTATTACT GTGCGAGAGAGGGGTATAGTAG TCCCTCCTATTATGGTATGGAC GTCTGGGGCCAAGGGACCACGG TCACCGTCTCCTCAG | |
| N442H | SEQ ID NO: 1 | SEQ ID NO: 2 | SEQ ID NO: 177 AREGYSSQSYYGMDV | SEQ ID NO: 254 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATAGTAG TCAGTCCTATTATGGTATGGAC GTCTGGGGCCAAGGGACCACGG TCACCGTCTCCTCAG | SEQ ID NO: 340 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSSQSYYG MDVWGQGTTVTVSS |
| N443H | SEQ ID NO: 1 | SEQ ID NO: 2 | SEQ ID NO: 178 AREGYSSRSYYGMDV | SEQ ID NO: 255 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATAGTAG TAGATCCTATTATGGTATGGAC GTCTGGGGCCAAGGGACCACGG TCACCGTCTCCTCAG | SEQ ID NO: 341 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSSRSYYG MDVWGQGTTVTVSS |
| N444H | SEQ ID NO: 1 | SEQ ID NO: 2 | SEQ ID NO: 179 AREGYSSTSYYGMDV | SEQ ID NO: 256 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATAGTAG TACCTCCTATTATGGTATGGAC GTCTGGGGCCAAGGGACCACGG TCACCGTCTCCTCAG | SEQ ID NO: 342 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSSTSYYG MDVWGQGTTVTVSS |
| N445H | SEQ ID NO: 1 | SEQ ID NO: 2 | SEQ ID NO: 180 AREGYSSVSYYGMDV | SEQ ID NO: 257 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA | SEQ ID NO: 343 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSSVSYYG MDVWGQGTTVTVSS |

TABLE 9A-continued

Anti-FIXa VH domain sequences and CDRs

| Ab VH | HCDR1 | HCDR2 | HCDR3 | VH nucleotide sequence | VH amino acid sequence |
|---|---|---|---|---|---|
| | | | | ACGCCAAGAAATCAGTGTATGT ACAAATGAACAGCCTGAGAGCC GAGGACACGGCTGTGTATTACT GTGCGAGAGAGGGGTATAGTAG TGTGTCCTATTATGGTATGGAC GTCTGGGGCCAAGGGACCACGG TCACCGTCTCCTCAG | |
| N446H | SEQ ID NO: 1 | SEQ ID NO: 2 | SEQ ID NO: 181 AREGYSSWSYYGMDV | SEQ ID NO: 258 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATAGTAG TTGGTCCTATTATGGTATGGAC GTCTGGGGCCAAGGGACCACGG TCACCGTCTCCTCAG | SEQ ID NO: 344 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSSWSYYG MDVWGQGTTVTVSS |
| N447H | SEQ ID NO: 1 | SEQ ID NO: 2 | SEQ ID NO: 182 AREGYSSYSYYGMDV | SEQ ID NO: 259 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATAGTAG TTACTCCTATTATGGTATGGAC GTCTGGGGCCAAGGGACCACGG TCACCGTCTCCTCAG | SEQ ID NO: 345 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSSYSYYG MDVWGQGTTVTVSS |
| N448H | SEQ ID NO: 1 | SEQ ID NO: 2 | SEQ ID NO: 183 AREGYSSSCYYGMDV | SEQ ID NO: 260 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATAGTAG TTCGTGCTATTATGGTATGGAC GTCTGGGGCCAAGGGACCACGG TCACCGTCTCCTCAG | SEQ ID NO: 346 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSSSCYYG MDVWGQGTTVTVSS |
| N449H | SEQ ID NO: 1 | SEQ ID NO: 2 | SEQ ID NO: 184 AREGYSSSDYYGMDV | SEQ ID NO: 261 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC | SEQ ID NO: 347 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSSSDYYG MDVWGQGTTVTVSS |

TABLE 9A-continued

Anti-FIXa VH domain sequences and CDRs

| Ab VH | HCDR1 | HCDR2 | HCDR3 | VH nucleotide sequence | VH amino acid sequence |
|---|---|---|---|---|---|
| | | | | CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATAGTAG TTCGGACTATTATGGTATGGAC GTCTGGGGCCAAGGGACCACGG TCACCGTCTCCTCAG | |
| N450H | SEQ ID NO: 1 | SEQ ID NO: 2 | SEQ ID NO: 185 AREGYSSSEYYGMDV | SEQ ID NO: 262 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATAGTAG TTCGGAGTATTATGGTATGGAC GTCTGGGGCCAAGGGACCACGG TCACCGTCTCCTCAG | SEQ ID NO: 348 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSSSEYYG MDVWGQGTTVTVSS |
| N451H | SEQ ID NO: 1 | SEQ ID NO: 2 | SEQ ID NO: 186 AREGYSSSFYYGMDV | SEQ ID NO: 263 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATAGTAG TTCGTTCTATTATGGTATGGAC GTCTGGGGCCAAGGGACCACGG TCACCGTCTCCTCAG | SEQ ID NO: 349 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSSSFYYG MDVWGQGTTVTVSS |
| N452H | SEQ ID NO: 1 | SEQ ID NO: 2 | SEQ ID NO: 187 AREGYSSSGYYGMDV | SEQ ID NO: 264 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATAGTAG TTCGGGCTATTATGGTATGGAC GTCTGGGGCCAAGGGACCACGG TCACCGTCTCCTCAG | SEQ ID NO: 350 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSSSGYYG MDVWGQGTTVTVSS |
| N453H | SEQ ID NO: 1 | SEQ ID NO: 2 | SEQ ID NO: 188 AREGYSSSHYYGMDV | SEQ ID NO: 265 GAGGTGCAGCTGGTGGAGTCTG GGGGAGGCTTTGTCCAGCCTGG GGGGTCCCTGAGACTCTCCTGT GCAGTCTCTGGATTCACCTTTA | SEQ ID NO: 351 EVQLVESGGGFVQPGGSL RLSCAVSGFTFNSYWMSW VRQAPGKGLEWVANINQD GSEKFYVASVKGRFTMSR |

TABLE 9A-continued

Anti-FIXa VH domain sequences and CDRs

| Ab VH | HCDR1 | HCDR2 | HCDR3 | VH nucleotide sequence | VH amino acid sequence |
|---|---|---|---|---|---|
| | | | | ATAGCTATTGGATGAGCTGGGT<br>CCGCCAGGCTCCAGGGAAGGGG<br>CTGGAGTGGGTGGCCAACATAA<br>ACCAAGATGGAAGTGAGAAATT<br>CTATGTGGCCTCTGTGAAGGGC<br>CGATTCACCATGTCCAGAGACA<br>ACGCCAAGAAATCAGTGTATGT<br>ACAAATGAACAGCCTGAGAGCC<br>GAGGACACGGCTGTGTATTACT<br>GTGCGAGAGAGGGGTATAGTAG<br>TTCGCACTATTATGGTATGGAC<br>GTCTGGGGCCAAGGGACCACGG<br>TCACCGTCTCCTCAG | DNAKKSVYVQMNSLRAED<br>TAVYYCAREGYSSSHYYG<br>MDVWGQGTTVTVSS |
| N454H | SEQ ID NO: 1 | SEQ ID NO: 2 | SEQ ID NO: 189<br>AREGYSSSIYYGMDV | SEQ ID NO: 266<br>GAGGTGCAGCTGGTGGAGTCTG<br>GGGGAGGCTTTGTCCAGCCTGG<br>GGGGTCCCTGAGACTCTCCTGT<br>GCAGTCTCTGGATTCACCTTTA<br>ATAGCTATTGGATGAGCTGGGT<br>CCGCCAGGCTCCAGGGAAGGGG<br>CTGGAGTGGGTGGCCAACATAA<br>ACCAAGATGGAAGTGAGAAATT<br>CTATGTGGCCTCTGTGAAGGGC<br>CGATTCACCATGTCCAGAGACA<br>ACGCCAAGAAATCAGTGTATGT<br>ACAAATGAACAGCCTGAGAGCC<br>GAGGACACGGCTGTGTATTACT<br>GTGCGAGAGAGGGGTATAGTAG<br>TTCGATCTATTATGGTATGGAC<br>GTCTGGGGCCAAGGGACCACGG<br>TCACCGTCTCCTCAG | SEQ ID NO: 352<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYSSSIYYG<br>MDVWGQGTTVTVSS |
| N455H | SEQ ID NO: 1 | SEQ ID NO: 2 | SEQ ID NO: 190<br>AREGYSSSKYYGMDV | SEQ ID NO: 267<br>GAGGTGCAGCTGGTGGAGTCTG<br>GGGGAGGCTTTGTCCAGCCTGG<br>GGGGTCCCTGAGACTCTCCTGT<br>GCAGTCTCTGGATTCACCTTTA<br>ATAGCTATTGGATGAGCTGGGT<br>CCGCCAGGCTCCAGGGAAGGGG<br>CTGGAGTGGGTGGCCAACATAA<br>ACCAAGATGGAAGTGAGAAATT<br>CTATGTGGCCTCTGTGAAGGGC<br>CGATTCACCATGTCCAGAGACA<br>ACGCCAAGAAATCAGTGTATGT<br>ACAAATGAACAGCCTGAGAGCC<br>GAGGACACGGCTGTGTATTACT<br>GTGCGAGAGAGGGGTATAGTAG<br>TTCGAAGTATTATGGTATGGAC<br>GTCTGGGGCCAAGGGACCACGG<br>TCACCGTCTCCTCAG | SEQ ID NO: 353<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYSSSKYYG<br>MDVWGQGTTVTVSS |
| N456H | SEQ ID NO: 1 | SEQ ID NO: 2 | SEQ ID NO: 191<br>AREGYSSLYYGMDV | SEQ ID NO: 268<br>GAGGTGCAGCTGGTGGAGTCTG<br>GGGGAGGCTTTGTCCAGCCTGG<br>GGGGTCCCTGAGACTCTCCTGT<br>GCAGTCTCTGGATTCACCTTTA<br>ATAGCTATTGGATGAGCTGGGT<br>CCGCCAGGCTCCAGGGAAGGGG<br>CTGGAGTGGGTGGCCAACATAA<br>ACCAAGATGGAAGTGAGAAATT<br>CTATGTGGCCTCTGTGAAGGGC<br>CGATTCACCATGTCCAGAGACA<br>ACGCCAAGAAATCAGTGTATGT<br>ACAAATGAACAGCCTGAGAGCC<br>GAGGACACGGCTGTGTATTACT<br>GTGCGAGAGAGGGGTATAGTAG<br>TTCGCTGTATTATGGTATGGAC<br>GTCTGGGGCCAAGGGACCACGG<br>TCACCGTCTCCTCAG | SEQ ID NO: 354<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYSSSLYYG<br>MDVWGQGTTVTVSS |

TABLE 9A-continued

Anti-FIXa VH domain sequences and CDRs

| Ab VH | HCDR1 | HCDR2 | HCDR3 | VH nucleotide sequence | VH amino acid sequence |
|---|---|---|---|---|---|
| N457H | SEQ ID NO: 1 | SEQ ID NO: 2 | SEQ ID NO: 192 AREGYSSSMYYGMDV | SEQ ID NO: 269 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATAGTAG TTCGATGTATTATGGTATGGAC GTCTGGGGCCAAGGGACCACGG TCACCGTCTCCTCAG | SEQ ID NO: 355 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSSSMYYG MDVWGQGTTVTVSS |
| N458H | SEQ ID NO: 1 | SEQ ID NO: 2 | SEQ ID NO: 193 AREGYSSSNYYGMDV | SEQ ID NO: 270 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATAGTAG TTCGAACTATTATGGTATGGAC GTCTGGGGCCAAGGGACCACGG TCACCGTCTCCTCAG | SEQ ID NO: 356 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSSSNYYG MDVWGQGTTVTVSS |
| N459H | SEQ ID NO: 1 | SEQ ID NO: 2 | SEQ ID NO: 194 AREGYSSSPYYGMDV | SEQ ID NO: 271 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATAGTAG TTCGCCCTATTATGGTATGGAC GTCTGGGGCCAAGGGACCACGG TCACCGTCTCCTCAG | SEQ ID NO: 357 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSSSPYYG MDVWGQGTTVTVSS |
| N460H | SEQ ID NO: 1 | SEQ ID NO: 2 | SEQ ID NO: 195 AREGYSSSQYYGMDV | SEQ ID NO: 272 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATAGTAG | SEQ ID NO: 358 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSSSQYYG MDVWGQGTTVTVSS |

TABLE 9A-continued

Anti-FIXa VH domain sequences and CDRs

| Ab VH | HCDR1 | HCDR2 | HCDR3 | VH nucleotide sequence | VH amino acid sequence |
|---|---|---|---|---|---|
| | | | | TTCGCAGTATTATGGTATGGAC GTCTGGGGCCAAGGGACCACGG TCACCGTCTCCTCAG | |
| N461H | SEQ ID NO: 1 | SEQ ID NO: 2 | SEQ ID NO: 196 AREGYSSSRYYGMDV | SEQ ID NO: 273 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATAGTAG TTCGAGATATTATGGTATGGAC GTCTGGGGCCAAGGGACCACGG TCACCGTCTCCTCAG | SEQ ID NO: 359 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSSSRYYG MDVWGQGTTVTVSS |
| N462H | SEQ ID NO: 1 | SEQ ID NO: 2 | SEQ ID NO: 197 AREGYSSSTYYGMDV | SEQ ID NO: 274 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATAGTAG TTCGACCTATTATGGTATGGAC GTCTGGGGCCAAGGGACCACGG TCACCGTCTCCTCAG | SEQ ID NO: 360 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSSSTYYG MDVWGQGTTVTVSS |
| N463H | SEQ ID NO: 1 | SEQ ID NO: 2 | SEQ ID NO: 198 AREGYSSSVYYGMDV | SEQ ID NO: 275 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATAGTAG TTCGGTGTATTATGGTATGGAC GTCTGGGGCCAAGGGACCACGG TCACCGTCTCCTCAG | SEQ ID NO: 361 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSSSVYYG MDVWGQGTTVTVSS |
| N464H | SEQ ID NO: 1 | SEQ ID NO: 2 | SEQ ID NO: 199 AREGYSSSWYYGMDV | SEQ ID NO: 276 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT | SEQ ID NO: 362 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSSSWYYG MDVWGQGTTVTVSS |

TABLE 9A-continued

Anti-FIXa VH domain sequences and CDRs

| Ab VH | HCDR1 | HCDR2 | HCDR3 | VH nucleotide sequence | VH amino acid sequence |
|---|---|---|---|---|---|
| | | | | GTGCGAGAGAGGGGTATAGTAG TTCGTGGTATTATGGTATGGAC GTCTGGGGCCAAGGGACCACGG TCACCGTCTCCTCAG | |
| N465H | SEQ ID NO: 1 | SEQ ID NO: 2 | SEQ ID NO: 200 AREGYSSSYYYGMDV | SEQ ID NO: 277 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATAGTAG TTCGTACTATTATGGTATGGAC GTCTGGGGCCAAGGGACCACGG TCACCGTCTCCTCAG | SEQ ID NO: 363 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSSSYYYG MDVWGQGTTVTVSS |
| N467H | SEQ ID NO: 1 | SEQ ID NO: 2 | SEQ ID NO: 201 AREGYCSSSYYYGMDV | SEQ ID NO: 278 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATTGCAG TTCGTCCTATTATGGTATGGAC GTCTGGGGCCAAGGGACCACGG TCACCGTCTCCTCAG | SEQ ID NO: 364 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYCSSSYYG MDVWGQGTTVTVSS |
| N468H | SEQ ID NO: 1 | SEQ ID NO: 2 | SEQ ID NO: 202 AREGYDSSSYYYGMDV | SEQ ID NO: 279 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATGACAG TTCGTCCTATTATGGTATGGAC GTCTGGGGCCAAGGGACCACGG TCACCGTCTCCTCAG | SEQ ID NO: 365 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYDSSSYYG MDVWGQGTTVTVSS |
| N469H | SEQ ID NO: 1 | SEQ ID NO: 2 | SEQ ID NO: 203 AREGYESSSYYYGMDV | SEQ ID NO: 280 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC | SEQ ID NO: 366 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYESSSYYG MDVWGQGTTVTVSS |

TABLE 9A-continued

Anti-FIXa VH domain sequences and CDRs

| Ab VH | HCDR1 | HCDR2 | HCDR3 | VH nucleotide sequence | VH amino acid sequence |
|---|---|---|---|---|---|
| | | | | GAGGACACGGCTGTGTATTACT GTGCGAGAGAGGGGTATGAGAG TTCGTCCTATTATGGTATGGAC GTCTGGGGCCAAGGGACCACGG TCACCGTCTCCTCAG | |
| N470H | SEQ ID NO: 1 | SEQ ID NO: 2 | SEQ ID NO: 204 AREGYFSSSYYGMDV | SEQ ID NO: 281 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATTTCAG TTCGTCCTATTATGGTATGGAC GTCTGGGGCCAAGGGACCACGG TCACCGTCTCCTCAG | SEQ ID NO: 367 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYFSSSYYG MDVWGQGTTVTVSS |
| N471H | SEQ ID NO: 1 | SEQ ID NO: 2 | SEQ ID NO: 205 AREGYGSSSYYGMDV | SEQ ID NO: 282 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATGGCAG TTCGTCCTATTATGGTATGGAC GTCTGGGGCCAAGGGACCACGG TCACCGTCTCCTCAG | SEQ ID NO: 368 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYGSSSYYG MDVWGQGTTVTVSS |
| N472H | SEQ ID NO: 1 | SEQ ID NO: 2 | SEQ ID NO: 206 AREGYHSSSYYGMDV | SEQ ID NO: 283 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATCACAG TTCGTCCTATTATGGTATGGAC GTCTGGGGCCAAGGGACCACGG TCACCGTCTCCTCAG | SEQ ID NO: 369 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYHSSSYYG MDVWGQGTTVTVSS |
| N473H | SEQ ID NO: 1 | SEQ ID NO: 2 | SEQ ID NO: 207 AREGYISSSYYGMDV | SEQ ID NO: 284 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT | SEQ ID NO: 370 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYISSSYYG MDVWGQGTTVTVSS |

TABLE 9A-continued

Anti-FIXa VH domain sequences and CDRs

| Ab VH | HCDR1 | HCDR2 | HCDR3 | VH nucleotide sequence | VH amino acid sequence |
|---|---|---|---|---|---|
| | | | | ACAAATGAACAGCCTGAGAGCC GAGGACACGGCTGTGTATTACT GTGCGAGAGAGGGGTATATCAG TTCGTCCTATTATGGTATGGAC GTCTGGGGCCAAGGGACCACGG TCACCGTCTCCTCAG | |
| N474H | SEQ ID NO: 1 | SEQ ID NO: 2 | SEQ ID NO: 208 AREGYKSSSYYGMDV | SEQ ID NO: 285 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATAAGAG TTCGTCCTATTATGGTATGGAC GTCTGGGGCCAAGGGACCACGG TCACCGTCTCCTCAG | SEQ ID NO: 371 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYKSSSYYG MDVWGQGTTVTVSS |
| N475H | SEQ ID NO: 1 | SEQ ID NO: 2 | SEQ ID NO: 209 AREGYLSSSYYGMDV | SEQ ID NO: 286 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATCTGAG TTCGTCCTATTATGGTATGGAC GTCTGGGGCCAAGGGACCACGG TCACCGTCTCCTCAG | SEQ ID NO: 372 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYLSSSYYG MDVWGQGTTVTVSS |
| N476H | SEQ ID NO: 1 | SEQ ID NO: 2 | SEQ ID NO: 210 AREGYMSSSYYGMDV | SEQ ID NO: 287 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATATGAG TTCGTCCTATTATGGTATGGAC GTCTGGGGCCAAGGGACCACGG TCACCGTCTCCTCAG | SEQ ID NO: 373 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYMSSSYYG MDVWGQGTTVTVSS |
| N477H | SEQ ID NO: 1 | SEQ ID NO: 2 | SEQ ID NO: 211 AREGYNSSSYYGMDV | SEQ ID NO: 288 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA | SEQ ID NO: 374 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYNSSSYYG MDVWGQGTTVTVSS |

TABLE 9A-continued

Anti-FIXa VH domain sequences and CDRs

| Ab VH | HCDR1 | HCDR2 | HCDR3 | VH nucleotide sequence | VH amino acid sequence |
|---|---|---|---|---|---|
| | | | | ACGCCAAGAAATCAGTGTATGT ACAAATGAACAGCCTGAGAGCC GAGGACACGGCTGTGTATTACT GTGCGAGAGAGGGGTATAACAG TTCGTCCTATTATGGTATGGAC GTCTGGGGCCAAGGGACCACGG TCACCGTCTCCTCAG | |
| N478H | SEQ ID NO: 1 | SEQ ID NO: 2 | SEQ ID NO: 212 AREGYPSSSYYGMDV | SEQ ID NO: 289 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATCCCAG TTCGTCCTATTATGGTATGGAC GTCTGGGGCCAAGGGACCACGG TCACCGTCTCCTCAG | SEQ ID NO: 375 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYPSSSYYG MDVWGQGTTVTVSS |
| N479H | SEQ ID NO: 1 | SEQ ID NO: 2 | SEQ ID NO: 213 AREGYQSSSYYGMDV | SEQ ID NO: 290 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATCAGAG TTCGTCCTATTATGGTATGGAC GTCTGGGGCCAAGGGACCACGG TCACCGTCTCCTCAG | SEQ ID NO: 376 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYQSSSYYG MDVWGQGTTVTVSS |
| N480H | SEQ ID NO: 1 | SEQ ID NO: 2 | SEQ ID NO: 214 AREGYRSSSYYGMDV | SEQ ID NO: 291 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATAGAAG TTCGTCCTATTATGGTATGGAC GTCTGGGGCCAAGGGACCACGG TCACCGTCTCCTCAG | SEQ ID NO: 377 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYRSSSYYG MDVWGQGTTVTVSS |
| N481H | SEQ ID NO: 1 | SEQ ID NO: 2 | SEQ ID NO: 215 AREGYTSSSYYGMDV | SEQ ID NO: 292 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC | SEQ ID NO: 378 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYTSSSYYG MDVWGQGTTVTVSS |

TABLE 9A-continued

Anti-FIXa VH domain sequences and CDRs

| Ab VH | HCDR1 | HCDR2 | HCDR3 | VH nucleotide sequence | VH amino acid sequence |
|---|---|---|---|---|---|
| | | | | CGATTCACCATGTCCAGAGACA ACGCCAAGAAATCAGTGTATGT ACAAATGAACAGCCTGAGAGCC GAGGACACGGCTGTGTATTACT GTGCGAGAGAGGGTATACCAG TTCGTCCTATTATGGTATGGAC GTCTGGGGCCAAGGGACCACGG TCACCGTCTCCTCAG | |
| N482H | SEQ ID NO: 1 | SEQ ID NO: 2 | SEQ ID NO: 216 AREGYVSSSYYGMDV | SEQ ID NO: 293 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATGTGAG TTCGTCCTATTATGGTATGGAC GTCTGGGGCCAAGGGACCACGG TCACCGTCTCCTCAG | SEQ ID NO: 379 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYVSSSYYG MDVWGQGTTVTVSS |
| N483H | SEQ ID NO: 1 | SEQ ID NO: 2 | SEQ ID NO: 217 AREGYWSSSYYGMDV | SEQ ID NO: 294 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATTGGAG TTCGTCCTATTATGGTATGGAC GTCTGGGGCCAAGGGACCACGG TCACCGTCTCCTCAG | SEQ ID NO: 380 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYWSSSYYG MDVWGQGTTVTVSS |
| N484H | SEQ ID NO: 1 | SEQ ID NO: 2 | SEQ ID NO: 218 AREGYYSSSYYGMDV | SEQ ID NO: 295 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATTACAG TTCGTCCTATTATGGTATGGAC GTCTGGGGCCAAGGGACCACGG TCACCGTCTCCTCAG | SEQ ID NO: 381 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYYSSSYYG MDVWGQGTTVTVSS |
| N485H | SEQ ID NO: 1 | SEQ ID NO: 2 | SEQ ID NO: 219 AREGYSCSSYYGMDV | SEQ ID NO: 296 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT | SEQ ID NO: 382 EVQLVESGGGFVQPGGSL RLSCAVSGFTFNSYWMSW VRQAPGKGLEWVANINQD GSEKFYVASVKGRFTMSR DNAKKSVYVQMNSLRAED |

TABLE 9A-continued

Anti-FIXa VH domain sequences and CDRs

| Ab VH | HCDR1 | HCDR2 | HCDR3 | VH nucleotide sequence | VH amino acid sequence |
|---|---|---|---|---|---|
| | | | | CCGCCAGGCTCCAGGGAAGGGG<br>CTGGAGTGGGTGGCCAACATAA<br>ACCAAGATGGAAGTGAGAAATT<br>CTATGTGGCCTCTGTGAAGGGC<br>CGATTCACCATGTCCAGAGACA<br>ACGCCAAGAAATCAGTGTATGT<br>ACAAATGAACAGCCTGAGAGCC<br>GAGGACACGGCTGTGTATTACT<br>GTGCGAGAGAGGGGTATAGTTG<br>CTCGTCCTATTATGGTATGGAC<br>GTCTGGGGCCAAGGGACCACGG<br>TCACCGTCTCCTCAG | TAVYYCAREGYSCSSYYG<br>MDVWGQGTTVTVSS |
| N486H | SEQ ID NO: 1 | SEQ ID NO: 2 | SEQ ID NO: 220<br>AREGYSDSSYYGMDV | SEQ ID NO: 297<br>GAGGTGCAGCTGGTGGAGTCTG<br>GGGGAGGCTTTGTCCAGCCTGG<br>GGGGTCCCTGAGACTCTCCTGT<br>GCAGTCTCTGGATTCACCTTTA<br>ATAGCTATTGGATGAGCTGGGT<br>CCGCCAGGCTCCAGGGAAGGGG<br>CTGGAGTGGGTGGCCAACATAA<br>ACCAAGATGGAAGTGAGAAATT<br>CTATGTGGCCTCTGTGAAGGGC<br>CGATTCACCATGTCCAGAGACA<br>ACGCCAAGAAATCAGTGTATGT<br>ACAAATGAACAGCCTGAGAGCC<br>GAGGACACGGCTGTGTATTACT<br>GTGCGAGAGAGGGGTATAGTGA<br>CTCGTCCTATTATGGTATGGAC<br>GTCTGGGGCCAAGGGACCACGG<br>TCACCGTCTCCTCAG | SEQ ID NO: 383<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYSDSSYYG<br>MDVWGQGTTVTVSS |
| N487H | SEQ ID NO: 1 | SEQ ID NO: 2 | SEQ ID NO: 221<br>AREGYSESSYYGMDV | SEQ ID NO: 298<br>GAGGTGCAGCTGGTGGAGTCTG<br>GGGGAGGCTTTGTCCAGCCTGG<br>GGGGTCCCTGAGACTCTCCTGT<br>GCAGTCTCTGGATTCACCTTTA<br>ATAGCTATTGGATGAGCTGGGT<br>CCGCCAGGCTCCAGGGAAGGGG<br>CTGGAGTGGGTGGCCAACATAA<br>ACCAAGATGGAAGTGAGAAATT<br>CTATGTGGCCTCTGTGAAGGGC<br>CGATTCACCATGTCCAGAGACA<br>ACGCCAAGAAATCAGTGTATGT<br>ACAAATGAACAGCCTGAGAGCC<br>GAGGACACGGCTGTGTATTACT<br>GTGCGAGAGAGGGGTATAGTGA<br>GTCGTCCTATTATGGTATGGAC<br>GTCTGGGGCCAAGGGACCACGG<br>TCACCGTCTCCTCAG | SEQ ID NO: 384<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYSESSYYG<br>MDVWGQGTTVTVSS |
| N488H | SEQ ID NO: 1 | SEQ ID NO: 2 | SEQ ID NO: 223<br>AREGYSFSSYYGMDV | SEQ ID NO: 299<br>GAGGTGCAGCTGGTGGAGTCTG<br>GGGGAGGCTTTGTCCAGCCTGG<br>GGGGTCCCTGAGACTCTCCTGT<br>GCAGTCTCTGGATTCACCTTTA<br>ATAGCTATTGGATGAGCTGGGT<br>CCGCCAGGCTCCAGGGAAGGGG<br>CTGGAGTGGGTGGCCAACATAA<br>ACCAAGATGGAAGTGAGAAATT<br>CTATGTGGCCTCTGTGAAGGGC<br>CGATTCACCATGTCCAGAGACA<br>ACGCCAAGAAATCAGTGTATGT<br>ACAAATGAACAGCCTGAGAGCC<br>GAGGACACGGCTGTGTATTACT<br>GTGCGAGAGAGGGGTATAGTTT<br>CTCGTCCTATTATGGTATGGAC<br>GTCTGGGGCCAAGGGACCACGG<br>TCACCGTCTCCTCAG | SEQ ID NO: 385<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYSFSSYYG<br>MDVWGQGTTVTVSS |
| N489H | SEQ ID NO: 1 | SEQ ID NO: 2 | SEQ ID NO: 224<br>AREGYSGSSYYGMDV | SEQ ID NO: 300<br>GAGGTGCAGCTGGTGGAGTCTG<br>GGGGAGGCTTTGTCCAGCCTGG<br>GGGGTCCCTGAGACTCTCCTGT<br>GCAGTCTCTGGATTCACCTTTA | SEQ ID NO: 386<br>EVQLVESGGGFVQPGGSL<br>RLSCAVSGFTFNSYWMSW<br>VRQAPGKGLEWVANINQD<br>GSEKFYVASVKGRFTMSR |

TABLE 9A-continued

Anti-FIXa VH domain sequences and CDRs

| Ab VH | HCDR1 | HCDR2 | HCDR3 | VH nucleotide sequence | VH amino acid sequence |
|---|---|---|---|---|---|
| | | | | ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATAGTGG CTCGTCCTATTATGGTATGGAC GTCTGGGGCCAAGGGACCACGG TCACCGTCTCCTCAG | DNAKKSVYVQMNSLRAED TAVYYCAREGYSGSSYYG MDVWGQGTTVTVSS |
| N490H | SEQ ID NO: 1 | SEQ ID NO: 2 | SEQ ID NO: 225 AREGYSHSSYYGMDV | SEQ ID NO: 301 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATAGTCA CTCGTCCTATTATGGTATGGAC GTCTGGGGCCAAGGGACCACGG TCACCGTCTCCTCAG | SEQ ID NO: 387 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSHSSYYG MDVWGQGTTVTVSS |
| N491H | SEQ ID NO: 1 | SEQ ID NO: 2 | SEQ ID NO: 226 AREGYSISSYYGMDV | SEQ ID NO: 302 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATAGTAT CTCGTCCTATTATGGTATGGAC GTCTGGGGCCAAGGGACCACGG TCACCGTCTCCTCAG | SEQ ID NO: 388 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSISSYYG MDVWGQGTTVTVSS |
| N492H | SEQ ID NO: 1 | SEQ ID NO: 2 | SEQ ID NO: 227 AREGYSKSSYYGMDV | SEQ ID NO: 303 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATAGTAA GTCGTCCTATTATGGTATGGAC GTCTGGGGCCAAGGGACCACGG TCACCGTCTCCTCAG | SEQ ID NO: 389 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSKSSYYG MDVWGQGTTVTVSS |
| N493H | SEQ ID NO: 1 | SEQ ID NO: 2 | SEQ ID NO: 228 AREGYSLSSYYGMDV | SEQ ID NO: 304 GAGGTGCAGCTGGTGGAGTCTG GGGGAGGCTTTGTCCAGCCTGG GGGGTCCCTGAGACTCTCCTGT | SEQ ID NO: 390 EVQLVESGGGFVQPGGSL RLSCAVSGFTFNSYWMSW VRQAPGKGLEWVANINQD |

TABLE 9A-continued

Anti-FIXa VH domain sequences and CDRs

| Ab VH | HCDR1 | HCDR2 | HCDR3 | VH nucleotide sequence | VH amino acid sequence |
|---|---|---|---|---|---|
| | | | | GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATAGTCT GTCGTCCTATTATGGTATGGAC GTCTGGGGCCAAGGGACCACGG TCACCGTCTCCTCAG | GSEKFYVASVKGRFTMSR DNAKKSVYVQMNSLRAED TAVYYCAREGYSLSSYYG MDVWGQGTTVTVSS |
| N494H | SEQ ID NO: 1 | SEQ ID NO: 2 | SEQ ID NO: 229 AREGYSMSSYYGMDV | SEQ ID NO: 305 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATAGTAT GTCGTCCTATTATGGTATGGAC GTCTGGGGCCAAGGGACCACGG TCACCGTCTCCTCAG | SEQ ID NO: 391 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSMSSYYG MDVWGQGTTVTVSS |
| N495H | SEQ ID NO: 1 | SEQ ID NO: 2 | SEQ ID NO: 230 AREGYSNSSYYGMDV | SEQ ID NO: 306 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATAGTAA CTCGTCCTATTATGGTATGGAC GTCTGGGGCCAAGGGACCACGG TCACCGTCTCCTCAG | SEQ ID NO: 392 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSNSSYYG MDVWGQGTTVTVSS |
| N496H | SEQ ID NO: 1 | SEQ ID NO: 2 | SEQ ID NO: 231 AREGYSPSSYYGMDV | SEQ ID NO: 307 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATAGTCC CTCGTCCTATTATGGTATGGAC GTCTGGGGCCAAGGGACCACGG TCACCGTCTCCTCAG | SEQ ID NO: 393 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSPSSYYG MDVWGQGTTVTVSS |

TABLE 9A-continued

Anti-FIXa VH domain sequences and CDRs

| Ab VH | HCDR1 | HCDR2 | HCDR3 | VH nucleotide sequence | VH amino acid sequence |
|---|---|---|---|---|---|
| N497H | SEQ ID NO: 1 | SEQ ID NO: 2 | SEQ ID NO: 232 AREGYSQSSYYGMDV | SEQ ID NO: 308 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGTATAGTCA GTCGTCCTATTATGGTATGGAC GTCTGGGGCCAAGGGACCACGG TCACCGTCTCCTCAG | SEQ ID NO: 394 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSQSSYYG MDVWGQGTTVTVSS |
| N498H | SEQ ID NO: 1 | SEQ ID NO: 2 | SEQ ID NO: 233 AREGYSRSSYYGMDV | SEQ ID NO: 309 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATAGTAG ATCGTCCTATTATGGTATGGAC GTCTGGGGCCAAGGGACCACGG TCACCGTCTCCTCAG | SEQ ID NO: 395 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSRSSYYG MDVWGQGTTVTVSS |
| N499H | SEQ ID NO: 1 | SEQ ID NO: 2 | SEQ ID NO: 234 AREGYSTSSYYGMDV | SEQ ID NO: 310 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATAGTAC CTCGTCCTATTATGGTATGGAC GTCTGGGGCCAAGGGACCACGG TCACCGTCTCCTCAG | SEQ ID NO: 396 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSTSSYYG MDVWGQGTTVTVSS |
| N500H | SEQ ID NO: 1 | SEQ ID NO: 2 | SEQ ID NO: 235 AREGYSVSSYYGMDV | SEQ ID NO: 311 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT | SEQ ID NO: 397 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSVSSYYG MDVWGQGTTVTVSS |

TABLE 9A-continued

Anti-FIXa VH domain sequences and CDRs

| Ab VH | HCDR1 | HCDR2 | HCDR3 | VH nucleotide sequence | VH amino acid sequence |
|---|---|---|---|---|---|
| | | | | GTGCGAGAGAGGGGTATAGTGT GTCGTCCTATTATGGTATGGAC GTCTGGGGCCAAGGGACCACGG TCACCGTCTCCTCAG | |
| N501H | SEQ ID NO: 1 | SEQ ID NO: 2 | SEQ ID NO: 236 AREGYSWSSYYGMDV | SEQ ID NO: 312 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATAGTTG GTCGTCCTATTATGGTATGGAC GTCTGGGGCCAAGGGACCACGG TCACCGTCTCCTCAG | SEQ ID NO: 398 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSWSSYYG MDVWGQGTTVTVSS |
| N502H | SEQ ID NO: 1 | SEQ ID NO: 2 | SEQ ID NO: 237 AREGYSYSSYYGMDV | SEQ ID NO: 313 GAGGTGCAGCTGGTGGAGTCTG GGGGAGGCTTTGTCCAGCCTGG GGGGTCCCTGAGACTCTCCTGT GCAGTCTCTGGATTCACCTTTA ATAGCTATTGGATGAGCTGGGT CCGCCAGGCTCCAGGGAAGGGG CTGGAGTGGGTGGCCAACATAA ACCAAGATGGAAGTGAGAAATT CTATGTGGCCTCTGTGAAGGGC CGATTCACCATGTCCAGAGACA ACGCCAAGAAATCAGTGTATGT ACAAATGAACAGCCTGAGAGCC GAGGACACGGCTGTGTATTACT GTGCGAGAGAGGGGTATAGTTA CTCGTCCTATTATGGTATGGAC GTCTGGGGCCAAGGGACCACGG TCACCGTCTCCTCAG | SEQ ID NO: 399 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSYSSYYG MDVWGQGTTVTVSS |
| | | | SEQ ID NO: 400 Consensus HCDR3 of N436 and selected variants with parent N128H AREGYSSXSYYGMDV X is I, L, V, R, W, Q, K, H, E, N, M, S Representing the N436H CDR3 sequence AREGYSSISYYGMDV in which the Ile is retained or replaced by Leu, Val, Arg, Trp, Gln, Lys, His, Glu, Asn, Met or Ser. SEQ ID NO: 401 Consensus HCDR3 of N436 and selected variants AREGYSSXSYYGMDV X is I, L, V, R, W, Q, K, H, E, N or M Representing the N436H CDR3 sequence AREGYSSISYYGMDV in which the Ile is retained or replaced by Leu, Val, Arg, Trp, Gln, Lys, His, Glu, Asn or Met. SEQ ID NO: 402 Consensus HCDR3 of N436 and selected hydrophobic or positively charged variants AREGYSSXSYYGMDV X is I, L, V, R, W, Q or K Representing the N436H CDR3 sequence AREGYSSISYYGMDV in which the Ile is retained or replaced by Leu, Val, Arg, Trp, Gln or Lys. | | |

TABLE 9A-continued

Anti-FIXa VH domain sequences and CDRs

| Ab VH | HCDR1 | HCDR2 | HCDR3 | VH nucleotide sequence | VH amino acid sequence |
|---|---|---|---|---|---|
| | | | SEQ ID NO: 403 Consensus HCDR3 of most active variants AREGYSSXSYYGMDV X is I, L or V Representing the N436H CDR3 sequence AREGYSSISYYGMDV in which the Ile is retained or replaced by Leu or Val. | | |

TABLE 9B

Anti-FIXa VH domain framework sequences

| Ab VH | FR1 | FR2 | FR3 | FR4 |
|---|---|---|---|---|
| N192H | SEQ ID NO: 148 EVQLVESGGGLVQPGGSLRLSCAAS | SEQ ID NO: 133 | SEQ ID NO: 149 YYVDSVKGRFTISRDNAKNSLY LQMNSLRAEDTAVYYC | SEQ ID NO: 135 |
| N212H | SEQ ID NO: 148 | SEQ ID NO: 133 | SEQ ID NO: 149 | SEQ ID NO: 135 |
| N205H | SEQ ID N: 150 EVQLVESGGGLVQPGGSLRLSCVAS | SEQ ID NO: 133 | SEQ ID NO: 149 | SEQ ID NO: 135 |
| N211H | SEQ ID NO: 151 EVQLVESGGGLVQPGGSLRLSCAVS | SEQ ID NO: 133 | SEQ ID NO: 152 FYVASVKGRFTISRDNAKNSVY LQMNSLRAEDTAVYYC | SEQ ID NO: 135 |
| N203H | SEQ ID NO: 151 | SEQ ID NO: 133 | SEQ ID NO: 153 FYVASVKGRFIISRDNAKNSVY LQMNSLRAEDTAVYYC | SEQ ID NO: 154 WGQGTTVSVSS |
| N128H | SEQ ID NO: 132 EVQLVESGGGFVQPGGSLRLSCAVS | SEQ ID NO: 133 MSWVRQAPGKGLEWVAN | SEQ ID NO: 134 FYVASVEGRFTMSRDNAKKSVY VQMNSLRAEDTAVYYC | SEQ ID NO: 135 WGQGTTVTVSS |
| N215H | SEQ ID NO: 148 | SEQ ID NO: 133 | SEQ ID NO: 149 | SEQ ID NO: 135 |
| N216H | SEQ ID NO: 132 | SEQ ID NO: 133 | SEQ ID NO: 152 | SEQ ID NO: 135 |
| N217H | SEQ ID NO: 151 | SEQ ID NO: 133 | SEQ ID NO: 155 FYVASVKGRFTMSRDNAKNSVY LQMNSLRAEDTAVYYC | SEQ ID NO: 135 |
| N218H | SEQ ID NO: 151 | SEQ ID NO: 133 | SEQ ID NO: 156 FYVASVEGRFTISRDNAKKSVY LQMNSLRAEDTAVYYC | SEQ ID NO: 135 |
| N219H | SEQ ID NO: 151 | SEQ ID NO: 133 | SEQ ID NO: 157 FYVASVKGRFTISRDNAKNSVY VQMNSLRAEDTAVYYC | SEQ ID NO: 135 |
| N220H | SEQ ID NO: 132 | SEQ ID NO: 133 | SEQ ID NO: 158 FYVASVEGRFTISRDNAKKSVY VQMNSLRAEDTAVYYC | SEQ ID NO: 135 |
| N221H | SEQ ID NO: 132 | SEQ ID NO: 133 | SEQ ID NO 159 FYVASVKGRFTMSRDNAKNSVY VQMNSLRAEDTAVYYC | SEQ ID NO: 135 |
| N222H | SEQ ID NO: 132 | SEQ ID NO: 133 | SEQ ID NO: 160 FYVASVEGRFTMSRDNAKKSVY LQMNSLRAEDTAVYYC | SEQ ID NO: 135 |
| N223H | SEQ ID NO: 151 | SEQ ID NO: 133 | SEQ ID NO: 134 | SEQ ID NO: 135 |
| N224H | SEQ ID NO: 132 | SEQ ID NO: 133 | SEQ ID NO: 155 | SEQ ID NO: 135 |
| N225H | SEQ ID NO: 132 | SEQ ID NO: 133 | SEQ ID NO: 156 | SEQ ID NO: 135 |
| N226H | SEQ ID NO: 132 | SEQ ID NO: 133 | SEQ ID NO: 157 | SEQ ID NO: 135 |
| N227H | SEQ ID NO: 151 | SEQ ID NO: 133 | SEQ ID NO: 160 | SEQ ID NO: 135 |

TABLE 9B-continued

Anti-FIXa VH domain framework sequences

| Ab VH | FR1 | FR2 | FR3 | FR4 |
|---|---|---|---|---|
| N228H | SEQ ID NO: 151 | SEQ ID NO: 133 | SEQ ID NO: 159 | SEQ ID NO: 135 |
| N229H | SEQ ID NO: 151 | SEQ ID NO: 133 | SEQ ID NO: 158 | SEQ ID NO: 135 |

TABLE 9C

Anti-FIXa VL domain sequences and CDRs

| Ab VL | LCDR1 | LCDR2 | LCDR3 | VL nucleotide sequence | VL amino acid sequence |
|---|---|---|---|---|---|
| N128L | SEQ ID NO: 6<br>NIGRKS | SEQ ID NO: 7<br>YDS | SEQ ID NO: 8<br>QVWDGSSDHWV | SEQ ID NO: 9<br>TCCTATGTGCTGACTCAGCCACCC<br>TCAGTGTCAGTGGCCCCAGGAGAG<br>ACGGCCAGGATTACCTGTGGGGGA<br>GACAACATTGGAAGGAAAAGTGTG<br>TACTGGTACCAGCAGAAGTCAGGC<br>CAGGCCCCTGTGCTGGTCATCTAT<br>TATGATAGCGACCGGCCCTCAGGG<br>ATCCCTGAGCGATTCTCTGGGTCC<br>AACTCTGGGAACACGGCGACCCTG<br>ACCATCAGCAGGGTCGAAGCCGGG<br>GATGAGGCCGACTATTACTGTCAG<br>GTGTGGGATGGAAGTAGTGATCAT<br>TGGGTGTTCGGCGGAGGGACCAAG<br>TTGACCGTCCTAG | SEQ ID NO: 10<br>SYVLTQPPSVSVAPGETA<br>RITCGGDNIGRKSVYWYQ<br>QKSGQAPVLVIYYDSDRP<br>SGIPERFSGSNSGNTATL<br>TISRVEAGDEADYYCQVW<br>DGSSDHWVFGGGTKLTVL |

TABLE 9D

Anti-FIXa VL domain framework sequences

| Ab VL | FR1 | FR2 | FR3 | FR4 |
|---|---|---|---|---|
| N128L | SEQ ID NO: 136<br>SYVLTQPPSV<br>SVAPGETARI<br>TCGGD | SEQ ID NO: 137<br>VYWYQQKSG<br>QAPVLVIY | SEQ ID NO: 138<br>DRPSGIPERF<br>SGSNSGNTAT<br>LTISRVEAGD<br>EADYYC | SEQ ID NO: 139<br>FGGGTKLTVL |

FX Binding Arm Polypeptide Sequences

TABLE 10A

Anti-FX VH domain sequences and CDRs

| Ab VH | HCDR1 | HCDR2 | HCDR3 | VH nucleotide sequence | VH amino acid sequence |
|---|---|---|---|---|---|
| T02 | SEQ ID NO: 57<br>GYTFTNYA | SEQ ID NO: 58<br>INAGNGFT | SEQ ID NO: 59<br>ARDWAAAISYYGMDV | SEQ ID NO: 60<br>CAGGTCCAGCTTGTGCAGTCTGGG<br>GCTGAGGTGAAGAGGCCTGGGGCC<br>TCAGTGAAGGTTTCCTGCAAGGCT<br>TCTGGATACACCTTCACTAACTAT<br>GCTATACATTGGGTGCGCCAGGCC<br>CCCGGACAGAGGCTTGAGTGGATG<br>GGATGGATCAACGCTGGCAATGGT<br>TTCACAAAATCTTCACAGAAGTTC<br>CGGGGCAGAGTCACCATTACCAGG<br>GACACATCCGCGAACACAGCCTAC<br>ATGGAACTGAGCAGCCTCAGATCT<br>GAAGACACGGCTATTTATTACTGT<br>GCGAGAGATTGGGCTGCTGCTATC<br>TCTTACTACGGTATGGACGTCTGG<br>GGCCAAGGGACCACGGTCACCGTC<br>TCCTCAG | SEQ ID NO: 61<br>QVQLVQSGAEVKRPGASV<br>KVSCKASGYTFTNYAIHW<br>VRQAPGQRLEWMGWINAG<br>NGFTKSSQKFRGRVTITR<br>DTSANTAYMELSSLRSED<br>TAIYYCARDWAAAISYYG<br>MDVWGQGTTVTVSS |
| T05 | SEQ ID NO: 67<br>GFTFSSYG | SEQ ID NO: 68<br>IWYDGTNK | SEQ ID NO: 69<br>ARSGYSSSWYGAMDV | SEQ ID NO: 70<br>CAGGTGCAGCTGGTGGAGTCTGGG<br>GGAGGCGTGGTCCAGCCTGGGAGG | SEQ ID NO: 71<br>QVQLVESGGGVVQPGRSL<br>RLSCAASGFTFSSYGMHW |

TABLE 10A-continued

Anti-FX VH domain sequences and CDRs

| Ab VH | HCDR1 | HCDR2 | HCDR3 | VH nucleotide sequence | VH amino acid sequence |
|---|---|---|---|---|---|
| | | | | TCCCTGAGACTCTCCTGTGCAGCG TCTGGATTCACCTTCAGTAGCTAT GGCATGCACTGGGTCCGCCAGGCT CCAGGCGAGGGGCTGGAGTGGGTG GCAGTTATATGGTATGATGGAACT AATAAATACTATGCAGACTCCTTG AAGGGCCGATTCACCATCTCCAGA GACAATTCCAAGAACACGCTCTAT CTGCAAATGAACAGGCTGAGAGCC GAGGACACGGCTGTGTATTACTGT GCGAGGTCCGGGTATAGCAGCAGC TGGTACGGCGCTATGGACGTCTGG GGCCAAGGGACCACGGTCACCGTC TCCTCAG | VRQAPGEGLEWVAVIWYD GTNKYYADSLKGRFTISR DNSKNTLYLQMNRLRAED TAVYYCARSGYSSSWYGA MDVWGQGTTVTVSS |
| T06 | SEQ ID NO: 77 GYTFTSYA | SEQ ID NO: 78 INAGNGIT | SEQ ID NO: 79 ARDWAAAITYYGMDV | SEQ ID NO: 80 CAGGTCCAGCTTGTGCAGTCTGGG GCTGAGGTGAAGAGGCCTGGGGCC TCAGTGAAGGTTTCCTGCAAGGCT TCTGGATACACCTTCACAAGCTAC GCCATACATTGGGTGCGCCAGGCC CCCGGACAGAGGCTTGAGTGGATG GGATGGATCAACGCTGGCAATGGT ATCACAAAATCTTCACAGAAGTTC CAGGGCAGAGTCACCATTACCAGG GACACATCCGCGAACACAGTTTAC CTGGAACTGAGCAGCCTCAGATCT GAAGACACGGCTGTTTATTATTGT GCGAGAGATTGGGCTGCTGCTATC ACCTACTACGGTATGGACGTCTGG GGCCAAGGGACCACGGTCACCGTC TCCTCAG | SEQ ID NO: 81 QVQLVQSGAEVKRPGASV KVSCKASGYTFTSYAIHW VRQAPGQRLEWMGWINAG NGITKSSQKFQGRVTITR DTSANTVYLELSSLRSED TAVYYCARDWAAAITYYG MDVWGQGTTVTVSS |
| T12 | SEQ ID NO: 86 EFTFSTAG | SEQ ID NO: 87 ISYDGSNK | SEQ ID NO: 88 AKDFTMVRGVIIMDV | SEQ ID NO: 89 CAGGTGCAGCTGGTGGAGTCTGGG GGGGGCGTACTCCAGCCTGGGAAG TCCCTGAGACTCTCCTGTGCAGCC TCTGAATTCACCTTCAGTACCGCT GGCATGCACTGGGTCCGCCAGGCT CCAGGCAAGGGGCTGGAGTGGGTG ACTTTTATATCATATGATGGAAGT AATAAATACTATGCAGACTCCGTG AAGGGCCGATTCACCATCTCCAGA GACAATTCCAAGGTGTATCTGCAA ATGAACAGCCTGAGAACTGAGGAC ACGGCTGTGTATTACTGTGCGAAA GATTTCACTATGGTTCGGGGAGTT ATTATAATGGACGTCTGGGGCCAA GGGACCACGGTCACCGTCTCCTCA G | SEQ ID NO: 90 QVQLVESGGGVLQPGKSL RLSCAASEFTFSTAGMHW VRQAPGKGLEWVTFISYD GSNKYYADSVKGRFTISR DNSKVYLQMNSLRTEDTA VYYCAKDFTMVRGVIIMD VWGQGTTVTVSS |
| T14 | SEQ ID NO: 96 GGSISSYY | SEQ ID NO: 97 IYYSGST | SEQ ID NO: 98 AKGAAGDY | SEQ ID NO: 99 CAGGTGCAGCTGCAGGAGTCGGGC CCAGGACTGGTGAAGCCTTCGGAG ACCCTGTCCCTCACCTGCACTGTC TCTGGTGGCTCCATCAGTAGTTAT TACTGGAGCTGGATCCGGCAGCCC CCAGGGAAGGGACTGGAGTGGATT GGGTATATCTATTACAGTGGGAGC ACCAACTATAACCCCTCCCTCAAG AGTCGAGTCAACATATCAGTAGAC ACGTCCAAGAACCAGTTCTCCCTG AGGCTGAGTTCTGTGACCGCTGCG GACACGGCCGTGTATTATTGTGCG AAAGGGGCAGCTGGGGACTACTGG GGCCAGGGAACCCTGGTCACCGTC TCCTCAG | SEQ ID NO: 100 QVQLQESGPGLVKPSETL SLTCTVSGGSISSYYWSW IRQPPGKGLEWIGYIYYS GSTNYNPSLKSRVNISVD TSKNQFSLRLSSVTAADT AVYYCAKGAAGDYWGQGT LVTVSS |

TABLE 10A-continued

Anti-FX VH domain sequences and CDRs

| Ab VH | HCDR1 | HCDR2 | HCDR3 | VH nucleotide sequence | VH amino acid sequence |
|---|---|---|---|---|---|
| T15 | SEQ ID NO: 105 GGSISKYY | SEQ ID NO: 106 IYYSGNT | SEQ ID NO: 107 ARGLGDY | SEQ ID NO: 108 CAGGTGCAGCTGCAGGAGTCGGGCCCAGGACTGGTGAAGCCTTCGGAGACCCTGTCCCTCACCTGCACTGTCTCTGGTGGCTCCATCAGTAAATACTACTGGAGCTGGATCCGGCAGCCCCCAGGGAAGGGACTGGAGTGGATTGGATATATCTATTACAGTGGGAACACCTACCAGAATCCCTCCCTCAAGAGTCGAGTCACCATATCAATAGACACGTCCAAGAACCAGATCTCCCTGAAGGTGAGCTCTGTGACCGCTGCGGACACGGCCGTCTATTACTGTGCGAGAGGGCTGGGGGACTACTGGGGCCAGGGAACCCTGGTCACCGTCTCCTCAG | SEQ ID NO: 109 QVQLQESGPGLVKPSETLSLTCTVSGGSISKYYWSWIRQPPGKGLEWIGYIYYSGNTYQNPSLKSRVTISIDTSKNQISLKVSSVTAADTAVYYCARGLGDYWGQGTLVTVSS |
| T23 | SEQ ID NO: 114 GGSISRYY | SEQ ID NO: 115 IYYSGTT | SEQ ID NO: 116 ARGLGDF | SEQ ID NO: 117 CAGGTGCAGCTGCAGGAGTCGGGCCCAGGACTGGTGAAGCCTTCGGAGACCCTGTCCCTCACCTGCAGTGTCTCTGGTGGCTCCATTAGTAGATATTACTGGAGCTGGATCCGGCAGCCCCCAGGGAAGGGACTGGAGTGGATTGGATATATCTATTACAGTGGGACCACCTACTATAACCCCTCCCTCAAGAGTCGAGTCACCTTTTCAGTAGACACGTCCAAGACCCAGTTCTCCCTGAAACTTAACTCTGTGACCGCTGCGGACACGGCCGTATATTACTGTGCGAGAGGACTGGGGGACTTCTGGGCCGGGGAACCCTGGTCACCGTCTCCTCAG | SEQ ID NO: 118 QVQLQESGPGLVKPSETLSLTCSVSGGSISRYYWSWIRQPPGKGLEWIGYIYYSGTTYYNPSLKSRVTFSVDTSKTQFSLKLNSVTAADTAVYYCARGLGDFWGRGTLVTVSS |
| T25 | SEQ ID NO: 122 GGSISSGIYY | SEQ ID NO: 123 INNSGNT | SEQ ID NO: 124 ARGGSGDY | SEQ ID NO: 125 CAGGTGCAGCTGCAGGAGTCGGGCCCAGGACTGGTGAAGCCTTCAGAGACCCTGTCCCTCACCTGCACTGTCTCTGGTGGCTCCATCAGTAGTGGTATATACTACTGGAGTTGGATCCGCCAGCACCCAGGGAAGGGCCTGGAGTGGATTGGATACATCAATAACAGTGGGAACACCTACTACAACCCGTCCCTCAAGGGTCGAGTTAACATATCAGTAGACACGTCTAAGAAACAGTTCTCCCTGAAGCTGAGCTCTGTGACTGACGCGGACACGGCCGTCTATTACTGTGCGAGGGGGGGATCGGGCGACTACTGGGGCCAGGGAACCCTGGTCACCGTCTCCTCAG | SEQ ID NO: 126 QVQLQESGPGLVKPSETLSLTCTVSGGSISSGIYYWSWIRQHPGKGLEWIGYINNSGNTYYNPSLKGRVNISVDTSKKQFSLKLSSVTADTAVYYCARGGSGDYWGQGTLVTVSS |

TABLE 10B

Anti-FXVL domain sequences and CDRs

| Ab VL | LCDR1 | LCDR2 | LCDR3 | VL nucleotide sequence | VL amino acid sequence |
|---|---|---|---|---|---|
| T02 | SEQ ID NO: 62 SSNIGSNY | SEQ ID NO: 63 RNT | SEQ ID NO: 64 ATWDDSLSAYV | SEQ ID NO: 65 CAGTCTGTCCTGACTCAGCCACCCTCAGCGTCTGGGACCCCCGGGCAGAGGGTCACCATCTCTTGTTCTGGAAGCAGCTCCAACATCGGAAGTAATTATGTATACTGGTACCAGCAGCTCCCAGGAACGGCCCCCAAACTCCTCATCTATAGGAATACTCAGCGGCCCTCAGAGGTCCCTGACCGATTCTCTGGCTCCAAGTCTGGCGCCTCAGCCTCCCTGGCCATCAGTGGGCTCCGGTCCGAGGATGAGACTGATTATTACTGTGCAACATGGGATGACAGCCTG | SEQ ID NO: 66 QSVLTQPPSASGTPGQRVTISCSGSSSNIGSNYVYWYQQLPGTAPKLLIYRNTQRPSEVPDRFSGSKSGASASLAISGLRSEDETDYYCATWDDSLSAYVFGTGTKVTVL |

TABLE 10B-continued

Anti-FXVL domain sequences and CDRs

| Ab VL | LCDR1 | LCDR2 | LCDR3 | VL nucleotide sequence | VL amino acid sequence |
|---|---|---|---|---|---|
| | | | | AGTGCTTATGTCTTCGGAACTGGG ACCAAAGTCACCGTCCTAG | |
| T05 | SEQ ID NO: 72 SSDVGGYYY | SEQ ID NO: 73 EVN | SEQ ID NO: 74 SSYAGSNTWV | SEQ ID NO: 75 CAGTCTGCCCTGACTCAGCCTCCC TCCGCGTCCGGGTCTCCTGGACAG TCAGTCACCATCTCCTGCACTGGA ACCAGCAGTGACGTTGGTGGTTAT TACTATGTCTCCTGGTACCAACAG CACCCAGGCAAAGCCCCCAAACTC ATGATTTATGAGGTCAATAAGCGG CCCTCAGGGGTCCCTGATCGCTTC TCTGGCTCCAAGTCTGGCATCACG GCCTCCCTGACCGTCTCTGGGCTC CAGTCTGAGGATGAGGCTGATTAT TACTGCAGCTCATATGCAGGCAGC AACACTTGGGTGTTCGGCGGAGGG ACCAAGCTGACCGTCCTAG | SEQ ID NO: 76 QSALTQPPSASGSPGQSVT ISCTGTSSDVGGYYVSWY QQHPGKAPKLMIYEVNKRP SGVPDRFSGSKSGITASLT VSGLQSEDEADYYCSSYAG SNTWVFGGGTKLTVL |
| T06 | SEQ ID NO: 62 SSNIGSNY | SEQ ID NO: 82 RNN | SEQ ID NO: 83 FGAGTKVTVL | SEQ ID NO: 84 CAGTCTGTGCTGACTCAGCCACCC TCAGTGTCTGGGACCCCCGGGCAG AGGGTCACCATCTCTTGTTCTGGA AGCAGCTCCAACATCGGAAGTAAT TATGTATACTGGTACCAGCAGTTC CCAGGAACGGCCCCCAAACTCCTC ATCTATAGGAATAATCAGCGGCCC TCAGAGGTCCCTGACCGATTCTCT GGCTCCAAGTCTGGCGCCTCAGCC TCCCTGGCCATCAGTGGGCTCCGG TCCGAGGATGAGACTGATTATTAC TGTGCAACATGGGATGACAGCCTG AGTGCTTATGTCTTCGGAGCTGGG ACCAAAGTCACCGTCCTAG | SEQ ID NO: 85 QSVLTQPPSVSGTPGQRVT ISCSGSSSNIGSNYVYWYQ QFPGTAPKLLIYRNNQRPS EVPDRFSGSKSGASASLAI SGLRSEDETDYYCATWDDS LSAYVFGAGTKVTVL |
| T12 | SEQ ID NO: 91 QDISNY | SEQ ID NO: 92 DAS | SEQ ID NO: 93 QQYDNLPIT | SEQ ID NO: 94 GACATCCAGATGACCCAGTCTCCA TCCTCCCTGTCTGTATCTGTAGGA GACAGAGTCACCATCACTTGCCAG GCGAGTCAGGACATTAGCAACTAT TTAAATTGGTATCAGCAGAAACCA GGGAAAGCCCCTAAGCTCCTGATC TACGATGCATCCAATTTGGAAACA GGGGTCCCATCAAGGTTCAGTGGA AGTGGATCTGGGACAGATTTTACT TTCATCATCAGCAGCCTGCAGCCT GAAGATATTGCAACATATTACTGT CAACAGTATGATAATCTCCCGATC ACCTTCGGCCAAGGGACACGACTG GAGATCAAAC | SEQ ID NO: 95 DIQMTQSPSSLSVSVGDRV TITCQASQDISNYLNWYQQ KPGKAPKLLIYDASNLETG VPSRFSGSGSGTDFTFIIS SLQPEDIATYYCQQYDNLP ITFGQGTRLEIK |
| T14 | SEQ ID NO: 101 QSVNSY | SEQ ID NO: 92 DAS | SEQ ID NO: 102 QQRNNWPIT | SEQ ID NO: 103 GAAATTGTGTTGGCACAGTCTCCA GCCACCCTGTCTTTGTCTCCAGGG GAAAGAGCCACCTTCTCCTGCAGG GCCAGTCAGAGTGTTAACAGCTAC TTAGCCTGGCACCAACAGAAACCT GGCCAGGCTCCCAGGCTCCTCATC TATGATGCATCCAACAGGGCCACT GGCATCCCAGCCAGGTTCAGTGGC AGTGGGTCCGGGACAGACTTCACT CTCACCATCAGCAGCCTAGAGCCT GAAGATTTTGCAGTTTATTACTGT CAGCAGCGTAACAACTGGCCTATC ACCTTCGGCCAAGGGACACGACTG GAGATCAAAC | SEQ ID NO: 104 EIVLAQSPATLSLSPGERA TFSCRASQSVNSYLAWHQQ KPGQAPRLLIYDASNRATG IPARFSGSGSGTDFTLTIS SLEPEDFAVYYCQQRNNWP ITFGQGTRLEIK |
| T15 | SEQ ID NO: 110 QSVSSY | SEQ ID NO: 92 DAS | SEQ ID NO: 111 QQRSNWPLT | SEQ ID NO: 112 GAAATTGTGTTGACACAGTCTCCA GCCACCCTGTCTTTGTCTCCAGGG GAAAGAGCCACCCTCTCCTGCAGG GCCAGTCAGAGTGTTAGCAGCTAC TTAGCCTGGCACCAACAGAAACCT GGCCAGGCTCCCAGGCTCCTCATC TATGATGCATCCAACAGGGCCACT | SEQ ID NO: 113 EIVLTQSPATLSLSPGERA TLSCRASQSVSSYLAWHQQ KPGQAPRLLIYDASNRATG IPARFSGSGSGTDFTLTIS SLEPEDFAVYYCQQRSNWP LTFGGGTKVEIK |

TABLE 10B-continued

Anti-FXVL domain sequences and CDRs

| Ab VL | LCDR1 | LCDR2 | LCDR3 | VL nucleotide sequence | VL amino acid sequence |
|---|---|---|---|---|---|
| | | | | GGCATCCCAGCCAGGTTCAGTGGC AGTGGGTCTGGGACAGACTTCACT CTCACCATCAGCAGCCTAGAGCCT GAAGATTTTGCAGTTTATTACTGT CAGCAACGTAGCAACTGGCCTCTC ACTTTCGGCGGAGGGACCAAGGTG GAGATCAAAC | |
| T23 | SEQ ID NO: 119<br>QSVSGY | SEQ ID NO: 92<br>DAS | SEQ ID NO: 111<br>QQRSNWPLT | SEQ ID NO: 120<br>GAAATTGTGTTGACTCAGTCTCCA GCCACCCTGTCATTGTCTCCAGGG GAAAGGGCCACCCTCTCTGCCGG GCCAGTCAGAGTGTTAGCGGCTAC TTAGCCTGGCACCAACAGAAACCT GGCCAGGCTCCCAGGCTCCTCATC TATGATGCATCCAACAGGGCCACT GGCATCCCAGCCAGATTCAGTGGC AGTGGGTCTGGGACAGACTTCACT CTCACCATCAGCAGCCTAGAGCCT GAAGATTTTGCAGTTTATTACTGT CAGCAACGTAGCAACTGGCCTCTC ACTTTCGGCGGAGGGACCAAGGTG GAGATCAAAC | SEQ ID NO: 121<br>EIVLTQSPATLSLSPGERA TLSCRASQSVSGYLAWHQQ KPGQAPRLLIYDASNRATG IPARFSGSGSGTDFTLTIS SLEPEDFAVYYCQQRSNWP LTFGGGTKVEIK |
| T25 | SEQ ID NO: 128<br>QSINNY | SEQ ID NO: 92<br>DAS | SEQ ID NO: 129<br>QQRNNWPPT | SEQ ID NO: 130<br>GAAATTGTGTTGACACAGTCTCCA GCCACCCTGTCTTTGTCTCCAGGG GAAAGAGCCACCCTCTCCTGCAGG ACCAGTCAGAGTATTAACAACTAC TTAGCCTGGTTCCAACAGAAACCT GGCCAGGCTCCCAGGCTCCTCATC TATGATGCATCCAACAGGGCCCCT GGCATCCCAGCCAGGTTCAGTGGC AGTGGGTCTGGGACAGACTTCACT CTCACCATCAGCAGCCTGGAGCCT GAAGATTTTGTAGTTTATTCTGT CAGCAGCGTAACAACTGGCCTCCG ACATTCGGCCAAGGGACCAAGGTG GAAATCAAAC | SEQ ID NO: 131<br>EIVLTQSPATLSLSPGERA TLSCRTSQSINNYLAWFQQ KPGQAPRLLIYDASNRAPG IPARFSGSGSGTDFTLTIS SLEPEDFVVYFCQQRNNWP PTFGQGTKVEIK |

TABLE 11

Antibody constant region sequences

| | |
|---|---|
| IgG4 PE human heavy chain constant region | SEQ ID NO: 143<br>ASTKGPSVFPLAPCSRSTSESTAALGCLVKDYFPEPVTVSWNSGALTSGVHTFPAVLQSSGL YSLSSVVTVPSSSLGTKTYTCNVDHKPSNTKVDKRVESKYGPPCPPCPAPEFEGGPSVFLFP FKPKDTLMISRTPEVTCVVVDVSQEDPEVUNWYVDGVEVHNAKTKPREEQFNSTYRVVSVLT VLHQDWLNGKEYKCKVSNKGLPSSIEKTISKAKGQPREPQVYTLPPSQEEMTKNQVSLTCLV KGFYPSDIAVEWESNGQPENNYKTTPPVLDSDGSFFLYSRLTVDKSRWQEGNVFSCSVMHEA LHNHYTQKSLSLSLGK |
| IgG4 human heavy chain constant region with knobs-into-holes mutations and hinge mutation. Type a (IgG4ra) | SEQ ID NO: 144<br>ASTKGPSVFPLAPCSRSTSESTAALGCLVKDYFPEPVTVSWNSGALTSGVHTFPAVLQSSGL YSLSSVVTVPSSSLGTKTYTCNVDHKPSNTKVDKRVESKYGPPCPPCPAPEFEGGPSVFLFP FKPKDTLMISRTPEVTCVVVDVSQEDPEVUNWYVDGVEVHNAKTKPREEQFNSTYRVVSVLT VLHQDWLNGKEYKCKVSNKGLPSSIEKTISKAKGQPREPQVCTLPPSQEEMTKNQVSLWCLV KGFYPSDIAVEWESNGQPENNYKTTPPVLDSDGSFFLYSRLTVDKSRWQEGNVFSCSVMHEA LHNHYTQKSLSLSLGK |
| IgG4 human heavy chain constant region with knobs-into-holes mutations and hinge mutation. Type b (IgG4yb) | SEQ ID NO: 145<br>ASTKGPSVFPLAPCSRSTSESTAALGCLVKDYFPEPVTVSWNSGALTSGVHTFPAVLQSSGL YSLSSVVTVPSSSLGTKTYTCNVDHKPSNTKVDKRVESKYGPPCPPCPAPEFEGGPSVFLFP FKPKDTLMISRTPEVTCVVVDVSQEDPEVUNWYVDGVEVHNAKTKPREEQFNSTYRVVSVLT VLHQDWLNGKEYKCKVSNKGLPSSIEKTISKAKGQPREPQVYTLPPSQCEMTKNQVSLSCAV KGFYPSDIAVEWESNGQPENNYKTTPPVLDSDGSFFLVSRLTVDKSRWQEGNVFSCSVMHEA LHNHYTQKSLSLSLGK |
| Human lambda light chain constant region | SEQ ID NO: 146<br>GQPKAAPSVTLFPPSSEELQANKATLVCLISDFYPGAVTVAWKADSSPVKAGVETTTPSKQS NNKYAASSYLSLTPEQWKSHKSYSCQVTHEGSTVEKTVAPTECS |

TABLE 11-continued

Antibody constant region sequences

| Human kappa light chain constant region | SEQ ID NO: 147<br>KRTVAAPSVFIFPPSDEQLKSGTASVVCLLNNFYPREAKVQWKVDNALQSGNSQESVTEQDS<br>KDSTYSLSSTLTLSKADYEKHKVYACEVTHQGLSSPVTKSFNRGEC |
|---|---|

TABLE 12

Corresponding germline v and j gene segments for antibody VH and VL domains

| Anti-FIX heavy chain | V -- J | Anti-FIX Light chain | V -- J |
|---|---|---|---|
| N128 | IGHV3-7*01--IGHJ6*02 | N128 | IGLV3-21*d01--IGLJ2*01 |
| N183 | IGHV3-48*02--IGHJ6*02 | N183 | IGLV3-16*01--IGLJ2*01 |

TABLE 12-continued

Corresponding germline v and j gene segments for antibody VH and VL domains

| Anti-FX heavy chain | V -- J | Anti-FX Light chain | V -- J |
|---|---|---|---|
| T02 | IGHV1-3*01--IGHJ6*02 | T02 | IGLV1-47*01--IGLJ1*01 |
| T05 | IGHV3-30*18--IGHJ6*02 | T05 | IGLV2-8*01--IGLJ2*01 |
| T06 | IGHV1-3*01--IGHJ6*02 | T06 | IGLV1-47*01--IGLJ6*01 |
| T12 | IGHV3-30*18--IGHJ6*02 | T12 | IGKV1D-33*01--IGKJ5*01 |
| T14 | IGHV4-61*01--IGHJ1*01 | T14 | IGKV3-11*01--IGKJ5*01 |
| T15 | IGHV4-61*01--IGHJ1*01 | T15 | IGKV3-11*01--IGKJ4*01 |
| T23 | IGKV3-11*01--IGKJ4*01 | T23 | IGHV4-61*01--IGHJ2*01 |
| T25 | IGHV4-31*03--IGHJ1*01 | T25 | IGKV3-11*01--IGKJ1*01 |

What is claimed is:

1. A bispecific antigen-binding molecule comprising:
a FIXa binding polypeptide arm comprising a FIXa binding site, and
a FX binding polypeptide arm comprising a FX binding site
wherein the FIXa binding site is provided by a set of complementarity determining regions (CDRs) in the FIXa binding polypeptide arm, the set of CDRs comprising HCDR1, HCDR2 and HCDR3, wherein HCDR1 is SEQ ID NO: 1, HCDR2 is SEQ ID NO: 2 and HCDR3 is SEQ ID NO: 171, and LCDR1, LCDR2 and LCDR3, wherein LCDR1 is SEQ ID NO: 6, LCDR2 is SEQ ID NO: 7 and LCDR3 is SEQ ID NO: 8;
wherein the FX binding site is provided by a set of CDRs in the FX binding polypeptide arm, the set of CDRs selected from the group consisting of:
(i) HCDR1 is SEQ ID NO: 67, HCDR2 is SEQ ID NO: 68 and HCDR3 is SEQ ID NO: 69, and LCDR1 is SEQ ID NO: 72, LCDR2 is SEQ ID NO: 73 and LCDR3 is SEQ ID NO: 74;
(ii) HCDR1 is SEQ ID NO: 57, HCDR2 is SEQ ID NO: 58 and HCDR3 is SEQ ID NO: 59, and LCDR1 is SEQ ID NO: 62, LCDR2 is SEQ ID NO: 63 and LCDR3 is SEQ ID NO: 64;
(iii) HCDR1 is SEQ ID NO: 96, HCDR2 is SEQ ID NO: 97 and HCDR3 is SEQ ID NO: 98, and LCDR1 is SEQ ID NO: 101, LCDR2 is SEQ ID NO: 92 and LCDR3 is SEQ ID NO: 102; and
(iv) HCDR1 is SEQ ID NO: 77, HCDR2 is SEQ ID NO: 78 and HCDR3 is SEQ ID NO: 79, and LCDR1 is SEQ ID NO: 62, LCDR2 is SEQ ID NO: 82 and LCDR3 is SEQ ID NO: 83.

2. The bispecific antigen-binding molecule according to claim 1, wherein the FIXa binding polypeptide arm and/or the FX binding polypeptide arm comprises
an antibody heavy chain comprising, from N to C terminus, a VH domain, a CH1 domain, a CH2 domain and a CH3 domain, and
an antibody light chain comprising, from N to C terminus, a VL domain and a CL domain.

3. The bispecific antigen-binding molecule according to claim 2, wherein the antigen-binding molecule is a tetrameric immunoglobulin comprising
a first heavy-light chain pair comprising a FIXa binding Fv region,
a second heavy-light chain pair comprising a FX binding Fv region,
wherein each heavy chain comprises a VH domain and a constant region, and each light chain comprises a VL domain and a constant region, and wherein the first and second heavy-light chain pairs associate to form the tetrameric immunoglobulin through heterodimerisation of their heavy chain constant regions.

4. The bispecific antigen-binding molecule according to claim 3, wherein the immunoglobulin is an IgG.

5. The composition comprising an antigen-binding molecule according to claim 1 in combination with a pharmaceutically acceptable excipient, wherein the antigen-binding molecule is in sterile aqueous solution.

6. The bispecific antigen-binding molecule according to claim 1 wherein
the FIXa binding polypeptide arm comprises a VH domain amino acid sequence SEQ ID NO: 324 and a VL domain amino acid sequence SEQ ID NO: 10, and
the FXa binding polypeptide arm comprises a VH domain amino acid sequence SEQ ID NO: 61 and a VL domain amino acid sequence SEQ ID NO: 66.

7. The bispecific antigen-binding molecule according to claim 1,
wherein
the FIXa binding polypeptide arm comprises a VH domain amino acid sequence SEQ ID NO: 324 and a VL domain amino acid sequence SEQ ID NO: 10, and
the FXa binding polypeptide arm comprises a VH domain amino acid sequence SEQ ID NO: 71 and a VL domain amino acid sequence SEQ ID NO: 76.

8. The bispecific antigen-binding molecule according to claim 1,
wherein
the FIXa binding polypeptide arm comprises a VH domain amino acid sequence SEQ ID NO: 324 and a VL domain amino acid sequence SEQ ID NO: 10, and
the FXa binding polypeptide arm comprises a VH domain amino acid sequence SEQ ID NO: 81 and a VL domain amino acid sequence SEQ ID NO: 85.

9. The bispecific antigen-binding molecule according to claim 1 wherein polypeptide arm comprises a VH domain amino acid sequence SEQ ID NO: 324 and a VL domain amino acid sequence SEQ ID NO: 10, and
the FXa binding polypeptide arm comprises a VH domain amino acid sequence SEQ ID NO: 100 and a VL domain amino acid sequence SEQ ID NO: 104.

* * * * *

SEQUENCE LISTING

```
<160> NUMBER OF SEQ ID NOS: 403

<210> SEQ ID NO 1
<211> LENGTH: 8
<212> TYPE: PRT
<213> ORGANISM: Homo sapiens

<400> SEQUENCE: 1

Gly Phe Thr Phe Asn Ser Tyr Trp
1               5

<210> SEQ ID NO 2
<211> LENGTH: 8
<212> TYPE: PRT
<213> ORGANISM: Homo sapiens

<400> SEQUENCE: 2

Ile Asn Gln Asp Gly Ser Glu Lys
1               5

<210> SEQ ID NO 3
<211> LENGTH: 15
<212> TYPE: PRT
<213> ORGANISM: Homo sapiens

<400> SEQUENCE: 3

Ala Arg Glu Gly Tyr Ser Ser Ser Ser Tyr Tyr Gly Met Asp Val
1               5                   10                  15

<210> SEQ ID NO 4
<211> LENGTH: 367
<212> TYPE: DNA
<213> ORGANISM: Homo sapiens

<400> SEQUENCE: 4
gaggtgcagc tggtggagtc tgggggaggc tttgtccagc ctggggggtc cctgagactc      60
tcctgtgcag tctctggatt cacctttaat agctattgga tgagctgggt ccgccaggct     120
```

| | |
|---|---|
| ccagggaagg ggctggagtg ggtggccaac ataaaccaag atggaagtga gaaattctat | 180 |
| gtggcctctg tgaagggccg attcaccatg tccagagaca acgccaagaa atcagtgtat | 240 |
| gtacaaatga acagcctgag agccgaggac acggctgtgt attactgtgc gagagagggg | 300 |
| tatagtagtt cgtcctatta tggtatggac gtctggggcc aagggaccac ggtcaccgtc | 360 |
| tcctcag | 367 |

<210> SEQ ID NO 5
<211> LENGTH: 122
<212> TYPE: PRT
<213> ORGANISM: Homo sapiens

<400> SEQUENCE: 5

Glu Val Gln Leu Val Glu Ser Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Ser Tyr Tyr Gly Met Asp Val Trp
            100                 105                 110

Gly Gln Gly Thr Thr Val Thr Val Ser Ser
        115                 120

<210> SEQ ID NO 6
<211> LENGTH: 6
<212> TYPE: PRT
<213> ORGANISM: Homo sapiens

<400> SEQUENCE: 6

Asn Ile Gly Arg Lys Ser
1               5

<210> SEQ ID NO 7
<211> LENGTH: 3
<212> TYPE: PRT
<213> ORGANISM: Homo sapiens

<400> SEQUENCE: 7

Tyr Asp Ser
1

<210> SEQ ID NO 8
<211> LENGTH: 11
<212> TYPE: PRT
<213> ORGANISM: Homo sapiens

<400> SEQUENCE: 8

Gln Val Trp Asp Gly Ser Ser Asp His Trp Val
1               5                   10

<210> SEQ ID NO 9
<211> LENGTH: 325
<212> TYPE: DNA
<213> ORGANISM: Homo sapiens

<400> SEQUENCE: 9

```
tcctatgtgc tgactcagcc accctcagtg tcagtggccc caggagagac ggccaggatt    60
acctgtgggg gagacaacat tggaaggaaa agtgtgtact ggtaccagca gaagtcaggc   120
caggcccctg tgctggtcat ctattatgat agcgaccggc cctcagggat ccctgagcga   180
ttctctgggt ccaactctgg gaacacggcg accctgacca tcagcagggt cgaagccggg   240
gatgaggccg actattactg tcaggtgtgg gatggaagta gtgatcattg ggtgttcggc   300
ggagggacca agttgaccgt cctag                                         325
```

<210> SEQ ID NO 10
<211> LENGTH: 108
<212> TYPE: PRT
<213> ORGANISM: Homo sapiens

<400> SEQUENCE: 10

Ser Tyr Val Leu Thr Gln Pro Pro Ser Val Ser Val Ala Pro Gly Glu
1               5                   10                  15

Thr Ala Arg Ile Thr Cys Gly Gly Asp Asn Ile Gly Arg Lys Ser Val
            20                  25                  30

Tyr Trp Tyr Gln Gln Lys Ser Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Gly Ser Ser Asp His
                85                  90                  95

Trp Val Phe Gly Gly Gly Thr Lys Leu Thr Val Leu
            100                 105

<210> SEQ ID NO 11
<211> LENGTH: 8
<212> TYPE: PRT
<213> ORGANISM: Homo sapiens

<400> SEQUENCE: 11

Gly Phe Thr Phe Ser Ser Tyr Trp
1               5

<210> SEQ ID NO 12
<211> LENGTH: 8
<212> TYPE: PRT
<213> ORGANISM: Homo sapiens

<400> SEQUENCE: 12

Ile Lys Gln Asp Gly Ser Glu Lys
1               5

<210> SEQ ID NO 13
<211> LENGTH: 15
<212> TYPE: PRT
<213> ORGANISM: Homo sapiens

```
<400> SEQUENCE: 13

Ala Arg Glu Gly Tyr Ser Ser Tyr Tyr Tyr Gly Met Asp Val
1               5                   10                  15

<210> SEQ ID NO 14
<211> LENGTH: 366
<212> TYPE: DNA
<213> ORGANISM: Homo sapiens

<400> SEQUENCE: 14
gaggtgcagc tggtggagtc tgggggaggc ttggtccagc ctgggggtc  cctgagactc    60 tcctgtgcag cctctggatt cacctttagt agctattgga tgagctgggt ccgccaggct   120
ccagggaagg ggctggagtg ggtggccaac ataaagcaag atggaagtga aaatactat    180 gtggactctg tgaagggccg attcaccatc tccagagaca cgccaagaa ctcactgtat    240 ctgcaaatga acagcctgag agccgaggac acggctgtgt attactgtgc gagagagggg   300
tatagcagtt actactacta cggtatggac gtctggggcc aagggaccac ggtcaccgtc   360
tcctca                                                              366

<210> SEQ ID NO 15
<211> LENGTH: 122
<212> TYPE: PRT
<213> ORGANISM: Homo sapiens

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Tyr Ser Ser Tyr Tyr Tyr Gly Met Asp Val Trp
            100                 105                 110

Gly Gln Gly Thr Thr Val Thr Val Ser Ser
        115                 120

<210> SEQ ID NO 16
<211> LENGTH: 366
<212> TYPE: DNA
<213> ORGANISM: Homo sapiens

<400> SEQUENCE: 16
gaggtgcagc tggtggagtc tgggggaggc ttggtccagc ctgggggtc  cctgagactc    60 tcctgtgcag cctctggatt cacctttagt agctattgga tgagctgggt ccgccaggct   120
ccagggaagg ggctggagtg ggtggccaac ataaaccaag atggaagtga aaatactat    180 gtggactctg tgaagggccg attcaccatc tccagagaca cgccaagaa ctcactgtat    240 ctacaaatga acagcctgag agccgaggac acggctgtgt attactgtgc gagagagggg   300
```

```
tatagtagtt cgtcctatta tggtatggac gtctggggcc aagggaccac ggtcaccgtc      360
tcctca                                                                 366
```

<210> SEQ ID NO 17
<211> LENGTH: 122
<212> TYPE: PRT
<213> ORGANISM: Homo sapiens

<400> SEQUENCE: 17

```
Glu Val Gln Leu Val Glu Ser Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Tyr Ser Ser Ser Tyr Tyr Gly Met Asp Val Trp
            100                 105                 110

Gly Gln Gly Thr Thr Val Thr Val Ser Ser
        115                 120
```

<210> SEQ ID NO 18
<211> LENGTH: 8
<212> TYPE: PRT
<213> ORGANISM: Homo sapiens

<400> SEQUENCE: 18

```
Gly Phe Ile Phe Ser Ser Tyr Trp
 1               5
```

<210> SEQ ID NO 19
<211> LENGTH: 366
<212> TYPE: DNA
<213> ORGANISM: Homo sapiens

<400> SEQUENCE: 19

```
gaggtgcagc tggtggagtc tgggggaggc ttggtccagc ctgggggtc cctgagactc       60 tcctgtgtag cctctggatt catctttagt agctattgga tgagctgggt ccgccaggct     120
ccagggaagg ggctggagtg ggtggccaat ataaatcaag atggaagtga gaaatactat    180
gtggactctg tgaagggccg attcaccatc tccagagaca cgccaagaa ctcactgtat     240 ctgcaaatga acagcctgag agccgaggac acggctgtgt attactgtgc gagagagggg   300
tatagcagtt cgtcctatta tggtatggac gtctggggcc aagggaccac ggtcaccgtc   360
tcctca                                                               366
```

<210> SEQ ID NO 20
<211> LENGTH: 122
<212> TYPE: PRT
<213> ORGANISM: Homo sapiens

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Val Ala Ser Gly Phe Ile Phe Ser Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Tyr Ser Ser Ser Tyr Tyr Gly Met Asp Val Trp
            100                 105                 110

Gly Gln Gly Thr Thr Val Thr Val Ser Ser
        115                 120

<210> SEQ ID NO 21
<211> LENGTH: 366
<212> TYPE: DNA
<213> ORGANISM: Homo sapiens

<400> SEQUENCE: 21
gaggtgcagc tggtggagtc tgggggaggc ttggtccagc ctggggggtc cctgagactc      60
tcctgtgcag tctctggatt cacctttaat agctattgga tgagctgggt ccgccaggct     120
ccagggaagg gctggagtg gtggccaac ataaaccaag atggaagtga gaaattctat     180
gtggcctctg tgaagggccg attcaccatc tccagagaca cgccaagaa ctcagtgtat     240 ctacaaatga acagcctgag agccgaggac acggctgtgt attactgtgc gagagagggg     300
tatagtagtt cgtcctatta tggtatggac gtctggggcc aagggaccac ggtcaccgtc     360
tcctca                                                                366

<210> SEQ ID NO 22
<211> LENGTH: 122
<212> TYPE: PRT
<213> ORGANISM: Homo sapiens

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Ile Ser Arg Asp Asn Ala Lys Asn Ser Val Tyr
65                  70                  75                  80

Leu Gln Met Asn Ser Leu Arg Ala Glu Asp Thr Ala Val Tyr Tyr Cys
                85                  90                  95

Ala Arg Glu Gly Tyr Ser Ser Ser Tyr Tyr Gly Met Asp Val Trp
            100                 105                 110

Gly Gln Gly Thr Thr Val Thr Val Ser Ser
        115                 120

```
<210> SEQ ID NO 23
<211> LENGTH: 8
<212> TYPE: PRT
<213> ORGANISM: Homo sapiens

<400> SEQUENCE: 23

Gly Phe Thr Phe Asn Asn Tyr Trp
1               5

<210> SEQ ID NO 24
<211> LENGTH: 15
<212> TYPE: PRT
<213> ORGANISM: Homo sapiens

<400> SEQUENCE: 24

Ala Arg Glu Gly Tyr Thr Asp Ser Ser Tyr Tyr Gly Met Asp Val
1               5                   10                  15

<210> SEQ ID NO 25
<211> LENGTH: 366
<212> TYPE: DNA
<213> ORGANISM: Homo sapiens

<400> SEQUENCE: 25
gaggtgcagc tggtggagtc tgggggaggc ctggtccagc ctgggggtc cctgagactc      60 tcctgtgcag tctctggatt cacctttaat aactattgga tgagctgggt ccgccaggct    120
ccagggaagg ggctggagtg ggtggccaac ataaaccaag atggaagtga gaaattctat    180
gtggcctctg tgaagggccg attcatcatc tccagagaca cgccaaaaa ttcagtgtat     240 ctacaaatga acagcctgag agccgaggac acggctgtgt attactgtgc gagagagggg    300
tataccgatt cgtcctatta tggaatggac gtctggggcc aagggaccac ggtctccgtc    360
tcctca                                                              366

<210> SEQ ID NO 26
<211> LENGTH: 122
<212> TYPE: PRT
<213> ORGANISM: Homo sapiens

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Asn Asn Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Ile Ile Ser Arg Asp Asn Ala Lys Asn Ser Val Tyr
65                  70                  75                  80

Leu Gln Met Asn Ser Leu Arg Ala Glu Asp Thr Ala Val Tyr Tyr Cys
                85                  90                  95

Ala Arg Glu Gly Tyr Thr Asp Ser Ser Tyr Tyr Gly Met Asp Val Trp
            100                 105                 110

Gly Gln Gly Thr Thr Val Ser Val Ser Ser
        115                 120
```

```
<210> SEQ ID NO 27
<211> LENGTH: 366
<212> TYPE: DNA
<213> ORGANISM: Homo sapiens

<400> SEQUENCE: 27
gaggtgcagc tggtggagtc tgggggaggc ttggtccagc ctgggggtc cctgagactc      60 tcctgtgcag cctctggatt cacctttagt agctattgga tgagctgggt ccgccaggct    120
ccagggaagg ggctggagtg ggtggccaac ataaagcaag atggaagtga aaatactat     180 gtggactctg tgaagggccg attcaccatc tccagagaca cgccaagaa ctcactgtat     240 ctgcaaatga acagcctgag agccgaggac acggctgtgt attactgtgc gagagaggg    300 tatagcagtt cgtcctacta cggtatggac gtctggggcc aagggaccac ggtcaccgtc   360
tcctca                                                              366

<210> SEQ ID NO 28
<211> LENGTH: 122
<212> TYPE: PRT
<213> ORGANISM: Homo sapiens

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Glu Gly Tyr Ser Ser Ser Tyr Tyr Gly Met Asp Val Trp
            100                 105                 110

Gly Gln Gly Thr Thr Val Thr Val Ser Ser
            115                 120

<210> SEQ ID NO 29
<211> LENGTH: 366
<212> TYPE: DNA
<213> ORGANISM: Homo sapiens

<400> SEQUENCE: 29
gaggtgcagc tggtggagtc tgggggaggc tttgtccagc ctgggggtc cctgagactc     60 tcctgtgcag tctctggatt cacctttaat agctattgga tgagctgggt ccgccaggct   120
ccagggaagg ggctggagtg ggtggccaac ataaaccaag atggaagtga aaattctat    180 gtggcctctg tgaagggccg attcaccatc tccagagaca cgccaagaa ctcagtgtat    240 ctacaaatga acagcctgag agccgaggac acggctgtgt attactgtgc gagagaggg    300 tatagtagtt cgtcctatta tggtatggac gtctggggcc aagggaccac ggtcaccgtc  360
tcctca                                                             366
```

```
<210> SEQ ID NO 30
<211> LENGTH: 122
<212> TYPE: PRT
<213> ORGANISM: Homo sapiens

<400> SEQUENCE: 30

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Ile Ser Arg Asp Asn Ala Lys Asn Ser Val Tyr
65                  70                  75                  80

Leu Gln Met Asn Ser Leu Arg Ala Glu Asp Thr Ala Val Tyr Tyr Cys
                85                  90                  95

Ala Arg Glu Gly Tyr Ser Ser Ser Tyr Tyr Gly Met Asp Val Trp
            100                 105                 110

Gly Gln Gly Thr Thr Val Thr Val Ser Ser
        115                 120

<210> SEQ ID NO 31
<211> LENGTH: 366
<212> TYPE: DNA
<213> ORGANISM: Homo sapiens

<400> SEQUENCE: 31
gaggtgcagc tggtggagtc tgggggaggc ttggtccagc ctggggggtc cctgagactc      60
tcctgtgcag tctctggatt cacctttaat agctattgga tgagctgggt ccgccaggct     120
ccagggaagg ggctggagtg ggtggccaac ataaaccaag atggaagtga gaaattctat     180
gtggcctctg tgaagggccg attcaccatg tccagagaca cgccaagaa ctcagtgtat      240 ctacaaatga acagcctgag agccgaggac acggctgtgt attactgtgc gagagaggg     300 tatagtagtt cgtcctatta tggtatggac gtctggggcc aagggaccac ggtcaccgtc     360
tcctca                                                                366

<210> SEQ ID NO 32
<211> LENGTH: 122
<212> TYPE: PRT
<213> ORGANISM: Homo sapiens

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Asn Ser Val Tyr
65                  70                  75                  80

Leu Gln Met Asn Ser Leu Arg Ala Glu Asp Thr Ala Val Tyr Tyr Cys
                85                  90                  95
```

```
            Ala Arg Glu Gly Tyr Ser Ser Ser Tyr Tyr Gly Met Asp Val Trp
                    100                 105                 110

Gly Gln Gly Thr Thr Val Thr Val Ser Ser
                    115                 120

<210> SEQ ID NO 33
<211> LENGTH: 366
<212> TYPE: DNA
<213> ORGANISM: Homo sapiens

<400> SEQUENCE: 33
gaggtgcagc tggtggagtc tgggggaggc ttggtccagc ctgggggtc cctgagactc      60 tcctgtgcag tctctggatt caccttaat agctattgga tgagctgggt ccgccaggct    120
ccagggaagg ggctggagtg ggtggccaac ataaaccaag atggaagtga aaattctat    180 gtggcctctg tgaagggccg attcaccatc tccagagaca cgccaagaa atcagtgtat    240 ctacaaatga acagcctgag agccgaggac acggctgtgt attactgtgc gagagagggg    300
tatagtagtt cgtcctatta tggtatggac gtctggggcc aagggaccac ggtcaccgtc    360
tcctca                                                                366

<210> SEQ ID NO 34
<211> LENGTH: 122
<212> TYPE: PRT
<213> ORGANISM: Homo sapiens

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Asn Ser Tyr
                20                  25                  30

Trp Met Ser Trp Val Arg Gln Ala Pro Gly Lys Gly Leu Glu Trp Val
            35                  40                  45

Ala Asn Ile Asn Gln Asp Gly Ser Glu Lys Phe Tyr Val Ala Ser Val
        50                  55                  60

Lys Gly Arg Phe Thr Ile Ser Arg Asp Asn Ala Lys Lys Ser Val Tyr
65                  70                  75                  80

Leu Gln Met Asn Ser Leu Arg Ala Glu Asp Thr Ala Val Tyr Tyr Cys
                85                  90                  95

Ala Arg Glu Gly Tyr Ser Ser Ser Tyr Tyr Gly Met Asp Val Trp
                100                 105                 110

Gly Gln Gly Thr Thr Val Thr Val Ser Ser
        115                 120

<210> SEQ ID NO 35
<211> LENGTH: 366
<212> TYPE: DNA
<213> ORGANISM: Homo sapiens

<400> SEQUENCE: 35
gaggtgcagc tggtggagtc tgggggaggc ttggtccagc ctgggggtc cctgagactc      60 tcctgtgcag tctctggatt caccttaat agctattgga tgagctgggt ccgccaggct    120
ccagggaagg ggctggagtg ggtggccaac ataaaccaag atggaagtga aaattctat    180 gtggcctctg tgaagggccg attcaccatc tccagagaca cgccaagaa ctcagtgtat    240 gtacaaatga acagcctgag agccgaggac acggctgtgt attactgtgc gagagagggg    300
```

```
tatagtagtt cgtcctatta tggtatggac gtctggggcc aagggaccac ggtcaccgtc    360
tcctca                                                                366
```

<210> SEQ ID NO 36
<211> LENGTH: 122
<212> TYPE: PRT
<213> ORGANISM: Homo sapiens

<400> SEQUENCE: 36

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Ile Ser Arg Asp Asn Ala Lys Asn Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Ser Tyr Tyr Gly Met Asp Val Trp
            100                 105                 110

Gly Gln Gly Thr Thr Val Thr Val Ser Ser
        115                 120

<210> SEQ ID NO 37
<211> LENGTH: 366
<212> TYPE: DNA
<213> ORGANISM: Homo sapiens

<400> SEQUENCE: 37

```
gaggtgcagc tggtggagtc tgggggaggc tttgtccagc ctggggggtc cctgagactc    60
tcctgtgcag tctctggatt cacctttaat agctattgga tgagctgggt ccgccaggct   120
ccagggaagg ggctggagtg gtggccaac ataaaccaag atggaagtga gaaattctat   180
gtggcctctg tgaagggccg attcaccatc tccagagaca acgccaagaa tcagtgtat   240 gtacaaatga acagcctgag agccgaggac acggctgtgt attactgtgc gagagagggg   300
tatagtagtt cgtcctatta tggtatggac gtctggggcc aagggaccac ggtcaccgtc   360
tcctca                                                              366
```

<210> SEQ ID NO 38
<211> LENGTH: 122
<212> TYPE: PRT
<213> ORGANISM: Homo sapiens

<400> SEQUENCE: 38

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

```
Lys Gly Arg Phe Thr Ile Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                 85                  90                  95

Ala Arg Glu Gly Tyr Ser Ser Ser Tyr Tyr Gly Met Asp Val Trp
            100                 105                 110

Gly Gln Gly Thr Thr Val Thr Val Ser Ser
        115                 120
```

```
<210> SEQ ID NO 39
<211> LENGTH: 366
<212> TYPE: DNA
<213> ORGANISM: Homo sapiens

<400> SEQUENCE: 39
gaggtgcagc tggtggagtc tgggggaggc tttgtccagc ctggggggtc cctgagactc      60
tcctgtgcag tctctggatt cacctttaat agctattgga tgagctgggt ccgccaggct     120
ccagggaagg ggctggagtg ggtggccaac ataaaccaag atggaagtga aaaattctat     180
gtggcctctg tgaagggccg attcaccatg tccagagaca cgccaagaa ctcagtgtat      240 gtacaaatga acagcctgag agccgaggac acggctgtgt attactgtgc gagagaggg     300 tatagtagtt cgtcctatta tggtatggac gtctggggcc aagggaccac ggtcaccgtc    360
tcctca                                                                366
```

```
<210> SEQ ID NO 40
<211> LENGTH: 122
<212> TYPE: PRT
<213> ORGANISM: Homo sapiens

<400> SEQUENCE: 40

Glu Val Gln Leu Val Glu Ser Gly Gly Gly Phe Val Gln Pro Gly Gly
 1               5                  10                  15

Ser Leu Arg Leu Ser Cys Ala Val Ser Gly Phe Thr Phe Asn Ser Tyr
                20                  25                  30

Trp Met Ser Trp Val Arg Gln Ala Pro Gly Lys Gly Leu Glu Trp Val
             35                  40                  45

Ala Asn Ile Asn Gln Asp Gly Ser Glu Lys Phe Tyr Val Ala Ser Val
 50                  55                  60

Lys Gly Arg Phe Thr Met Ser Arg Asp Asn Ala Lys Asn Ser Val Tyr
 65                  70                  75                  80

Val Gln Met Asn Ser Leu Arg Ala Glu Asp Thr Ala Val Tyr Tyr Cys
                 85                  90                  95

Ala Arg Glu Gly Tyr Ser Ser Ser Tyr Tyr Gly Met Asp Val Trp
            100                 105                 110

Gly Gln Gly Thr Thr Val Thr Val Ser Ser
        115                 120
```

```
<210> SEQ ID NO 41
<211> LENGTH: 366
<212> TYPE: DNA
<213> ORGANISM: Homo sapiens

<400> SEQUENCE: 41
gaggtgcagc tggtggagtc tgggggaggc tttgtccagc ctggggggtc cctgagactc      60
tcctgtgcag tctctggatt cacctttaat agctattgga tgagctgggt ccgccaggct    120
ccagggaagg ggctggagtg ggtggccaac ataaaccaag atggaagtga aaaattctat    180
```

```
gtggcctctg tgaagggccg attcaccatg tccagagaca cgccaagaa atcagtgtat    240 ctacaaatga acagcctgag agccgaggac acggctgtgt attactgtgc gagagagggg    300
tatagtagtt cgtcctatta tggtatggac gtctggggcc aagggaccac ggtcaccgtc    360
tcctca                                                                366
```

<210> SEQ ID NO 42
<211> LENGTH: 122
<212> TYPE: PRT
<213> ORGANISM: Homo sapiens

<400> SEQUENCE: 42

```
Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Leu Gln Met Asn Ser Leu Arg Ala Glu Asp Thr Ala Val Tyr Tyr Cys
                85                  90                  95

Ala Arg Glu Gly Tyr Ser Ser Ser Tyr Tyr Gly Met Asp Val Trp
            100                 105                 110

Gly Gln Gly Thr Thr Val Thr Val Ser Ser
        115                 120
```

<210> SEQ ID NO 43
<211> LENGTH: 366
<212> TYPE: DNA
<213> ORGANISM: Homo sapiens

<400> SEQUENCE: 43

```
gaggtgcagc tggtggagtc tgggggaggc ttggtccagc ctggggggtc cctgagactc    60
tcctgtgcag tctctggatt cacctttaat agctattgga tgagctgggt ccgccaggct    120
ccagggaagg ggctggagtg gtggccaac ataaaccaag atggaagtga gaaattctat    180
gtggcctctg tgaagggccg attcaccatg tccagagaca cgccaagaa atcagtgtat    240 gtacaaatga acagcctgag agccgaggac acggctgtgt attactgtgc gagagagggg    300
tatagtagtt cgtcctatta tggtatggac gtctggggcc aagggaccac ggtcaccgtc    360
tcctca                                                                366
```

<210> SEQ ID NO 44
<211> LENGTH: 122
<212> TYPE: PRT
<213> ORGANISM: Homo sapiens

<400> SEQUENCE: 44

```
Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45
```

```
Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                 85                  90                  95

Ala Arg Glu Gly Tyr Ser Ser Ser Tyr Tyr Gly Met Asp Val Trp
            100                 105                 110

Gly Gln Gly Thr Thr Val Thr Val Ser Ser
        115                 120
```

<210> SEQ ID NO 45
<211> LENGTH: 366
<212> TYPE: DNA
<213> ORGANISM: Homo sapiens

<400> SEQUENCE: 45

```
gaggtgcagc tggtggagtc tgggggaggc tttgtccagc ctggggggtc cctgagactc    60
tcctgtgcag tctctggatt caccttaat agctattgga tgagctgggt ccgccaggct   120
ccagggaagg ggctggagtg ggtggccaac ataaaccaag atggaagtga gaaattctat   180
gtggcctctg tgaagggccg attcaccatg tccagagaca cgccaagaa ctcagtgtat    240 ctacaaatga acagcctgag agccgaggac acggctgtgt attactgtgc gagagaggg   300 tatagtagtt cgtcctatta tggtatggac gtctggggcc aagggaccac ggtcaccgtc   360
tcctca                                                              366
```

<210> SEQ ID NO 46
<211> LENGTH: 122
<212> TYPE: PRT
<213> ORGANISM: Homo sapiens

<400> SEQUENCE: 46

```
Glu Val Gln Leu Val Glu Ser Gly Gly Gly Phe Val Gln Pro Gly Gly
 1               5                  10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
         35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Asn Ser Val Tyr
 65                  70                  75                  80

Leu Gln Met Asn Ser Leu Arg Ala Glu Asp Thr Ala Val Tyr Tyr Cys
                 85                  90                  95

Ala Arg Glu Gly Tyr Ser Ser Ser Tyr Tyr Gly Met Asp Val Trp
            100                 105                 110

Gly Gln Gly Thr Thr Val Thr Val Ser Ser
        115                 120
```

<210> SEQ ID NO 47
<211> LENGTH: 366
<212> TYPE: DNA
<213> ORGANISM: Homo sapiens

<400> SEQUENCE: 47

```
gaggtgcagc tggtggagtc tgggggaggc tttgtccagc ctggggggtc cctgagactc    60
tcctgtgcag tctctggatt cacctttaat agctattgga tgagctgggt ccgccaggct   120
ccagggaagg ggctggagtg ggtggccaac ataaaccaag atggaagtga gaaattctat   180
gtggcctctg tgaagggccg attcaccatc tccagagaca cgccaagaa  atcagtgtat   240 ctacaaatga acagcctgag agccgaggac acggctgtgt attactgtgc gagagagggg   300
tatagtagtt cgtcctatta tggtatggac gtctggggcc aagggaccac ggtcaccgtc   360
tcctca                                                              366
```

<210> SEQ ID NO 48
<211> LENGTH: 122
<212> TYPE: PRT
<213> ORGANISM: Homo sapiens

<400> SEQUENCE: 48

```
Glu Val Gln Leu Val Glu Ser Gly Gly Gly Phe Val Gln Pro Gly Gly
 1               5                  10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Ile Ser Arg Asp Asn Ala Lys Lys Ser Val Tyr
65                  70                  75                  80

Leu Gln Met Asn Ser Leu Arg Ala Glu Asp Thr Ala Val Tyr Tyr Cys
                85                  90                  95

Ala Arg Glu Gly Tyr Ser Ser Ser Ser Tyr Tyr Gly Met Asp Val Trp
            100                 105                 110

Gly Gln Gly Thr Thr Val Thr Val Ser Ser
        115                 120
```

<210> SEQ ID NO 49
<211> LENGTH: 366
<212> TYPE: DNA
<213> ORGANISM: Homo sapiens

<400> SEQUENCE: 49

```
gaggtgcagc tggtggagtc tgggggaggc tttgtccagc ctggggggtc cctgagactc    60
tcctgtgcag tctctggatt cacctttaat agctattgga tgagctgggt ccgccaggct   120
ccagggaagg ggctggagtg ggtggccaac ataaaccaag atggaagtga gaaattctat   180
gtggcctctg tgaagggccg attcaccatc tccagagaca cgccaagaa  ctcagtgtat   240 gtacaaatga acagcctgag agccgaggac acggctgtgt attactgtgc gagagagggg   300
tatagtagtt cgtcctatta tggtatggac gtctggggcc aagggaccac ggtcaccgtc   360
tcctca                                                              366
```

<210> SEQ ID NO 50
<211> LENGTH: 122
<212> TYPE: PRT
<213> ORGANISM: Homo sapiens -continued

```
<400> SEQUENCE: 50

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Ile Ser Arg Asp Asn Ala Lys Asn Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Ser Tyr Tyr Gly Met Asp Val Trp
            100                 105                 110

Gly Gln Gly Thr Thr Val Thr Val Ser Ser
        115                 120

<210> SEQ ID NO 51
<211> LENGTH: 366
<212> TYPE: DNA
<213> ORGANISM: Homo sapiens

<400> SEQUENCE: 51
gaggtgcagc tggtggagtc tgggggaggc ttggtccagc ctggggggtc cctgagactc     60
tcctgtgcag tctctggatt cacctttaat agctattgga tgagctgggt ccgccaggct   120
ccagggaagg gctggagtg gtggccaac ataaaccaag atggaagtga gaaattctat    180
gtggcctctg tgaagggccg attcaccatg tccagagaca cgccaagaa atcagtgtat    240 ctacaaatga acagcctgag agccgaggac acggctgtgt attactgtgc gagagagggg   300
tatagtagtt cgtcctatta tggtatggac gtctggggcc aagggaccac ggtcaccgtc   360
tcctca                                                              366

<210> SEQ ID NO 52
<211> LENGTH: 122
<212> TYPE: PRT
<213> ORGANISM: Homo sapiens

<400> SEQUENCE: 52

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Leu Gln Met Asn Ser Leu Arg Ala Glu Asp Thr Ala Val Tyr Tyr Cys
                85                  90                  95

Ala Arg Glu Gly Tyr Ser Ser Ser Tyr Tyr Gly Met Asp Val Trp
            100                 105                 110

Gly Gln Gly Thr Thr Val Thr Val Ser Ser
        115                 120
```

<210> SEQ ID NO 53
<211> LENGTH: 366
<212> TYPE: DNA
<213> ORGANISM: Homo sapiens

<400> SEQUENCE: 53

```
gaggtgcagc tggtggagtc tgggggaggc ttggtccagc ctggggggtc cctgagactc      60
tcctgtgcag tctctggatt cacctttaat agctattgga tgagctgggt ccgccaggct     120
ccagggaagg ggctggagtg ggtggccaac ataaaccaag atggaagtga aaattctat      180 gtggcctctg tgaagggccg attcaccatg tccagagaca cgccaagaa ctcagtgtat      240 gtacaaatga acagcctgag agccgaggac acggctgtgt attactgtgc gagagagggg    300
tatagtagtt cgtcctatta tggtatggac gtctggggcc aagggaccac ggtcaccgtc    360
tcctca                                                                366
```

<210> SEQ ID NO 54
<211> LENGTH: 122
<212> TYPE: PRT
<213> ORGANISM: Homo sapiens

<400> SEQUENCE: 54

```
Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Asn Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Ser Tyr Tyr Gly Met Asp Val Trp
            100                 105                 110

Gly Gln Gly Thr Thr Val Thr Val Ser Ser
        115                 120
```

<210> SEQ ID NO 55
<211> LENGTH: 366
<212> TYPE: DNA
<213> ORGANISM: Homo sapiens

<400> SEQUENCE: 55

```
gaggtgcagc tggtggagtc tgggggaggc ttggtccagc ctggggggtc cctgagactc      60
tcctgtgcag tctctggatt cacctttaat agctattgga tgagctgggt ccgccaggct     120
ccagggaagg ggctggagtg ggtggccaac ataaaccaag atggaagtga aaattctat      180 gtggcctctg tgaagggccg attcaccatc tccagagaca cgccaagaa atcagtgtat      240 gtacaaatga acagcctgag agccgaggac acggctgtgt attactgtgc gagagagggg    300
tatagtagtt cgtcctatta tggtatggac gtctggggcc aagggaccac ggtcaccgtc    360
tcctca                                                                366
```

-continued

```
<210> SEQ ID NO 56
<211> LENGTH: 122
<212> TYPE: PRT
<213> ORGANISM: Homo sapiens

<400> SEQUENCE: 56

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Ile Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Ser Tyr Tyr Gly Met Asp Val Trp
            100                 105                 110

Gly Gln Gly Thr Thr Val Thr Val Ser Ser
        115                 120

<210> SEQ ID NO 57
<211> LENGTH: 8
<212> TYPE: PRT
<213> ORGANISM: Homo sapiens

<400> SEQUENCE: 57

Gly Tyr Thr Phe Thr Asn Tyr Ala
1               5

<210> SEQ ID NO 58
<211> LENGTH: 8
<212> TYPE: PRT
<213> ORGANISM: Homo sapiens

<400> SEQUENCE: 58

Ile Asn Ala Gly Asn Gly Phe Thr
1               5

<210> SEQ ID NO 59
<211> LENGTH: 15
<212> TYPE: PRT
<213> ORGANISM: Homo sapiens

<400> SEQUENCE: 59

Ala Arg Asp Trp Ala Ala Ala Ile Ser Tyr Tyr Gly Met Asp Val
1               5                   10                  15

<210> SEQ ID NO 60
<211> LENGTH: 367
<212> TYPE: DNA
<213> ORGANISM: Homo sapiens

<400> SEQUENCE: 60
caggtccagc ttgtgcagtc tggggctgag gtgaagaggc ctggggcctc agtgaaggtt        60
tcctgcaagg cttctggata caccttcact aactatgcta tacattgggt gcgccaggcc       120
cccggacaga ggcttgagtg gatgggatgg atcaacgctg gcaatggttt cacaaaatct       180
tcacagaagt tccggggcag agtcaccatt accaggacag acatccgcga aacagcctac       240
```

```
atggaactga gcagcctcag atctgaagac acggctattt attactgtgc gagagattgg      300
gctgctgcta tctcttacta cggtatggac gtctggggcc aagggaccac ggtcaccgtc      360
tcctcag                                                                367
```

<210> SEQ ID NO 61
<211> LENGTH: 122
<212> TYPE: PRT
<213> ORGANISM: Homo sapiens

<400> SEQUENCE: 61

Gln Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Asn Tyr
            20                  25                  30

Ala Ile His Trp Val Arg Gln Ala Pro Gly Gln Arg Leu Glu Trp Met
        35                  40                  45

Gly Trp Ile Asn Ala Gly Asn Gly Phe Thr Lys Ser Gln Lys Phe
    50                  55                  60

Arg Gly Arg Val Thr Ile Thr Arg Asp Thr Ser Ala Asn Thr Ala Tyr
65                  70                  75                  80

Met Glu Leu Ser Ser Leu Arg Ser Glu Asp Thr Ala Ile Tyr Tyr Cys
                85                  90                  95

Ala Arg Asp Trp Ala Ala Ala Ile Ser Tyr Tyr Gly Met Asp Val Trp
            100                 105                 110

Gly Gln Gly Thr Thr Val Thr Val Ser Ser
        115                 120

<210> SEQ ID NO 62
<211> LENGTH: 8
<212> TYPE: PRT
<213> ORGANISM: Homo sapiens

<400> SEQUENCE: 62

Ser Ser Asn Ile Gly Ser Asn Tyr
1               5

<210> SEQ ID NO 63
<211> LENGTH: 3
<212> TYPE: PRT
<213> ORGANISM: Homo sapiens

<400> SEQUENCE: 63

Arg Asn Thr
1

<210> SEQ ID NO 64
<211> LENGTH: 11
<212> TYPE: PRT
<213> ORGANISM: Homo sapiens

<400> SEQUENCE: 64

Ala Thr Trp Asp Asp Ser Leu Ser Ala Tyr Val
1               5                   10

<210> SEQ ID NO 65
<211> LENGTH: 331
<212> TYPE: DNA
<213> ORGANISM: Homo sapiens

```
<400> SEQUENCE: 65
cagtctgtcc tgactcagcc accctcagcg tctgggaccc ccgggcagag ggtcaccatc     60
tcttgttctg gaagcagctc caacatcgga agtaattatg tatactggta ccagcagctc    120
ccaggaacgg cccccaaact cctcatctat aggaatactc agcggccctc agaggtccct    180
gaccgattct ctggctccaa gtctggcgcc tcagcctccc tggccatcag tgggctccgg    240
tccgaggatg agactgatta ttactgtgca acatgggatg acagcctgag tgcttatgtc    300
ttcggaactg ggaccaaagt caccgtccta g                                   331

<210> SEQ ID NO 66
<211> LENGTH: 110
<212> TYPE: PRT
<213> ORGANISM: Homo sapiens

<400> SEQUENCE: 66

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Arg Asn Thr Gln Arg Pro Ser Glu Val Pro Asp Arg Phe Ser
    50                  55                  60

Gly Ser Lys Ser Gly Ala Ser Ala Ser Leu Ala Ile Ser Gly Leu Arg
65                  70                  75                  80

Ser Glu Asp Glu Thr Asp Tyr Tyr Cys Ala Thr Trp Asp Asp Ser Leu
                85                  90                  95

Ser Ala Tyr Val Phe Gly Thr Gly Thr Lys Val Thr Val Leu
            100                 105                 110

<210> SEQ ID NO 67
<211> LENGTH: 8
<212> TYPE: PRT
<213> ORGANISM: Homo sapiens

<400> SEQUENCE: 67

Gly Phe Thr Phe Ser Ser Tyr Gly
1               5

<210> SEQ ID NO 68
<211> LENGTH: 8
<212> TYPE: PRT
<213> ORGANISM: Homo sapiens

<400> SEQUENCE: 68

Ile Trp Tyr Asp Gly Thr Asn Lys
1               5

<210> SEQ ID NO 69
<211> LENGTH: 15
<212> TYPE: PRT
<213> ORGANISM: Homo sapiens

<400> SEQUENCE: 69

Ala Arg Ser Gly Tyr Ser Ser Ser Trp Tyr Gly Ala Met Asp Val
1               5                   10                  15
```

-continued

```
<210> SEQ ID NO 70
<211> LENGTH: 367
<212> TYPE: DNA
<213> ORGANISM: Homo sapiens

<400> SEQUENCE: 70
caggtgcagc tggtggagtc tgggggaggc gtggtccagc ctgggaggtc cctgagactc      60
tcctgtgcag cgtctggatt caccttcagt agctatggca tgcactgggt ccgccaggct     120
ccaggcgagg ggctggagtg ggtggcagtt atatggtatg atggaactaa taaatactat     180
gcagactcct tgaagggccg attcaccatc tccagagaca attccaagaa cacgctctat     240
ctgcaaatga acaggctgag agccgaggac acggctgtgt attactgtgc gaggtccggg     300
tatagcagca gctggtacgg cgctatggac gtctggggcc aagggaccac ggtcaccgtc     360
tcctcag                                                              367

<210> SEQ ID NO 71
<211> LENGTH: 122
<212> TYPE: PRT
<213> ORGANISM: Homo sapiens

<400> SEQUENCE: 71

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Glu Gly Leu Glu Trp Val
        35                  40                  45

Ala Val Ile Trp Tyr Asp Gly Thr Asn Lys Tyr Tyr Ala Asp Ser Leu
    50                  55                  60

Lys Gly Arg Phe Thr Ile Ser Arg Asp Asn Ser Lys Asn Thr Leu Tyr
65                  70                  75                  80

Leu Gln Met Asn Arg Leu Arg Ala Glu Asp Thr Ala Val Tyr Tyr Cys
                85                  90                  95

Ala Arg Ser Gly Tyr Ser Ser Ser Trp Tyr Gly Ala Met Asp Val Trp
            100                 105                 110

Gly Gln Gly Thr Thr Val Thr Val Ser Ser
        115                 120

<210> SEQ ID NO 72
<211> LENGTH: 9
<212> TYPE: PRT
<213> ORGANISM: Homo sapiens

<400> SEQUENCE: 72

Ser Ser Asp Val Gly Gly Tyr Tyr Tyr
1               5

<210> SEQ ID NO 73
<211> LENGTH: 3
<212> TYPE: PRT
<213> ORGANISM: Homo sapiens

<400> SEQUENCE: 73

Glu Val Asn
1
```

```
<210> SEQ ID NO 74
<211> LENGTH: 10
<212> TYPE: PRT
<213> ORGANISM: Homo sapiens

<400> SEQUENCE: 74

Ser Ser Tyr Ala Gly Ser Asn Thr Trp Val
1               5                   10

<210> SEQ ID NO 75
<211> LENGTH: 331
<212> TYPE: DNA
<213> ORGANISM: Homo sapiens

<400> SEQUENCE: 75
cagtctgccc tgactcagcc tccctccgcg tccgggtctc ctggacagtc agtcaccatc      60
tcctgcactg gaaccagcag tgacgttggt ggttattact atgtctcctg gtaccaacag     120
cacccaggca aagcccccaa actcatgatt tatgaggtca ataagcggcc ctcaggggtc     180
cctgatcgct tctctggctc caagtctggc atcacggcct ccctgaccgt ctctgggctc     240
cagtctgagg atgaggctga ttattactgc agctcatatg caggcagcaa cacttgggtg     300
ttcggcggag ggaccaagct gaccgtccta g                                    331

<210> SEQ ID NO 76
<211> LENGTH: 110
<212> TYPE: PRT
<213> ORGANISM: Homo sapiens

<400> SEQUENCE: 76

Gln Ser Ala Leu Thr Gln Pro Pro Ser Ala Gly Ser Pro Gly Gln
1               5                   10                  15

Ser Val Thr Ile Ser Cys Thr Gly Thr Ser Ser Asp Val Gly Gly Tyr
            20                  25                  30

Tyr Tyr Val Ser Trp Tyr Gln Gln His Pro Gly Lys Ala Pro Lys Leu
        35                  40                  45

Met Ile Tyr Glu Val Asn Lys Arg Pro Ser Gly Val Pro Asp Arg Phe
    50                  55                  60

Ser Gly Ser Lys Ser Gly Ile Thr Ala Ser Leu Thr Val Ser Gly Leu
65                  70                  75                  80

Gln Ser Glu Asp Glu Ala Asp Tyr Tyr Cys Ser Ser Tyr Ala Gly Ser
                85                  90                  95

Asn Thr Trp Val Phe Gly Gly Gly Thr Lys Leu Thr Val Leu
            100                 105                 110

<210> SEQ ID NO 77
<211> LENGTH: 8
<212> TYPE: PRT
<213> ORGANISM: Homo sapiens

<400> SEQUENCE: 77

Gly Tyr Thr Phe Thr Ser Tyr Ala
1               5

<210> SEQ ID NO 78
<211> LENGTH: 8
<212> TYPE: PRT
<213> ORGANISM: Homo sapiens
```

-continued

```
<400> SEQUENCE: 78

Ile Asn Ala Gly Asn Gly Ile Thr
1               5

<210> SEQ ID NO 79
<211> LENGTH: 15
<212> TYPE: PRT
<213> ORGANISM: Homo sapiens

<400> SEQUENCE: 79

Ala Arg Asp Trp Ala Ala Ala Ile Thr Tyr Tyr Gly Met Asp Val
1               5                   10                  15

<210> SEQ ID NO 80
<211> LENGTH: 367
<212> TYPE: DNA
<213> ORGANISM: Homo sapiens

<400> SEQUENCE: 80
caggtccagc ttgtgcagtc tggggctgag gtgaagaggc ctggggcctc agtgaaggtt      60
tcctgcaagg cttctggata caccttcaca agctacgcca tacattgggt gcgccaggcc     120
cccggacaga ggcttgagtg gatgggatgg atcaacgctg gcaatggtat cacaaaatct     180
tcacagaagt tccagggcag agtcaccatt accaggcaca catccgcgaa cacagtttac     240
ctggaactga gcagcctcag atctgaagac acggctgttt attattgtgc gagagattgg     300
gctgctgcta tcacctacta cggtatggac gtctggggcc aagggaccac ggtcaccgtc     360
tcctcag                                                               367

<210> SEQ ID NO 81
<211> LENGTH: 122
<212> TYPE: PRT
<213> ORGANISM: Homo sapiens

<400> SEQUENCE: 81

Gln Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Ser Tyr
                20                  25                  30

Ala Ile His Trp Val Arg Gln Ala Pro Gly Gln Arg Leu Glu Trp Met
            35                  40                  45

Gly Trp Ile Asn Ala Gly Asn Gly Ile Thr Lys Ser Ser Gln Lys Phe
        50                  55                  60

Gln Gly Arg Val Thr Ile Thr Arg Asp Thr Ser Ala Asn Thr Val Tyr
65                  70                  75                  80

Leu Glu Leu Ser Ser Leu Arg Ser Glu Asp Thr Ala Val Tyr Tyr Cys
                85                  90                  95

Ala Arg Asp Trp Ala Ala Ala Ile Thr Tyr Tyr Gly Met Asp Val Trp
                100                 105                 110

Gly Gln Gly Thr Thr Val Thr Val Ser Ser
            115                 120

<210> SEQ ID NO 82
<211> LENGTH: 3
<212> TYPE: PRT
<213> ORGANISM: Homo sapiens
```

<400> SEQUENCE: 82

Arg Asn Asn
1

<210> SEQ ID NO 83
<211> LENGTH: 10
<212> TYPE: PRT
<213> ORGANISM: Homo sapiens

<400> SEQUENCE: 83

Phe Gly Ala Gly Thr Lys Val Thr Val Leu
1               5                   10

<210> SEQ ID NO 84
<211> LENGTH: 331
<212> TYPE: DNA
<213> ORGANISM: Homo sapiens

<400> SEQUENCE: 84
cagtctgtgc tgactcagcc accctcagtg tctgggaccc ccgggcagag ggtcaccatc      60
tcttgttctg gaagcagctc caacatcgga agtaattatg tatactggta ccagcagttc     120
ccaggaacgg cccccaaact cctcatctat aggaataatc agcggccctc agaggtccct     180
gaccgattct ctggctccaa gtctggcgcc tcagcctccc tggccatcag tgggctccgg     240
tccgaggatg agactgatta ttactgtgca acatgggatg acagcctgag tgcttatgtc     300
ttcggagctg ggaccaaagt caccgtccta g                                    331

<210> SEQ ID NO 85
<211> LENGTH: 110
<212> TYPE: PRT
<213> ORGANISM: Homo sapiens

<400> SEQUENCE: 85

Gln Ser Val Leu Thr Gln Pro Pro Ser Val Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Tyr Trp Tyr Gln Gln Phe Pro Gly Thr Ala Pro Lys Leu Leu
        35                  40                  45

Ile Tyr Arg Asn Asn Gln Arg Pro Ser Glu Val Pro Asp Arg Phe Ser
    50                  55                  60

Gly Ser Lys Ser Gly Ala Ser Ala Ser Leu Ala Ile Ser Gly Leu Arg
65                  70                  75                  80

Ser Glu Asp Glu Thr Asp Tyr Tyr Cys Ala Thr Trp Asp Asp Ser Leu
                85                  90                  95

Ser Ala Tyr Val Phe Gly Ala Gly Thr Lys Val Thr Val Leu
            100                 105                 110

<210> SEQ ID NO 86
<211> LENGTH: 8
<212> TYPE: PRT
<213> ORGANISM: Homo sapiens

<400> SEQUENCE: 86

Glu Phe Thr Phe Ser Thr Ala Gly
1               5

<210> SEQ ID NO 87
<211> LENGTH: 8
<212> TYPE: PRT
<213> ORGANISM: Homo sapiens

<400> SEQUENCE: 87

Ile Ser Tyr Asp Gly Ser Asn Lys
1               5

<210> SEQ ID NO 88
<211> LENGTH: 15
<212> TYPE: PRT
<213> ORGANISM: Homo sapiens

<400> SEQUENCE: 88

Ala Lys Asp Phe Thr Met Val Arg Gly Val Ile Ile Met Asp Val
1               5                   10                  15

<210> SEQ ID NO 89
<211> LENGTH: 361
<212> TYPE: DNA
<213> ORGANISM: Homo sapiens

<400> SEQUENCE: 89
caggtgcagc tggtggagtc tggggggggc gtactccagc ctgggaagtc cctgagactc      60
tcctgtgcag cctctgaatt caccttcagt accgctggca tgcactgggt ccgccaggct     120
ccaggcaagg ggctggagtg ggtgactttt atatcatatg atggaagtaa taaatactat     180
gcagactccg tgaagggccg attcaccatc tccagagaca attccaaggt gtatctgcaa     240
atgaacagcc tgagaactga ggacacggct gtgtattact gtgcgaaaga tttcactatg     300
gttcggggag ttattataat ggacgtctgg ggccaaggga ccacggtcac cgtctcctca     360
g                                                                    361

<210> SEQ ID NO 90
<211> LENGTH: 120
<212> TYPE: PRT
<213> ORGANISM: Homo sapiens

<400> SEQUENCE: 90

Gln Val Gln Leu Val Glu Ser Gly Gly Gly Val Leu Gln Pro Gly Lys
1               5                   10                  15

Ser Leu Arg Leu Ser Cys Ala Ala Ser Glu Phe Thr Phe Ser Thr Ala
            20                  25                  30

Gly Met His Trp Val Arg Gln Ala Pro Gly Lys Gly Leu Glu Trp Val
        35                  40                  45

Thr Phe Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Val Tyr Leu Gln
65                  70                  75                  80

Met Asn Ser Leu Arg Thr Glu Asp Thr Ala Val Tyr Tyr Cys Ala Lys
                85                  90                  95

Asp Phe Thr Met Val Arg Gly Val Ile Ile Met Asp Val Trp Gly Gln
            100                 105                 110

Gly Thr Thr Val Thr Val Ser Ser
        115                 120

-continued

<210> SEQ ID NO 91
<211> LENGTH: 6
<212> TYPE: PRT
<213> ORGANISM: Homo sapiens

<400> SEQUENCE: 91

Gln Asp Ile Ser Asn Tyr
1               5

<210> SEQ ID NO 92
<211> LENGTH: 3
<212> TYPE: PRT
<213> ORGANISM: Homo sapiens

<400> SEQUENCE: 92

Asp Ala Ser
1

<210> SEQ ID NO 93
<211> LENGTH: 9
<212> TYPE: PRT
<213> ORGANISM: Homo sapiens

<400> SEQUENCE: 93

Gln Gln Tyr Asp Asn Leu Pro Ile Thr
1               5

<210> SEQ ID NO 94
<211> LENGTH: 322
<212> TYPE: DNA
<213> ORGANISM: Homo sapiens

<400> SEQUENCE: 94
gacatccaga tgacccagtc tccatcctcc ctgtctgtat ctgtaggaga cagagtcacc      60
atcacttgcc aggcgagtca ggacattagc aactatttaa attggtatca gcagaaacca     120
gggaaagccc ctaagctcct gatctacgat gcatccaatt tggaaacagg ggtcccatca     180
aggttcagtg gaagtggatc tgggacagat tttactttca tcatcagcag cctgcagcct     240
gaagatattg caacatatta ctgtcaacag tatgataatc tcccgatcac cttcggccaa     300
gggacacgac tggagatcaa ac                                              322

<210> SEQ ID NO 95
<211> LENGTH: 107
<212> TYPE: PRT
<213> ORGANISM: Homo sapiens

<400> SEQUENCE: 95

Asp Ile Gln Met Thr Gln Ser Pro Ser Ser Leu Ser Val Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Ile Ile Ser Ser Leu Gln Pro
65                  70                  75                  80

-continued

Glu Asp Ile Ala Thr Tyr Tyr Cys Gln Gln Tyr Asp Asn Leu Pro Ile
                85                  90                  95
Thr Phe Gly Gln Gly Thr Arg Leu Glu Ile Lys
            100                 105

<210> SEQ ID NO 96
<211> LENGTH: 8
<212> TYPE: PRT
<213> ORGANISM: Homo sapiens

<400> SEQUENCE: 96

Gly Gly Ser Ile Ser Ser Tyr Tyr
1               5

<210> SEQ ID NO 97
<211> LENGTH: 7
<212> TYPE: PRT
<213> ORGANISM: Homo sapiens

<400> SEQUENCE: 97

Ile Tyr Tyr Ser Gly Ser Thr
1               5

<210> SEQ ID NO 98
<211> LENGTH: 8
<212> TYPE: PRT
<213> ORGANISM: Homo sapiens

<400> SEQUENCE: 98

Ala Lys Gly Ala Ala Gly Asp Tyr
1               5

<210> SEQ ID NO 99
<211> LENGTH: 343
<212> TYPE: DNA
<213> ORGANISM: Homo sapiens

<400> SEQUENCE: 99
caggtgcagc tgcaggagtc gggcccagga ctggtgaagc cttcggagac cctgtccctc      60
acctgcactg tctctggtgg ctccatcagt agttattact ggagctggat ccggcagccc     120
ccagggaagg gactggagtg gattgggtat atctattaca gtgggagcac caactataac     180
ccctccctca agagtcgagt caacatatca gtagacacgt ccaagaacca gttctccctg     240
aggctgagtt ctgtgaccgc tgcggacacg gccgtgtatt attgtgcgaa aggggcagct     300
ggggactact ggggccaggg aaccctggtc accgtctcct cag                      343

<210> SEQ ID NO 100
<211> LENGTH: 114
<212> TYPE: PRT
<213> ORGANISM: Homo sapiens

<400> SEQUENCE: 100

Gln Val Gln Leu Gln Glu Ser Gly Pro Gly Leu Val Lys Pro Ser Glu
1               5                   10                  15
Thr Leu Ser Leu Thr Cys Thr Val Ser Gly Gly Ser Ile Ser Ser Tyr
            20                  25                  30
Tyr Trp Ser Trp Ile Arg Gln Pro Pro Gly Lys Gly Leu Glu Trp Ile
        35                  40                  45
Gly Tyr Ile Tyr Tyr Ser Gly Ser Thr Asn Tyr Asn Pro Ser Leu Lys
    50                  55                  60

```
Ser Arg Val Asn Ile Ser Val Asp Thr Ser Lys Asn Gln Phe Ser Leu
 65                  70                  75                  80

Arg Leu Ser Ser Val Thr Ala Ala Asp Thr Ala Val Tyr Tyr Cys Ala
                 85                  90                  95

Lys Gly Ala Ala Gly Asp Tyr Trp Gly Gln Gly Thr Leu Val Thr Val
            100                 105                 110

Ser Ser

<210> SEQ ID NO 101
<211> LENGTH: 6
<212> TYPE: PRT
<213> ORGANISM: Homo sapiens

<400> SEQUENCE: 101

Gln Ser Val Asn Ser Tyr
 1               5

<210> SEQ ID NO 102
<211> LENGTH: 9
<212> TYPE: PRT
<213> ORGANISM: Homo sapiens

<400> SEQUENCE: 102

Gln Gln Arg Asn Asn Trp Pro Ile Thr
 1               5

<210> SEQ ID NO 103
<211> LENGTH: 322
<212> TYPE: DNA
<213> ORGANISM: Homo sapiens

<400> SEQUENCE: 103
gaaattgtgt tggcacagtc tccagccacc ctgtctttgt ctccagggga aagagccacg    60
ttctcctgca gggccagtca gagtgttaac agctacttag cctggcacca acagaaacct   120
ggccaggctc ccaggctcct catctatgat gcatccaaca gggccactgg catcccagcc   180
aggttcagtg gcagtgggtc cgggacagac ttcactctca ccatcagcag cctagagcct   240
gaagattttg cagtttatta ctgtcagcag cgtaacaact ggcctatcac cttcggccaa   300
gggacacgac tggagatcaa ac                                            322

<210> SEQ ID NO 104
<211> LENGTH: 107
<212> TYPE: PRT
<213> ORGANISM: Homo sapiens

<400> SEQUENCE: 104

Glu Ile Val Leu Ala Gln Ser Pro Ala Thr Leu Ser Leu Ser Pro Gly
 1               5                  10                  15

Glu Arg Ala Thr Phe Ser Cys Arg Ala Ser Gln Ser Val Asn Ser Tyr
                 20                  25                  30

Leu Ala Trp His Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
         50                  55                  60

Ser Gly Ser Gly Thr Asp Phe Thr Leu Thr Ile Ser Ser Leu Glu Pro
 65                  70                  75                  80
```

Glu Asp Phe Ala Val Tyr Tyr Cys Gln Gln Arg Asn Asn Trp Pro Ile
            85                  90                  95

Thr Phe Gly Gln Gly Thr Arg Leu Glu Ile Lys
            100                 105

<210> SEQ ID NO 105
<211> LENGTH: 8
<212> TYPE: PRT
<213> ORGANISM: Homo sapiens

<400> SEQUENCE: 105

Gly Gly Ser Ile Ser Lys Tyr Tyr
1               5

<210> SEQ ID NO 106
<211> LENGTH: 7
<212> TYPE: PRT
<213> ORGANISM: Homo sapiens

<400> SEQUENCE: 106

Ile Tyr Tyr Ser Gly Asn Thr
1               5

<210> SEQ ID NO 107
<211> LENGTH: 7
<212> TYPE: PRT
<213> ORGANISM: Homo sapiens

<400> SEQUENCE: 107

Ala Arg Gly Leu Gly Asp Tyr
1               5

<210> SEQ ID NO 108
<211> LENGTH: 340
<212> TYPE: DNA
<213> ORGANISM: Homo sapiens

<400> SEQUENCE: 108
caggtgcagc tgcaggagtc gggcccagga ctggtgaagc cttcggagac cctgtccctc      60
acctgcactg tctctggtgg ctccatcagt aaatactact ggagctggat ccggcagccc     120
ccagggaagg gactggagtg gattggatat atctattaca gtgggaacac ctaccagaat     180
ccctccctca gagtcgagt caccatatca atagacacgt ccaagaacca gatctccctg     240
aaggtgagct ctgtgaccgc tgcggacacg gccgtctatt actgtgcgag agggctgggg     300
gactactggg gccagggaac cctggtcacc gtctcctcag                           340

<210> SEQ ID NO 109
<211> LENGTH: 113
<212> TYPE: PRT
<213> ORGANISM: Homo sapiens

<400> SEQUENCE: 109

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Lys Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Asn Thr Tyr Gln Asn Pro Ser Leu Lys
    50                  55                  60

```
Ser Arg Val Thr Ile Ser Ile Asp Thr Ser Lys Asn Gln Ile Ser Leu
 65                  70                  75                  80

Lys Val Ser Ser Val Thr Ala Ala Asp Thr Ala Val Tyr Tyr Cys Ala
                 85                  90                  95

Arg Gly Leu Gly Asp Tyr Trp Gly Gln Gly Thr Leu Val Thr Val Ser
            100                 105                 110

Ser
```

<210> SEQ ID NO 110
<211> LENGTH: 6
<212> TYPE: PRT
<213> ORGANISM: Homo sapiens

<400> SEQUENCE: 110

```
Gln Ser Val Ser Ser Tyr
1               5
```

<210> SEQ ID NO 111
<211> LENGTH: 9
<212> TYPE: PRT
<213> ORGANISM: Homo sapiens

<400> SEQUENCE: 111

```
Gln Gln Arg Ser Asn Trp Pro Leu Thr
1               5
```

<210> SEQ ID NO 112
<211> LENGTH: 322
<212> TYPE: DNA
<213> ORGANISM: Homo sapiens

<400> SEQUENCE: 112

```
gaaattgtgt tgacacagtc tccagccacc ctgtctttgt ctccagggga aagagccacc      60
ctctcctgca gggccagtca gagtgttagc agctacttag cctggcacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcaa cgtagcaact ggcctctcac tttcggcgga     300
gggaccaagg tggagatcaa ac                                              322
```

<210> SEQ ID NO 113
<211> LENGTH: 107
<212> TYPE: PRT
<213> ORGANISM: Homo sapiens

<400> SEQUENCE: 113

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp His Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80
```

Glu Asp Phe Ala Val Tyr Tyr Cys Gln Gln Arg Ser Asn Trp Pro Leu
            85                  90                  95
Thr Phe Gly Gly Gly Thr Lys Val Glu Ile Lys
            100                 105

<210> SEQ ID NO 114
<211> LENGTH: 8
<212> TYPE: PRT
<213> ORGANISM: Homo sapiens

<400> SEQUENCE: 114

Gly Gly Ser Ile Ser Arg Tyr Tyr
1               5

<210> SEQ ID NO 115
<211> LENGTH: 7
<212> TYPE: PRT
<213> ORGANISM: Homo sapiens

<400> SEQUENCE: 115

Ile Tyr Tyr Ser Gly Thr Thr
1               5

<210> SEQ ID NO 116
<211> LENGTH: 7
<212> TYPE: PRT
<213> ORGANISM: Homo sapiens

<400> SEQUENCE: 116

Ala Arg Gly Leu Gly Asp Phe
1               5

<210> SEQ ID NO 117
<211> LENGTH: 340
<212> TYPE: DNA
<213> ORGANISM: Homo sapiens

<400> SEQUENCE: 117
caggtgcagc tgcaggagtc gggcccagga ctggtgaagc cttcggagac cctgtccctc      60
acctgcagtg tctctggtgg ctccattagt agatattact ggagctggat ccggcagccc     120
ccagggaagg gactggagtg gattggatat atctattaca gtgggaccac ctactataac     180
ccctccctca agagtcgagt cacctttttca gtagacacgt ccaagaccca gttctccctg    240
aaacttaact ctgtgaccgc tgcggacacg gccgtatatt actgtgcgag aggactgggg    300
gacttctggg gccggggaac cctggtcacc gtctcctcag                           340

<210> SEQ ID NO 118
<211> LENGTH: 113
<212> TYPE: PRT
<213> ORGANISM: Homo sapiens

<400> SEQUENCE: 118

Gln Val Gln Leu Gln Glu Ser Gly Pro Gly Leu Val Lys Pro Ser Glu
1               5                   10                  15

Thr Leu Ser Leu Thr Cys Ser Val Ser Gly Gly Ser Ile Ser Arg Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Thr Thr Tyr Tyr Asn Pro Ser Leu Lys
    50                  55                  60

```
Ser Arg Val Thr Phe Ser Val Asp Thr Ser Lys Thr Gln Phe Ser Leu
 65                  70                  75                  80

Lys Leu Asn Ser Val Thr Ala Ala Asp Thr Ala Val Tyr Tyr Cys Ala
                 85                  90                  95

Arg Gly Leu Gly Asp Phe Trp Gly Arg Gly Thr Leu Val Thr Val Ser
            100                 105                 110

Ser

<210> SEQ ID NO 119
<211> LENGTH: 6
<212> TYPE: PRT
<213> ORGANISM: Homo sapiens

<400> SEQUENCE: 119

Gln Ser Val Ser Gly Tyr
1               5

<210> SEQ ID NO 120
<211> LENGTH: 322
<212> TYPE: DNA
<213> ORGANISM: Homo sapiens

<400> SEQUENCE: 120
gaaattgtgt tgactcagtc tccagccacc ctgtcattgt ctccagggga aagggccacc      60
ctctcctgcc gggccagtca gagtgttagc ggctacttag cctggcacca acagaaacct    120
ggccaggctc ccaggctcct catctatgat gcatccaaca gggccactgg catcccagcc    180
agattcagtg gcagtgggtc tgggacagac ttcactctca ccatcagcag cctagagcct    240
gaagattttg cagtttatta ctgtcagcaa cgtagcaact ggcctctcac tttcggcgga    300
gggaccaagg tggagatcaa ac                                             322

<210> SEQ ID NO 121
<211> LENGTH: 107
<212> TYPE: PRT
<213> ORGANISM: Homo sapiens

<400> SEQUENCE: 121

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Gly Tyr
                20                  25                  30

Leu Ala Trp His Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Leu
                 85                  90                  95

Thr Phe Gly Gly Gly Thr Lys Val Glu Ile Lys
            100                 105

<210> SEQ ID NO 122
<211> LENGTH: 10
<212> TYPE: PRT
<213> ORGANISM: Homo sapiens
```

<400> SEQUENCE: 122

Gly Gly Ser Ile Ser Ser Gly Ile Tyr Tyr
1               5                   10

<210> SEQ ID NO 123
<211> LENGTH: 7
<212> TYPE: PRT
<213> ORGANISM: Homo sapiens

<400> SEQUENCE: 123

Ile Asn Asn Ser Gly Asn Thr
1               5

<210> SEQ ID NO 124
<211> LENGTH: 8
<212> TYPE: PRT
<213> ORGANISM: Homo sapiens

<400> SEQUENCE: 124

Ala Arg Gly Gly Ser Gly Asp Tyr
1               5

<210> SEQ ID NO 125
<211> LENGTH: 349
<212> TYPE: DNA
<213> ORGANISM: Homo sapiens

<400> SEQUENCE: 125
caggtgcagc tgcaggagtc gggcccagga ctggtgaagc cttcagagac cctgtccctc      60
acctgcactg tctctggtgg ctccatcagt agtggtatat actactggag ttggatccgc     120
cagcacccag ggaagggcct ggagtggatt ggatacatca ataacagtgg aacacctac     180
tacaacccgt ccctcaaggg tcgagttaac atatcagtag acacgtctaa gaaacagttc     240
tccctgaagc tgagctctgt gactgacgcg gacacggccg tctattactg tgcgaggggg     300
ggatcgggcg actactgggg ccagggaacc ctggtcaccg tctcctcag                349

<210> SEQ ID NO 126
<211> LENGTH: 116
<212> TYPE: PRT
<213> ORGANISM: Homo sapiens

<400> SEQUENCE: 126

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Ile Tyr Tyr Trp Ser Trp Ile Arg Gln His Pro Gly Lys Gly Leu Glu
        35                  40                  45

Trp Ile Gly Tyr Ile Asn Asn Ser Gly Asn Thr Tyr Tyr Asn Pro Ser
    50                  55                  60

Leu Lys Gly Arg Val Asn Ile Ser Val Asp Thr Ser Lys Lys Gln Phe
65                  70                  75                  80

Ser Leu Lys Leu Ser Ser Val Thr Asp Ala Asp Thr Ala Val Tyr Tyr
                85                  90                  95

Cys Ala Arg Gly Gly Ser Gly Asp Tyr Trp Gly Gln Gly Thr Leu Val
            100                 105                 110

Thr Val Ser Ser
        115

<210> SEQ ID NO 127
<211> LENGTH: 28
<212> TYPE: PRT
<213> ORGANISM: Homo sapiens

<400> SEQUENCE: 127

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys
            20                  25

<210> SEQ ID NO 128
<211> LENGTH: 6
<212> TYPE: PRT
<213> ORGANISM: Homo sapiens

<400> SEQUENCE: 128

Gln Ser Ile Asn Asn Tyr
1               5

<210> SEQ ID NO 129
<211> LENGTH: 9
<212> TYPE: PRT
<213> ORGANISM: Homo sapiens

<400> SEQUENCE: 129

Gln Gln Arg Asn Asn Trp Pro Pro Thr
1               5

<210> SEQ ID NO 130
<211> LENGTH: 322
<212> TYPE: DNA
<213> ORGANISM: Homo sapiens

<400> SEQUENCE: 130
gaaattgtgt tgacacagtc tccagccacc ctgtctttgt ctccagggga aagagccacc    60
ctctcctgca ggaccagtca gagtattaac aactacttag cctggttcca acagaaacct   120
ggccaggctc ccaggctcct catctatgat gcatccaaca gggcccctgg catcccagcc   180
aggttcagtg gcagtgggtc tgggacagac ttcactctca ccatcagcag cctggagcct   240
gaagattttg tagtttattt ctgtcagcag cgtaacaact ggcctccgac attcggccaa   300
gggaccaagg tggaaatcaa ac                                            322

<210> SEQ ID NO 131
<211> LENGTH: 107
<212> TYPE: PRT
<213> ORGANISM: Homo sapiens

<400> SEQUENCE: 131

Glu Ile Val Leu Thr Gln Ser Pro Ala Thr Leu Ser Leu Ser Pro Gly
1               5                   10                  15

Glu Arg Ala Thr Leu Ser Cys Arg Thr Ser Gln Ser Ile Asn Asn Tyr
            20                  25                  30

Leu Ala Trp Phe Gln Gln Lys Pro Gly Gln Ala Pro Arg Leu Leu Ile
        35                  40                  45

Tyr Asp Ala Ser Asn Arg Ala Pro Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

```
Glu Asp Phe Val Val Tyr Phe Cys Gln Gln Arg Asn Asn Trp Pro Pro
                    85                  90                  95

Thr Phe Gly Gln Gly Thr Lys Val Glu Ile Lys
            100                 105

<210> SEQ ID NO 132
<211> LENGTH: 25
<212> TYPE: PRT
<213> ORGANISM: Homo sapiens

<400> SEQUENCE: 132

Glu Val Gln Leu Val Glu Ser Gly Gly Gly Phe Val Gln Pro Gly Gly
1               5                   10                  15

Ser Leu Arg Leu Ser Cys Ala Val Ser
            20                  25

<210> SEQ ID NO 133
<211> LENGTH: 17
<212> TYPE: PRT
<213> ORGANISM: Homo sapiens

<400> SEQUENCE: 133

Met Ser Trp Val Arg Gln Ala Pro Gly Lys Gly Leu Glu Trp Val Ala
1               5                   10                  15

Asn

<210> SEQ ID NO 134
<211> LENGTH: 38
<212> TYPE: PRT
<213> ORGANISM: Homo sapiens

<400> SEQUENCE: 134

Phe Tyr Val Ala Ser Val Lys Gly Arg Phe Thr Met Ser Arg Asp Asn
1               5                   10                  15

Ala Lys Lys Ser Val Tyr Val Gln Met Asn Ser Leu Arg Ala Glu Asp
            20                  25                  30

Thr Ala Val Tyr Tyr Cys
            35

<210> SEQ ID NO 135
<211> LENGTH: 11
<212> TYPE: PRT
<213> ORGANISM: Homo sapiens

<400> SEQUENCE: 135

Trp Gly Gln Gly Thr Thr Val Thr Val Ser Ser
1               5                   10

<210> SEQ ID NO 136
<211> LENGTH: 25
<212> TYPE: PRT
<213> ORGANISM: Homo sapiens

<400> SEQUENCE: 136

Ser Tyr Val Leu Thr Gln Pro Pro Ser Val Ser Val Ala Pro Gly Glu
1               5                   10                  15

Thr Ala Arg Ile Thr Cys Gly Gly Asp
            20                  25
```

```
<210> SEQ ID NO 137
<211> LENGTH: 17
<212> TYPE: PRT
<213> ORGANISM: Homo sapiens

<400> SEQUENCE: 137

Val Tyr Trp Tyr Gln Gln Lys Ser Gly Gln Ala Pro Val Leu Val Ile
1               5                   10                  15

Tyr

<210> SEQ ID NO 138
<211> LENGTH: 36
<212> TYPE: PRT
<213> ORGANISM: Homo sapiens

<400> SEQUENCE: 138

Asp Arg Pro Ser Gly Ile Pro Glu Arg Phe Ser Gly Ser Asn Ser Gly
1               5                   10                  15

Asn Thr Ala Thr Leu Thr Ile Ser Arg Val Glu Ala Gly Asp Glu Ala
            20                  25                  30

Asp Tyr Tyr Cys
        35

<210> SEQ ID NO 139
<211> LENGTH: 10
<212> TYPE: PRT
<213> ORGANISM: Homo sapiens

<400> SEQUENCE: 139

Phe Gly Gly Gly Thr Lys Leu Thr Val Leu
1               5                   10

<210> SEQ ID NO 140
<211> LENGTH: 8
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa = Thr or Ile
<220> FEATURE:
<221> NAME/KEY: MISC_FEATURE
<222> LOCATION: (5)..(5)
<223> OTHER INFORMATION: Xaa = Ser or Asn
<220> FEATURE:
<221> NAME/KEY: MISC_FEATURE
<222> LOCATION: (6)..(6)
<223> OTHER INFORMATION: Xaa = Ser or Asn

<400> SEQUENCE: 140

Gly Phe Xaa Phe Xaa Xaa Tyr Met
1               5

<210> SEQ ID NO 141
<211> LENGTH: 8
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = Asn or Lys

<400> SEQUENCE: 141

Ile Xaa Gln Asp Gly Ser Glu Lys
1               5
```

```
<210> SEQ ID NO 142
<211> LENGTH: 13
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: Xaa = Ser or Thr
<220> FEATURE:
<221> NAME/KEY: MISC_FEATURE
<222> LOCATION: (7)..(7)
<223> OTHER INFORMATION: Xaa = Ser or Asp
<220> FEATURE:
<221> NAME/KEY: MISC_FEATURE
<222> LOCATION: (8)..(8)
<223> OTHER INFORMATION: Xaa = Ser or Tyr
<220> FEATURE:
<221> NAME/KEY: MISC_FEATURE
<222> LOCATION: (9)..(9)
<223> OTHER INFORMATION: Xaa = Ser or Tyr

<400> SEQUENCE: 142

Ala Arg Glu Gly Tyr Xaa Xaa Xaa Xaa Gly Met Asp Val
1               5                   10

<210> SEQ ID NO 143
<211> LENGTH: 327
<212> TYPE: PRT
<213> ORGANISM: Artificial Sequence
<220> FEATURE:
<223> OTHER INFORMATION: IgG4 PE

<400> SEQUENCE: 143

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220
```

```
Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 144
<211> LENGTH: 327
<212> TYPE: PRT
<213> ORGANISM: Artificial Sequence
<220> FEATURE:
<223> OTHER INFORMATION: IgG4ra

<400> SEQUENCE: 144

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Cys Thr Leu Pro Pro Ser Gln Glu Glu Met Thr Lys
225                 230                 235                 240

Asn Gln Val Ser Leu Trp Cys Leu Val Lys Gly Phe Tyr Pro Ser Asp
                245                 250                 255
```

-continued

Ile Ala Val Glu Trp Glu Ser Asn Gly Gln Pro Glu Asn Asn Tyr Lys
           260                 265                 270

Thr Thr Pro Pro Val Leu Asp Ser Asp Gly Ser Phe Phe Leu Tyr Ser
           275                 280                 285

Arg Leu Thr Val Asp Lys Ser Arg Trp Gln Glu Gly Asn Val Phe Ser
           290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 145
<211> LENGTH: 327
<212> TYPE: PRT
<213> ORGANISM: Artificial Sequence
<220> FEATURE:
<223> OTHER INFORMATION: IgG4yb

<400> SEQUENCE: 145

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Cys Glu Met Thr Lys
225                 230                 235                 240

Asn Gln Val Ser Leu Ser Cys Ala Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Val Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 146
<211> LENGTH: 106
<212> TYPE: PRT
<213> ORGANISM: Homo sapiens

<400> SEQUENCE: 146

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Lys Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 147
<211> LENGTH: 108
<212> TYPE: PRT
<213> ORGANISM: Homo sapiens

<400> SEQUENCE: 147

Lys Arg Thr Val Ala Ala Pro Ser Val Phe Ile Phe Pro Pro Ser Asp
1               5                   10                  15

Glu Gln Leu Lys Ser Gly Thr Ala Ser Val Val Cys Leu Leu Asn Asn
            20                  25                  30

Phe Tyr Pro Arg Glu Ala Lys Val Gln Trp Lys Val Asp Asn Ala Leu
        35                  40                  45

Gln Ser Gly Asn Ser Gln Glu Ser Val Thr Glu Gln Asp Ser Lys Asp
    50                  55                  60

Ser Thr Tyr Ser Leu Ser Ser Thr Leu Thr Leu Ser Lys Ala Asp Tyr
65                  70                  75                  80

Glu Lys His Lys Val Tyr Ala Cys Glu Val Thr His Gln Gly Leu Ser
                85                  90                  95

Ser Pro Val Thr Lys Ser Phe Asn Arg Gly Glu Cys
            100                 105

<210> SEQ ID NO 148
<211> LENGTH: 25
<212> TYPE: PRT
<213> ORGANISM: Homo sapiens

<400> SEQUENCE: 148

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 149
<211> LENGTH: 38
<212> TYPE: PRT
<213> ORGANISM: Homo sapiens

<400> SEQUENCE: 149

Tyr Tyr Val Asp Ser Val Lys Gly Arg Phe Thr Ile Ser Arg Asp Asn
1               5                   10                  15

Ala Lys Asn Ser Leu Tyr Leu Gln Met Asn Ser Leu Arg Ala Glu Asp
            20                  25                  30

Thr Ala Val Tyr Tyr Cys
                35

<210> SEQ ID NO 150
<211> LENGTH: 25
<212> TYPE: PRT
<213> ORGANISM: Homo sapiens

<400> SEQUENCE: 150

Glu Val Gln Leu Val Glu Ser Gly Gly Gly Leu Val Gln Pro Gly Gly
1               5                   10                  15

Ser Leu Arg Leu Ser Cys Val Ala Ser
            20                  25

<210> SEQ ID NO 151
<211> LENGTH: 25
<212> TYPE: PRT
<213> ORGANISM: Homo sapiens

<400> SEQUENCE: 151

Glu Val Gln Leu Val Glu Ser Gly Gly Gly Leu Val Gln Pro Gly Gly
1               5                   10                  15

Ser Leu Arg Leu Ser Cys Ala Val Ser
            20                  25

<210> SEQ ID NO 152
<211> LENGTH: 38
<212> TYPE: PRT
<213> ORGANISM: Homo sapiens

<400> SEQUENCE: 152

Phe Tyr Val Ala Ser Val Lys Gly Arg Phe Thr Ile Ser Arg Asp Asn
1               5                   10                  15

Ala Lys Asn Ser Val Tyr Leu Gln Met Asn Ser Leu Arg Ala Glu Asp
            20                  25                  30

Thr Ala Val Tyr Tyr Cys
                35

<210> SEQ ID NO 153
<211> LENGTH: 38
<212> TYPE: PRT
<213> ORGANISM: Homo sapiens

<400> SEQUENCE: 153

Phe Tyr Val Ala Ser Val Lys Gly Arg Phe Ile Ile Ser Arg Asp Asn
1               5                   10                  15

Ala Lys Asn Ser Val Tyr Leu Gln Met Asn Ser Leu Arg Ala Glu Asp
            20                  25                  30

Thr Ala Val Tyr Tyr Cys
        35

<210> SEQ ID NO 154
<211> LENGTH: 11
<212> TYPE: PRT
<213> ORGANISM: Homo sapiens

<400> SEQUENCE: 154

Trp Gly Gln Gly Thr Thr Val Ser Val Ser Ser
1               5                   10

<210> SEQ ID NO 155
<211> LENGTH: 38
<212> TYPE: PRT
<213> ORGANISM: Homo sapiens

<400> SEQUENCE: 155

Phe Tyr Val Ala Ser Val Lys Gly Arg Phe Thr Met Ser Arg Asp Asn
1               5                   10                  15

Ala Lys Asn Ser Val Tyr Leu Gln Met Asn Ser Leu Arg Ala Glu Asp
            20                  25                  30

Thr Ala Val Tyr Tyr Cys
        35

<210> SEQ ID NO 156
<211> LENGTH: 38
<212> TYPE: PRT
<213> ORGANISM: Homo sapiens

<400> SEQUENCE: 156

Phe Tyr Val Ala Ser Val Lys Gly Arg Phe Thr Ile Ser Arg Asp Asn
1               5                   10                  15

Ala Lys Lys Ser Val Tyr Leu Gln Met Asn Ser Leu Arg Ala Glu Asp
            20                  25                  30

Thr Ala Val Tyr Tyr Cys
        35

<210> SEQ ID NO 157
<211> LENGTH: 38
<212> TYPE: PRT
<213> ORGANISM: Homo sapiens

<400> SEQUENCE: 157

Phe Tyr Val Ala Ser Val Lys Gly Arg Phe Thr Ile Ser Arg Asp Asn
1               5                   10                  15

Ala Lys Asn Ser Val Tyr Val Gln Met Asn Ser Leu Arg Ala Glu Asp
            20                  25                  30

Thr Ala Val Tyr Tyr Cys
        35

<210> SEQ ID NO 158
<211> LENGTH: 38
<212> TYPE: PRT
<213> ORGANISM: Homo sapiens

```
<400> SEQUENCE: 158

Phe Tyr Val Ala Ser Val Lys Gly Arg Phe Thr Ile Ser Arg Asp Asn
1               5                   10                  15

Ala Lys Lys Ser Val Tyr Val Gln Met Asn Ser Leu Arg Ala Glu Asp
            20                  25                  30

Thr Ala Val Tyr Tyr Cys
        35

<210> SEQ ID NO 159
<211> LENGTH: 38
<212> TYPE: PRT
<213> ORGANISM: Homo sapiens

<400> SEQUENCE: 159

Phe Tyr Val Ala Ser Val Lys Gly Arg Phe Thr Met Ser Arg Asp Asn
1               5                   10                  15

Ala Lys Asn Ser Val Tyr Val Gln Met Asn Ser Leu Arg Ala Glu Asp
            20                  25                  30

Thr Ala Val Tyr Tyr Cys
        35

<210> SEQ ID NO 160
<211> LENGTH: 38
<212> TYPE: PRT
<213> ORGANISM: Homo sapiens

<400> SEQUENCE: 160

Phe Tyr Val Ala Ser Val Lys Gly Arg Phe Thr Met Ser Arg Asp Asn
1               5                   10                  15

Ala Lys Lys Ser Val Tyr Leu Gln Met Asn Ser Leu Arg Ala Glu Asp
            20                  25                  30

Thr Ala Val Tyr Tyr Cys
        35

<210> SEQ ID NO 161
<211> LENGTH: 15
<212> TYPE: PRT
<213> ORGANISM: Homo sapiens

<400> SEQUENCE: 161

Ala Arg Glu Gly Tyr Ala Ser Ser Ser Tyr Tyr Gly Met Asp Val
1               5                   10                  15

<210> SEQ ID NO 162
<211> LENGTH: 15
<212> TYPE: PRT
<213> ORGANISM: Homo sapiens

<400> SEQUENCE: 162

Ala Arg Glu Gly Tyr Ser Ala Ser Ser Tyr Tyr Gly Met Asp Val
1               5                   10                  15

<210> SEQ ID NO 163
<211> LENGTH: 15
<212> TYPE: PRT
```

<400> SEQUENCE: 163

Ala Arg Glu Gly Tyr Ser Ser Ala Ser Tyr Tyr Gly Met Asp Val
1               5                   10                  15

<210> SEQ ID NO 164
<211> LENGTH: 15
<212> TYPE: PRT
<213> ORGANISM: Homo sapiens

<400> SEQUENCE: 164

Ala Arg Glu Gly Tyr Ser Ser Ser Ala Tyr Tyr Gly Met Asp Val
1               5                   10                  15

<210> SEQ ID NO 165
<211> LENGTH: 15
<212> TYPE: PRT
<213> ORGANISM: Homo sapiens

<400> SEQUENCE: 165

Ala Arg Glu Gly Tyr Ser Ser Cys Ser Tyr Tyr Gly Met Asp Val
1               5                   10                  15

<210> SEQ ID NO 166
<211> LENGTH: 15
<212> TYPE: PRT
<213> ORGANISM: Homo sapiens

<400> SEQUENCE: 166

Ala Arg Glu Gly Tyr Ser Ser Asp Ser Tyr Tyr Gly Met Asp Val
1               5                   10                  15

<210> SEQ ID NO 167
<211> LENGTH: 15
<212> TYPE: PRT
<213> ORGANISM: Homo sapiens

<400> SEQUENCE: 167

Ala Arg Glu Gly Tyr Ser Ser Glu Ser Tyr Tyr Gly Met Asp Val
1               5                   10                  15

<210> SEQ ID NO 168
<211> LENGTH: 15
<212> TYPE: PRT
<213> ORGANISM: Homo sapiens

<400> SEQUENCE: 168

Ala Arg Glu Gly Tyr Ser Ser Phe Ser Tyr Tyr Gly Met Asp Val
1               5                   10                  15

<210> SEQ ID NO 169
<211> LENGTH: 15
<212> TYPE: PRT
<213> ORGANISM: Homo sapiens

<400> SEQUENCE: 169

Ala Arg Glu Gly Tyr Ser Ser Gly Ser Tyr Tyr Gly Met Asp Val
1               5                   10                  15

<210> SEQ ID NO 170
<211> LENGTH: 15
<212> TYPE: PRT
<213> ORGANISM: Homo sapiens

```
<400> SEQUENCE: 170

Ala Arg Glu Gly Tyr Ser Ser His Ser Tyr Tyr Gly Met Asp Val
1               5                   10                  15

<210> SEQ ID NO 171
<211> LENGTH: 15
<212> TYPE: PRT
<213> ORGANISM: Homo sapiens

<400> SEQUENCE: 171

Ala Arg Glu Gly Tyr Ser Ser Ile Ser Tyr Tyr Gly Met Asp Val
1               5                   10                  15

<210> SEQ ID NO 172
<211> LENGTH: 15
<212> TYPE: PRT
<213> ORGANISM: Homo sapiens

<400> SEQUENCE: 172

Ala Arg Glu Gly Tyr Ser Ser Lys Ser Tyr Tyr Gly Met Asp Val
1               5                   10                  15

<210> SEQ ID NO 173
<211> LENGTH: 15
<212> TYPE: PRT
<213> ORGANISM: Homo sapiens

<400> SEQUENCE: 173

Ala Arg Glu Gly Tyr Ser Ser Leu Ser Tyr Tyr Gly Met Asp Val
1               5                   10                  15

<210> SEQ ID NO 174
<211> LENGTH: 15
<212> TYPE: PRT
<213> ORGANISM: Homo sapiens

<400> SEQUENCE: 174

Ala Arg Glu Gly Tyr Ser Ser Met Ser Tyr Tyr Gly Met Asp Val
1               5                   10                  15

<210> SEQ ID NO 175
<211> LENGTH: 15
<212> TYPE: PRT
<213> ORGANISM: Homo sapiens

<400> SEQUENCE: 175

Ala Arg Glu Gly Tyr Ser Ser Asn Ser Tyr Tyr Gly Met Asp Val
1               5                   10                  15

<210> SEQ ID NO 176
<211> LENGTH: 15
<212> TYPE: PRT
<213> ORGANISM: Homo sapiens

<400> SEQUENCE: 176

Ala Arg Glu Gly Tyr Ser Ser Pro Ser Tyr Tyr Gly Met Asp Val
1               5                   10                  15

<210> SEQ ID NO 177
<211> LENGTH: 15
<212> TYPE: PRT
<213> ORGANISM: Homo sapiens
```

```
<400> SEQUENCE: 177

Ala Arg Glu Gly Tyr Ser Ser Gln Ser Tyr Tyr Gly Met Asp Val
1               5                   10                  15

<210> SEQ ID NO 178
<211> LENGTH: 15
<212> TYPE: PRT
<213> ORGANISM: Homo sapiens

<400> SEQUENCE: 178

Ala Arg Glu Gly Tyr Ser Ser Arg Ser Tyr Tyr Gly Met Asp Val
1               5                   10                  15

<210> SEQ ID NO 179
<211> LENGTH: 15
<212> TYPE: PRT
<213> ORGANISM: Homo sapiens

<400> SEQUENCE: 179

Ala Arg Glu Gly Tyr Ser Ser Thr Ser Tyr Tyr Gly Met Asp Val
1               5                   10                  15

<210> SEQ ID NO 180
<211> LENGTH: 15
<212> TYPE: PRT
<213> ORGANISM: Homo sapiens

<400> SEQUENCE: 180

Ala Arg Glu Gly Tyr Ser Ser Val Ser Tyr Tyr Gly Met Asp Val
1               5                   10                  15

<210> SEQ ID NO 181
<211> LENGTH: 15
<212> TYPE: PRT
<213> ORGANISM: Homo sapiens

<400> SEQUENCE: 181

Ala Arg Glu Gly Tyr Ser Ser Trp Ser Tyr Tyr Gly Met Asp Val
1               5                   10                  15

<210> SEQ ID NO 182
<211> LENGTH: 15
<212> TYPE: PRT
<213> ORGANISM: Homo sapiens

<400> SEQUENCE: 182

Ala Arg Glu Gly Tyr Ser Ser Tyr Ser Tyr Tyr Gly Met Asp Val
1               5                   10                  15

<210> SEQ ID NO 183
<211> LENGTH: 15
<212> TYPE: PRT
<213> ORGANISM: Homo sapiens

<400> SEQUENCE: 183

Ala Arg Glu Gly Tyr Ser Ser Cys Tyr Tyr Gly Met Asp Val
1               5                   10                  15

<210> SEQ ID NO 184
<211> LENGTH: 15
<212> TYPE: PRT
```

```
<400> SEQUENCE: 184

Ala Arg Glu Gly Tyr Ser Ser Ser Asp Tyr Tyr Gly Met Asp Val
1               5                   10                  15

<210> SEQ ID NO 185
<211> LENGTH: 15
<212> TYPE: PRT
<213> ORGANISM: Homo sapiens

<400> SEQUENCE: 185

Ala Arg Glu Gly Tyr Ser Ser Ser Glu Tyr Tyr Gly Met Asp Val
1               5                   10                  15

<210> SEQ ID NO 186
<211> LENGTH: 15
<212> TYPE: PRT
<213> ORGANISM: Homo sapiens

<400> SEQUENCE: 186

Ala Arg Glu Gly Tyr Ser Ser Ser Phe Tyr Tyr Gly Met Asp Val
1               5                   10                  15

<210> SEQ ID NO 187
<211> LENGTH: 15
<212> TYPE: PRT
<213> ORGANISM: Homo sapiens

<400> SEQUENCE: 187

Ala Arg Glu Gly Tyr Ser Ser Ser Gly Tyr Tyr Gly Met Asp Val
1               5                   10                  15

<210> SEQ ID NO 188
<211> LENGTH: 15
<212> TYPE: PRT
<213> ORGANISM: Homo sapiens

<400> SEQUENCE: 188

Ala Arg Glu Gly Tyr Ser Ser Ser His Tyr Tyr Gly Met Asp Val
1               5                   10                  15

<210> SEQ ID NO 189
<211> LENGTH: 15
<212> TYPE: PRT
<213> ORGANISM: Homo sapiens

<400> SEQUENCE: 189

Ala Arg Glu Gly Tyr Ser Ser Ser Ile Tyr Tyr Gly Met Asp Val
1               5                   10                  15

<210> SEQ ID NO 190
<211> LENGTH: 15
<212> TYPE: PRT
<213> ORGANISM: Homo sapiens

<400> SEQUENCE: 190

Ala Arg Glu Gly Tyr Ser Ser Ser Lys Tyr Tyr Gly Met Asp Val
1               5                   10                  15

<210> SEQ ID NO 191
<211> LENGTH: 15
<212> TYPE: PRT
<213> ORGANISM: Homo sapiens
```

<400> SEQUENCE: 191

Ala Arg Glu Gly Tyr Ser Ser Ser Leu Tyr Tyr Gly Met Asp Val
1               5                   10                  15

<210> SEQ ID NO 192
<211> LENGTH: 15
<212> TYPE: PRT
<213> ORGANISM: Homo sapiens

<400> SEQUENCE: 192

Ala Arg Glu Gly Tyr Ser Ser Ser Met Tyr Tyr Gly Met Asp Val
1               5                   10                  15

<210> SEQ ID NO 193
<211> LENGTH: 15
<212> TYPE: PRT
<213> ORGANISM: Homo sapiens

<400> SEQUENCE: 193

Ala Arg Glu Gly Tyr Ser Ser Ser Asn Tyr Tyr Gly Met Asp Val
1               5                   10                  15

<210> SEQ ID NO 194
<211> LENGTH: 15
<212> TYPE: PRT
<213> ORGANISM: Homo sapiens

<400> SEQUENCE: 194

Ala Arg Glu Gly Tyr Ser Ser Ser Pro Tyr Tyr Gly Met Asp Val
1               5                   10                  15

<210> SEQ ID NO 195
<211> LENGTH: 15
<212> TYPE: PRT
<213> ORGANISM: Homo sapiens

<400> SEQUENCE: 195

Ala Arg Glu Gly Tyr Ser Ser Ser Gln Tyr Tyr Gly Met Asp Val
1               5                   10                  15

<210> SEQ ID NO 196
<211> LENGTH: 15
<212> TYPE: PRT
<213> ORGANISM: Homo sapiens

<400> SEQUENCE: 196

Ala Arg Glu Gly Tyr Ser Ser Ser Arg Tyr Tyr Gly Met Asp Val
1               5                   10                  15

<210> SEQ ID NO 197
<211> LENGTH: 15
<212> TYPE: PRT
<213> ORGANISM: Homo sapiens

<400> SEQUENCE: 197

Ala Arg Glu Gly Tyr Ser Ser Ser Thr Tyr Tyr Gly Met Asp Val
1               5                   10                  15

<210> SEQ ID NO 198
<211> LENGTH: 15
<212> TYPE: PRT
<213> ORGANISM: Homo sapiens

```
<400> SEQUENCE: 198

Ala Arg Glu Gly Tyr Ser Ser Ser Val Tyr Tyr Gly Met Asp Val
1               5                   10                  15

<210> SEQ ID NO 199
<211> LENGTH: 15
<212> TYPE: PRT
<213> ORGANISM: Homo sapiens

<400> SEQUENCE: 199

Ala Arg Glu Gly Tyr Ser Ser Ser Trp Tyr Tyr Gly Met Asp Val
1               5                   10                  15

<210> SEQ ID NO 200
<211> LENGTH: 15
<212> TYPE: PRT
<213> ORGANISM: Homo sapiens

<400> SEQUENCE: 200

Ala Arg Glu Gly Tyr Ser Ser Ser Tyr Tyr Tyr Gly Met Asp Val
1               5                   10                  15

<210> SEQ ID NO 201
<211> LENGTH: 15
<212> TYPE: PRT
<213> ORGANISM: Homo sapiens

<400> SEQUENCE: 201

Ala Arg Glu Gly Tyr Cys Ser Ser Tyr Tyr Gly Met Asp Val
1               5                   10                  15

<210> SEQ ID NO 202
<211> LENGTH: 15
<212> TYPE: PRT
<213> ORGANISM: Homo sapiens

<400> SEQUENCE: 202

Ala Arg Glu Gly Tyr Asp Ser Ser Tyr Tyr Gly Met Asp Val
1               5                   10                  15

<210> SEQ ID NO 203
<211> LENGTH: 15
<212> TYPE: PRT
<213> ORGANISM: Homo sapiens

<400> SEQUENCE: 203

Ala Arg Glu Gly Tyr Glu Ser Ser Tyr Tyr Gly Met Asp Val
1               5                   10                  15

<210> SEQ ID NO 204
<211> LENGTH: 15
<212> TYPE: PRT
<213> ORGANISM: Homo sapiens

<400> SEQUENCE: 204

Ala Arg Glu Gly Tyr Phe Ser Ser Tyr Tyr Gly Met Asp Val
1               5                   10                  15

<210> SEQ ID NO 205
<211> LENGTH: 15
<212> TYPE: PRT
<213> ORGANISM: Homo sapiens

<400> SEQUENCE: 205
```

Ala Arg Glu Gly Tyr Gly Ser Ser Ser Tyr Tyr Gly Met Asp Val
1               5                   10                  15

<210> SEQ ID NO 206
<211> LENGTH: 15
<212> TYPE: PRT
<213> ORGANISM: Homo sapiens

<400> SEQUENCE: 206

Ala Arg Glu Gly Tyr His Ser Ser Ser Tyr Tyr Gly Met Asp Val
1               5                   10                  15

<210> SEQ ID NO 207
<211> LENGTH: 15
<212> TYPE: PRT
<213> ORGANISM: Homo sapiens

<400> SEQUENCE: 207

Ala Arg Glu Gly Tyr Ile Ser Ser Ser Tyr Tyr Gly Met Asp Val
1               5                   10                  15

<210> SEQ ID NO 208
<211> LENGTH: 15
<212> TYPE: PRT
<213> ORGANISM: Homo sapiens

<400> SEQUENCE: 208

Ala Arg Glu Gly Tyr Lys Ser Ser Ser Tyr Tyr Gly Met Asp Val
1               5                   10                  15

<210> SEQ ID NO 209
<211> LENGTH: 15
<212> TYPE: PRT
<213> ORGANISM: Homo sapiens

<400> SEQUENCE: 209

Ala Arg Glu Gly Tyr Leu Ser Ser Ser Tyr Tyr Gly Met Asp Val
1               5                   10                  15

<210> SEQ ID NO 210
<211> LENGTH: 15
<212> TYPE: PRT
<213> ORGANISM: Homo sapiens

<400> SEQUENCE: 210

Ala Arg Glu Gly Tyr Met Ser Ser Ser Tyr Tyr Gly Met Asp Val
1               5                   10                  15

<210> SEQ ID NO 211
<211> LENGTH: 15
<212> TYPE: PRT
<213> ORGANISM: Homo sapiens

<400> SEQUENCE: 211

Ala Arg Glu Gly Tyr Asn Ser Ser Ser Tyr Tyr Gly Met Asp Val
1               5                   10                  15

<210> SEQ ID NO 212
<211> LENGTH: 15
<212> TYPE: PRT
<213> ORGANISM: Homo sapiens

<400> SEQUENCE: 212

Ala Arg Glu Gly Tyr Pro Ser Ser Ser Tyr Tyr Gly Met Asp Val
1               5                   10                  15

<210> SEQ ID NO 213
<211> LENGTH: 15
<212> TYPE: PRT
<213> ORGANISM: Homo sapiens

<400> SEQUENCE: 213

Ala Arg Glu Gly Tyr Gln Ser Ser Tyr Tyr Gly Met Asp Val
1               5                   10                  15

<210> SEQ ID NO 214
<211> LENGTH: 15
<212> TYPE: PRT
<213> ORGANISM: Homo sapiens

<400> SEQUENCE: 214

Ala Arg Glu Gly Tyr Arg Ser Ser Tyr Tyr Gly Met Asp Val
1               5                   10                  15

<210> SEQ ID NO 215
<211> LENGTH: 15
<212> TYPE: PRT
<213> ORGANISM: Homo sapiens

<400> SEQUENCE: 215

Ala Arg Glu Gly Tyr Thr Ser Ser Tyr Tyr Gly Met Asp Val
1               5                   10                  15

<210> SEQ ID NO 216
<211> LENGTH: 15
<212> TYPE: PRT
<213> ORGANISM: Homo sapiens

<400> SEQUENCE: 216

Ala Arg Glu Gly Tyr Val Ser Ser Tyr Tyr Gly Met Asp Val
1               5                   10                  15

<210> SEQ ID NO 217
<211> LENGTH: 15
<212> TYPE: PRT
<213> ORGANISM: Homo sapiens

<400> SEQUENCE: 217

Ala Arg Glu Gly Tyr Trp Ser Ser Tyr Tyr Gly Met Asp Val
1               5                   10                  15

<210> SEQ ID NO 218
<211> LENGTH: 15
<212> TYPE: PRT
<213> ORGANISM: Homo sapiens

<400> SEQUENCE: 218

Ala Arg Glu Gly Tyr Tyr Ser Ser Tyr Tyr Gly Met Asp Val
1               5                   10                  15

<210> SEQ ID NO 219
<211> LENGTH: 15
<212> TYPE: PRT
<213> ORGANISM: Homo sapiens

<400> SEQUENCE: 219

Ala Arg Glu Gly Tyr Ser Cys Ser Ser Tyr Tyr Gly Met Asp Val
1               5                   10                  15

-continued

```
<210> SEQ ID NO 220
<211> LENGTH: 15
<212> TYPE: PRT
<213> ORGANISM: Homo sapiens

<400> SEQUENCE: 220

Ala Arg Glu Gly Tyr Ser Asp Ser Ser Tyr Tyr Gly Met Asp Val
1               5                   10                  15

<210> SEQ ID NO 221
<211> LENGTH: 15
<212> TYPE: PRT
<213> ORGANISM: Homo sapiens

<400> SEQUENCE: 221

Ala Arg Glu Gly Tyr Ser Glu Ser Ser Tyr Tyr Gly Met Asp Val
1               5                   10                  15

<210> SEQ ID NO 222
<211> LENGTH: 18
<212> TYPE: PRT
<213> ORGANISM: Homo sapiens

<400> SEQUENCE: 222

Thr Val Phe Leu Asp His Glu Asn Ala Asn Lys Ile Leu Asn Arg Pro
1               5                   10                  15

Lys Arg

<210> SEQ ID NO 223
<211> LENGTH: 15
<212> TYPE: PRT
<213> ORGANISM: Homo sapiens

<400> SEQUENCE: 223

Ala Arg Glu Gly Tyr Ser Phe Ser Ser Tyr Tyr Gly Met Asp Val
1               5                   10                  15

<210> SEQ ID NO 224
<211> LENGTH: 15
<212> TYPE: PRT
<213> ORGANISM: Homo sapiens

<400> SEQUENCE: 224

Ala Arg Glu Gly Tyr Ser Gly Ser Ser Tyr Tyr Gly Met Asp Val
1               5                   10                  15

<210> SEQ ID NO 225
<211> LENGTH: 15
<212> TYPE: PRT
<213> ORGANISM: Homo sapiens

<400> SEQUENCE: 225

Ala Arg Glu Gly Tyr Ser His Ser Ser Tyr Tyr Gly Met Asp Val
1               5                   10                  15

<210> SEQ ID NO 226
<211> LENGTH: 15
<212> TYPE: PRT
<213> ORGANISM: Homo sapiens

<400> SEQUENCE: 226

Ala Arg Glu Gly Tyr Ser Ile Ser Ser Tyr Tyr Gly Met Asp Val
1               5                   10                  15
```

<210> SEQ ID NO 227
<211> LENGTH: 15
<212> TYPE: PRT
<213> ORGANISM: Homo sapiens

<400> SEQUENCE: 227

Ala Arg Glu Gly Tyr Ser Lys Ser Ser Tyr Tyr Gly Met Asp Val
1               5                   10                  15

<210> SEQ ID NO 228
<211> LENGTH: 15
<212> TYPE: PRT
<213> ORGANISM: Homo sapiens

<400> SEQUENCE: 228

Ala Arg Glu Gly Tyr Ser Leu Ser Ser Tyr Tyr Gly Met Asp Val
1               5                   10                  15

<210> SEQ ID NO 229
<211> LENGTH: 15
<212> TYPE: PRT
<213> ORGANISM: Homo sapiens

<400> SEQUENCE: 229

Ala Arg Glu Gly Tyr Ser Met Ser Ser Tyr Tyr Gly Met Asp Val
1               5                   10                  15

<210> SEQ ID NO 230
<211> LENGTH: 15
<212> TYPE: PRT
<213> ORGANISM: Homo sapiens

<400> SEQUENCE: 230

Ala Arg Glu Gly Tyr Ser Asn Ser Ser Tyr Tyr Gly Met Asp Val
1               5                   10                  15

<210> SEQ ID NO 231
<211> LENGTH: 15
<212> TYPE: PRT
<213> ORGANISM: Homo sapiens

<400> SEQUENCE: 231

Ala Arg Glu Gly Tyr Ser Pro Ser Ser Tyr Tyr Gly Met Asp Val
1               5                   10                  15

<210> SEQ ID NO 232
<211> LENGTH: 15
<212> TYPE: PRT
<213> ORGANISM: Homo sapiens

<400> SEQUENCE: 232

Ala Arg Glu Gly Tyr Ser Gln Ser Ser Tyr Tyr Gly Met Asp Val
1               5                   10                  15

<210> SEQ ID NO 233
<211> LENGTH: 15
<212> TYPE: PRT
<213> ORGANISM: Homo sapiens

<400> SEQUENCE: 233

Ala Arg Glu Gly Tyr Ser Arg Ser Ser Tyr Tyr Gly Met Asp Val
1               5                   10                  15

<210> SEQ ID NO 234
<211> LENGTH: 15

<212> TYPE: PRT
<213> ORGANISM: Homo sapiens

<400> SEQUENCE: 234

Ala Arg Glu Gly Tyr Ser Thr Ser Ser Tyr Tyr Gly Met Asp Val
1               5                   10                  15

<210> SEQ ID NO 235
<211> LENGTH: 15
<212> TYPE: PRT
<213> ORGANISM: Homo sapiens

<400> SEQUENCE: 235

Ala Arg Glu Gly Tyr Ser Val Ser Ser Tyr Tyr Gly Met Asp Val
1               5                   10                  15

<210> SEQ ID NO 236
<211> LENGTH: 15
<212> TYPE: PRT
<213> ORGANISM: Homo sapiens

<400> SEQUENCE: 236

Ala Arg Glu Gly Tyr Ser Trp Ser Ser Tyr Tyr Gly Met Asp Val
1               5                   10                  15

<210> SEQ ID NO 237
<211> LENGTH: 15
<212> TYPE: PRT
<213> ORGANISM: Homo sapiens

<400> SEQUENCE: 237

Ala Arg Glu Gly Tyr Ser Tyr Ser Ser Tyr Tyr Gly Met Asp Val
1               5                   10                  15

<210> SEQ ID NO 238
<211> LENGTH: 367
<212> TYPE: DNA
<213> ORGANISM: Homo sapiens

<400> SEQUENCE: 238
gaggtgcagc tggtggagtc tgggggaggc tttgtccagc ctggggggtc cctgagactc      60
tcctgtgcag tctctggatt cacctttaat agctattgga tgagctgggt ccgccaggct    120
ccagggaagg ggctggagtg ggtggccaac ataaaccaag atggaagtga aaattctat     180 gtggcctctg tgaagggccg attcaccatg tccagagaca cgccaagaa atcagtgtat    240 gtacaaatga acagcctgag agccgaggac acggctgtgt attactgtgc gagagaggg     300 tatgccagtt cgtcctatta tggtatggac gtctggggcc aagggaccac ggtcaccgtc    360
tcctcag                                                              367

<210> SEQ ID NO 239
<211> LENGTH: 367
<212> TYPE: DNA
<213> ORGANISM: Homo sapiens

<400> SEQUENCE: 239
gaggtgcagc tggtggagtc tgggggaggc tttgtccagc ctggggggtc cctgagactc      60
tcctgtgcag tctctggatt cacctttaat agctattgga tgagctgggt ccgccaggct    120
ccagggaagg ggctggagtg ggtggccaac ataaaccaag atggaagtga aaattctat     180 gtggcctctg tgaagggccg attcaccatg tccagagaca cgccaagaa atcagtgtat    240

```
gtacaaatga acagcctgag agccgaggac acggctgtgt attactgtgc gagagagggg    300
tatagtgcct cgtcctatta tggtatggac gtctggggcc aagggaccac ggtcaccgtc    360
tcctcag                                                              367
```

<210> SEQ ID NO 240
<211> LENGTH: 367
<212> TYPE: DNA
<213> ORGANISM: Homo sapiens

<400> SEQUENCE: 240

```
gaggtgcagc tggtggagtc tgggggaggc tttgtccagc ctgggggtc cctgagactc    60 tcctgtgcag tctctggatt cacctttaat agctattgga tgagctgggt ccgccaggct    120
ccagggaagg ggctggagtg ggtggccaac ataaaccaag atggaagtga gaaattctat    180
gtggcctctg tgaagggccg attcaccatg tccagagaca acgccaagaa atcagtgtat    240
gtacaaatga acagcctgag agccgaggac acggctgtgt attactgtgc gagagagggg    300
tatagtagtg cctcctatta tggtatggac gtctggggcc aagggaccac ggtcaccgtc    360
tcctcag                                                              367
```

<210> SEQ ID NO 241
<211> LENGTH: 367
<212> TYPE: DNA
<213> ORGANISM: Homo sapiens

<400> SEQUENCE: 241

```
gaggtgcagc tggtggagtc tgggggaggc tttgtccagc ctgggggtc cctgagactc    60 tcctgtgcag tctctggatt cacctttaat agctattgga tgagctgggt ccgccaggct    120
ccagggaagg ggctggagtg ggtggccaac ataaaccaag atggaagtga gaaattctat    180
gtggcctctg tgaagggccg attcaccatg tccagagaca acgccaagaa atcagtgtat    240
gtacaaatga acagcctgag agccgaggac acggctgtgt attactgtgc gagagagggg    300
tatagtagtt cggcctatta tggtatggac gtctggggcc aagggaccac ggtcaccgtc    360
tcctcag                                                              367
```

<210> SEQ ID NO 242
<211> LENGTH: 367
<212> TYPE: DNA
<213> ORGANISM: Homo sapiens

<400> SEQUENCE: 242

```
gaggtgcagc tggtggagtc tgggggaggc tttgtccagc ctgggggtc cctgagactc    60 tcctgtgcag tctctggatt cacctttaat agctattgga tgagctgggt ccgccaggct    120
ccagggaagg ggctggagtg ggtggccaac ataaaccaag atggaagtga gaaattctat    180
gtggcctctg tgaagggccg attcaccatg tccagagaca acgccaagaa atcagtgtat    240
gtacaaatga acagcctgag agccgaggac acggctgtgt attactgtgc gagagagggg    300
tatagtagtt gctcctatta tggtatggac gtctggggcc aagggaccac ggtcaccgtc    360
tcctcag                                                              367
```

<210> SEQ ID NO 243
<211> LENGTH: 367
<212> TYPE: DNA
<213> ORGANISM: Homo sapiens

<400> SEQUENCE: 243

```
gaggtgcagc tggtggagtc tggggagggc tttgtccagc ctggggggtc cctgagactc      60
tcctgtgcag tctctggatt cacctttaat agctattgga tgagctgggt ccgccaggct     120
ccagggaagg ggctggagtg ggtggccaac ataaaccaag atggaagtga gaaattctat     180
gtggcctctg tgaagggccg attcaccatg tccagagaca acgccaagaa atcagtgtat     240
gtacaaatga acagcctgag agccgaggac acggctgtgt attactgtgc gagagagggg     300
tatagtagtg actcctatta tggtatggac gtctggggcc aagggaccac ggtcaccgtc     360
tcctcag                                                               367
```

<210> SEQ ID NO 244
<211> LENGTH: 367
<212> TYPE: DNA
<213> ORGANISM: Homo sapiens

<400> SEQUENCE: 244

```
gaggtgcagc tggtggagtc tggggagggc tttgtccagc ctggggggtc cctgagactc      60
tcctgtgcag tctctggatt cacctttaat agctattgga tgagctgggt ccgccaggct     120
ccagggaagg ggctggagtg ggtggccaac ataaaccaag atggaagtga gaaattctat     180
gtggcctctg tgaagggccg attcaccatg tccagagaca acgccaagaa atcagtgtat     240
gtacaaatga acagcctgag agccgaggac acggctgtgt attactgtgc gagagagggg     300
tatagtagtg agtcctatta tggtatggac gtctggggcc aagggaccac ggtcaccgtc     360
tcctcag                                                               367
```

<210> SEQ ID NO 245
<211> LENGTH: 367
<212> TYPE: DNA
<213> ORGANISM: Homo sapiens

<400> SEQUENCE: 245

```
gaggtgcagc tggtggagtc tggggagggc tttgtccagc ctggggggtc cctgagactc      60
tcctgtgcag tctctggatt cacctttaat agctattgga tgagctgggt ccgccaggct     120
ccagggaagg ggctggagtg ggtggccaac ataaaccaag atggaagtga gaaattctat     180
gtggcctctg tgaagggccg attcaccatg tccagagaca acgccaagaa atcagtgtat     240
gtacaaatga acagcctgag agccgaggac acggctgtgt attactgtgc gagagagggg     300
tatagtagtt ctcctatta tggtatggac gtctggggcc aagggaccac ggtcaccgtc     360
tcctcag                                                               367
```

<210> SEQ ID NO 246
<211> LENGTH: 367
<212> TYPE: DNA
<213> ORGANISM: Homo sapiens

<400> SEQUENCE: 246

```
gaggtgcagc tggtggagtc tggggagggc tttgtccagc ctggggggtc cctgagactc      60
tcctgtgcag tctctggatt cacctttaat agctattgga tgagctgggt ccgccaggct     120
ccagggaagg ggctggagtg ggtggccaac ataaaccaag atggaagtga gaaattctat     180
gtggcctctg tgaagggccg attcaccatg tccagagaca acgccaagaa atcagtgtat     240
gtacaaatga acagcctgag agccgaggac acggctgtgt attactgtgc gagagagggg     300
tatagtagtg gctcctatta tggtatggac gtctggggcc aagggaccac ggtcaccgtc     360
tcctcag                                                               367
```

<210> SEQ ID NO 247
<211> LENGTH: 367
<212> TYPE: DNA
<213> ORGANISM: Homo sapiens

<400> SEQUENCE: 247

```
gaggtgcagc tggtggagtc tgggggaggc tttgtccagc ctggggggtc cctgagactc    60
tcctgtgcag tctctggatt cacctttaat agctattgga tgagctgggt ccgccaggct   120
ccagggaagg ggctggagtg ggtggccaac ataaaccaag atggaagtga gaaattctat   180
gtggcctctg tgaagggccg attcaccatg tccagagaca cgccaagaa atcagtgtat    240
gtacaaatga acagcctgag agccgaggac acggctgtgt attactgtgc gagagagggg   300
tatagtagtc actcctatta tggtatggac gtctggggcc aagggaccac ggtcaccgtc   360
tcctcag                                                             367
```

<210> SEQ ID NO 248
<211> LENGTH: 367
<212> TYPE: DNA
<213> ORGANISM: Homo sapiens

<400> SEQUENCE: 248

```
gaggtgcagc tggtggagtc tgggggaggc tttgtccagc ctggggggtc cctgagactc    60
tcctgtgcag tctctggatt cacctttaat agctattgga tgagctgggt ccgccaggct   120
ccagggaagg ggctggagtg ggtggccaac ataaaccaag atggaagtga gaaattctat   180
gtggcctctg tgaagggccg attcaccatg tccagagaca cgccaagaa atcagtgtat    240
gtacaaatga acagcctgag agccgaggac acggctgtgt attactgtgc gagagagggg   300
tatagtagta tctcctatta tggtatggac gtctggggcc aagggaccac ggtcaccgtc   360
tcctcag                                                             367
```

<210> SEQ ID NO 249
<211> LENGTH: 367
<212> TYPE: DNA
<213> ORGANISM: Homo sapiens

<400> SEQUENCE: 249

```
gaggtgcagc tggtggagtc tgggggaggc tttgtccagc ctggggggtc cctgagactc    60
tcctgtgcag tctctggatt cacctttaat agctattgga tgagctgggt ccgccaggct   120
ccagggaagg ggctggagtg ggtggccaac ataaaccaag atggaagtga gaaattctat   180
gtggcctctg tgaagggccg attcaccatg tccagagaca cgccaagaa atcagtgtat    240
gtacaaatga acagcctgag agccgaggac acggctgtgt attactgtgc gagagagggg   300
tatagtagta agtcctatta tggtatggac gtctggggcc aagggaccac ggtcaccgtc   360
tcctcag                                                             367
```

<210> SEQ ID NO 250
<211> LENGTH: 367
<212> TYPE: DNA
<213> ORGANISM: Homo sapiens

<400> SEQUENCE: 250

```
gaggtgcagc tggtggagtc tgggggaggc tttgtccagc ctggggggtc cctgagactc    60
tcctgtgcag tctctggatt cacctttaat agctattgga tgagctgggt ccgccaggct   120
```

-continued

| | |
|---|---|
| ccagggaagg ggctggagtg ggtggccaac ataaaccaag atggaagtga gaaattctat | 180 |
| gtggcctctg tgaagggccg attcaccatg tccagagaca acgccaagaa atcagtgtat | 240 |
| gtacaaatga acagcctgag agccgaggac acggctgtgt attactgtgc gagagagggg | 300 |
| tatagtagtc tgtcctatta tggtatggac gtctggggcc aagggaccac ggtcaccgtc | 360 |
| tcctcag | 367 |

<210> SEQ ID NO 251
<211> LENGTH: 367
<212> TYPE: DNA
<213> ORGANISM: Homo sapiens

<400> SEQUENCE: 251

| | |
|---|---|
| gaggtgcagc tggtggagtc tgggggaggc tttgtccagc ctggggggtc cctgagactc | 60 |
| tcctgtgcag tctctggatt cacctttaat agctattgga tgagctgggt ccgccaggct | 120 |
| ccagggaagg ggctggagtg ggtggccaac ataaaccaag atggaagtga gaaattctat | 180 |
| gtggcctctg tgaagggccg attcaccatg tccagagaca acgccaagaa atcagtgtat | 240 |
| gtacaaatga acagcctgag agccgaggac acggctgtgt attactgtgc gagagagggg | 300 |
| tatagtagta tgtcctatta tggtatggac gtctggggcc aagggaccac ggtcaccgtc | 360 |
| tcctcag | 367 |

<210> SEQ ID NO 252
<211> LENGTH: 367
<212> TYPE: DNA
<213> ORGANISM: Homo sapiens

<400> SEQUENCE: 252

| | |
|---|---|
| gaggtgcagc tggtggagtc tgggggaggc tttgtccagc ctggggggtc cctgagactc | 60 |
| tcctgtgcag tctctggatt cacctttaat agctattgga tgagctgggt ccgccaggct | 120 |
| ccagggaagg ggctggagtg ggtggccaac ataaaccaag atggaagtga gaaattctat | 180 |
| gtggcctctg tgaagggccg attcaccatg tccagagaca acgccaagaa atcagtgtat | 240 |
| gtacaaatga acagcctgag agccgaggac acggctgtgt attactgtgc gagagagggg | 300 |
| tatagtagta actcctatta tggtatggac gtctggggcc aagggaccac ggtcaccgtc | 360 |
| tcctcag | 367 |

<210> SEQ ID NO 253
<211> LENGTH: 367
<212> TYPE: DNA
<213> ORGANISM: Homo sapiens

<400> SEQUENCE: 253

| | |
|---|---|
| gaggtgcagc tggtggagtc tgggggaggc tttgtccagc ctggggggtc cctgagactc | 60 |
| tcctgtgcag tctctggatt cacctttaat agctattgga tgagctgggt ccgccaggct | 120 |
| ccagggaagg ggctggagtg ggtggccaac ataaaccaag atggaagtga gaaattctat | 180 |
| gtggcctctg tgaagggccg attcaccatg tccagagaca acgccaagaa atcagtgtat | 240 |
| gtacaaatga acagcctgag agccgaggac acggctgtgt attactgtgc gagagagggg | 300 |
| tatagtagtc cctcctatta tggtatggac gtctggggcc aagggaccac ggtcaccgtc | 360 |
| tcctcag | 367 |

<210> SEQ ID NO 254
<211> LENGTH: 367

```
<212> TYPE: DNA
<213> ORGANISM: Homo sapiens

<400> SEQUENCE: 254
gaggtgcagc tggtggagtc tgggggaggc tttgtccagc ctggggggtc cctgagactc      60
tcctgtgcag tctctggatt cacctttaat agctattgga tgagctgggt ccgccaggct     120
ccagggaagg ggctggagtg ggtggccaac ataaaccaag atggaagtga gaaattctat     180
gtggcctctg tgaagggccg attcaccatg tccagagaca acgccaagaa atcagtgtat     240
gtacaaatga acagcctgag agccgaggac acggctgtgt attactgtgc gagagagggg     300
tatagtagtc agtcctatta tggtatggac gtctggggcc aagggaccac ggtcaccgtc     360
tcctcag                                                               367

<210> SEQ ID NO 255
<211> LENGTH: 367
<212> TYPE: DNA
<213> ORGANISM: Homo sapiens

<400> SEQUENCE: 255
gaggtgcagc tggtggagtc tgggggaggc tttgtccagc ctggggggtc cctgagactc      60
tcctgtgcag tctctggatt cacctttaat agctattgga tgagctgggt ccgccaggct     120
ccagggaagg ggctggagtg ggtggccaac ataaaccaag atggaagtga gaaattctat     180
gtggcctctg tgaagggccg attcaccatg tccagagaca acgccaagaa atcagtgtat     240
gtacaaatga acagcctgag agccgaggac acggctgtgt attactgtgc gagagagggg     300
tatagtagta gatcctatta tggtatggac gtctggggcc aagggaccac ggtcaccgtc     360
tcctcag                                                               367

<210> SEQ ID NO 256
<211> LENGTH: 367
<212> TYPE: DNA
<213> ORGANISM: Homo sapiens

<400> SEQUENCE: 256
gaggtgcagc tggtggagtc tgggggaggc tttgtccagc ctggggggtc cctgagactc      60
tcctgtgcag tctctggatt cacctttaat agctattgga tgagctgggt ccgccaggct     120
ccagggaagg ggctggagtg ggtggccaac ataaaccaag atggaagtga gaaattctat     180
gtggcctctg tgaagggccg attcaccatg tccagagaca acgccaagaa atcagtgtat     240
gtacaaatga acagcctgag agccgaggac acggctgtgt attactgtgc gagagagggg     300
tatagtagta cctcctatta tggtatggac gtctggggcc aagggaccac ggtcaccgtc     360
tcctcag                                                               367

<210> SEQ ID NO 257
<211> LENGTH: 367
<212> TYPE: DNA
<213> ORGANISM: Homo sapiens

<400> SEQUENCE: 257
gaggtgcagc tggtggagtc tgggggaggc tttgtccagc ctggggggtc cctgagactc      60
tcctgtgcag tctctggatt cacctttaat agctattgga tgagctgggt ccgccaggct     120
ccagggaagg ggctggagtg ggtggccaac ataaaccaag atggaagtga gaaattctat     180
gtggcctctg tgaagggccg attcaccatg tccagagaca acgccaagaa atcagtgtat     240
```

| | |
|---|---|
| gtacaaatga acagcctgag agccgaggac acggctgtgt attactgtgc gagagagggg | 300 |
| tatagtagtg tgtcctatta tggtatggac gtctggggcc aagggaccac ggtcaccgtc | 360 |
| tcctcag | 367 |

<210> SEQ ID NO 258
<211> LENGTH: 367
<212> TYPE: DNA
<213> ORGANISM: Homo sapiens

<400> SEQUENCE: 258

| | |
|---|---|
| gaggtgcagc tggtggagtc tgggggaggc tttgtccagc ctgggggtc cctgagactc | 60 |
| tcctgtgcag tctctggatt cacctttaat agctattgga tgagctgggt ccgccaggct | 120 |
| ccagggaagg ggctggagtg ggtggccaac ataaaccaag atggaagtga gaaattctat | 180 |
| gtggcctctg tgaagggccg attcaccatg tccagagaca acgccaagaa atcagtgtat | 240 |
| gtacaaatga acagcctgag agccgaggac acggctgtgt attactgtgc gagagagggg | 300 |
| tatagtagtt ggtcctatta tggtatggac gtctggggcc aagggaccac ggtcaccgtc | 360 |
| tcctcag | 367 |

<210> SEQ ID NO 259
<211> LENGTH: 367
<212> TYPE: DNA
<213> ORGANISM: Homo sapiens

<400> SEQUENCE: 259

| | |
|---|---|
| gaggtgcagc tggtggagtc tgggggaggc tttgtccagc ctgggggtc cctgagactc | 60 |
| tcctgtgcag tctctggatt cacctttaat agctattgga tgagctgggt ccgccaggct | 120 |
| ccagggaagg ggctggagtg ggtggccaac ataaaccaag atggaagtga gaaattctat | 180 |
| gtggcctctg tgaagggccg attcaccatg tccagagaca acgccaagaa atcagtgtat | 240 |
| gtacaaatga acagcctgag agccgaggac acggctgtgt attactgtgc gagagagggg | 300 |
| tatagtagtt actcctatta tggtatggac gtctggggcc aagggaccac ggtcaccgtc | 360 |
| tcctcag | 367 |

<210> SEQ ID NO 260
<211> LENGTH: 367
<212> TYPE: DNA
<213> ORGANISM: Homo sapiens

<400> SEQUENCE: 260

| | |
|---|---|
| gaggtgcagc tggtggagtc tgggggaggc tttgtccagc ctgggggtc cctgagactc | 60 |
| tcctgtgcag tctctggatt cacctttaat agctattgga tgagctgggt ccgccaggct | 120 |
| ccagggaagg ggctggagtg ggtggccaac ataaaccaag atggaagtga gaaattctat | 180 |
| gtggcctctg tgaagggccg attcaccatg tccagagaca acgccaagaa atcagtgtat | 240 |
| gtacaaatga acagcctgag agccgaggac acggctgtgt attactgtgc gagagagggg | 300 |
| tatagtagtt cgtgctatta tggtatggac gtctggggcc aagggaccac ggtcaccgtc | 360 |
| tcctcag | 367 |

<210> SEQ ID NO 261
<211> LENGTH: 367
<212> TYPE: DNA
<213> ORGANISM: Homo sapiens

<400> SEQUENCE: 261

```
gaggtgcagc tggtggagtc tgggggaggc tttgtccagc ctgggggtc cctgagactc      60 tcctgtgcag tctctggatt cacctttaat agctattgga tgagctgggt ccgccaggct    120
ccagggaagg ggctggagtg ggtggccaac ataaaccaag atggaagtga gaaattctat    180
gtggcctctg tgaagggccg attcaccatg tccagagaca acgccaagaa atcagtgtat    240
gtacaaatga acagcctgag agccgaggac acggctgtgt attactgtgc gagagagggg    300
tatagtagtt cggactatta tggtatggac gtctggggcc aagggaccac ggtcaccgtc    360
tcctcag                                                              367
```

<210> SEQ ID NO 262
<211> LENGTH: 367
<212> TYPE: DNA
<213> ORGANISM: Homo sapiens

<400> SEQUENCE: 262

```
gaggtgcagc tggtggagtc tgggggaggc tttgtccagc ctgggggtc cctgagactc      60 tcctgtgcag tctctggatt cacctttaat agctattgga tgagctgggt ccgccaggct    120
ccagggaagg ggctggagtg ggtggccaac ataaaccaag atggaagtga gaaattctat    180
gtggcctctg tgaagggccg attcaccatg tccagagaca acgccaagaa atcagtgtat    240
gtacaaatga acagcctgag agccgaggac acggctgtgt attactgtgc gagagagggg    300
tatagtagtt cggagtatta tggtatggac gtctggggcc aagggaccac ggtcaccgtc    360
tcctcag                                                              367
```

<210> SEQ ID NO 263
<211> LENGTH: 367
<212> TYPE: DNA
<213> ORGANISM: Homo sapiens

<400> SEQUENCE: 263

```
gaggtgcagc tggtggagtc tgggggaggc tttgtccagc ctgggggtc cctgagactc      60 tcctgtgcag tctctggatt cacctttaat agctattgga tgagctgggt ccgccaggct    120
ccagggaagg ggctggagtg ggtggccaac ataaaccaag atggaagtga gaaattctat    180
gtggcctctg tgaagggccg attcaccatg tccagagaca acgccaagaa atcagtgtat    240
gtacaaatga acagcctgag agccgaggac acggctgtgt attactgtgc gagagagggg    300
tatagtagtt cgttctatta tggtatggac gtctggggcc aagggaccac ggtcaccgtc    360
tcctcag                                                              367
```

<210> SEQ ID NO 264
<211> LENGTH: 367
<212> TYPE: DNA
<213> ORGANISM: Homo sapiens

<400> SEQUENCE: 264

```
gaggtgcagc tggtggagtc tgggggaggc tttgtccagc ctgggggtc cctgagactc      60 tcctgtgcag tctctggatt cacctttaat agctattgga tgagctgggt ccgccaggct    120
ccagggaagg ggctggagtg ggtggccaac ataaaccaag atggaagtga gaaattctat    180
gtggcctctg tgaagggccg attcaccatg tccagagaca acgccaagaa atcagtgtat    240
gtacaaatga acagcctgag agccgaggac acggctgtgt attactgtgc gagagagggg    300
tatagtagtt cgggctatta tggtatggac gtctggggcc aagggaccac ggtcaccgtc    360
```

```
tcctcag                                                                367
```

<210> SEQ ID NO 265
<211> LENGTH: 367
<212> TYPE: DNA
<213> ORGANISM: Homo sapiens

<400> SEQUENCE: 265

```
gaggtgcagc tggtggagtc tggggaggc tttgtccagc ctggggggtc cctgagactc      60
tcctgtgcag tctctggatt cacctttaat agctattgga tgagctgggt ccgccaggct    120
ccagggaagg gctggagtg gtggccaac ataaaccaag atggaagtga gaaattctat     180
gtggcctctg tgaagggccg attcaccatg tccagagaca acgccaagaa atcagtgtat   240
gtacaaatga acagcctgag agccgaggac acggctgtgt attactgtgc gagagagggg   300
tatagtagtt cgcactatta tggtatggac gtctggggcc aagggaccac ggtcaccgtc   360
tcctcag                                                              367
```

<210> SEQ ID NO 266
<211> LENGTH: 367
<212> TYPE: DNA
<213> ORGANISM: Homo sapiens

<400> SEQUENCE: 266

```
gaggtgcagc tggtggagtc tggggaggc tttgtccagc ctggggggtc cctgagactc      60
tcctgtgcag tctctggatt cacctttaat agctattgga tgagctgggt ccgccaggct    120
ccagggaagg gctggagtg gtggccaac ataaaccaag atggaagtga gaaattctat     180
gtggcctctg tgaagggccg attcaccatg tccagagaca acgccaagaa atcagtgtat   240
gtacaaatga acagcctgag agccgaggac acggctgtgt attactgtgc gagagagggg   300
tatagtagtt cgatctatta tggtatggac gtctggggcc aagggaccac ggtcaccgtc   360
tcctcag                                                              367
```

<210> SEQ ID NO 267
<211> LENGTH: 367
<212> TYPE: DNA
<213> ORGANISM: Homo sapiens

<400> SEQUENCE: 267

```
gaggtgcagc tggtggagtc tggggaggc tttgtccagc ctggggggtc cctgagactc      60
tcctgtgcag tctctggatt cacctttaat agctattgga tgagctgggt ccgccaggct    120
ccagggaagg gctggagtg gtggccaac ataaaccaag atggaagtga gaaattctat     180
gtggcctctg tgaagggccg attcaccatg tccagagaca acgccaagaa atcagtgtat   240
gtacaaatga acagcctgag agccgaggac acggctgtgt attactgtgc gagagagggg   300
tatagtagtt cgaagtatta tggtatggac gtctggggcc aagggaccac ggtcaccgtc   360
tcctcag                                                              367
```

<210> SEQ ID NO 268
<211> LENGTH: 367
<212> TYPE: DNA
<213> ORGANISM: Homo sapiens

<400> SEQUENCE: 268

```
gaggtgcagc tggtggagtc tggggaggc tttgtccagc ctggggggtc cctgagactc      60
tcctgtgcag tctctggatt cacctttaat agctattgga tgagctgggt ccgccaggct    120
```

```
ccagggaagg ggctggagtg ggtggccaac ataaaccaag atggaagtga gaaattctat    180
gtggcctctg tgaagggccg attcaccatg tccagagaca acgccaagaa atcagtgtat    240
gtacaaatga acagcctgag agccgaggac acggctgtgt attactgtgc gagagagggg    300
tatagtagtt cgctgtatta tggtatggac gtctggggcc aagggaccac ggtcaccgtc    360
tcctcag                                                              367

<210> SEQ ID NO 269
<211> LENGTH: 367
<212> TYPE: DNA
<213> ORGANISM: Homo sapiens

<400> SEQUENCE: 269
gaggtgcagc tggtggagtc tgggggaggc tttgtccagc ctgggggtc cctgagactc      60 tcctgtgcag tctctggatt cacctttaat agctattgga tgagctgggt ccgccaggct    120
ccagggaagg ggctggagtg ggtggccaac ataaaccaag atggaagtga gaaattctat    180
gtggcctctg tgaagggccg attcaccatg tccagagaca acgccaagaa atcagtgtat    240
gtacaaatga acagcctgag agccgaggac acggctgtgt attactgtgc gagagagggg    300
tatagtagtt cgatgtatta tggtatggac gtctggggcc aagggaccac ggtcaccgtc    360
tcctcag                                                              367

<210> SEQ ID NO 270
<211> LENGTH: 367
<212> TYPE: DNA
<213> ORGANISM: Homo sapiens

<400> SEQUENCE: 270
gaggtgcagc tggtggagtc tgggggaggc tttgtccagc ctgggggtc cctgagactc      60 tcctgtgcag tctctggatt cacctttaat agctattgga tgagctgggt ccgccaggct    120
ccagggaagg ggctggagtg ggtggccaac ataaaccaag atggaagtga gaaattctat    180
gtggcctctg tgaagggccg attcaccatg tccagagaca acgccaagaa atcagtgtat    240
gtacaaatga acagcctgag agccgaggac acggctgtgt attactgtgc gagagagggg    300
tatagtagtt cgaactatta tggtatggac gtctggggcc aagggaccac ggtcaccgtc    360
tcctcag                                                              367

<210> SEQ ID NO 271
<211> LENGTH: 367
<212> TYPE: DNA
<213> ORGANISM: Homo sapiens

<400> SEQUENCE: 271
gaggtgcagc tggtggagtc tgggggaggc tttgtccagc ctgggggtc cctgagactc      60 tcctgtgcag tctctggatt cacctttaat agctattgga tgagctgggt ccgccaggct    120
ccagggaagg ggctggagtg ggtggccaac ataaaccaag atggaagtga gaaattctat    180
gtggcctctg tgaagggccg attcaccatg tccagagaca acgccaagaa atcagtgtat    240
gtacaaatga acagcctgag agccgaggac acggctgtgt attactgtgc gagagagggg    300
tatagtagtt cgccctatta tggtatggac gtctggggcc aagggaccac ggtcaccgtc    360
tcctcag                                                              367
```

```
<210> SEQ ID NO 272
<211> LENGTH: 367
<212> TYPE: DNA
<213> ORGANISM: Homo sapiens

<400> SEQUENCE: 272
gaggtgcagc tggtggagtc tgggggaggc tttgtccagc ctgggggtc  cctgagactc      60 tcctgtgcag tctctggatt cacctttaat agctattgga tgagctgggt  ccgccaggct     120
ccagggaagg ggctggagtg ggtggccaac ataaaccaag atggaagtga  gaaattctat    180
gtggcctctg tgaagggccg attcaccatg tccagagaca cgccaagaa  atcagtgtat     240 gtacaaatga acagcctgag agccgaggac acggctgtgt attactgtgc  gagagagggg    300
tatagtagtt cgcagtatta tggtatggac gtctggggcc aagggaccac  ggtcaccgtc    360
tcctcag                                                                 367

<210> SEQ ID NO 273
<211> LENGTH: 367
<212> TYPE: DNA
<213> ORGANISM: Homo sapiens

<400> SEQUENCE: 273
gaggtgcagc tggtggagtc tgggggaggc tttgtccagc ctgggggtc  cctgagactc      60 tcctgtgcag tctctggatt cacctttaat agctattgga tgagctgggt  ccgccaggct     120
ccagggaagg ggctggagtg ggtggccaac ataaaccaag atggaagtga  gaaattctat    180
gtggcctctg tgaagggccg attcaccatg tccagagaca cgccaagaa  atcagtgtat     240 gtacaaatga acagcctgag agccgaggac acggctgtgt attactgtgc  gagagagggg    300
tatagtagtt cgagatatta tggtatggac gtctggggcc aagggaccac  ggtcaccgtc    360
tcctcag                                                                 367

<210> SEQ ID NO 274
<211> LENGTH: 367
<212> TYPE: DNA
<213> ORGANISM: Homo sapiens

<400> SEQUENCE: 274
gaggtgcagc tggtggagtc tgggggaggc tttgtccagc ctgggggtc  cctgagactc      60 tcctgtgcag tctctggatt cacctttaat agctattgga tgagctgggt  ccgccaggct     120
ccagggaagg ggctggagtg ggtggccaac ataaaccaag atggaagtga  gaaattctat    180
gtggcctctg tgaagggccg attcaccatg tccagagaca cgccaagaa  atcagtgtat     240 gtacaaatga acagcctgag agccgaggac acggctgtgt attactgtgc  gagagagggg    300
tatagtagtt cgacctatta tggtatggac gtctggggcc aagggaccac  ggtcaccgtc    360
tcctcag                                                                 367

<210> SEQ ID NO 275
<211> LENGTH: 367
<212> TYPE: DNA
<213> ORGANISM: Homo sapiens

<400> SEQUENCE: 275
gaggtgcagc tggtggagtc tgggggaggc tttgtccagc ctgggggtc  cctgagactc      60 tcctgtgcag tctctggatt cacctttaat agctattgga tgagctgggt  ccgccaggct     120
ccagggaagg ggctggagtg ggtggccaac ataaaccaag atggaagtga  gaaattctat    180
```

```
gtggcctctg tgaagggccg attcaccatg tccagagaca acgccaagaa atcagtgtat    240
gtacaaatga acagcctgag agccgaggac acggctgtgt attactgtgc gagagagggg    300
tatagtagtt cggtgtatta tggtatggac gtctggggcc aagggaccac ggtcaccgtc    360
tcctcag                                                              367
```

<210> SEQ ID NO 276
<211> LENGTH: 367
<212> TYPE: DNA
<213> ORGANISM: Homo sapiens

<400> SEQUENCE: 276

```
gaggtgcagc tggtggagtc tgggggaggc tttgtccagc ctggggggtc cctgagactc    60
tcctgtgcag tctctggatt cacctttaat agctattgga tgagctgggt ccgccaggct    120
ccagggaagg ggctggagtg ggtggccaac ataaaccaag atggaagtga gaaattctat    180
gtggcctctg tgaagggccg attcaccatg tccagagaca acgccaagaa atcagtgtat    240
gtacaaatga acagcctgag agccgaggac acggctgtgt attactgtgc gagagagggg    300
tatagtagtt cgtggtatta tggtatggac gtctggggcc aagggaccac ggtcaccgtc    360
tcctcag                                                              367
```

<210> SEQ ID NO 277
<211> LENGTH: 367
<212> TYPE: DNA
<213> ORGANISM: Homo sapiens

<400> SEQUENCE: 277

```
gaggtgcagc tggtggagtc tgggggaggc tttgtccagc ctggggggtc cctgagactc    60
tcctgtgcag tctctggatt cacctttaat agctattgga tgagctgggt ccgccaggct    120
ccagggaagg ggctggagtg ggtggccaac ataaaccaag atggaagtga gaaattctat    180
gtggcctctg tgaagggccg attcaccatg tccagagaca acgccaagaa atcagtgtat    240
gtacaaatga acagcctgag agccgaggac acggctgtgt attactgtgc gagagagggg    300
tatagtagtt cgtactatta tggtatggac gtctggggcc aagggaccac ggtcaccgtc    360
tcctcag                                                              367
```

<210> SEQ ID NO 278
<211> LENGTH: 367
<212> TYPE: DNA
<213> ORGANISM: Homo sapiens

<400> SEQUENCE: 278

```
gaggtgcagc tggtggagtc tgggggaggc tttgtccagc ctggggggtc cctgagactc    60
tcctgtgcag tctctggatt cacctttaat agctattgga tgagctgggt ccgccaggct    120
ccagggaagg ggctggagtg ggtggccaac ataaaccaag atggaagtga gaaattctat    180
gtggcctctg tgaagggccg attcaccatg tccagagaca acgccaagaa atcagtgtat    240
gtacaaatga acagcctgag agccgaggac acggctgtgt attactgtgc gagagagggg    300
tattgcagtt cgtcctatta tggtatggac gtctggggcc aagggaccac ggtcaccgtc    360
tcctcag                                                              367
```

<210> SEQ ID NO 279
<211> LENGTH: 367
<212> TYPE: DNA
<213> ORGANISM: Homo sapiens

<400> SEQUENCE: 279

```
gaggtgcagc tggtggagtc tgggggaggc tttgtccagc ctggggggtc cctgagactc    60
tcctgtgcag tctctggatt cacctttaat agctattgga tgagctgggt ccgccaggct   120
ccagggaagg ggctggagtg ggtggccaac ataaaccaag atggaagtga gaaattctat   180
gtggcctctg tgaagggccg attcaccatg tccagagaca cgccaagaa atcagtgtat   240
gtacaaatga acagcctgag agccgaggac acggctgtgt attactgtgc gagagagggg   300
tatgacagtt cgtcctatta tggtatggac gtctggggcc aagggaccac ggtcaccgtc   360
tcctcag                                                              367
```

<210> SEQ ID NO 280
<211> LENGTH: 367
<212> TYPE: DNA
<213> ORGANISM: Homo sapiens

<400> SEQUENCE: 280

```
gaggtgcagc tggtggagtc tgggggaggc tttgtccagc ctggggggtc cctgagactc    60
tcctgtgcag tctctggatt cacctttaat agctattgga tgagctgggt ccgccaggct   120
ccagggaagg ggctggagtg ggtggccaac ataaaccaag atggaagtga gaaattctat   180
gtggcctctg tgaagggccg attcaccatg tccagagaca cgccaagaa atcagtgtat   240
gtacaaatga acagcctgag agccgaggac acggctgtgt attactgtgc gagagagggg   300
tatgagagtt cgtcctatta tggtatggac gtctggggcc aagggaccac ggtcaccgtc   360
tcctcag                                                              367
```

<210> SEQ ID NO 281
<211> LENGTH: 367
<212> TYPE: DNA
<213> ORGANISM: Homo sapiens

<400> SEQUENCE: 281

```
gaggtgcagc tggtggagtc tgggggaggc tttgtccagc ctggggggtc cctgagactc    60
tcctgtgcag tctctggatt cacctttaat agctattgga tgagctgggt ccgccaggct   120
ccagggaagg ggctggagtg ggtggccaac ataaaccaag atggaagtga gaaattctat   180
gtggcctctg tgaagggccg attcaccatg tccagagaca cgccaagaa atcagtgtat   240
gtacaaatga acagcctgag agccgaggac acggctgtgt attactgtgc gagagagggg   300
tatttcagtt cgtcctatta tggtatggac gtctggggcc aagggaccac ggtcaccgtc   360
tcctcag                                                              367
```

<210> SEQ ID NO 282
<211> LENGTH: 367
<212> TYPE: DNA
<213> ORGANISM: Homo sapiens

<400> SEQUENCE: 282

```
gaggtgcagc tggtggagtc tgggggaggc tttgtccagc ctggggggtc cctgagactc    60
tcctgtgcag tctctggatt cacctttaat agctattgga tgagctgggt ccgccaggct   120
ccagggaagg ggctggagtg ggtggccaac ataaaccaag atggaagtga gaaattctat   180
gtggcctctg tgaagggccg attcaccatg tccagagaca cgccaagaa atcagtgtat   240
gtacaaatga acagcctgag agccgaggac acggctgtgt attactgtgc gagagagggg   300
```

<210> SEQ ID NO 283
<211> LENGTH: 367
<212> TYPE: DNA
<213> ORGANISM: Homo sapiens

<400> SEQUENCE: 283

```
gaggtgcagc tggtggagtc tgggggaggc tttgtccagc ctgggggtc cctgagactc      60
tcctgtgcag tctctggatt cacctttaat agctattgga tgagctgggt ccgccaggct    120
ccagggaagg gctggagtg gtggccaac ataaaccaag atggaagtga gaaattctat     180
gtggcctctg tgaagggccg attcaccatg tccagagaca cgccaagaa atcagtgtat   240
gtacaaatga acagcctgag agccgaggac acggctgtgt attactgtgc gagagagggg    300
tatcacagtt cgtcctatta tggtatggac gtctggggcc aagggaccac ggtcaccgtc    360
tcctcag                                                               367
```

<210> SEQ ID NO 284
<211> LENGTH: 367
<212> TYPE: DNA
<213> ORGANISM: Homo sapiens

<400> SEQUENCE: 284

```
gaggtgcagc tggtggagtc tgggggaggc tttgtccagc ctgggggtc cctgagactc      60
tcctgtgcag tctctggatt cacctttaat agctattgga tgagctgggt ccgccaggct    120
ccagggaagg gctggagtg gtggccaac ataaaccaag atggaagtga gaaattctat     180
gtggcctctg tgaagggccg attcaccatg tccagagaca cgccaagaa atcagtgtat   240
gtacaaatga acagcctgag agccgaggac acggctgtgt attactgtgc gagagagggg    300
tatatcagtt cgtcctatta tggtatggac gtctggggcc aagggaccac ggtcaccgtc    360
tcctcag                                                               367
```

<210> SEQ ID NO 285
<211> LENGTH: 367
<212> TYPE: DNA
<213> ORGANISM: Homo sapiens

<400> SEQUENCE: 285

```
gaggtgcagc tggtggagtc tgggggaggc tttgtccagc ctgggggtc cctgagactc      60
tcctgtgcag tctctggatt cacctttaat agctattgga tgagctgggt ccgccaggct    120
ccagggaagg gctggagtg gtggccaac ataaaccaag atggaagtga gaaattctat     180
gtggcctctg tgaagggccg attcaccatg tccagagaca cgccaagaa atcagtgtat   240
gtacaaatga acagcctgag agccgaggac acggctgtgt attactgtgc gagagagggg    300
tataagagtt cgtcctatta tggtatggac gtctggggcc aagggaccac ggtcaccgtc    360
tcctcag                                                               367
```

<210> SEQ ID NO 286
<211> LENGTH: 367
<212> TYPE: DNA
<213> ORGANISM: Homo sapiens

<400> SEQUENCE: 286

```
gaggtgcagc tggtggagtc tgggggaggc tttgtccagc ctgggggtc cctgagactc      60
```

```
tcctgtgcag tctctggatt cacctttaat agctattgga tgagctgggt ccgccaggct    120
ccagggaagg ggctggagtg ggtggccaac ataaaccaag atggaagtga gaaattctat    180
gtggcctctg tgaagggccg attcaccatg tccagagaca cgccaagaa atcagtgtat     240 gtacaaatga acagcctgag agccgaggac acggctgtgt attactgtgc gagagagggg    300
tatctgagtt cgtcctatta tggtatggac gtctggggcc aagggaccac ggtcaccgtc    360
tcctcag                                                              367
```

<210> SEQ ID NO 287
<211> LENGTH: 367
<212> TYPE: DNA
<213> ORGANISM: Homo sapiens

<400> SEQUENCE: 287

```
gaggtgcagc tggtggagtc tgggggaggc tttgtccagc ctgggggtc cctgagactc     60 tcctgtgcag tctctggatt cacctttaat agctattgga tgagctgggt ccgccaggct    120
ccagggaagg ggctggagtg ggtggccaac ataaaccaag atggaagtga gaaattctat    180
gtggcctctg tgaagggccg attcaccatg tccagagaca cgccaagaa atcagtgtat     240 gtacaaatga acagcctgag agccgaggac acggctgtgt attactgtgc gagagagggg    300
tatatgagtt cgtcctatta tggtatggac gtctggggcc aagggaccac ggtcaccgtc    360
tcctcag                                                              367
```

<210> SEQ ID NO 288
<211> LENGTH: 367
<212> TYPE: DNA
<213> ORGANISM: Homo sapiens

<400> SEQUENCE: 288

```
gaggtgcagc tggtggagtc tgggggaggc tttgtccagc ctgggggtc cctgagactc     60 tcctgtgcag tctctggatt cacctttaat agctattgga tgagctgggt ccgccaggct    120
ccagggaagg ggctggagtg ggtggccaac ataaaccaag atggaagtga gaaattctat    180
gtggcctctg tgaagggccg attcaccatg tccagagaca cgccaagaa atcagtgtat     240 gtacaaatga acagcctgag agccgaggac acggctgtgt attactgtgc gagagagggg    300
tataacagtt cgtcctatta tggtatggac gtctggggcc aagggaccac ggtcaccgtc    360
tcctcag                                                              367
```

<210> SEQ ID NO 289
<211> LENGTH: 367
<212> TYPE: DNA
<213> ORGANISM: Homo sapiens

<400> SEQUENCE: 289

```
gaggtgcagc tggtggagtc tgggggaggc tttgtccagc ctgggggtc cctgagactc     60 tcctgtgcag tctctggatt cacctttaat agctattgga tgagctgggt ccgccaggct    120
ccagggaagg ggctggagtg ggtggccaac ataaaccaag atggaagtga gaaattctat    180
gtggcctctg tgaagggccg attcaccatg tccagagaca cgccaagaa atcagtgtat     240 gtacaaatga acagcctgag agccgaggac acggctgtgt attactgtgc gagagagggg    300
tatcccagtt cgtcctatta tggtatggac gtctggggcc aagggaccac ggtcaccgtc    360
tcctcag                                                              367
```

<210> SEQ ID NO 290
<211> LENGTH: 367
<212> TYPE: DNA
<213> ORGANISM: Homo sapiens

<400> SEQUENCE: 290

| gaggtgcagc tggtggagtc tgggggaggc tttgtccagc ctggggggtc cctgagactc | 60 |
| tcctgtgcag tctctggatt cacctttaat agctattgga tgagctgggt ccgccaggct | 120 |
| ccagggaagg ggctggagtg ggtggccaac ataaaccaag atggaagtga gaaattctat | 180 |
| gtggcctctg tgaagggccg attcaccatg tccagagaca acgccaagaa atcagtgtat | 240 |
| gtacaaatga acagcctgag agccgaggac acggctgtgt attactgtgc gagagagggg | 300 |
| tatcagagtt cgtcctatta tggtatggac gtctggggcc aagggaccac ggtcaccgtc | 360 |
| tcctcag | 367 |

<210> SEQ ID NO 291
<211> LENGTH: 367
<212> TYPE: DNA
<213> ORGANISM: Homo sapiens

<400> SEQUENCE: 291

| gaggtgcagc tggtggagtc tgggggaggc tttgtccagc ctggggggtc cctgagactc | 60 |
| tcctgtgcag tctctggatt cacctttaat agctattgga tgagctgggt ccgccaggct | 120 |
| ccagggaagg ggctggagtg ggtggccaac ataaaccaag atggaagtga gaaattctat | 180 |
| gtggcctctg tgaagggccg attcaccatg tccagagaca acgccaagaa atcagtgtat | 240 |
| gtacaaatga acagcctgag agccgaggac acggctgtgt attactgtgc gagagagggg | 300 |
| tatagaagtt cgtcctatta tggtatggac gtctggggcc aagggaccac ggtcaccgtc | 360 |
| tcctcag | 367 |

<210> SEQ ID NO 292
<211> LENGTH: 367
<212> TYPE: DNA
<213> ORGANISM: Homo sapiens

<400> SEQUENCE: 292

| gaggtgcagc tggtggagtc tgggggaggc tttgtccagc ctggggggtc cctgagactc | 60 |
| tcctgtgcag tctctggatt caccttaat agctattgga tgagctgggt ccgccaggct | 120 |
| ccagggaagg ggctggagtg ggtggccaac ataaaccaag atggaagtga gaaattctat | 180 |
| gtggcctctg tgaagggccg attcaccatg tccagagaca acgccaagaa atcagtgtat | 240 |
| gtacaaatga acagcctgag agccgaggac acggctgtgt attactgtgc gagagagggg | 300 |
| tataccagtt cgtcctatta tggtatggac gtctggggcc aagggaccac ggtcaccgtc | 360 |
| tcctcag | 367 |

<210> SEQ ID NO 293
<211> LENGTH: 367
<212> TYPE: DNA
<213> ORGANISM: Homo sapiens

<400> SEQUENCE: 293

| gaggtgcagc tggtggagtc tgggggaggc tttgtccagc ctggggggtc cctgagactc | 60 |
| tcctgtgcag tctctggatt cacctttaat agctattgga tgagctgggt ccgccaggct | 120 |
| ccagggaagg ggctggagtg ggtggccaac ataaaccaag atggaagtga gaaattctat | 180 |

```
gtggcctctg tgaagggccg attcaccatg tccagagaca acgccaagaa atcagtgtat    240
gtacaaatga acagcctgag agccgaggac acggctgtgt attactgtgc gagagagggg    300
tatgtgagtt cgtcctatta tggtatggac gtctggggcc aagggaccac ggtcaccgtc    360
tcctcag                                                              367
```

<210> SEQ ID NO 294
<211> LENGTH: 367
<212> TYPE: DNA
<213> ORGANISM: Homo sapiens

<400> SEQUENCE: 294

```
gaggtgcagc tggtggagtc tgggggaggc tttgtccagc ctggggggtc cctgagactc    60
tcctgtgcag tctctggatt cacctttaat agctattgga tgagctgggt ccgccaggct    120
ccagggaagg ggctggagtg ggtggccaac ataaaccaag atggaagtga gaaattctat    180
gtggcctctg tgaagggccg attcaccatg tccagagaca acgccaagaa atcagtgtat    240
gtacaaatga acagcctgag agccgaggac acggctgtgt attactgtgc gagagagggg    300
tattggagtt cgtcctatta tggtatggac gtctggggcc aagggaccac ggtcaccgtc    360
tcctcag                                                              367
```

<210> SEQ ID NO 295
<211> LENGTH: 367
<212> TYPE: DNA
<213> ORGANISM: Homo sapiens

<400> SEQUENCE: 295

```
gaggtgcagc tggtggagtc tgggggaggc tttgtccagc ctggggggtc cctgagactc    60
tcctgtgcag tctctggatt cacctttaat agctattgga tgagctgggt ccgccaggct    120
ccagggaagg ggctggagtg ggtggccaac ataaaccaag atggaagtga gaaattctat    180
gtggcctctg tgaagggccg attcaccatg tccagagaca acgccaagaa atcagtgtat    240
gtacaaatga acagcctgag agccgaggac acggctgtgt attactgtgc gagagagggg    300
tattacagtt cgtcctatta tggtatggac gtctggggcc aagggaccac ggtcaccgtc    360
tcctcag                                                              367
```

<210> SEQ ID NO 296
<211> LENGTH: 367
<212> TYPE: DNA
<213> ORGANISM: Homo sapiens

<400> SEQUENCE: 296

```
gaggtgcagc tggtggagtc tgggggaggc tttgtccagc ctggggggtc cctgagactc    60
tcctgtgcag tctctggatt cacctttaat agctattgga tgagctgggt ccgccaggct    120
ccagggaagg ggctggagtg ggtggccaac ataaaccaag atggaagtga gaaattctat    180
gtggcctctg tgaagggccg attcaccatg tccagagaca acgccaagaa atcagtgtat    240
gtacaaatga acagcctgag agccgaggac acggctgtgt attactgtgc gagagagggg    300
tatagttgct cgtcctatta tggtatggac gtctggggcc aagggaccac ggtcaccgtc    360
tcctcag                                                              367
```

<210> SEQ ID NO 297
<211> LENGTH: 367
<212> TYPE: DNA
<213> ORGANISM: Homo sapiens

<400> SEQUENCE: 297

| | | | | | |
|---|---|---|---|---|---|
| gaggtgcagc | tggtggagtc | tggggaggc | tttgtccagc | ctgggggtc | cctgagactc | 60 |
| tcctgtgcag | tctctggatt | cacctttaat | agctattgga | tgagctgggt | ccgccaggct | 120 |
| ccagggaagg | ggctggagtg | ggtggccaac | ataaaccaag | atggaagtga | gaaattctat | 180 |
| gtggcctctg | tgaagggccg | attcaccatg | tccagagaca | acgccaagaa | atcagtgtat | 240 |
| gtacaaatga | acagcctgag | agccgaggac | acggctgtgt | attactgtgc | gagagagggg | 300 |
| tatagtgact | cgtcctatta | tggtatggac | gtctggggcc | aagggaccac | ggtcaccgtc | 360 |
| tcctcag | | | | | | 367 |

<210> SEQ ID NO 298
<211> LENGTH: 367
<212> TYPE: DNA
<213> ORGANISM: Homo sapiens

<400> SEQUENCE: 298

| | | | | | |
|---|---|---|---|---|---|
| gaggtgcagc | tggtggagtc | tggggaggc | tttgtccagc | ctgggggtc | cctgagactc | 60 |
| tcctgtgcag | tctctggatt | caccttaat | agctattgga | tgagctgggt | ccgccaggct | 120 |
| ccagggaagg | ggctggagtg | ggtggccaac | ataaaccaag | atggaagtga | gaaattctat | 180 |
| gtggcctctg | tgaagggccg | attcaccatg | tccagagaca | acgccaagaa | atcagtgtat | 240 |
| gtacaaatga | acagcctgag | agccgaggac | acggctgtgt | attactgtgc | gagagagggg | 300 |
| tatagtgagt | cgtcctatta | tggtatggac | gtctggggcc | aagggaccac | ggtcaccgtc | 360 |
| tcctcag | | | | | | 367 |

<210> SEQ ID NO 299
<211> LENGTH: 367
<212> TYPE: DNA
<213> ORGANISM: Homo sapiens

<400> SEQUENCE: 299

| | | | | | |
|---|---|---|---|---|---|
| gaggtgcagc | tggtggagtc | tggggaggc | tttgtccagc | ctgggggtc | cctgagactc | 60 |
| tcctgtgcag | tctctggatt | cacctttaat | agctattgga | tgagctgggt | ccgccaggct | 120 |
| ccagggaagg | ggctggagtg | ggtggccaac | ataaaccaag | atggaagtga | gaaattctat | 180 |
| gtggcctctg | tgaagggccg | attcaccatg | tccagagaca | acgccaagaa | atcagtgtat | 240 |
| gtacaaatga | acagcctgag | agccgaggac | acggctgtgt | attactgtgc | gagagaggg | 300 |
| tatagttct | cgtcctatta | tggtatggac | gtctggggcc | aagggaccac | ggtcaccgtc | 360 |
| tcctcag | | | | | | 367 |

<210> SEQ ID NO 300
<211> LENGTH: 367
<212> TYPE: DNA
<213> ORGANISM: Homo sapiens

<400> SEQUENCE: 300

| | | | | | |
|---|---|---|---|---|---|
| gaggtgcagc | tggtggagtc | tggggaggc | tttgtccagc | ctgggggtc | cctgagactc | 60 |
| tcctgtgcag | tctctggatt | cacctttaat | agctattgga | tgagctgggt | ccgccaggct | 120 |
| ccagggaagg | ggctggagtg | ggtggccaac | ataaaccaag | atggaagtga | gaaattctat | 180 |
| gtggcctctg | tgaagggccg | attcaccatg | tccagagaca | acgccaagaa | atcagtgtat | 240 |
| gtacaaatga | acagcctgag | agccgaggac | acggctgtgt | attactgtgc | gagagagggg | 300 |

```
tatagtggct cgtcctatta tggtatggac gtctggggcc aagggaccac ggtcaccgtc    360
tcctcag                                                              367
```

<210> SEQ ID NO 301
<211> LENGTH: 367
<212> TYPE: DNA
<213> ORGANISM: Homo sapiens

<400> SEQUENCE: 301

```
gaggtgcagc tggtggagtc tgggggaggc tttgtccagc ctgggggtc cctgagactc     60 tcctgtgcag tctctggatt cacctttaat agctattgga tgagctgggt ccgccaggct   120
ccagggaagg ggctggagtg ggtggccaac ataaaccaag atggaagtga gaaattctat   180
gtggcctctg tgaagggccg attcaccatg tccagagaca acgccaagaa ctcagtgtat   240
gtacaaatga acagcctgag agccgaggac acggctgtgt attactgtgc gagagagggg   300
tatagtcact cgtcctatta tggtatggac gtctggggcc aagggaccac ggtcaccgtc   360
tcctcag                                                             367
```

<210> SEQ ID NO 302
<211> LENGTH: 367
<212> TYPE: DNA
<213> ORGANISM: Homo sapiens

<400> SEQUENCE: 302

```
gaggtgcagc tggtggagtc tgggggaggc tttgtccagc ctgggggtc cctgagactc     60 tcctgtgcag tctctggatt cacctttaat agctattgga tgagctgggt ccgccaggct   120
ccagggaagg ggctggagtg ggtggccaac ataaaccaag atggaagtga gaaattctat   180
gtggcctctg tgaagggccg attcaccatg tccagagaca acgccaagaa ctcagtgtat   240
gtacaaatga acagcctgag agccgaggac acggctgtgt attactgtgc gagagagggg   300
tatagtatct cgtcctatta tggtatggac gtctggggcc aagggaccac ggtcaccgtc   360
tcctcag                                                             367
```

<210> SEQ ID NO 303
<211> LENGTH: 367
<212> TYPE: DNA
<213> ORGANISM: Homo sapiens

<400> SEQUENCE: 303

```
gaggtgcagc tggtggagtc tgggggaggc tttgtccagc ctgggggtc cctgagactc     60 tcctgtgcag tctctggatt cacctttaat agctattgga tgagctgggt ccgccaggct   120
ccagggaagg ggctggagtg ggtggccaac ataaaccaag atggaagtga gaaattctat   180
gtggcctctg tgaagggccg attcaccatg tccagagaca acgccaagaa ctcagtgtat   240
gtacaaatga acagcctgag agccgaggac acggctgtgt attactgtgc gagagagggg   300
tatagtaagt cgtcctatta tggtatggac gtctggggcc aagggaccac ggtcaccgtc   360
tcctcag                                                             367
```

<210> SEQ ID NO 304
<211> LENGTH: 367
<212> TYPE: DNA
<213> ORGANISM: Homo sapiens

<400> SEQUENCE: 304

```
gaggtgcagc tggtggagtc tggggaggc tttgtccagc ctgggggtc cctgagactc      60
tcctgtgcag tctctggatt cacctttaat agctattgga tgagctgggt ccgccaggct    120
ccagggaagg ggctggagtg ggtggccaac ataaaccaag atggaagtga gaaattctat    180
gtggcctctg tgaagggccg attcaccatg tccagagaca acgccaagaa atcagtgtat    240
gtacaaatga acagcctgag agccgaggac acggctgtgt attactgtgc gagagagggg    300
tatagtctgt cgtcctatta tggtatggac gtctggggcc aagggaccac ggtcaccgtc    360
tcctcag                                                              367
```

<210> SEQ ID NO 305
<211> LENGTH: 367
<212> TYPE: DNA
<213> ORGANISM: Homo sapiens

<400> SEQUENCE: 305

```
gaggtgcagc tggtggagtc tggggaggc tttgtccagc ctgggggtc cctgagactc      60
tcctgtgcag tctctggatt cacctttaat agctattgga tgagctgggt ccgccaggct    120
ccagggaagg ggctggagtg ggtggccaac ataaaccaag atggaagtga gaaattctat    180
gtggcctctg tgaagggccg attcaccatg tccagagaca acgccaagaa atcagtgtat    240
gtacaaatga acagcctgag agccgaggac acggctgtgt attactgtgc gagagagggg    300
tatagtatgt cgtcctatta tggtatggac gtctggggcc aagggaccac ggtcaccgtc    360
tcctcag                                                              367
```

<210> SEQ ID NO 306
<211> LENGTH: 367
<212> TYPE: DNA
<213> ORGANISM: Homo sapiens

<400> SEQUENCE: 306

```
gaggtgcagc tggtggagtc tggggaggc tttgtccagc ctgggggtc cctgagactc      60
tcctgtgcag tctctggatt cacctttaat agctattgga tgagctgggt ccgccaggct    120
ccagggaagg ggctggagtg ggtggccaac ataaaccaag atggaagtga gaaattctat    180
gtggcctctg tgaagggccg attcaccatg tccagagaca acgccaagaa atcagtgtat    240
gtacaaatga acagcctgag agccgaggac acggctgtgt attactgtgc gagagagggg    300
tatagtaact cgtcctatta tggtatggac gtctggggcc aagggaccac ggtcaccgtc    360
tcctcag                                                              367
```

<210> SEQ ID NO 307
<211> LENGTH: 367
<212> TYPE: DNA
<213> ORGANISM: Homo sapiens

<400> SEQUENCE: 307

```
gaggtgcagc tggtggagtc tggggaggc tttgtccagc ctgggggtc cctgagactc      60
tcctgtgcag tctctggatt cacctttaat agctattgga tgagctgggt ccgccaggct    120
ccagggaagg ggctggagtg ggtggccaac ataaaccaag atggaagtga gaaattctat    180
gtggcctctg tgaagggccg attcaccatg tccagagaca acgccaagaa atcagtgtat    240
gtacaaatga acagcctgag agccgaggac acggctgtgt attactgtgc gagagagggg    300
```

```
tatagtccct cgtcctatta tggtatggac gtctggggcc aagggaccac ggtcaccgtc    360
tcctcag                                                              367

<210> SEQ ID NO 308
<211> LENGTH: 367
<212> TYPE: DNA
<213> ORGANISM: Homo sapiens

<400> SEQUENCE: 308
gaggtgcagc tggtggagtc tgggggaggc tttgtccagc ctgggggtc cctgagactc     60 tcctgtgcag tctctggatt cacctttaat agctattgga tgagctgggt ccgccaggct   120
ccagggaagg ggctggagtg ggtggccaac ataaaccaag atggaagtga gaaattctat   180
gtggcctctg tgaagggccg attcaccatg tccagagaca cgccaagaa atcagtgtat    240 gtacaaatga acagcctgag agccgaggac acggctgtgt attactgtgc gagagagggg   300
tatagtcagt cgtcctatta tggtatggac gtctggggcc aagggaccac ggtcaccgtc   360
tcctcag                                                              367

<210> SEQ ID NO 309
<211> LENGTH: 367
<212> TYPE: DNA
<213> ORGANISM: Homo sapiens

<400> SEQUENCE: 309
gaggtgcagc tggtggagtc tgggggaggc tttgtccagc ctgggggtc cctgagactc     60 tcctgtgcag tctctggatt cacctttaat agctattgga tgagctgggt ccgccaggct   120
ccagggaagg ggctggagtg ggtggccaac ataaaccaag atggaagtga gaaattctat   180
gtggcctctg tgaagggccg attcaccatg tccagagaca cgccaagaa atcagtgtat    240 gtacaaatga acagcctgag agccgaggac acggctgtgt attactgtgc gagagagggg   300
tatagtagat cgtcctatta tggtatggac gtctggggcc aagggaccac ggtcaccgtc   360
tcctcag                                                              367

<210> SEQ ID NO 310
<211> LENGTH: 367
<212> TYPE: DNA
<213> ORGANISM: Homo sapiens

<400> SEQUENCE: 310
gaggtgcagc tggtggagtc tgggggaggc tttgtccagc ctgggggtc cctgagactc     60 tcctgtgcag tctctggatt cacctttaat agctattgga tgagctgggt ccgccaggct   120
ccagggaagg ggctggagtg ggtggccaac ataaaccaag atggaagtga gaaattctat   180
gtggcctctg tgaagggccg attcaccatg tccagagaca cgccaagaa atcagtgtat    240 gtacaaatga acagcctgag agccgaggac acggctgtgt attactgtgc gagagagggg   300
tatagtacct cgtcctatta tggtatggac gtctggggcc aagggaccac ggtcaccgtc   360
tcctcag                                                              367

<210> SEQ ID NO 311
<211> LENGTH: 367
<212> TYPE: DNA
<213> ORGANISM: Homo sapiens
```

-continued

<400> SEQUENCE: 311

```
gaggtgcagc tggtggagtc tgggggaggc tttgtccagc ctggggggtc cctgagactc    60
tcctgtgcag tctctggatt cacctttaat agctattgga tgagctgggt ccgccaggct   120
ccagggaagg ggctggagtg ggtggccaac ataaaccaag atggaagtga gaaattctat   180
gtggcctctg tgaagggccg attcaccatg tccagagaca acgccaagaa atcagtgtat   240
gtacaaatga acagcctgag agccgaggac acggctgtgt attactgtgc gagagagggg   300
tatagtgtgt cgtcctatta tggtatggac gtctggggcc aagggaccac ggtcaccgtc   360
tcctcag                                                             367
```

<210> SEQ ID NO 312
<211> LENGTH: 367
<212> TYPE: DNA
<213> ORGANISM: Homo sapiens

<400> SEQUENCE: 312

```
gaggtgcagc tggtggagtc tgggggaggc tttgtccagc ctggggggtc cctgagactc    60
tcctgtgcag tctctggatt cacctttaat agctattgga tgagctgggt ccgccaggct   120
ccagggaagg ggctggagtg ggtggccaac ataaaccaag atggaagtga gaaattctat   180
gtggcctctg tgaagggccg attcaccatg tccagagaca acgccaagaa atcagtgtat   240
gtacaaatga acagcctgag agccgaggac acggctgtgt attactgtgc gagagagggg   300
tatagttggt cgtcctatta tggtatggac gtctggggcc aagggaccac ggtcaccgtc   360
tcctcag                                                             367
```

<210> SEQ ID NO 313
<211> LENGTH: 367
<212> TYPE: DNA
<213> ORGANISM: Homo sapiens

<400> SEQUENCE: 313

```
gaggtgcagc tggtggagtc tgggggaggc tttgtccagc ctggggggtc cctgagactc    60
tcctgtgcag tctctggatt caccttttaat agctattgga tgagctgggt ccgccaggct  120
ccagggaagg ggctggagtg ggtggccaac ataaaccaag atggaagtga gaaattctat   180
gtggcctctg tgaagggccg attcaccatg tccagagaca acgccaagaa atcagtgtat   240
gtacaaatga acagcctgag agccgaggac acggctgtgt attactgtgc gagagagggg   300
tatagttact cgtcctatta tggtatggac gtctggggcc aagggaccac ggtcaccgtc   360
tcctcag                                                             367
```

<210> SEQ ID NO 314
<211> LENGTH: 122
<212> TYPE: PRT
<213> ORGANISM: Homo sapiens

<400> SEQUENCE: 314

```
Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60
```

-continued

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ala Ser Ser Tyr Tyr Gly Met Asp Val Trp
            100                 105                 110

Gly Gln Gly Thr Thr Val Thr Val Ser Ser
        115                 120

<210> SEQ ID NO 315
<211> LENGTH: 122
<212> TYPE: PRT
<213> ORGANISM: Homo sapiens

<400> SEQUENCE: 315

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ala Ser Ser Tyr Tyr Gly Met Asp Val Trp
            100                 105                 110

Gly Gln Gly Thr Thr Val Thr Val Ser Ser
        115                 120

<210> SEQ ID NO 316
<211> LENGTH: 122
<212> TYPE: PRT
<213> ORGANISM: Homo sapiens

<400> SEQUENCE: 316

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Ala Ser Tyr Tyr Gly Met Asp Val Trp
            100                 105                 110

Gly Gln Gly Thr Thr Val Thr Val Ser Ser
        115                 120

```
<210> SEQ ID NO 317
<211> LENGTH: 122
<212> TYPE: PRT
<213> ORGANISM: Homo sapiens

<400> SEQUENCE: 317

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Ala Tyr Tyr Gly Met Asp Val Trp
            100                 105                 110

Gly Gln Gly Thr Thr Val Thr Val Ser Ser
        115                 120

<210> SEQ ID NO 318
<211> LENGTH: 122
<212> TYPE: PRT
<213> ORGANISM: Homo sapiens

<400> SEQUENCE: 318

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Cys Ser Tyr Tyr Gly Met Asp Val Trp
            100                 105                 110

Gly Gln Gly Thr Thr Val Thr Val Ser Ser
        115                 120

<210> SEQ ID NO 319
<211> LENGTH: 122
<212> TYPE: PRT
<213> ORGANISM: Homo sapiens

<400> SEQUENCE: 319

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45
```

-continued

```
Ala Asn Ile Asn Gln Asp Gly Ser Glu Lys Phe Tyr Val Ala Ser Val
 50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                 85                  90                  95

Ala Arg Glu Gly Tyr Ser Ser Asp Ser Tyr Tyr Gly Met Asp Val Trp
             100                 105                 110

Gly Gln Gly Thr Thr Val Thr Val Ser Ser
         115                 120
```

<210> SEQ ID NO 320
<211> LENGTH: 122
<212> TYPE: PRT
<213> ORGANISM: Homo sapiens

<400> SEQUENCE: 320

```
Glu Val Gln Leu Val Glu Ser Gly Gly Phe Val Gln Pro Gly Gly
 1               5                  10                  15

Ser Leu Arg Leu Ser Cys Ala Val Ser Gly Phe Thr Phe Asn Ser Tyr
                 20                  25                  30

Trp Met Ser Trp Val Arg Gln Ala Pro Gly Lys Gly Leu Glu Trp Val
             35                  40                  45

Ala Asn Ile Asn Gln Asp Gly Ser Glu Lys Phe Tyr Val Ala Ser Val
 50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                 85                  90                  95

Ala Arg Glu Gly Tyr Ser Ser Glu Ser Tyr Tyr Gly Met Asp Val Trp
             100                 105                 110

Gly Gln Gly Thr Thr Val Thr Val Ser Ser
         115                 120
```

<210> SEQ ID NO 321
<211> LENGTH: 122
<212> TYPE: PRT
<213> ORGANISM: Homo sapiens

<400> SEQUENCE: 321

```
Glu Val Gln Leu Val Glu Ser Gly Gly Phe Val Gln Pro Gly Gly
 1               5                  10                  15

Ser Leu Arg Leu Ser Cys Ala Val Ser Gly Phe Thr Phe Asn Ser Tyr
                 20                  25                  30

Trp Met Ser Trp Val Arg Gln Ala Pro Gly Lys Gly Leu Glu Trp Val
             35                  40                  45

Ala Asn Ile Asn Gln Asp Gly Ser Glu Lys Phe Tyr Val Ala Ser Val
 50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                 85                  90                  95

Ala Arg Glu Gly Tyr Ser Ser Phe Ser Tyr Tyr Gly Met Asp Val Trp
             100                 105                 110

Gly Gln Gly Thr Thr Val Thr Val Ser Ser
         115                 120
```

```
<210> SEQ ID NO 322
<211> LENGTH: 122
<212> TYPE: PRT
<213> ORGANISM: Homo sapiens

<400> SEQUENCE: 322

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Gly Ser Tyr Tyr Gly Met Asp Val Trp
            100                 105                 110

Gly Gln Gly Thr Thr Val Thr Val Ser Ser
        115                 120

<210> SEQ ID NO 323
<211> LENGTH: 122
<212> TYPE: PRT
<213> ORGANISM: Homo sapiens

<400> SEQUENCE: 323

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser His Ser Tyr Tyr Gly Met Asp Val Trp
            100                 105                 110

Gly Gln Gly Thr Thr Val Thr Val Ser Ser
        115                 120

<210> SEQ ID NO 324
<211> LENGTH: 122
<212> TYPE: PRT
<213> ORGANISM: Homo sapiens

<400> SEQUENCE: 324

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45
```

Ala Asn Ile Asn Gln Asp Gly Ser Glu Lys Phe Tyr Val Ala Ser Val
            50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Ile Ser Tyr Tyr Gly Met Asp Val Trp
                100                 105                 110

Gly Gln Gly Thr Thr Val Thr Val Ser Ser
            115                 120

<210> SEQ ID NO 325
<211> LENGTH: 122
<212> TYPE: PRT
<213> ORGANISM: Homo sapiens

<400> SEQUENCE: 325

Glu Val Gln Leu Val Glu Ser Gly Gly Gly Phe Val Gln Pro Gly Gly
 1               5                  10                  15

Ser Leu Arg Leu Ser Cys Ala Val Ser Gly Phe Thr Phe Asn Ser Tyr
                20                  25                  30

Trp Met Ser Trp Val Arg Gln Ala Pro Gly Lys Gly Leu Glu Trp Val
            35                  40                  45

Ala Asn Ile Asn Gln Asp Gly Ser Glu Lys Phe Tyr Val Ala Ser Val
        50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Lys Ser Tyr Tyr Gly Met Asp Val Trp
                100                 105                 110

Gly Gln Gly Thr Thr Val Thr Val Ser Ser
            115                 120

<210> SEQ ID NO 326
<211> LENGTH: 122
<212> TYPE: PRT
<213> ORGANISM: Homo sapiens

<400> SEQUENCE: 326

Glu Val Gln Leu Val Glu Ser Gly Gly Gly Phe Val Gln Pro Gly Gly
 1               5                  10                  15

Ser Leu Arg Leu Ser Cys Ala Val Ser Gly Phe Thr Phe Asn Ser Tyr
                20                  25                  30

Trp Met Ser Trp Val Arg Gln Ala Pro Gly Lys Gly Leu Glu Trp Val
            35                  40                  45

Ala Asn Ile Asn Gln Asp Gly Ser Glu Lys Phe Tyr Val Ala Ser Val
        50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Leu Ser Tyr Tyr Gly Met Asp Val Trp
                100                 105                 110

Gly Gln Gly Thr Thr Val Thr Val Ser Ser
            115                 120

<210> SEQ ID NO 327
<211> LENGTH: 122
<212> TYPE: PRT
<213> ORGANISM: Homo sapiens

<400> SEQUENCE: 327

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Met Ser Tyr Tyr Gly Met Asp Val Trp
            100                 105                 110

Gly Gln Gly Thr Thr Val Thr Val Ser Ser
        115                 120

<210> SEQ ID NO 328
<211> LENGTH: 122
<212> TYPE: PRT
<213> ORGANISM: Homo sapiens

<400> SEQUENCE: 328

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Asn Ser Tyr Tyr Gly Met Asp Val Trp
            100                 105                 110

Gly Gln Gly Thr Thr Val Thr Val Ser Ser
        115                 120

<210> SEQ ID NO 329
<211> LENGTH: 122
<212> TYPE: PRT
<213> ORGANISM: Homo sapiens

<400> SEQUENCE: 329

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

```
Ala Asn Ile Asn Gln Asp Gly Ser Glu Lys Phe Tyr Val Ala Ser Val
        50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                 85                  90                  95

Ala Arg Glu Gly Tyr Ser Ser Pro Ser Tyr Tyr Gly Met Asp Val Trp
            100                 105                 110

Gly Gln Gly Thr Thr Val Thr Val Ser Ser
            115                 120

<210> SEQ ID NO 330
<211> LENGTH: 145
<212> TYPE: PRT
<213> ORGANISM: Homo sapiens

<400> SEQUENCE: 330

Tyr Asn Ser Gly Lys Leu Glu Glu Phe Val Gln Gly Asn Leu Glu Arg
  1               5                  10                  15

Glu Cys Met Glu Glu Lys Cys Ser Phe Glu Glu Ala Arg Glu Val Phe
                 20                  25                  30

Glu Asn Thr Glu Arg Thr Thr Glu Phe Trp Lys Gln Tyr Val Asp Gly
             35                  40                  45

Asp Gln Cys Glu Ser Asn Pro Cys Leu Asn Gly Gly Ser Cys Lys Asp
 50                  55                  60

Asp Ile Asn Ser Tyr Glu Cys Trp Cys Pro Phe Gly Phe Glu Gly Lys
 65                  70                  75                  80

Asn Cys Glu Leu Asp Val Thr Cys Asn Ile Lys Asn Gly Arg Cys Glu
                 85                  90                  95

Gln Phe Cys Lys Asn Ser Ala Asp Asn Lys Val Val Cys Ser Cys Thr
            100                 105                 110

Glu Gly Tyr Arg Leu Ala Glu Asn Gln Lys Ser Cys Glu Pro Ala Val
        115                 120                 125

Pro Phe Pro Cys Gly Arg Val Ser Val Ser Gln Thr Ser Lys Leu Thr
    130                 135                 140

Arg
145

<210> SEQ ID NO 331
<211> LENGTH: 270
<212> TYPE: PRT
<213> ORGANISM: Homo sapiens

<400> SEQUENCE: 331

Ala Glu Thr Val Phe Pro Asp Val Asp Tyr Val Asn Ser Thr Glu Ala
  1               5                  10                  15

Glu Thr Ile Leu Asp Asn Ile Thr Gln Ser Thr Gln Ser Phe Asn Asp
                 20                  25                  30

Phe Thr Arg Val Val Gly Gly Glu Asp Ala Lys Pro Gly Gln Phe Pro
             35                  40                  45

Trp Gln Val Val Leu Asn Gly Lys Val Asp Ala Phe Cys Gly Gly Ser
 50                  55                  60

Ile Val Asn Glu Lys Trp Ile Val Thr Ala Ala His Cys Val Glu Thr
 65                  70                  75                  80

Gly Val Lys Ile Thr Val Val Ala Gly Glu His Asn Ile Glu Glu Thr
                 85                  90                  95
```

-continued

```
Glu His Thr Glu Gln Lys Arg Asn Val Ile Arg Ile Ile Pro His His
                100                 105                 110

Asn Tyr Asn Ala Ala Ile Asn Lys Tyr Asn His Asp Ile Ala Leu Leu
            115                 120                 125

Glu Leu Asp Glu Pro Leu Val Leu Asn Ser Tyr Val Thr Pro Ile Cys
        130                 135                 140

Ile Ala Asp Lys Glu Tyr Thr Asn Ile Phe Leu Lys Phe Gly Ser Gly
145                 150                 155                 160

Tyr Val Ser Gly Trp Gly Arg Val Phe His Lys Gly Arg Ser Ala Leu
                165                 170                 175

Val Leu Gln Tyr Leu Arg Val Pro Leu Val Asp Arg Ala Thr Cys Leu
            180                 185                 190

Arg Ser Thr Lys Phe Thr Ile Tyr Asn Asn Met Phe Cys Ala Gly Phe
        195                 200                 205

His Glu Gly Gly Arg Asp Ser Cys Gln Gly Asp Ser Gly Gly Pro His
210                 215                 220

Val Thr Glu Val Glu Gly Thr Ser Phe Leu Thr Gly Ile Ile Ser Trp
225                 230                 235                 240

Gly Glu Glu Cys Ala Met Lys Gly Lys Tyr Gly Ile Tyr Thr Lys Val
                245                 250                 255

Ser Arg Tyr Val Asn Trp Ile Lys Glu Lys Thr Lys Leu Thr
            260                 265                 270

<210> SEQ ID NO 332
<211> LENGTH: 235
<212> TYPE: PRT
<213> ORGANISM: Homo sapiens

<400> SEQUENCE: 332

Val Val Gly Gly Glu Asp Ala Lys Pro Gly Gln Phe Pro Trp Gln Val
1               5                   10                  15

Val Leu Asn Gly Lys Val Asp Ala Phe Cys Gly Gly Ser Ile Val Asn
            20                  25                  30

Glu Lys Trp Ile Val Thr Ala Ala His Cys Val Glu Thr Gly Val Lys
        35                  40                  45

Ile Thr Val Val Ala Gly Glu His Asn Ile Glu Glu Thr Glu His Thr
50                  55                  60

Glu Gln Lys Arg Asn Val Ile Arg Ile Ile Pro His His Asn Tyr Asn
65                  70                  75                  80

Ala Ala Ile Asn Lys Tyr Asn His Asp Ile Ala Leu Leu Glu Leu Asp
                85                  90                  95

Glu Pro Leu Val Leu Asn Ser Tyr Val Thr Pro Ile Cys Ile Ala Asp
            100                 105                 110

Lys Glu Tyr Thr Asn Ile Phe Leu Lys Phe Gly Ser Gly Tyr Val Ser
        115                 120                 125

Gly Trp Gly Arg Val Phe His Lys Gly Arg Ser Ala Leu Val Leu Gln
    130                 135                 140

Tyr Leu Arg Val Pro Leu Val Asp Arg Ala Thr Cys Leu Arg Ser Thr
145                 150                 155                 160

Lys Phe Thr Ile Tyr Asn Asn Met Phe Cys Ala Gly Phe His Glu Gly
                165                 170                 175

Gly Arg Asp Ser Cys Gln Gly Asp Ser Gly Gly Pro His Val Thr Glu
            180                 185                 190

Val Glu Gly Thr Ser Phe Leu Thr Gly Ile Ile Ser Trp Gly Glu Glu
        195                 200                 205
```

Cys Ala Met Lys Gly Lys Tyr Gly Ile Tyr Thr Lys Val Ser Arg Tyr
            210                 215                 220

Val Asn Trp Ile Lys Glu Lys Thr Lys Leu Thr
225                 230                 235

<210> SEQ ID NO 333
<211> LENGTH: 35
<212> TYPE: PRT
<213> ORGANISM: Homo sapiens

<400> SEQUENCE: 333

Ala Glu Thr Val Phe Pro Asp Val Asp Tyr Val Asn Ser Thr Glu Ala
1               5                   10                  15

Glu Thr Ile Leu Asp Asn Ile Thr Gln Ser Thr Gln Ser Phe Asn Asp
            20                  25                  30

Phe Thr Arg
        35

<210> SEQ ID NO 334
<211> LENGTH: 461
<212> TYPE: PRT
<213> ORGANISM: Homo sapiens

<400> SEQUENCE: 334

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

```
Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Pro His His Asn
    290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
            340                 345                 350

Val Ser Gly Trp Gly Arg Val Phe His Lys Gly Arg Ser Ala Leu Val
        355                 360                 365

Leu Gln Tyr Leu Arg Val Pro Leu Val Asp Arg Ala Thr Cys Leu Arg
    370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
                405                 410                 415

Thr Glu Val Glu Gly Thr Ser Phe Leu Thr Gly Ile Ile Ser Trp Gly
            420                 425                 430

Glu Glu Cys Ala Met Lys Gly Lys Tyr Gly Ile Tyr Thr Lys Val Ser
        435                 440                 445

Arg Tyr Val Asn Trp Ile Lys Glu Lys Thr Lys Leu Thr
    450                 455                 460

<210> SEQ ID NO 335
<211> LENGTH: 488
<212> TYPE: PRT
<213> ORGANISM: Homo sapiens

<400> SEQUENCE: 335

Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala Asn
            20                  25                  30

Asn Ile Leu Ala Arg Val Thr Arg Ala Asn Ser Phe Leu Glu Glu Met
        35                  40                  45

Lys Lys Gly His Leu Glu Arg Glu Cys Met Glu Glu Thr Cys Ser Tyr
    50                  55                  60

Glu Glu Ala Arg Glu Val Phe Glu Asp Ser Asp Lys Thr Asn Glu Phe
65                  70                  75                  80

Trp Asn Lys Tyr Lys Asp Gly Asp Gln Cys Glu Thr Ser Pro Cys Gln
                85                  90                  95

Asn Gln Gly Lys Cys Lys Asp Gly Leu Gly Glu Tyr Thr Cys Thr Cys
            100                 105                 110

Leu Glu Gly Phe Glu Gly Lys Asn Cys Glu Leu Phe Thr Arg Lys Leu
        115                 120                 125

Cys Ser Leu Asp Asn Gly Asp Cys Asp Gln Phe Cys His Glu Glu Gln
    130                 135                 140

Asn Ser Val Val Cys Ser Cys Ala Arg Gly Tyr Thr Leu Ala Asp Asn
145                 150                 155                 160

Gly Lys Ala Cys Ile Pro Thr Gly Pro Tyr Pro Cys Gly Lys Gln Thr
                165                 170                 175
```

```
Leu Glu Arg Arg Lys Arg Ser Val Ala Gln Ala Thr Ser Ser Ser Gly
            180                 185                 190

Glu Ala Pro Asp Ser Ile Thr Trp Lys Pro Tyr Asp Ala Ala Asp Leu
        195                 200                 205

Asp Pro Thr Glu Asn Pro Phe Asp Leu Leu Asp Phe Asn Gln Thr Gln
210                 215                 220

Pro Glu Arg Gly Asp Asn Asn Leu Thr Arg Ile Val Gly Gly Gln Glu
225                 230                 235                 240

Cys Lys Asp Gly Glu Cys Pro Trp Gln Ala Leu Leu Ile Asn Glu Glu
                245                 250                 255

Asn Glu Gly Phe Cys Gly Gly Thr Ile Leu Ser Glu Phe Tyr Ile Leu
            260                 265                 270

Thr Ala Ala His Cys Leu Tyr Gln Ala Lys Arg Phe Lys Val Arg Val
        275                 280                 285

Gly Asp Arg Asn Thr Glu Gln Glu Glu Gly Gly Glu Ala Val His Glu
290                 295                 300

Val Glu Val Val Ile Lys His Asn Arg Phe Thr Lys Glu Thr Tyr Asp
305                 310                 315                 320

Phe Asp Ile Ala Val Leu Arg Leu Lys Thr Pro Ile Thr Phe Arg Met
                325                 330                 335

Asn Val Ala Pro Ala Cys Leu Pro Glu Arg Asp Trp Ala Glu Ser Thr
            340                 345                 350

Leu Met Thr Gln Lys Thr Gly Ile Val Ser Gly Phe Gly Arg Thr His
        355                 360                 365

Glu Lys Gly Arg Gln Ser Thr Arg Leu Lys Met Leu Glu Val Pro Tyr
370                 375                 380

Val Asp Arg Asn Ser Cys Lys Leu Ser Ser Ser Phe Ile Ile Thr Gln
385                 390                 395                 400

Asn Met Phe Cys Ala Gly Tyr Asp Thr Lys Gln Glu Asp Ala Cys Gln
                405                 410                 415

Gly Asp Ser Gly Gly Pro His Val Thr Arg Phe Lys Asp Thr Tyr Phe
            420                 425                 430

Val Thr Gly Ile Val Ser Trp Gly Glu Gly Cys Ala Arg Lys Gly Lys
        435                 440                 445

Tyr Gly Ile Tyr Thr Lys Val Thr Ala Phe Leu Lys Trp Ile Asp Arg
450                 455                 460

Ser Met Lys Thr Arg Gly Leu Pro Lys Ala Lys Ser His Ala Pro Glu
465                 470                 475                 480

Val Ile Thr Ser Ser Pro Leu Lys
                485

<210> SEQ ID NO 336
<211> LENGTH: 31
<212> TYPE: PRT
<213> ORGANISM: Homo sapiens

<400> SEQUENCE: 336

Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala
            20                  25                  30

<210> SEQ ID NO 337
<211> LENGTH: 9
<212> TYPE: PRT
<213> ORGANISM: Homo sapiens
```

<400> SEQUENCE: 337

Asn Asn Ile Leu Ala Arg Val Thr Arg
1               5

<210> SEQ ID NO 338
<211> LENGTH: 139
<212> TYPE: PRT
<213> ORGANISM: Homo sapiens

<400> SEQUENCE: 338

Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
            20                  25                  30

Asp Ser Asp Lys Thr Asn Glu Phe Trp Asn Lys Tyr Lys Asp Gly Asp
        35                  40                  45

Gln Cys Glu Thr Ser Pro Cys Gln Asn Gln Gly Lys Cys Lys Asp Gly
    50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
                85                  90                  95

Asp Gln Phe Cys His Glu Glu Gln Asn Ser Val Val Cys Ser Cys Ala
            100                 105                 110

Arg Gly Tyr Thr Leu Ala Asp Asn Gly Lys Ala Cys Ile Pro Thr Gly
        115                 120                 125

Pro Tyr Pro Cys Gly Lys Gln Thr Leu Glu Arg
    130                 135

<210> SEQ ID NO 339
<211> LENGTH: 254
<212> TYPE: PRT
<213> ORGANISM: Homo sapiens

<400> SEQUENCE: 339

Ile Val Gly Gly Gln Glu Cys Lys Asp Gly Glu Cys Pro Trp Gln Ala
1               5                   10                  15

Leu Leu Ile Asn Glu Glu Asn Glu Gly Phe Cys Gly Gly Thr Ile Leu
            20                  25                  30

Ser Glu Phe Tyr Ile Leu Thr Ala Ala His Cys Leu Tyr Gln Ala Lys
        35                  40                  45

Arg Phe Lys Val Arg Val Gly Asp Arg Asn Thr Glu Gln Glu Glu Gly
    50                  55                  60

Gly Glu Ala Val His Glu Val Glu Val Ile Lys His Asn Arg Phe
65                  70                  75                  80

Thr Lys Glu Thr Tyr Asp Phe Asp Ile Ala Val Leu Arg Leu Lys Thr
                85                  90                  95

Pro Ile Thr Phe Arg Met Asn Val Ala Pro Ala Cys Leu Pro Glu Arg
            100                 105                 110

Asp Trp Ala Glu Ser Thr Leu Met Thr Gln Lys Thr Gly Ile Val Ser
        115                 120                 125

Gly Phe Gly Arg Thr His Glu Lys Gly Arg Gln Ser Thr Arg Leu Lys
    130                 135                 140

Met Leu Glu Val Pro Tyr Val Asp Arg Asn Ser Cys Lys Leu Ser
145                 150                 155                 160

```
Ser Phe Ile Ile Thr Gln Asn Met Phe Cys Ala Gly Tyr Asp Thr Lys
                165                 170                 175

Gln Glu Asp Ala Cys Gln Gly Asp Ser Gly Gly Pro His Val Thr Arg
            180                 185                 190

Phe Lys Asp Thr Tyr Phe Val Thr Gly Ile Val Ser Trp Gly Glu Gly
            195                 200                 205

Cys Ala Arg Lys Gly Lys Tyr Gly Ile Tyr Thr Lys Val Thr Ala Phe
            210                 215                 220

Leu Lys Trp Ile Asp Arg Ser Met Lys Thr Arg Gly Leu Pro Lys Ala
225                 230                 235                 240

Lys Ser His Ala Pro Glu Val Ile Thr Ser Ser Pro Leu Lys
            245                 250

<210> SEQ ID NO 340
<211> LENGTH: 122
<212> TYPE: PRT
<213> ORGANISM: Homo sapiens

<400> SEQUENCE: 340

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Gln Ser Tyr Tyr Gly Met Asp Val Trp
            100                 105                 110

Gly Gln Gly Thr Thr Val Thr Val Ser Ser
        115                 120

<210> SEQ ID NO 341
<211> LENGTH: 122
<212> TYPE: PRT
<213> ORGANISM: Homo sapiens

<400> SEQUENCE: 341

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95
```

Ala Arg Glu Gly Tyr Ser Ser Arg Ser Tyr Tyr Gly Met Asp Val Trp
            100                 105                 110

Gly Gln Gly Thr Thr Val Thr Val Ser Ser
            115                 120

<210> SEQ ID NO 342
<211> LENGTH: 122
<212> TYPE: PRT
<213> ORGANISM: Homo sapiens

<400> SEQUENCE: 342

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Thr Ser Tyr Tyr Gly Met Asp Val Trp
            100                 105                 110

Gly Gln Gly Thr Thr Val Thr Val Ser Ser
            115                 120

<210> SEQ ID NO 343
<211> LENGTH: 122
<212> TYPE: PRT
<213> ORGANISM: Homo sapiens

<400> SEQUENCE: 343

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Val Ser Tyr Tyr Gly Met Asp Val Trp
            100                 105                 110

Gly Gln Gly Thr Thr Val Thr Val Ser Ser
            115                 120

<210> SEQ ID NO 344
<211> LENGTH: 122
<212> TYPE: PRT
<213> ORGANISM: Homo sapiens -continued

<400> SEQUENCE: 344

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Trp Ser Tyr Tyr Gly Met Asp Val Trp
            100                 105                 110

Gly Gln Gly Thr Thr Val Thr Val Ser Ser
        115                 120

<210> SEQ ID NO 345
<211> LENGTH: 122
<212> TYPE: PRT
<213> ORGANISM: Homo sapiens

<400> SEQUENCE: 345

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Tyr Ser Tyr Tyr Gly Met Asp Val Trp
            100                 105                 110

Gly Gln Gly Thr Thr Val Thr Val Ser Ser
        115                 120

<210> SEQ ID NO 346
<211> LENGTH: 122
<212> TYPE: PRT
<213> ORGANISM: Homo sapiens

<400> SEQUENCE: 346

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

```
Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                 85                  90                  95

Ala Arg Glu Gly Tyr Ser Ser Cys Tyr Tyr Gly Met Asp Val Trp
            100                 105                 110

Gly Gln Gly Thr Thr Val Thr Val Ser Ser
            115                 120

<210> SEQ ID NO 347
<211> LENGTH: 122
<212> TYPE: PRT
<213> ORGANISM: Homo sapiens

<400> SEQUENCE: 347

Glu Val Gln Leu Val Glu Ser Gly Gly Gly Phe Val Gln Pro Gly Gly
  1               5                  10                  15

Ser Leu Arg Leu Ser Cys Ala Val Ser Gly Phe Thr Phe Asn Ser Tyr
                 20                  25                  30

Trp Met Ser Trp Val Arg Gln Ala Pro Gly Lys Gly Leu Glu Trp Val
             35                  40                  45

Ala Asn Ile Asn Gln Asp Gly Ser Glu Lys Phe Tyr Val Ala Ser Val
         50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                 85                  90                  95

Ala Arg Glu Gly Tyr Ser Ser Ser Asp Tyr Tyr Gly Met Asp Val Trp
            100                 105                 110

Gly Gln Gly Thr Thr Val Thr Val Ser Ser
            115                 120

<210> SEQ ID NO 348
<211> LENGTH: 122
<212> TYPE: PRT
<213> ORGANISM: Homo sapiens

<400> SEQUENCE: 348

Glu Val Gln Leu Val Glu Ser Gly Gly Gly Phe Val Gln Pro Gly Gly
  1               5                  10                  15

Ser Leu Arg Leu Ser Cys Ala Val Ser Gly Phe Thr Phe Asn Ser Tyr
                 20                  25                  30

Trp Met Ser Trp Val Arg Gln Ala Pro Gly Lys Gly Leu Glu Trp Val
             35                  40                  45

Ala Asn Ile Asn Gln Asp Gly Ser Glu Lys Phe Tyr Val Ala Ser Val
         50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                 85                  90                  95

Ala Arg Glu Gly Tyr Ser Ser Ser Glu Tyr Tyr Gly Met Asp Val Trp
            100                 105                 110

Gly Gln Gly Thr Thr Val Thr Val Ser Ser
            115                 120

<210> SEQ ID NO 349
<211> LENGTH: 122
```

```
<212> TYPE: PRT
<213> ORGANISM: Homo sapiens

<400> SEQUENCE: 349

Glu Val Gln Leu Val Glu Ser Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Ser Phe Tyr Tyr Gly Met Asp Val Trp
            100                 105                 110

Gly Gln Gly Thr Thr Val Thr Val Ser Ser
        115                 120

<210> SEQ ID NO 350
<211> LENGTH: 122
<212> TYPE: PRT
<213> ORGANISM: Homo sapiens

<400> SEQUENCE: 350

Glu Val Gln Leu Val Glu Ser Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Ser Gly Tyr Tyr Gly Met Asp Val Trp
            100                 105                 110

Gly Gln Gly Thr Thr Val Thr Val Ser Ser
        115                 120

<210> SEQ ID NO 351
<211> LENGTH: 122
<212> TYPE: PRT
<213> ORGANISM: Homo sapiens

<400> SEQUENCE: 351

Glu Val Gln Leu Val Glu Ser Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45
```

```
Ala Asn Ile Asn Gln Asp Gly Ser Glu Lys Phe Tyr Val Ala Ser Val
 50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                 85                  90                  95

Ala Arg Glu Gly Tyr Ser Ser His Tyr Tyr Gly Met Asp Val Trp
             100                 105                 110

Gly Gln Gly Thr Thr Val Thr Val Ser Ser
        115                 120
```

<210> SEQ ID NO 352
<211> LENGTH: 122
<212> TYPE: PRT
<213> ORGANISM: Homo sapiens

<400> SEQUENCE: 352

```
Glu Val Gln Leu Val Glu Ser Gly Gly Gly Phe Val Gln Pro Gly Gly
 1               5                   10                  15

Ser Leu Arg Leu Ser Cys Ala Val Ser Gly Phe Thr Phe Asn Ser Tyr
             20                  25                  30

Trp Met Ser Trp Val Arg Gln Ala Pro Gly Lys Gly Leu Glu Trp Val
         35                  40                  45

Ala Asn Ile Asn Gln Asp Gly Ser Glu Lys Phe Tyr Val Ala Ser Val
 50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                 85                  90                  95

Ala Arg Glu Gly Tyr Ser Ser Ile Tyr Tyr Gly Met Asp Val Trp
             100                 105                 110

Gly Gln Gly Thr Thr Val Thr Val Ser Ser
        115                 120
```

<210> SEQ ID NO 353
<211> LENGTH: 122
<212> TYPE: PRT
<213> ORGANISM: Homo sapiens

<400> SEQUENCE: 353

```
Glu Val Gln Leu Val Glu Ser Gly Gly Gly Phe Val Gln Pro Gly Gly
 1               5                   10                  15

Ser Leu Arg Leu Ser Cys Ala Val Ser Gly Phe Thr Phe Asn Ser Tyr
             20                  25                  30

Trp Met Ser Trp Val Arg Gln Ala Pro Gly Lys Gly Leu Glu Trp Val
         35                  40                  45

Ala Asn Ile Asn Gln Asp Gly Ser Glu Lys Phe Tyr Val Ala Ser Val
 50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                 85                  90                  95

Ala Arg Glu Gly Tyr Ser Ser Lys Tyr Tyr Gly Met Asp Val Trp
             100                 105                 110

Gly Gln Gly Thr Thr Val Thr Val Ser Ser
        115                 120
```

```
<210> SEQ ID NO 354
<211> LENGTH: 122
<212> TYPE: PRT
<213> ORGANISM: Homo sapiens

<400> SEQUENCE: 354

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Ser Leu Tyr Tyr Gly Met Asp Val Trp
            100                 105                 110

Gly Gln Gly Thr Thr Val Thr Val Ser Ser
        115                 120

<210> SEQ ID NO 355
<211> LENGTH: 122
<212> TYPE: PRT
<213> ORGANISM: Homo sapiens

<400> SEQUENCE: 355

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Ser Met Tyr Tyr Gly Met Asp Val Trp
            100                 105                 110

Gly Gln Gly Thr Thr Val Thr Val Ser Ser
        115                 120

<210> SEQ ID NO 356
<211> LENGTH: 122
<212> TYPE: PRT
<213> ORGANISM: Homo sapiens

<400> SEQUENCE: 356

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45
```

-continued

Ala Asn Ile Asn Gln Asp Gly Ser Glu Lys Phe Tyr Val Ala Ser Val
 50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                 85                  90                  95

Ala Arg Glu Gly Tyr Ser Ser Asn Tyr Tyr Gly Met Asp Val Trp
            100                 105                 110

Gly Gln Gly Thr Thr Val Thr Val Ser Ser
            115                 120

<210> SEQ ID NO 357
<211> LENGTH: 122
<212> TYPE: PRT
<213> ORGANISM: Homo sapiens

<400> SEQUENCE: 357

Glu Val Gln Leu Val Glu Ser Gly Gly Gly Phe Val Gln Pro Gly Gly
 1               5                  10                  15

Ser Leu Arg Leu Ser Cys Ala Val Ser Gly Phe Thr Phe Asn Ser Tyr
             20                  25                  30

Trp Met Ser Trp Val Arg Gln Ala Pro Gly Lys Gly Leu Glu Trp Val
         35                  40                  45

Ala Asn Ile Asn Gln Asp Gly Ser Glu Lys Phe Tyr Val Ala Ser Val
 50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                 85                  90                  95

Ala Arg Glu Gly Tyr Ser Ser Pro Tyr Tyr Gly Met Asp Val Trp
            100                 105                 110

Gly Gln Gly Thr Thr Val Thr Val Ser Ser
            115                 120

<210> SEQ ID NO 358
<211> LENGTH: 122
<212> TYPE: PRT
<213> ORGANISM: Homo sapiens

<400> SEQUENCE: 358

Glu Val Gln Leu Val Glu Ser Gly Gly Gly Phe Val Gln Pro Gly Gly
 1               5                  10                  15

Ser Leu Arg Leu Ser Cys Ala Val Ser Gly Phe Thr Phe Asn Ser Tyr
             20                  25                  30

Trp Met Ser Trp Val Arg Gln Ala Pro Gly Lys Gly Leu Glu Trp Val
         35                  40                  45

Ala Asn Ile Asn Gln Asp Gly Ser Glu Lys Phe Tyr Val Ala Ser Val
 50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                 85                  90                  95

Ala Arg Glu Gly Tyr Ser Ser Ser Gln Tyr Tyr Gly Met Asp Val Trp
            100                 105                 110

Gly Gln Gly Thr Thr Val Thr Val Ser Ser
            115                 120

<210> SEQ ID NO 359
<211> LENGTH: 122
<212> TYPE: PRT
<213> ORGANISM: Homo sapiens

<400> SEQUENCE: 359

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Arg Tyr Tyr Gly Met Asp Val Trp
            100                 105                 110

Gly Gln Gly Thr Thr Val Thr Val Ser Ser
        115                 120

<210> SEQ ID NO 360
<211> LENGTH: 122
<212> TYPE: PRT
<213> ORGANISM: Homo sapiens

<400> SEQUENCE: 360

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Ser Thr Tyr Tyr Gly Met Asp Val Trp
            100                 105                 110

Gly Gln Gly Thr Thr Val Thr Val Ser Ser
        115                 120

<210> SEQ ID NO 361
<211> LENGTH: 122
<212> TYPE: PRT
<213> ORGANISM: Homo sapiens

<400> SEQUENCE: 361

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

-continued

Ala Asn Ile Asn Gln Asp Gly Ser Glu Lys Phe Tyr Val Ala Ser Val
 50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                 85                  90                  95

Ala Arg Glu Gly Tyr Ser Ser Val Tyr Tyr Gly Met Asp Val Trp
            100                 105                 110

Gly Gln Gly Thr Thr Val Thr Val Ser Ser
            115                 120

<210> SEQ ID NO 362
<211> LENGTH: 122
<212> TYPE: PRT
<213> ORGANISM: Homo sapiens

<400> SEQUENCE: 362

Glu Val Gln Leu Val Glu Ser Gly Gly Gly Phe Val Gln Pro Gly Gly
 1               5                   10                  15

Ser Leu Arg Leu Ser Cys Ala Val Ser Gly Phe Thr Phe Asn Ser Tyr
             20                  25                  30

Trp Met Ser Trp Val Arg Gln Ala Pro Gly Lys Gly Leu Glu Trp Val
         35                  40                  45

Ala Asn Ile Asn Gln Asp Gly Ser Glu Lys Phe Tyr Val Ala Ser Val
 50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                 85                  90                  95

Ala Arg Glu Gly Tyr Ser Ser Trp Tyr Tyr Gly Met Asp Val Trp
            100                 105                 110

Gly Gln Gly Thr Thr Val Thr Val Ser Ser
            115                 120

<210> SEQ ID NO 363
<211> LENGTH: 122
<212> TYPE: PRT
<213> ORGANISM: Homo sapiens

<400> SEQUENCE: 363

Glu Val Gln Leu Val Glu Ser Gly Gly Gly Phe Val Gln Pro Gly Gly
 1               5                   10                  15

Ser Leu Arg Leu Ser Cys Ala Val Ser Gly Phe Thr Phe Asn Ser Tyr
             20                  25                  30

Trp Met Ser Trp Val Arg Gln Ala Pro Gly Lys Gly Leu Glu Trp Val
         35                  40                  45

Ala Asn Ile Asn Gln Asp Gly Ser Glu Lys Phe Tyr Val Ala Ser Val
 50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                 85                  90                  95

Ala Arg Glu Gly Tyr Ser Ser Ser Tyr Tyr Gly Met Asp Val Trp
            100                 105                 110

Gly Gln Gly Thr Thr Val Thr Val Ser Ser
            115                 120

```
<210> SEQ ID NO 364
<211> LENGTH: 122
<212> TYPE: PRT
<213> ORGANISM: Homo sapiens

<400> SEQUENCE: 364

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Cys Ser Ser Tyr Tyr Gly Met Asp Val Trp
            100                 105                 110

Gly Gln Gly Thr Thr Val Thr Val Ser Ser
        115                 120

<210> SEQ ID NO 365
<211> LENGTH: 122
<212> TYPE: PRT
<213> ORGANISM: Homo sapiens

<400> SEQUENCE: 365

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Asp Ser Ser Tyr Tyr Gly Met Asp Val Trp
            100                 105                 110

Gly Gln Gly Thr Thr Val Thr Val Ser Ser
        115                 120

<210> SEQ ID NO 366
<211> LENGTH: 122
<212> TYPE: PRT
<213> ORGANISM: Homo sapiens

<400> SEQUENCE: 366

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45
```

Ala Asn Ile Asn Gln Asp Gly Ser Glu Lys Phe Tyr Val Ala Ser Val
            50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                85                  90                  95

Ala Arg Glu Gly Tyr Glu Ser Ser Tyr Tyr Gly Met Asp Val Trp
            100                 105                 110

Gly Gln Gly Thr Thr Val Thr Val Ser Ser
            115                 120

<210> SEQ ID NO 367
<211> LENGTH: 122
<212> TYPE: PRT
<213> ORGANISM: Homo sapiens

<400> SEQUENCE: 367

Glu Val Gln Leu Val Glu Ser Gly Gly Gly Phe Val Gln Pro Gly Gly
 1               5                   10                  15

Ser Leu Arg Leu Ser Cys Ala Val Ser Gly Phe Thr Phe Asn Ser Tyr
                20                  25                  30

Trp Met Ser Trp Val Arg Gln Ala Pro Gly Lys Gly Leu Glu Trp Val
            35                  40                  45

Ala Asn Ile Asn Gln Asp Gly Ser Glu Lys Phe Tyr Val Ala Ser Val
            50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                85                  90                  95

Ala Arg Glu Gly Tyr Phe Ser Ser Tyr Tyr Gly Met Asp Val Trp
            100                 105                 110

Gly Gln Gly Thr Thr Val Thr Val Ser Ser
            115                 120

<210> SEQ ID NO 368
<211> LENGTH: 122
<212> TYPE: PRT
<213> ORGANISM: Homo sapiens

<400> SEQUENCE: 368

Glu Val Gln Leu Val Glu Ser Gly Gly Gly Phe Val Gln Pro Gly Gly
 1               5                   10                  15

Ser Leu Arg Leu Ser Cys Ala Val Ser Gly Phe Thr Phe Asn Ser Tyr
                20                  25                  30

Trp Met Ser Trp Val Arg Gln Ala Pro Gly Lys Gly Leu Glu Trp Val
            35                  40                  45

Ala Asn Ile Asn Gln Asp Gly Ser Glu Lys Phe Tyr Val Ala Ser Val
            50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                85                  90                  95

Ala Arg Glu Gly Tyr Gly Ser Ser Tyr Tyr Gly Met Asp Val Trp
            100                 105                 110

Gly Gln Gly Thr Thr Val Thr Val Ser Ser
            115                 120

-continued

<210> SEQ ID NO 369
<211> LENGTH: 122
<212> TYPE: PRT
<213> ORGANISM: Homo sapiens

<400> SEQUENCE: 369

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr His Ser Ser Tyr Tyr Gly Met Asp Val Trp
            100                 105                 110

Gly Gln Gly Thr Thr Val Thr Val Ser Ser
        115                 120

<210> SEQ ID NO 370
<211> LENGTH: 122
<212> TYPE: PRT
<213> ORGANISM: Homo sapiens

<400> SEQUENCE: 370

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ile Ser Ser Tyr Tyr Gly Met Asp Val Trp
            100                 105                 110

Gly Gln Gly Thr Thr Val Thr Val Ser Ser
        115                 120

<210> SEQ ID NO 371
<211> LENGTH: 122
<212> TYPE: PRT
<213> ORGANISM: Homo sapiens

<400> SEQUENCE: 371

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
            50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                 85                  90                  95

Ala Arg Glu Gly Tyr Lys Ser Ser Tyr Tyr Gly Met Asp Val Trp
            100                 105                 110

Gly Gln Gly Thr Thr Val Thr Val Ser Ser
            115                 120

<210> SEQ ID NO 372
<211> LENGTH: 122
<212> TYPE: PRT
<213> ORGANISM: Homo sapiens

<400> SEQUENCE: 372

Glu Val Gln Leu Val Glu Ser Gly Gly Gly Phe Val Gln Pro Gly Gly
 1               5                  10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
            50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                 85                  90                  95

Ala Arg Glu Gly Tyr Leu Ser Ser Tyr Tyr Gly Met Asp Val Trp
            100                 105                 110

Gly Gln Gly Thr Thr Val Thr Val Ser Ser
            115                 120

<210> SEQ ID NO 373
<211> LENGTH: 122
<212> TYPE: PRT
<213> ORGANISM: Homo sapiens

<400> SEQUENCE: 373

Glu Val Gln Leu Val Glu Ser Gly Gly Gly Phe Val Gln Pro Gly Gly
 1               5                  10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
            50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                 85                  90                  95

Ala Arg Glu Gly Tyr Met Ser Ser Tyr Tyr Gly Met Asp Val Trp
            100                 105                 110

Gly Gln Gly Thr Thr Val Thr Val Ser Ser
            115                 120

<210> SEQ ID NO 374
<211> LENGTH: 122
<212> TYPE: PRT
<213> ORGANISM: Homo sapiens

<400> SEQUENCE: 374

Glu Val Gln Leu Val Glu Ser Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Asn Ser Ser Tyr Tyr Gly Met Asp Val Trp
            100                 105                 110

Gly Gln Gly Thr Thr Val Thr Val Ser Ser
        115                 120

<210> SEQ ID NO 375
<211> LENGTH: 122
<212> TYPE: PRT
<213> ORGANISM: Homo sapiens

<400> SEQUENCE: 375

Glu Val Gln Leu Val Glu Ser Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Pro Ser Ser Tyr Tyr Gly Met Asp Val Trp
            100                 105                 110

Gly Gln Gly Thr Thr Val Thr Val Ser Ser
        115                 120

<210> SEQ ID NO 376
<211> LENGTH: 122
<212> TYPE: PRT
<213> ORGANISM: Homo sapiens

<400> SEQUENCE: 376

Glu Val Gln Leu Val Glu Ser Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

-continued

Trp Met Ser Trp Val Arg Gln Ala Pro Gly Lys Gly Leu Glu Trp Val
            35                  40                  45

Ala Asn Ile Asn Gln Asp Gly Ser Glu Lys Phe Tyr Val Ala Ser Val
 50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                85                  90                  95

Ala Arg Glu Gly Tyr Gln Ser Ser Tyr Tyr Gly Met Asp Val Trp
                100                 105                 110

Gly Gln Gly Thr Thr Val Thr Val Ser Ser
            115                 120

<210> SEQ ID NO 377
<211> LENGTH: 122
<212> TYPE: PRT
<213> ORGANISM: Homo sapiens

<400> SEQUENCE: 377

Glu Val Gln Leu Val Glu Ser Gly Gly Gly Phe Val Gln Pro Gly Gly
 1               5                  10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
            35                  40                  45

Ala Asn Ile Asn Gln Asp Gly Ser Glu Lys Phe Tyr Val Ala Ser Val
 50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                85                  90                  95

Ala Arg Glu Gly Tyr Arg Ser Ser Tyr Tyr Gly Met Asp Val Trp
                100                 105                 110

Gly Gln Gly Thr Thr Val Thr Val Ser Ser
            115                 120

<210> SEQ ID NO 378
<211> LENGTH: 122
<212> TYPE: PRT
<213> ORGANISM: Homo sapiens

<400> SEQUENCE: 378

Glu Val Gln Leu Val Glu Ser Gly Gly Gly Phe Val Gln Pro Gly Gly
 1               5                  10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
            35                  40                  45

Ala Asn Ile Asn Gln Asp Gly Ser Glu Lys Phe Tyr Val Ala Ser Val
 50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                85                  90                  95

Ala Arg Glu Gly Tyr Thr Ser Ser Tyr Tyr Gly Met Asp Val Trp
            100                 105                 110

Gly Gln Gly Thr Thr Val Thr Val Ser Ser
            115                 120

<210> SEQ ID NO 379
<211> LENGTH: 122
<212> TYPE: PRT
<213> ORGANISM: Homo sapiens

<400> SEQUENCE: 379

Glu Val Gln Leu Val Glu Ser Gly Gly Phe Val Gln Pro Gly Gly
1               5                   10                  15

Ser Leu Arg Leu Ser Cys Ala Val Ser Gly Phe Thr Phe Asn Ser Tyr
                20                  25                  30

Trp Met Ser Trp Val Arg Gln Ala Pro Gly Lys Gly Leu Glu Trp Val
            35                  40                  45

Ala Asn Ile Asn Gln Asp Gly Ser Glu Lys Phe Tyr Val Ala Ser Val
        50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Val Ser Ser Tyr Tyr Gly Met Asp Val Trp
            100                 105                 110

Gly Gln Gly Thr Thr Val Thr Val Ser Ser
            115                 120

<210> SEQ ID NO 380
<211> LENGTH: 122
<212> TYPE: PRT
<213> ORGANISM: Homo sapiens

<400> SEQUENCE: 380

Glu Val Gln Leu Val Glu Ser Gly Gly Phe Val Gln Pro Gly Gly
1               5                   10                  15

Ser Leu Arg Leu Ser Cys Ala Val Ser Gly Phe Thr Phe Asn Ser Tyr
                20                  25                  30

Trp Met Ser Trp Val Arg Gln Ala Pro Gly Lys Gly Leu Glu Trp Val
            35                  40                  45

Ala Asn Ile Asn Gln Asp Gly Ser Glu Lys Phe Tyr Val Ala Ser Val
        50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Trp Ser Ser Tyr Tyr Gly Met Asp Val Trp
            100                 105                 110

Gly Gln Gly Thr Thr Val Thr Val Ser Ser
            115                 120

<210> SEQ ID NO 381
<211> LENGTH: 122
<212> TYPE: PRT
<213> ORGANISM: Homo sapiens -continued

<400> SEQUENCE: 381

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Tyr Ser Ser Ser Tyr Tyr Gly Met Asp Val Trp
            100                 105                 110

Gly Gln Gly Thr Thr Val Thr Val Ser Ser
        115                 120

<210> SEQ ID NO 382
<211> LENGTH: 122
<212> TYPE: PRT
<213> ORGANISM: Homo sapiens

<400> SEQUENCE: 382

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Cys Ser Ser Tyr Tyr Gly Met Asp Val Trp
            100                 105                 110

Gly Gln Gly Thr Thr Val Thr Val Ser Ser
        115                 120

<210> SEQ ID NO 383
<211> LENGTH: 105
<212> TYPE: PRT
<213> ORGANISM: Homo sapiens

<400> SEQUENCE: 383

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

-continued

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Asp Ser Ser
            100                 105

<210> SEQ ID NO 384
<211> LENGTH: 122
<212> TYPE: PRT
<213> ORGANISM: Homo sapiens

<400> SEQUENCE: 384

Glu Val Gln Leu Val Glu Ser Gly Gly Phe Val Gln Pro Gly Gly
1               5                   10                  15

Ser Leu Arg Leu Ser Cys Ala Val Ser Gly Phe Thr Phe Asn Ser Tyr
                20                  25                  30

Trp Met Ser Trp Val Arg Gln Ala Pro Gly Lys Gly Leu Glu Trp Val
            35                  40                  45

Ala Asn Ile Asn Gln Asp Gly Ser Glu Lys Phe Tyr Val Ala Ser Val
        50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Glu Ser Tyr Tyr Gly Met Asp Val Trp
            100                 105                 110

Gly Gln Gly Thr Thr Val Thr Val Ser Ser
            115                 120

<210> SEQ ID NO 385
<211> LENGTH: 122
<212> TYPE: PRT
<213> ORGANISM: Homo sapiens

<400> SEQUENCE: 385

Glu Val Gln Leu Val Glu Ser Gly Gly Phe Val Gln Pro Gly Gly
1               5                   10                  15

Ser Leu Arg Leu Ser Cys Ala Val Ser Gly Phe Thr Phe Asn Ser Tyr
                20                  25                  30

Trp Met Ser Trp Val Arg Gln Ala Pro Gly Lys Gly Leu Glu Trp Val
            35                  40                  45

Ala Asn Ile Asn Gln Asp Gly Ser Glu Lys Phe Tyr Val Ala Ser Val
        50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Phe Ser Tyr Tyr Gly Met Asp Val Trp
            100                 105                 110

Gly Gln Gly Thr Thr Val Thr Val Ser Ser
            115                 120

<210> SEQ ID NO 386
<211> LENGTH: 122
<212> TYPE: PRT
<213> ORGANISM: Homo sapiens

<400> SEQUENCE: 386

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Gly Ser Tyr Tyr Gly Met Asp Val Trp
            100                 105                 110

Gly Gln Gly Thr Thr Val Thr Val Ser Ser
        115                 120

<210> SEQ ID NO 387
<211> LENGTH: 122
<212> TYPE: PRT
<213> ORGANISM: Homo sapiens

<400> SEQUENCE: 387

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser His Ser Ser Tyr Tyr Gly Met Asp Val Trp
            100                 105                 110

Gly Gln Gly Thr Thr Val Thr Val Ser Ser
        115                 120

<210> SEQ ID NO 388
<211> LENGTH: 122
<212> TYPE: PRT
<213> ORGANISM: Homo sapiens

<400> SEQUENCE: 388

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

```
Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                 85                  90                  95

Ala Arg Glu Gly Tyr Ser Ile Ser Ser Tyr Tyr Gly Met Asp Val Trp
            100                 105                 110

Gly Gln Gly Thr Thr Val Thr Val Ser Ser
            115                 120

<210> SEQ ID NO 389
<211> LENGTH: 122
<212> TYPE: PRT
<213> ORGANISM: Homo sapiens

<400> SEQUENCE: 389

Glu Val Gln Leu Val Glu Ser Gly Gly Gly Phe Val Gln Pro Gly Gly
 1               5                  10                  15

Ser Leu Arg Leu Ser Cys Ala Val Ser Gly Phe Thr Phe Asn Ser Tyr
                 20                  25                  30

Trp Met Ser Trp Val Arg Gln Ala Pro Gly Lys Gly Leu Glu Trp Val
             35                  40                  45

Ala Asn Ile Asn Gln Asp Gly Ser Glu Lys Phe Tyr Val Ala Ser Val
     50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                 85                  90                  95

Ala Arg Glu Gly Tyr Ser Lys Ser Ser Tyr Tyr Gly Met Asp Val Trp
            100                 105                 110

Gly Gln Gly Thr Thr Val Thr Val Ser Ser
            115                 120

<210> SEQ ID NO 390
<211> LENGTH: 122
<212> TYPE: PRT
<213> ORGANISM: Homo sapiens

<400> SEQUENCE: 390

Glu Val Gln Leu Val Glu Ser Gly Gly Gly Phe Val Gln Pro Gly Gly
 1               5                  10                  15

Ser Leu Arg Leu Ser Cys Ala Val Ser Gly Phe Thr Phe Asn Ser Tyr
                 20                  25                  30

Trp Met Ser Trp Val Arg Gln Ala Pro Gly Lys Gly Leu Glu Trp Val
             35                  40                  45

Ala Asn Ile Asn Gln Asp Gly Ser Glu Lys Phe Tyr Val Ala Ser Val
     50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                 85                  90                  95

Ala Arg Glu Gly Tyr Ser Leu Ser Ser Tyr Tyr Gly Met Asp Val Trp
            100                 105                 110

Gly Gln Gly Thr Thr Val Thr Val Ser Ser
            115                 120

<210> SEQ ID NO 391
<211> LENGTH: 122
```

```
<212> TYPE: PRT
<213> ORGANISM: Homo sapiens

<400> SEQUENCE: 391

Glu Val Gln Leu Val Glu Ser Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Met Ser Ser Tyr Tyr Gly Met Asp Val Trp
            100                 105                 110

Gly Gln Gly Thr Thr Val Thr Val Ser Ser
        115                 120

<210> SEQ ID NO 392
<211> LENGTH: 122
<212> TYPE: PRT
<213> ORGANISM: Homo sapiens

<400> SEQUENCE: 392

Glu Val Gln Leu Val Glu Ser Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Asn Ser Ser Tyr Tyr Gly Met Asp Val Trp
            100                 105                 110

Gly Gln Gly Thr Thr Val Thr Val Ser Ser
        115                 120

<210> SEQ ID NO 393
<211> LENGTH: 122
<212> TYPE: PRT
<213> ORGANISM: Homo sapiens

<400> SEQUENCE: 393

Glu Val Gln Leu Val Glu Ser Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45
```

Ala Asn Ile Asn Gln Asp Gly Ser Glu Lys Phe Tyr Val Ala Ser Val
            50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                 85                  90                  95

Ala Arg Glu Gly Tyr Ser Pro Ser Tyr Tyr Gly Met Asp Val Trp
                100                 105                 110

Gly Gln Gly Thr Thr Val Thr Val Ser Ser
            115                 120

<210> SEQ ID NO 394
<211> LENGTH: 122
<212> TYPE: PRT
<213> ORGANISM: Homo sapiens

<400> SEQUENCE: 394

Glu Val Gln Leu Val Glu Ser Gly Gly Gly Phe Val Gln Pro Gly Gly
  1               5                  10                  15

Ser Leu Arg Leu Ser Cys Ala Val Ser Gly Phe Thr Phe Asn Ser Tyr
                 20                  25                  30

Trp Met Ser Trp Val Arg Gln Ala Pro Gly Lys Gly Leu Glu Trp Val
             35                  40                  45

Ala Asn Ile Asn Gln Asp Gly Ser Glu Lys Phe Tyr Val Ala Ser Val
            50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                 85                  90                  95

Ala Arg Glu Gly Tyr Ser Gln Ser Tyr Tyr Gly Met Asp Val Trp
                100                 105                 110

Gly Gln Gly Thr Thr Val Thr Val Ser Ser
            115                 120

<210> SEQ ID NO 395
<211> LENGTH: 122
<212> TYPE: PRT
<213> ORGANISM: Homo sapiens

<400> SEQUENCE: 395

Glu Val Gln Leu Val Glu Ser Gly Gly Gly Phe Val Gln Pro Gly Gly
  1               5                  10                  15

Ser Leu Arg Leu Ser Cys Ala Val Ser Gly Phe Thr Phe Asn Ser Tyr
                 20                  25                  30

Trp Met Ser Trp Val Arg Gln Ala Pro Gly Lys Gly Leu Glu Trp Val
             35                  40                  45

Ala Asn Ile Asn Gln Asp Gly Ser Glu Lys Phe Tyr Val Ala Ser Val
            50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                 85                  90                  95

Ala Arg Glu Gly Tyr Ser Arg Ser Tyr Tyr Gly Met Asp Val Trp
                100                 105                 110

Gly Gln Gly Thr Thr Val Thr Val Ser Ser
            115                 120

```
<210> SEQ ID NO 396
<211> LENGTH: 122
<212> TYPE: PRT
<213> ORGANISM: Homo sapiens

<400> SEQUENCE: 396

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Thr Ser Tyr Tyr Gly Met Asp Val Trp
            100                 105                 110

Gly Gln Gly Thr Thr Val Thr Val Ser Ser
        115                 120

<210> SEQ ID NO 397
<211> LENGTH: 122
<212> TYPE: PRT
<213> ORGANISM: Homo sapiens

<400> SEQUENCE: 397

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Val Ser Tyr Tyr Gly Met Asp Val Trp
            100                 105                 110

Gly Gln Gly Thr Thr Val Thr Val Ser Ser
        115                 120

<210> SEQ ID NO 398
<211> LENGTH: 122
<212> TYPE: PRT
<213> ORGANISM: Homo sapiens

<400> SEQUENCE: 398

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45
```

```
Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Trp Ser Ser Tyr Tyr Gly Met Asp Val Trp
            100                 105                 110

Gly Gln Gly Thr Thr Val Thr Val Ser Ser
        115                 120

<210> SEQ ID NO 399
<211> LENGTH: 122
<212> TYPE: PRT
<213> ORGANISM: Homo sapiens

<400> SEQUENCE: 399

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Tyr Ser Ser Tyr Tyr Gly Met Asp Val Trp
            100                 105                 110

Gly Gln Gly Thr Thr Val Thr Val Ser Ser
        115                 120

<210> SEQ ID NO 400
<211> LENGTH: 15
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: Xaa is Ile, Leu, Val, Arg, Trp, Gln, Lys, His,
      Glu, Asn, Met or Ser.

<400> SEQUENCE: 400

Ala Arg Glu Gly Tyr Ser Ser Xaa Ser Tyr Tyr Gly Met Asp Val
1               5                   10                  15

<210> SEQ ID NO 401
<211> LENGTH: 15
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: Xaa is Ile, Leu, Val, Arg, Trp, Gln, Lys, His,
      Glu, Asn or Met.

<400> SEQUENCE: 401

Ala Arg Glu Gly Tyr Ser Ser Xaa Ser Tyr Tyr Gly Met Asp Val
1               5                   10                  15
```

```
<210> SEQ ID NO 402
<211> LENGTH: 15
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: Xaa is Ile, Leu, Val, Arg, Trp, Gln or Lys.

<400> SEQUENCE: 402

Ala Arg Glu Gly Tyr Ser Ser Xaa Ser Tyr Tyr Gly Met Asp Val
1               5                   10                  15

<210> SEQ ID NO 403
<211> LENGTH: 15
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: Xaa is Ile, Leu or Val

<400> SEQUENCE: 403

Ala Arg Glu Gly Tyr Ser Ser Xaa Ser Tyr Tyr Gly Met Asp Val
1               5                   10                  15
```